US012577257B2

(12) United States Patent
Kuhn et al.

(10) Patent No.: US 12,577,257 B2
(45) Date of Patent: Mar. 17, 2026

(54) HETEROCYCLIC COMPOUNDS

(71) Applicant: Hoffmann-La Roche Inc., Little Falls, NJ (US)

(72) Inventors: Bernd Kuhn, Basel (CH); Uwe Grether, Basel (CH); Benoit Hornsperger, Basel (CH); Hans Richter, Basel (CH); Carsten Kroll, Basel (CH); Katrin Groebke Zbinden, Basel (CH); Fionn O'Hara, Basel (CH); Didier Rombach, Basel (CH); Marius Daniel Rinaldo Lutz, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 1180 days.

(21) Appl. No.: 17/325,934

(22) Filed: May 20, 2021

(65) Prior Publication Data

US 2021/0387999 A1 Dec. 16, 2021

Related U.S. Application Data

(63) Continuation of application No. PCT/EP2019/081870, filed on Nov. 20, 2019.

(30) Foreign Application Priority Data

Nov. 22, 2018 (EP) .................................... 18207725

(51) Int. Cl.
*C07D 498/04* (2006.01)
*C07D 519/00* (2006.01)

(52) U.S. Cl.
CPC ......... *C07D 498/04* (2013.01); *C07D 519/00* (2013.01)

(58) Field of Classification Search
CPC ..... C07D 498/04; C07D 519/00; A61P 25/28; A61P 29/00; A61P 35/00; A61K 31/5383
See application file for complete search history.

(56) References Cited

U.S. PATENT DOCUMENTS

| | | | |
|---|---|---|---|
| 5,214,038 A | 5/1993 | Effland et al. |
| 8,431,695 B2 | 4/2013 | O'Connor et al. |
| 10,106,556 B2 | 10/2018 | Ikeda et al. |
| 10,610,520 B2 | 4/2020 | Ikeda et al. |
| 11,390,610 B2 | 7/2022 | Benz et al. |
| 11,420,961 B2 | 8/2022 | Benz et al. |
| 11,608,347 B2 | 3/2023 | Petersen et al. |
| 11,802,133 B2 | 10/2023 | Bell et al. |
| 11,814,375 B2 | 11/2023 | Benz et al. |
| 11,981,661 B2 | 5/2024 | Benz et al. |
| 2010/0035893 A1 | 2/2010 | Hoornaert et al. |
| 2010/0280240 A1 | 11/2010 | Allison et al. |
| 2011/0059118 A1 | 3/2011 | Fidalgo et al. |
| 2011/0251169 A1 | 10/2011 | Green et al. |
| 2013/0046097 A1 | 2/2013 | Tomesch et al. |
| 2014/0275015 A1 | 9/2014 | Vaca et al. |
| 2014/0309218 A1 | 10/2014 | Hubschwerlen et al. |
| 2015/0018335 A1 | 1/2015 | Cisar et al. |
| 2017/0029390 A1 | 2/2017 | Butler et al. |
| 2019/0135778 A1 | 5/2019 | Bertozzi et al. |
| 2020/0255439 A1 | 8/2020 | Kamata et al. |
| 2020/0299277 A1 | 9/2020 | Benz et al. |
| 2020/0308158 A1 | 10/2020 | Bell et al. |
| 2020/0308190 A1 | 10/2020 | Bell et al. |
| 2020/0392125 A1 | 12/2020 | Benz et al. |
| 2021/0024546 A1 | 1/2021 | Petersen et al. |
| 2021/0094943 A1 | 4/2021 | Benz et al. |
| 2021/0094971 A1 | 4/2021 | Grether et al. |
| 2021/0094972 A1 | 4/2021 | Benz et al. |
| 2021/0094973 A1 | 4/2021 | Gobbi et al. |
| 2021/0107920 A1 | 4/2021 | Bell et al. |
| 2021/0107921 A1 | 4/2021 | Benz et al. |
| 2021/0277020 A1 | 9/2021 | Anselm et al. |
| 2021/0387999 A1 | 12/2021 | Kuhn et al. |

(Continued)

FOREIGN PATENT DOCUMENTS

| | | |
|---|---|---|
| EA | 009645 B1 | 2/2008 |
| EA | 018521 B1 | 8/2013 |

(Continued)

OTHER PUBLICATIONS

Anderson, A.C., "The Process of Structure-Based Drug Design" Chem Biol 10(9):787-797 (Sep. 1, 2003).
Belikov, V.G. Pharmaceutical Chemistry—Tutorial "Part I: General Pharmaceutical Chemistry" (Eng. Transl.), Fourth, Revised edition, Moscow-RU:MEDPress-Inform,:27-29 (2007).
Cisar, J., et al., "Identification of ABX-1431, a Selective Inhibitor of Monoacylglycerol Lipase and Clinical Candidate for Treatment of Neurological Disorders" ACS J Med Chem 61(20):9062-9084 (Aug. 1, 2018).

(Continued)

*Primary Examiner* — Danah Al-Awadi
*Assistant Examiner* — Chantal Adlam
(74) *Attorney, Agent, or Firm* — Zong-Qiang Bill Tian

(57) ABSTRACT

The invention provides new heterocyclic compounds having the general formula (I)

(I)

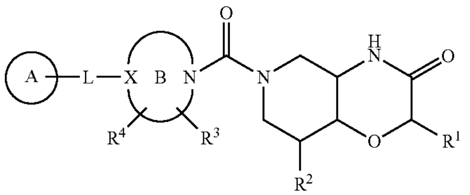

wherein A, B, L, X, $R^1$, $R^2$, $R^3$ and $R^4$ are as described herein, compositions including the compounds, processes of manufacturing the compounds and methods of using the compounds.

25 Claims, No Drawings

(56) References Cited

U.S. PATENT DOCUMENTS

| | | | | |
|---|---|---|---|---|
| 2022/0098176 | A1 | 3/2022 | Benz et al. | |
| 2022/0106328 | A1 | 4/2022 | Benz et al. | |
| 2022/0135591 | A1 | 5/2022 | Benz et al. | |
| 2022/0202963 | A1* | 6/2022 | Collin | A61B 6/037 |
| 2022/0213093 | A1 | 7/2022 | Benz et al. | |
| 2022/0220373 | A1 | 7/2022 | Benz et al. | |
| 2022/0242876 | A1 | 8/2022 | Kroll et al. | |
| 2022/0267349 | A1 | 8/2022 | Benz et al. | |
| 2022/0275005 | A1 | 9/2022 | Grether et al. | |
| 2023/0117324 | A1 | 4/2023 | Bell et al. | |
| 2023/0183224 | A1 | 6/2023 | Bell et al. | |
| 2023/0203056 | A1 | 6/2023 | Benz et al. | |
| 2024/0150373 | A1 | 5/2024 | Bell et al. | |
| 2024/0199587 | A1 | 6/2024 | Amoussa et al. | |

FOREIGN PATENT DOCUMENTS

| | | | |
|---|---|---|---|
| EP | 3279191 | A1 | 7/2018 |
| JP | 2010-524907 | A | 7/2010 |
| RU | 2042680 | C1 | 8/1995 |
| RU | 2009 142 430 | | 4/2008 |
| RU | 2 558 141 | | 7/2015 |
| WO | 2005/019215 | A1 | 3/2005 |
| WO | 2005/066187 | A1 | 7/2005 |
| WO | 2006/101496 | | 9/2006 |
| WO | 2007/002057 | A1 | 1/2007 |
| WO | 2007/098418 | A1 | 8/2007 |
| WO | 2007/117557 | A2 | 10/2007 |
| WO | 2008/145842 | | 12/2008 |
| WO | 2009/097287 | A1 | 8/2009 |
| WO | 2009/145456 | | 12/2009 |
| WO | 2010/049302 | | 5/2010 |
| WO | 2011/058766 | A1 | 5/2011 |
| WO | 2011/059118 | A1 | 5/2011 |
| WO | 2012/155199 | A1 | 11/2012 |
| WO | 2013/059118 | A1 | 4/2013 |
| WO | 2013/093849 | A1 | 6/2013 |
| WO | 2013/179024 | A1 | 12/2013 |
| WO | 2014/102630 | A1 | 7/2014 |
| WO | 2014/170821 | | 10/2014 |
| WO | 2016/109501 | A1 | 7/2016 |
| WO | 2016/180536 | A1 | 11/2016 |
| WO | 2016/185279 | A1 | 11/2016 |
| WO | 2016/205590 | A1 | 12/2016 |
| WO | 2017/021805 | | 2/2017 |
| WO | 2017/087858 | A1 | 5/2017 |
| WO | 2017/087863 | A1 | 5/2017 |
| WO | 2017/170830 | A1 | 10/2017 |
| WO | 2017/171100 | A1 | 10/2017 |
| WO | 2018/002220 | | 1/2018 |
| WO | 2018/093949 | | 5/2018 |
| WO | 2018/093953 | | 5/2018 |
| WO | 2018/169880 | A1 | 9/2018 |
| WO | 2018/228934 | A1 | 12/2018 |
| WO | 2019/072785 | A1 | 4/2019 |
| WO | 2019/105915 | A1 | 6/2019 |
| WO | 2019/115660 | A1 | 6/2019 |
| WO | 2019/134985 | A1 | 7/2019 |
| WO | 2019/180185 | A1 | 9/2019 |
| WO | 2019/180185 | A8 | 9/2019 |
| WO | 2020/035424 | A1 | 2/2020 |
| WO | 2020/035425 | A1 | 2/2020 |
| WO | 2020/104494 | A1 | 5/2020 |
| WO | 2021/058445 | A1 | 4/2021 |

OTHER PUBLICATIONS

Damasio, A., "Alzheimer's Disease and Related Dementias" Cecil Textbook of Medicine 20(2):1992-1996 (Jan. 1, 1996).

Durnov and GOLDBENKO, "Children's Oncology" Medicine (English machine translation),:139 ( 2002).

Gura, T., "Systems for Identifying New Drugs Are Often Faulty" Science 278(5340):1041-1042 (Nov. 7, 1997).

"International Preliminary Report on Patentability—PCT/EP2020/076346" (Report Issuance Date: Mar. 15, 2022; Chapter I),:pp. 1-9 (Apr. 7, 2022).

"International Preliminary Report on Patentability—PCT/EP2020/074897" (Report Issuance Date: Mar. 9, 2022; Chapter I),:pp. 1-8 (Mar. 17, 2022).

"International Preliminary Report on Patentability—PCT/EP2020/076228" (Report Issuance Date: Mar. 15, 2022; Chapter I),:pp. 1-9 (Apr. 7, 2022).

Janssen, F., et al., "Inhibitors of diacylglycerol lipases in neurodegenerative and metabolic disorders" Bioorg Med Chem Lett 26(16):3831-3837 (Aug. 15, 2016).

Johnson, J.I., et al., "Relationships between drug activity in NCI preclinical in vitro and in vivo models and early clinical trials" Brit J Cancer 84(10):1424-1431 (May 1, 2001).

Kayacelebi, A., et al., "Cross-validated stable-isotope dilution GC-MS and LC-MS/MS assays for monoacylglycerol lipase (MAGL) activity by measuring arachidonic acid released from the endocannabinoid 2-arachidonoyl glycerol" J Chromatogr B Analyt Technol Biomed Life Sci (Epub: Aug. 3, 2016), 1047:151-159 (Mar. 15, 2017).

Korhonen, J., et al., "Piperazine and piperidine carboxamides and carbamates as inhibitors of fatty acid amide hydrolase (FAAH) and monoacylglycerol lipase (Magl)" Bioorg Med Chem 22(23):6694-6705 (Dec. 1, 2014).

Kummerer, K., "Pharmaceuticals in the Environment" Ann Rev Environ Res 35:57-75 (Nov. 1, 2010).

Layzer, R., "Section Five: Degenerative Diseases of the Nervous System" Cecil Textbook of Medicine 20(2):2050-2057 (Jan. 1, 1996).

Marino, S., et al., "JZL184, A Monoacylglycerol Lipase Inhibitor, Induces Bone Loss in a Multiple Myeloma Model of Immunocompetent Mice" Calcif Tissue Int 107(1):72-85 (Jul. 1, 2020).

Merck Manual et al. Merck Manual—Online Professional "Acute Leukemia" Kenilworth, N.J.-USA:Merck and Company, Inc.,:1-6 (Jul. 10, 2013).

Pearce, H., et al. Cancer Drug Design and Discovery "Chapter 18: Failure modes in anticancer drug discovery and development" Neidle, S., ed., 1st edition, New York, NY-USA:Academic Presss,:424-435 ( 2008).

Simone, J.V.,, "Oncology: Introduction" Cecil Textbook of Medicine 1(20):1004-1010 (Jan. 1, 1996).

Thiel, K.,, "Structure-aided drug design's next generation" Nat Biotechnol 22(5):513-519 (May 1, 2004).

Williams, D., et al. Foye's Principles of Medicinal Chemistry, Chapter 2(5th edition):59-63 ( 2002).

"Written Opinion of the International Searching Authority—PCT/EP2019/071520":pp. 1-6 (Sep. 17, 2019).

Alpar, A., et al., "Endocannabinoids modulate cortical development by configuring Slit2/Robo1 signaling" Nat Commun 5(4421):1-13 (Jul. 17, 2014).

Ashton, K., et al., "Design and synthesis of novel amide AKT1 inhibitors with selectivity over CDK2" Bioorg Med Chem Lett 21(18):5191-5196 (Sep. 15, 2011).

Barney, C., et al., "A convenient synthesis of hindered amines and α-trifluoromethylamines from ketones" Tetrahedron Lett 31(39):5547-5550 (1990).

Bernal-Chico, A., et al., "Blockade of Monoacylglycerol Lipase Inhibits Oligodendrocyte Excitotoxicity and Prevents Demyelination In Vivo" GLIA 63(1):163-176 (Jan. 1, 2015).

Chanda, P.K., et al., "Monoacylglycerol Lipase Activity Is a Critical Modulator of the Tone and Integrity of the Endocannabinoid System" Mol Pharmacol 78(6):996-1003 (Dec. 1, 2010).

Chang, J. et al., "Highly Selective Inhibitors of Monoacylglycerol Lipase Bearing a Reactive Group that Is Bioisosteric with Endocannabinoid Substrates" Chem Biol 19(5):579-588 (May 1, 2012).

Dugar, S. et al., "A Concise and Efficient Synthesis of Substituted Morpholines" Synthesis 47:712-720 (2015).

Duncan, M., et al., "Review article: endocannabinoids and their receptors in the enteric nervous system" Aliment Pharmacol Ther 22(8):667-683 (Oct. 15, 2005).

(56) References Cited

OTHER PUBLICATIONS

Evano, G., et al., "Copper-Mediated Coupling Reactions and Their Applications in Natural Products and Designed Biomolecules Synthesis" Chem Rev 108(8):3054-3131 (Aug. 13, 2008).
Feliu, A., et al., "2-Arachidonoylglycerol Reduces Proteoglycans and Enhances Remyelination in a Progressive Model of Demyelination" J Neurosci 37(35):8385-8398 (Aug. 30, 2017).
Fray, M., et al., "Second generation N-(1,2-diphenylethyl)piperazines as dual serotonin and noradrenaline reuptake inhibitors: improving metabolic stability and reducing ion channel activity" Bioorg Med Chem Lett 20(12):3788-3792 (Jun. 15, 2010).
Fray, M., et al., "Structure-activity relationships of N-substituted piperazine amine reuptake inhibitors" Bioorg Med Chem Lett 16(16):4349-4353 (Aug. 15, 2006).
Gavryushin, A., et al., "Efficient Cross-Coupling of Functionalized Arylzinc Halides Catalyzed by a Nickel Chloride-Diethyl Phosphite System" Org Lett 7(22):4871-4874 (Oct. 7, 2005).
Grill, M., et al., "Members of the endocannabinoid system are distinctly regulated in inflammatory bowel disease and colorectal cancer" Sci Rep 9(2358):1-13 (Feb. 20, 2019).
Haas, D., et al., "Recent Developments in Negishi Cross-Coupling Reactions" ACS Catal 6(3):1540-1552 (Feb. 3, 2016).
He, S., et al., "High-Affinity Small-Molecule Inhibitors of the Menin-Mixed Lineage Leukemia (MLL) Interaction Closely Mimic a Natural Protein-Protein Interaction" J Med Chem 57(4):1543-1556 (Feb. 27, 2014).
Heravi, M., et al., "Buchwald-Hartwig reaction: An overview" J Organometallic Chem 861:17-104 (Apr. 15, 2018).
Hutchings, K., et al., "Synthesis and antibacterial activity of the C-7 side chain of 3-aminoquinazolinediones" Bioorg Med Chem Lett 18(18):5087-5090 (Sep. 15, 2008).
Iannotti, F. A., et al., "Endocannabinoids and endocannabinoid-related mediators: Targets, metabolism and role in neurological disorders" Prog Lipid Res 62:107-128 (Apr. 1, 2016).
Ignatowska-Jankowska, B., et al., "Selective Monoacylglycerol Lipase Inhibitors: Antinociceptive versus Cannabimimetic Effects in Mice" J Pharmacol Exp Ther 353(2):424-432 (May 1, 2015).
"International Preliminary Report on Patentability—PCT/EP2019/081870" (Report Issuance Date: May 25, 2021; Chapter I),:pp. 1-8 (Jun. 3, 2021).
"International Preliminary Report on Patentability—PCT/EP2019/071520" (Report Issuance Date: Feb. 16, 2021, Chapter I),:pp. 1-8 (Feb. 25, 2021).
"International Preliminary Report on Patentability—PCT/EP2019/071522" (Report Issuance Date: Feb. 16, 2021, Chapter I),:pp. 1-9 (Feb. 25, 2021).
"International Preliminary Report on Patentability—PCT/EP2019/057174" (Report Issuance Date: Sep. 22, 2020—Chapter I),:pp. 1-9 (Oct. 1, 2020).
"International Search Report—PCT/EP2019/057174" (w/Written Opinion), :pp. 1-6 (Jul. 3, 2019).
"International Search Report—PCT/EP2019/071520" (w/Written Opinion), :pp. 1-14 (Sep. 17, 2019).
"International Search Report—PCT/EP2019/071522" (w/Written Opinion), :pp. 1-15 (Sep. 17, 2019).
"International Search Report—PCT/EP2019/081870" (w/Written Opinion), :pp. 1-12 (Jan. 14, 2020).
"International Search Report—PCT/EP2020/074897" (w/Written Opinion), :pp. 1-15 (Nov. 18, 2020).
"International Search Report—PCT/EP2020/075260" (w/Written Opinion), :pp. 1-14 (Nov. 18, 2020).
"International Search Report—PCT/EP2020/076228" (w/Written Opinion), :pp. 1-14 (Nov. 12, 2020).
"International Search Report—PCT/EP2020/076346" (w/Written Opinion), :pp. 1-16 (Nov. 13, 2020).
"International Search Report—PCT/EP2020/076347" (w/Written Opinion), :pp. 1-16 (Nov. 30, 2020).
Ishichi, Y., et al., "Novel triple reuptake inhibitors with low risk of CAD associated liabilities: design, synthesis and biological activities of 4-[(1S)-1-(3,4-dichlorophenyl)-2-methoxyethyl] piperidine and related compounds" Bioorg Med Chem 21(15):4600-4613 (Aug. 1, 2013).
Keenan, M., et al., "Design, structure-activity relationship and in vivo efficacy of piperazine analogues of fenarimol as inhibitors of Trypanosoma cruzi" Bioorg Med Chem 21(7):1756-1763 (Apr. 1, 2013).
Kitbunnadaj, R., et al., "Synthesis and structure-activity relationships of conformationally constrained histamine H(3) receptor agonists" J Med Chem 46(25):5445-5457 (Dec. 4, 2003).
Liu, F., et al., "Structure-Based Optimization of Pyridoxal 5'-Phosphate-Dependent Transaminase Enzyme (BioA) Inhibitors that Target Biotin Biosynthesis in Mycobacterium tuberculosis" J Med Chem 60(13):5507-5520 (Jul. 13, 2017).
Liu, Y. et al., "Discovery of 4-benzoylpiperidine and 3-(piperidin-4-yl)benzo[d]isoxazole derivatives as potential and selective GlyT1 inhibitors" RSC ADV 5(51):40964-40977 (Apr. 30, 2015).
Lleo, A., et al., "Molecular targets of non-steroidal anti-inflammatory drugs in neurodegenerative diseases" Cell Mol Life Sci 64(11):1403-1418 (Apr. 20, 2007).
Long, J.Z., et al., "Selective blockade of 2-arachidonoylglycerol hydrolysis produces cannabinoid behavioral effects" Nat Chem Biol 5(1):37-44 (Jan. 1, 2009).
Marquez, L., et al., "Ulcerative Colitis Induces Changes on the Expression of the Endocannabinoid System in the Human Colonic Tissue" PLOS One 4(9):(e6893) 1-13 (Sep. 4, 2009).
McAllister, L., et al., "Discovery of Trifluoromethyl Glycol Carbamates as Potent and Selective Covalent Monoacylglycerol Lipase (MAGL) Inhibitors for Treatment of Neuroinflammation" J Med Chem 61(7):3008-3026 (Apr. 12, 2018).
Muccioli, G., et al., "CAY10499, a Novel Monoglyceride Lipase Inhibitor Evidenced by an Expeditious MGL Assay" Chem Bio Chem 9(16):2704-2710 (Nov. 3, 2008).
Mulvihill, M., et al., "Therapeutic Potential of Monoacylglycerol Lipase Inhibitors" Life Sci 92(8-9):492-497 (Nov. 8, 2013).
Negishi, E., "Palladium- or Nickel-Catalyzed Cross Coupling. A New Selective Method for Carbon-Carbon Bond Formation" Acc Chem Res 15(11):340-348 (Nov. 1, 1982).
Nomura, D.K., et al., "Endocannabinoid Hydrolysis Generates Brain Prostaglandins That Promote Neuroinflammation" Science 334(6057):809-813 (Nov. 11, 2011).
Nomura, D.K., et al., "Monoacylglycerol Lipase Exerts Dual Control over Endocannabinoid and Fatty Acid Pathways to Support Prostate Cancer" Chem Biol 18(7):846-856 (Jul. 29, 2011).
Nomura, D.K., et al., "Monoacylglycerol Lipase Regulates a Fatty Acid Network that Promotes Cancer Pathogenesis" Cell 140(1):49-61 (Jan. 8, 2010).
Patel, J. et al., "Loratadine analogues as MAGL inhibitors" Bioorg Med Chem Lett 25(7):1436-1442 (Feb. 24, 2015).
Perisetti, A., et al., "Role of cannabis in inflammatory bowel diseases" Ann Gastroenterol 33(2):134-144 (Feb. 12, 2020).
Qin, H., et al., "The role of monoacylglycerol lipase (MAGL) in the cancer progress" Cell Biochem Biophys 70:33-36 (Mar. 16, 2014).
Rafinski, Z. et al., "Enantioselective Synthesis of Chromanones Bearing Quaternary Substituted Stereocenters Catalyzed by (1R)-Camphor-Derived N-Heterocyclic Carbenes" J Org Chem 80(15):7468-7476 (Aug. 7, 2015).
Scalvini, L., et al., "Monoglyceride lipase: Structure and inhibitors" Chem Phys Lipids 197:13-24 (Jul. 26, 2015).
Senter, T., et al., "Progress towards small molecule menin-mixed lineage leukemia (MLL) interaction inhibitors with in vivo utility" Bioorg Med Chem Lett 25(13):2720-2725 (Jul. 1, 2015).
Surry, D., et al., "Biaryl Phosphane Ligands in Palladium-Catalyzed Amination" Angew Chem Int Ed Engl 47(34):6338-6361 (Aug. 11, 2008).
Ukrorgsyntez, Ltd., CAS Registry Database, 1941372-36-6, (Stereosearch—C20 H27 N3 O3), pp. 1 Creation Date Jun. 29, 2016.
USPTO, "U.S. Appl. No. 17/174,000, filed Feb. 11, 2021" (Feb. 11, 2021).
Viader, A., et al., "Metabolic Interplay between Astrocytes and Neurons Regulates Endocannabinoid Action" Cell Rep 12(5):798-808 (Aug. 4, 2015).

(56) References Cited

OTHER PUBLICATIONS

Walsh, D., et al., "Synthesis and antiallergy activity of 4-(diarylhydroxymethyl)-1-[3-(aryloxy)propyl]piperidines and structurally related compounds" J Med Chem 32(1):105-118 (Jan. 1, 1989).
Wang, J., et al., "Effect of monoacylglycerol lipase inhibition on intestinal permeability in chronic stress model" Biochem Biophys Res Commun 525(4):962-967 (May 14, 2020).
Wright, K., et al., "Differential expression of cannabinoid receptors in the human colon: cannabinoids promote epithelial wound healing" Gastroenterology 129(2):437-453 (Aug. 1, 2005).
Wu, W., et al., "Synthesis and structure-activity relationships of piperidine-based melanin-concentrating hormone receptor 1 antagonists" Bioorg Med Chem Lett 16(14):3668-3673 (Jul. 15, 2006).
Yin, J., et al., "ARS2/MAGL signaling in glioblastoma stem cells promotes self-renewal and M2-like polarization of tumor-associated macrophages" Nat Commun 11(1 Suppl 2978):1-15 (Jun. 11, 2020).
Zhang, P., et al., "Silyl Radical Activation of Alkyl Halides in Metallaphotoredox Catalysis: A Unique Pathway for Cross-Electrophile Coupling" J Am Chem Soc 138(26):8084-8087 (Jul. 6, 2016).
Zhang, X., et al., "Direct Aldehyde C—H Arylation and Alkylation via the Combination of Nickel, Hydrogen Atom Transfer, and Photoredox Catalysis" J Am Chem Soc 139(33):11353-11356 (Aug. 23, 2017).
Zhong, P., et al., "Monoacylglycerol Lipase Inhibition Blocks Chronic Stress-Induced Depressive-Like Behaviors via Activation of mTOR Signaling" Neuropsychopharmacology 39(7):1763-1776 (Feb. 19, 2014).
Granchi, C., et al., "A patent review of monoacylglycerol lipase (MAGL) inhibitors" Expert Opin Ther Pat 27(12): 1341-1351 (Dec. 1, 2017).

* cited by examiner

HETEROCYCLIC COMPOUNDS

CROSS-REFERENCE TO RELATED APPLICATIONS

This application is a continuation of International Application No. PCT/EP2019/081870, filed Nov. 20, 2019, which claims priority to EP Application No. 18207725.5, filed Nov. 22, 2018, the disclosures of which are incorporated herein by reference in their entireties.

FIELD OF THE INVENTION

The present invention relates to organic compounds useful for therapy or prophylaxis in a mammal, and in particular to monoacylglycerol lipase (MAGL) inhibitors for the treatment or prophylaxis of neuroinflammation, neurodegenerative diseases, pain, cancer, mental disorders, multiple sclerosis, Alzheimer's disease, Parkinson's disease, amyotrophic lateral sclerosis, traumatic brain injury, neurotoxicity, stroke, epilepsy, anxiety, migraine and/or depression in a mammal.

BACKGROUND OF THE INVENTION

Endocannabinoids (ECs) are signaling lipids that exert their biological actions by interacting with cannabinoid receptors (CBRs), CB1 and CB2. They modulate multiple physiological processes including neuroinflammation, neurodegeneration and tissue regeneration (Iannotti, F. A., et al., *Progress in lipid research* 2016, 62, 107-28). In the brain, the main endocannabinoid, 2-arachidonoylglycerol (2-AG), is produced by diacyglycerol lipases (DAGL) and hydrolyzed by the monoacylglycerol lipase, MAGL. MAGL hydrolyses 85% of 2-AG; the remaining 15% being hydrolysed by ABHD6 and ABDH12 (Nomura, D. K., et al., *Science* 2011, 334, 809). MAGL is expressed throughout the brain and in most brain cell types, including neurons, astrocytes, oligodendrocytes and microglia cells (Chanda, P. K., et al., *Molecular pharmacology* 2010, 78, 996; Viader, A., et al., *Cell reports* 2015, 12, 798). 2-AG hydrolysis results in the formation of arachidonic acid (AA), the precursor of prostaglandins (PGs) and leukotrienes (LTs). Oxidative metabolism of AA is increased in inflamed tissues. There are two principal enzyme pathways of arachidonic acid oxygenation involved in inflammatory processes, the cyclo-oxygenase which produces PGs and the 5-lipoxygenase which produces LTs. Of the various cyclooxygenase products formed during inflammation, PGE2 is one of the most important. These products have been detected at sites of inflammation, e.g. in the cerebrospinal fluid of patients suffering from neurodegenerative disorders and are believed to contribute to inflammatory response and disease progression. Mice lacking MAGL (Mgll−/−) exhibit dramatically reduced 2-AG hydrolase activity and elevated 2-AG levels in the nervous system while other arachidonoyl-containing phospho- and neutral lipid species including anandamide (AEA), as well as other free fatty acids, are unaltered. Conversely, levels of AA and AA-derived prostaglandins and other eicosanoids, including prostaglandin E2 (PGE2), D2 (PGD2), F2 (PGF2), and thromboxane B2 (TXB2), are strongly decreased. Phospholipase $A_2$ ($PLA_2$) enzymes have been viewed as the principal source of AA, but $cPLA_2$-deficient mice have unaltered AA levels in their brain, reinforcing the key role of MAGL in the brain for AA production and regulation of the brain inflammatory process.

Neuroinflammation is a common pathological change characteristic of diseases of the brain including, but not restricted to, neurodegenerative diseases (e.g. multiple sclerosis, Alzheimer's disease, Parkinson disease, amyotrophic lateral sclerosis, traumatic brain injury, neurotoxicity, stroke, epilepsy and mental disorders such as anxiety and migraine). In the brain, production of eicosanoids and prostaglandins controls the neuroinflammation process. The pro-inflammatory agent lipopolysaccharide (LPS) produces a robust, time-dependent increase in brain eicosanoids that is markedly blunted in Mgll−/− mice. LPS treatment also induces a widespread elevation in pro-inflammatory cytokines including interleukin-1-a (IL-1-a), IL-1b, IL-6, and tumor necrosis factor-a (TNF-a) that is prevented in Mgll−/− mice.

Neuroinflammation is characterized by the activation of the innate immune cells of the central nervous system, the microglia and the astrocytes. It has been reported that anti-inflammatory drugs can suppress in preclinical models the activation of glia cells and the progression of disease including Alzheimer's disease and multiple sclerosis (Lleo A., *Cell Mol Life Sci.* 2007, 64, 1403). Importantly, genetic and/or pharmacological disruption of MAGL activity also blocks LPS-induced activation of microglial cells in the brain (Nomura, D. K., et al., *Science* 2011, 334, 809).

In addition, genetic and/or pharmacological disruption of MAGL activity was shown to be protective in several animal models of neurodegeneration including, but not restricted to, Alzheimer's disease, Parkinson's disease and multiple sclerosis. For example, an irreversible MAGL inhibitor has been widely used in preclinical models of neuroinflammation and neurodegeneration (Long, J. Z., et al., *Nature chemical biology* 2009, 5, 37). Systemic injection of such inhibitor recapitulates the Mgll−/− mice phenotype in the brain, including an increase in 2-AG levels, a reduction in AA levels and related eicosanoids production, as well as the prevention of cytokines production and microglia activation following LPS-induced neuroinflammation (Nomura, D. K., et al., *Science* 2011, 334, 809), altogether confirming that MAGL is a druggable target.

Consecutive to the genetic and/or pharmacological disruption of MAGL activity, the endogenous levels of the MAGL natural substrate in the brain, 2-AG, are increased. 2-AG has been reported to show beneficial effects on pain with, for example, anti-nociceptive effects in mice (Ignatowska-Jankowska B. et al., *J. Pharmacol. Exp. Ther.* 2015, 353, 424.) and on mental disorders, such as depression in chronic stress models (Zhong P. et al., *Neuropsychopharmacology* 2014, 39, 1763).

Furthermore, oligodendrocytes (OLs), the myelinating cells of the central nervous system, and their precursors (OPCs) express the cannabinoid receptor 2 (CB2) on their membrane. 2-AG is the endogenous ligand of CB1 and CB2 receptors. It has been reported that both cannabinoids and pharmacological inhibition of MAGL attenuate OLs's and OPCs's vulnerability to excitotoxic insults and therefore may be neuroprotective (Bernal-Chico, A., et al., *Glia* 2015, 63, 163). Additionally, pharmacological inhibition of MAGL increases the number of myelinating OLs in the brain of mice, suggesting that MAGL inhibition may promote differentiation of OPCs in myelinating OLs in vivo (Alpar, A., et al., *Nature communications* 2014, 5, 4421). Inhibition of MAGL was also shown to promote remyelination and functional recovery in a mouse model of progressive multiple sclerosis (Feliu A. et al., *Journal of Neuroscience* 2017, 37(35), 8385).

Finally, in recent years, metabolism is talked highly important in cancer research, especially the lipid metabolism. Researchers believe that the de novo fatty acid synthesis plays an important role in tumor development. Many studies illustrated that endocannabinoids have anti-tumorigenic actions, including anti-proliferation, apoptosis induction and anti-metastatic effects. MAGL as an important decomposing enzyme for both lipid metabolism and the endocannabinoids system, additionally as a part of a gene expression signature, contributes to different aspects of tumourigenesis (Qin, H., et al., *Cell Biochem. Biophys.* 2014, 70, 33; Nomura D K et al., *Cell* 2009, 140(1), 49-61; Nomura D K et al., *Chem. Biol.* 2011, 18(7), 846-856).

In conclusion, suppressing the action and/or the activation of MAGL is a promising new therapeutic strategy for the treatment or prevention of neuroinflammation, neurodegenerative diseases, pain, cancer and mental disorders. Furthermore, suppressing the action and/or the activation of MAGL is a promising new therapeutic strategy for providing neuroprotection and myelin regeneration. Accordingly, there is a high unmet medical need for new MAGL inhibitors.

SUMMARY OF THE INVENTION

In a first aspect, the present invention provides a compound of formula (I)

(I)

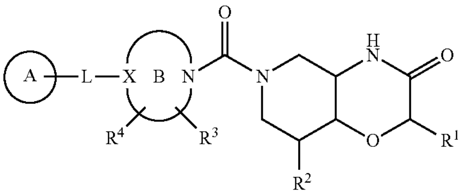

wherein A, B, L, X, $R^1$, $R^2$, $R^3$ and $R^4$ are as described herein.

In one aspect, the present invention provides a process of manufacturing the urea compounds of formula (I) described herein, and pharmaceutically acceptable salts thereof, comprising:

(a) reacting a first amine of formula 1, wherein $R^1$ and $R^2$ are as described herein, preferably wherein $R^1$ and $R^2$ are hydrogen,

1

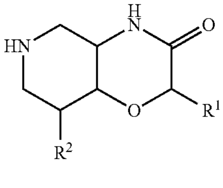

with a secondary amine 2, wherein A, B, L, X, $R^3$ and $R^4$ are as described herein

2

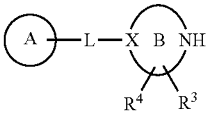

in the presence of a base and a urea forming reagent, to form said compound of formula (I); and optionally (b) transforming said compound of formula (I) to a pharmaceutically acceptable salts thereof.

In a further aspect, the present invention provides a compound of formula (I) as described herein, when manufactured according to the processes described herein.

In a further aspect, the present invention provides a compound of formula (I) as described herein, for use as therapeutically active substance.

In a further aspect, the present invention provides a pharmaceutical composition comprising a compound of formula (I) as described herein and a therapeutically inert carrier.

In a further aspect, the present invention provides a compound of formula (I) as described herein or a pharmaceutical composition described herein for use in a method of inhibiting monoacylglycerol lipase in a mammal.

In a further aspect, the present invention provides a compound of formula (I) as described herein or a pharmaceutical composition described herein for use in the treatment or prophylaxis of neuroinflammation, neurodegenerative diseases, pain, cancer and/or mental disorders in a mammal.

In a further aspect, the present invention provides a compound of formula (I) as described herein or a pharmaceutical composition described herein, for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

DETAILED DESCRIPTION OF THE INVENTION

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "alkyl" refers to a mono- or multivalent, e.g., a mono- or bivalent, linear or branched saturated hydrocarbon group of 1 to 6 carbon atoms ("$C_1$-$C_6$-alkyl"), e.g., 1, 2, 3, 4, 5, or 6 carbon atoms. In some embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, sec-butyl, tert-butyl, and 2,2-dimethylpropyl. A particularly preferred, yet non-limiting example of alkyl is methyl.

The term "alkoxy" refers to an alkyl group, as previously defined, attached to the parent molecular moiety via an oxygen atom. Unless otherwise specified, the alkoxy group contains 1 to 6 carbon atoms ("$C_1$-$C_6$-alkoxy"). In some preferred embodiments, the alkoxy group contains 1 to 4 carbon atoms. In still other embodiments, the alkoxy group contains 1 to 3 carbon atoms. Some non-limiting examples of alkoxy groups include methoxy, ethoxy, n-propoxy, isopropoxy, n-butoxy, isobutoxy and tert-butoxy. A particularly preferred, yet non-limiting example of alkoxy is methoxy.

The term "halogen" or "halo" refers to fluoro (F), chloro (Cl), bromo (Br), or iodo (I). Preferably, the term "halogen" or "halo" refers to fluoro (F), chloro (Cl) or bromo (Br). Particularly preferred, yet non-limiting examples of "halogen" or "halo" are fluoro (F) and chloro (Cl).

The term "bicyclic spirocycle" refers to a chemical entity consisting of two heterocyclyl or two cycloalkyl moieties as defined herein, or to a combination of one heterocyclyl and one cycloalkyl moiety, having one ring atom in common, i.e., the two rings are connected via one common ring atom. Some preferred, yet non-limiting examples of bicyclic spirocycles include 2-azaspiro[3.3]heptane, 2,6-diazaspiro[3.3]heptane, 2,7-diazaspiro[3.5]nonane, 7-azaspiro[3.5]nonane, 1-oxa-8-azaspiro[4.5]decane, 2,7-diazaspiro[4.4]nonane and 2,7-diazaspiro[3.4]octane.

The term "heterocyclyl" refers to a saturated or partly unsaturated monocyclic ring system of 3 to 14 ring atoms, preferably 3 to 10 ring atoms, more preferably 3 to 8 ring atoms, wherein 1, 2, or 3 of said ring atoms are heteroatoms selected from N, O and S, the remaining ring atoms being carbon. Preferably, 1 to 2 of said ring atoms are selected from N and O, the remaining ring atoms being carbon. Some non-limiting examples of heterocyclyl groups include azetidin-3-yl, azetidin-2-yl, oxetan-3-yl, oxetan-2-yl, 2-oxopyrrolidin-1-yl, 2-oxopyrrolidin-3-yl, 5-oxopyrrolidin-2-yl, 5-oxopyrrolidin-3-yl, 2-oxo-1-piperidyl, 2-oxo-3-piperidyl, 2-oxo-4-piperidyl, 6-oxo-2-piperidyl, 6-oxo-3-piperidyl, 1-piperidinyl, 2-piperidinyl, 3-piperidinyl, 4-piperidinyl, morpholino, morpholin-2-yl, morpholin-3-yl, pyrrolidin-1-yl, pyrrolidin-2-yl, and pyrrolidin-3-yl.

The term "cycloalkyl" as used herein refers to a saturated or partly unsaturated monocyclic hydrocarbon group of 3 to 10 ring carbon atoms ("$C_{3-10}$-cycloalkyl"). In some preferred embodiments, the cycloalkyl group is a saturated monocyclic hydrocarbon group of 3 to 8 ring carbon atoms. Preferably, the cycloalkyl group is a saturated monocyclic hydrocarbon group of 3 to 6 ring carbon atoms, e.g., of 3, 4, 5 or 6 carbon atoms. Some non-limiting examples of cycloalkyl include cyclopropyl, cyclobutyl, cyclopentyl, cyclohexyl and cycloheptyl. A preferred, yet non-limiting example of cycloalkyl is cyclopropyl.

The term "aryl" refers to a monocyclic, bicyclic, or tricyclic carbocyclic ring system having a total of 6 to 14 ring members ("$C_{6-14}$-aryl"), preferably, 6 to 12 ring members, and more preferably 6 to 10 ring members, and wherein at least one ring in the system is aromatic. A particularly preferred, yet non-limiting example of aryl is phenyl.

The term "heteroaryl" refers to a mono- or multivalent, monocyclic or bicyclic, preferably bicyclic ring system having a total of 5 to 14 ring members, preferably, 5 to 12 ring members, and more preferably 5 to 10 ring members, wherein at least one ring in the system is aromatic, and at least one ring in the system contains one or more heteroatoms. Preferably, "heteroaryl" refers to a 5-10 membered heteroaryl comprising 1, 2, 3 or 4 heteroatoms independently selected from O, S and N. Most preferably, "heteroaryl" refers to a 5-10 membered heteroaryl comprising 1 to 2 heteroatoms independently selected from O and N. Some non-limiting examples of heteroaryl include 2-pyridyl, 3-pyridyl, 4-pyridyl, indol-1-yl, 1H-indol-2-yl, 1H-indol-3-yl, 1H-indol-4-yl, 1H-indol-5-yl, 1H-indol-6-yl, 1H-indol-7-yl, 1,2-benzoxazol-3-yl, 1,2-benzoxazol-4-yl, 1,2-benzoxazol-5-yl, 1,2-benzoxazol-6-yl, 1,2-benzoxazol-7-yl, 1H-indazol-3-yl, 1H-indazol-4-yl, 1H-indazol-5-yl, 1H-indazol-6-yl, 1H-indazol-7-yl, pyrazol-1-yl, 1H-pyrazol-3-yl, 1H-pyrazol-4-yl, 1H-pyrazol-5-yl, imidazol-1-yl, 1H-imidazol-2-yl, 1H-imidazol-4-yl, 1H-imidazol-5-yl, oxazol-2-yl, oxazol-4-yl and oxazol-5-yl. A particularly preferred, yet non-limiting example of heteroaryl is indolyl, in particular 1H-indol-3-yl.

The term "hydroxy" refers to an —OH group.

The term "cyano" refers to a —CN (nitrile) group.

The term "carbonyl" refers to a C(O) group.

The term "oxo" refers to an oxygen atom bound to the parent molecule through a double bond (=O).

The term "alkoxycarbonyl" refers to a —C(O)—O-alkyl group (i.e., an alkyl ester). A particularly preferred, yet non-limiting example of alkoxycarbonyl is tert-butoxycarbonyl.

The term "aryloxycarbonyl" refers to a —C(O)—O-aryl group (i.e., an aryl ester). A particularly preferred, yet non-limiting example of alkoxycarbonyl is phenoxycarbonyl.

The term "heteroaryloxycarbonyl" refers to a —C(O)—O-heteroaryl group (i.e., a heteroaryl ester). A particularly preferred, yet non-limiting example of alkoxycarbonyl is pyridyloxycarbonyl.

The term "haloalkyl" refers to an alkyl group, wherein at least one of the hydrogen atoms of the alkyl group has been replaced by a halogen atom, preferably fluoro. Preferably, "haloalkyl" refers to an alkyl group wherein 1, 2 or 3 hydrogen atoms of the alkyl group have been replaced by a halogen atom, most preferably fluoro. A particularly preferred, yet non-limiting example of haloalkyl is trifluoromethyl ($CF_3$).

The term "haloalkoxy" refers to an alkoxy group, wherein at least one of the hydrogen atoms of the alkoxy group has been replaced by a halogen atom, preferably fluoro. Preferably, "haloalkoxy" refers to an alkoxy group wherein 1, 2 or 3 hydrogen atoms of the alkoxy group have been replaced by a halogen atom, most preferably fluoro. A particularly preferred, yet non-limiting example of haloalkoxy is trifluoromethoxy ($—OCF_3$).

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid.

Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are hydrochloride salts.

The term "protective group" (PG) denotes the group which selectively blocks a reactive site in a multifunctional compound such that a chemical reaction can be carried out selectively at another unprotected reactive site in the meaning conventionally associated with it in synthetic chemistry. Protective groups can be removed at the appropriate point. Exemplary protective groups are amino-protective groups, carboxy-protective groups or hydroxy-protective groups. Particular protective groups are the tert-butoxycarbonyl (Boc), benzyloxycarbonyl (Cbz), fluorenylmethoxycarbonyl (Fmoc) and benzyl (Bn). Further particular protective groups are the tert-butoxycarbonyl (Boc) and the fluorenylmethoxycarbonyl (Fmoc). More particular protective group is the tert-butoxycarbonyl (Boc). Exemplary protective groups and their application in organic synthesis are described, for example, in "Protective Groups in Organic Chemistry" by T. W. Greene and P. G. M. Wutts, 5th Ed., 2014, John Wiley & Sons, N.Y.

The term "urea forming reagent" refers to a chemical compound that is able to render a first amine to a species that will react with a second amine, thereby forming an urea derivative. Non-limiting examples of urea forming reagents include bis(trichloromethyl) carbonate, phosgene, trichloromethyl chloroformate, (4-nitrophenyl)carbonate and 1,1'-carbonyldiimidazole. The urea forming reagents described in G. Sartori et al., *Green Chemistry* 2000, 2, 140 are incorporated herein by reference.

The compounds of formula (I) can contain several asymmetric centers and can be present in the form of optically pure enantiomers, mixtures of enantiomers such as, for example, racemates, optically pure diastereioisomers, mixtures of diastereoisomers, diastereoisomeric racemates or mixtures of diastereoisomeric racemates. In a preferred embodiment, the compound of formula (I) according to the invention is a cis-enantiomer of formula (Ia) or (Ib), respectively, as described herein.

According to the Cahn-Ingold-Prelog Convention, the asymmetric carbon atom can be of the "R" or "S" configuration.

The abbreviation "MAGL" refers to the enzyme monoacylglycerol lipase. The terms "MAGL" and "monoacylglycerol lipase" are used herein interchangeably.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human that may be afflicted with or predisposed to the state, disorder or condition but does not yet experience or display clinical or subclinical symptoms of the state, disorder or condition.

The term "neuroinflammation" as used herein relates to acute and chronic inflammation of the nervous tissue, which is the main tissue component of the two parts of the nervous system; the brain and spinal cord of the central nervous system (CNS), and the branching peripheral nerves of the peripheral nervous system (PNS). Chronic neuroinflammation is associated with neurodegenerative diseases such as Alzheimer's disease, Parkinson's disease and multiple sclerosis. Acute neuroinflammation usually follows injury to the central nervous system immediately, e.g., as a result of traumatic brain injury (TBI).

The term "traumatic brain injury" ("TBI", also known as "intracranial injury"), relates to damage to the brain resulting from external mechanical force, such as rapid acceleration or deceleration, impact, blast waves, or penetration by a projectile.

The term "neurodegenerative diseases" relates to diseases that are related to the progressive loss of structure or function of neurons, including death of neurons. Examples of neurodegenerative diseases include, but are not limited to, multiple sclerosis, Alzheimer's disease, Parkinson's disease and amyotrophic lateral sclerosis.

The term "mental disorders" (also called mental illnesses or psychiatric disorders) relates to behavioral or mental patterns that may cause suffering or a poor ability to function in life. Such features may be persistent, relapsing and remitting, or occur as a single episode. Examples of mental disorders include, but are not limited to, anxiety and depression.

The term "pain" relates to an unpleasant sensory and emotional experience associated with actual or potential tissue damage. Examples of pain include, but are not limited to, nociceptive pain, chronic pain (including idiopathic pain), neuropathic pain including chemotherapy induced neuropathy, phantom pain and psychogenic pain. A particular example of pain is neuropathic pain, which is caused by damage or disease affecting any part of the nervous system involved in bodily feelings (i.e., the somatosensory system). In one embodiment, "pain" is neuropathic pain resulting from amputation or thoracotomy. In one embodiment, "pain" is chemotherapy induced neuropathy.

The term "neurotoxicity" relates to toxicity in the nervous system. It occurs when exposure to natural or artificial toxic substances (neurotoxins) alter the normal activity of the nervous system in such a way as to cause damage to nervous tissue. Examples of neurotoxicity include, but are not limited to, neurotoxicity resulting from exposure to substances used in chemotherapy, radiation treatment, drug therapies, drug abuse, and organ transplants, as well as exposure to heavy metals, certain foods and food additives, pesticides, industrial and/or cleaning solvents, cosmetics, and some naturally occurring substances.

The term "cancer" refers to a disease characterized by the presence of a neoplasm or tumor resulting from abnormal uncontrolled growth of cells (such cells being "cancer cells"). As used herein, the term cancer explicitly includes, but is not limited to, hepatocellular carcinoma, colon carcinogenesis and ovarian cancer.

The term "mammal" as used herein includes both humans and non-humans and includes but is not limited to humans, non-human primates, canines, felines, murines, bovines, equines, and porcines. In a particularly preferred embodiment, the term "mammal" refers to humans.

Compounds of the Invention

In a first aspect, the present invention provides a compound of formula (I)

(I)

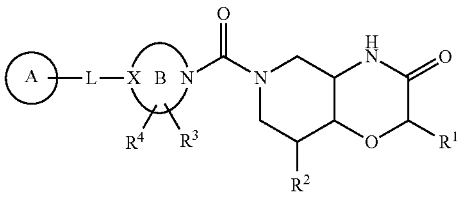

or a pharmaceutically acceptable salt thereof, wherein:

(i) X is C—$R^5$;

L is a covalent bond, —$(CH_2)_n$—N($C_{1-6}$-alkyl)-, —$(CH_2)_n$—NH—, —N($C_{1-6}$-alkyl)-$(CH_2)_p$—, —NH—$(CH_2)_p$—, —$(CH_2)_n$—O—, —O—$(CH_2)_p$—, —$SO_2$—N($C_{1-6}$-alkyl)-, —$SO_2$—NH—, —N($C_{1-6}$-alkyl)-$SO_2$—, —NH—$SO_2$—, carbonyl, —$(CH_2)_n$—, —CH$R^6$—, —$CF_2$—$(CH_2)_n$—, —$(CH_2)_p$—$CF_2$—, —$(CH_2)_n$—S—, —S—$(CH_2)_p$—, —$SO_2$—, —C(O)—NH—, —C(O)—N($C_{1-6}$-alkyl)-, —NH—C(O)— or —N($C_{1-6}$-alkyl)-C(O)—; and A is:

(i) $C_{6-14}$-aryl substituted with $R^7$, $R^8$ and $R^9$; or (ii) 5-14 membered heteroaryl substituted with $R^{10}$, $R^{11}$ and $R^{12}$; or (ii) X is N;

L is a covalent bond, —$(CH_2)_n$—, —CH$R^6$—, —$SO_2$—, carbonyl, —N($C_{1-6}$-alkyl)-$(CH_2)_p$—, —NH—$(CH_2)_p$—, —O—$(CH_2)_p$—, —$CF_2$—$CH_2$—, —N($C_{1-6}$-alkyl)-$SO_2$—, —NH—$SO_2$—, —NH—C(O)— or —N($C_{1-6}$-alkyl)-C(O)—; and A is:

(i) $C_{6-14}$-aryl substituted with $R^7$, $R^8$ and $R^9$; or (ii) 5-14 membered heteroaryl substituted with $R^{10}$, $R^{11}$ and $R^{12}$; or (iii) X is N;

L is $C_{1-6}$-alkoxycarbonyl, $C_{6-14}$-aryloxycarbonyl or 5-14 membered heteroaryloxycarbonyl; and A is absent;

B is a bicyclic spirocycle;

$R^1$, $R^2$, $R^3$, $R^4$ and $R^5$ are independently hydrogen, halogen, hydroxy, $C_{1-6}$-alkyl or halo-$C_{1-6}$-alkyl;

$R^6$ is $C_{6-14}$-aryl or 5-14 membered heteroaryl;

$R^7$, $R^8$, $R^9$, $R^{10}$, $R^{11}$ and $R^{12}$ are each at each occurrence independently hydrogen, hydroxy, $C_{1-6}$-alkyl, halo-$C_{1-6}$-alkyl, halogen, $C_{1-6}$-alkoxy, halo-$C_{1-6}$-alkoxy, $SF_5$, $C_{1-6}$-alkylsulfonyl, cyano or a group

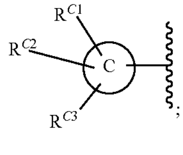

;

C is 5-14 membered heteroaryl, 3-14 membered heterocyclyl or $C_{3-10}$-cycloalkyl;

$R^{C1}$, $R^{C2}$ and $R^{C3}$ are each independently hydrogen, $C_{1-6}$-alkyl, halo-$C_{1-6}$-alkyl, oxo, halogen, hydroxy, $C_{1-6}$-alkoxy or halo-$C_{1-6}$-alkoxy;

each occurrence of n is independently 0, 1, 2 or 3;

each occurrence of p is independently 1, 2 or 3; and q is 0, 1 or 2.

In one embodiment, the present invention provides a compound of formula (I) or a pharmaceutically acceptable salt thereof, wherein:

(i) X is C—$R^5$;

L is —$(CH_2)_n$—N($C_{1-6}$-alkyl)-, —$(CH_2)_n$—NH—, —N($C_{1-6}$-alkyl)-$(CH_2)_p$—, —NH—$(CH_2)_p$—, —$(CH_2)_n$—O—, —O—$(CH_2)_p$—, —$SO_2$—N($C_{1-6}$-alkyl)-, —$SO_2$—NH—, —N($C_{1-6}$-alkyl)-$SO_2$—, —NH—$SO_2$—, carbonyl, —$(CH_2)_n$—, —CH$R^6$—, —$CF_2$—$(CH_2)_n$—, —$(CH_2)_p$—$CF_2$—, —$(CH_2)_n$—S—, —S—$(CH_2)_p$—, —$SO_2$—, —C(O)—NH—, —C(O)—N($C_{1-6}$-alkyl)-, —NH—C(O)— or —N($C_{1-6}$-alkyl)-C(O)—; and A is:

(i) $C_{6-14}$-aryl substituted with $R^7$, $R^8$ and $R^9$; or (ii) 5-14 membered heteroaryl substituted with $R^{10}$, $R^{11}$ and $R^{12}$; or (ii) X is N;

L is —$(CH_2)_n$—, —CH$R^6$—, —$SO_2$—, carbonyl, —N($C_{1-6}$-alkyl)-$(CH_2)_p$—, —NH—$(CH_2)_p$—, —O—$(CH_2)_p$—, —$CF_2$—$CH_2$—, —N($C_{1-6}$-alkyl)-$SO_2$—, —NH—$SO_2$—, —NH—C(O)— or —N($C_{1-6}$-alkyl)-C(O)—; and A is:

(i) $C_{6-14}$-aryl substituted with $R^7$, $R^8$ and $R^9$; or (ii) 5-14 membered heteroaryl substituted with $R^{10}$, $R^{11}$ and $R^{12}$; or (iii) X is N;

L is $C_{1-6}$-alkoxycarbonyl, $C_{6-14}$-aryloxycarbonyl or 5-14 membered heteroaryloxycarbonyl; and A is absent;

B is a bicyclic spirocycle;

$R^1$ is hydrogen or $C_{1-4}$-alkyl;

$R^2$ is hydrogen or $C_{1-6}$-alkyl;

$R^3$ is hydrogen, $C_{1-6}$-alkyl, halo-$C_{1-6}$-alkyl, halogen or hydroxy;

$R^4$ is hydrogen, $C_{1-6}$-alkyl, halo-$C_{1-6}$-alkyl, halogen or hydroxy;

$R^5$ is hydrogen, $C_{1-6}$-alkyl, halo-$C_{1-6}$-alkyl, halogen or hydroxy;

$R^6$ is $C_{6-14}$-aryl or 5-14 membered heteroaryl;

$R^7$, $R^8$, $R^9$, $R^{10}$, $R^{11}$ and $R^{12}$ are each at each occurrence independently hydrogen, $C_{1-6}$-alkyl, halo-$C_{1-6}$-alkyl, halogen, $C_{1-6}$-alkoxy, halo-$C_{1-6}$-alkoxy, $SF_5$, $SO_2CH_3$, cyano, a group

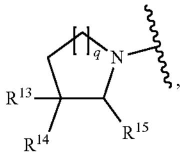

, a group

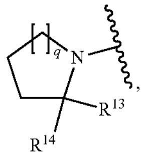

, a group

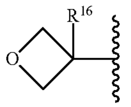

or a group

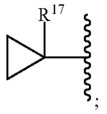

$R^{13}$ is hydrogen, $C_{1-6}$-alkyl, halo-$C_{1-6}$-alkyl, halogen, hydroxy or $C_{1-6}$-alkoxy; and $R^{14}$ is hydrogen, $C_{1-6}$-alkyl, halo-$C_{1-6}$-alkyl, halogen, hydroxy, $C_{1-6}$-alkoxy; or $R^{13}$ and $R^{14}$, taken together with the carbon atom to which they are attached, form a 4-6-membered ring containing 0, 1 or 2 heteroatoms selected from oxygen and $NR^{18}$.

$R^{15}$ is hydrogen, $C_{1-6}$-alkyl or halo-$C_{1-6}$-alkyl;

$R^{16}$ is hydrogen, $C_{1-6}$-alkyl, halo-$C_{1-6}$-alkyl, hydroxy or cyano;

$R^{17}$ is hydrogen, hydroxy, cyano, halo-$C_{1-6}$-alkyl or $C_{1-6}$-alkyl;

$R^{18}$ is hydrogen or $C_{1-6}$-alkyl;

each occurrence of n is independently 0, 1, 2 or 3;

each occurrence of p is independently 1, 2 or 3; and q is 0, 1 or 2.

In one embodiment, the present invention provides a compound of formula (I) as described herein, or a pharmaceutically acceptable salt thereof, wherein $R^1$ is hydrogen.

In one embodiment, the present invention provides a compound of formula (I) as described herein, or a pharmaceutically acceptable salt thereof, wherein $R^2$ is hydrogen.

In one embodiment, the present invention provides a compound of formula (I) as described herein, or a pharmaceutically acceptable salt thereof, wherein $R^1$ and $R^2$ are both hydrogen.

In one embodiment, the present invention provides a compound of formula (I) as described herein, or a pharmaceutically acceptable salt thereof, wherein $R^3$ is hydrogen. In one embodiment, the present invention provides a compound of formula (I) as described herein, or a pharmaceutically acceptable salt thereof, wherein $R^4$ is hydrogen.

In one embodiment, the present invention provides a compound of formula (I) as described herein, or a pharmaceutically acceptable salt thereof, wherein $R^3$ and $R^4$ are both hydrogen.

In one embodiment, the present invention provides a compound of formula (I) as described herein, or a pharmaceutically acceptable salt thereof, wherein $R^1$, $R^2$, $R^3$ and $R^4$ are all hydrogen.

In one embodiment, the present invention provides a compound of formula (I) as described herein, or a pharmaceutically acceptable salt thereof, wherein $R^5$ is hydrogen or halo-$C_{1-6}$-alkyl.

In one embodiment, the present invention provides a compound of formula (I) as described herein, or a pharmaceutically acceptable salt thereof, wherein $R^5$ is hydrogen.

In one embodiment, the present invention provides a compound of formula (I) as described herein, or a pharmaceutically acceptable salt thereof, wherein $R^6$ is $C_{6-14}$-aryl.

In one embodiment, the present invention provides a compound of formula (I) as described herein, or a pharmaceutically acceptable salt thereof, wherein $R^7$ is hydrogen, hydroxy, $C_{1-6}$-alkyl, halo-$C_{1-6}$-alkyl, halogen, $C_{1-6}$-alkoxy, halo-$C_{1-6}$-alkoxy, $SF_5$ or a group

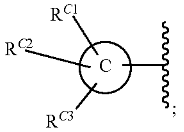

wherein

C is 5-14 membered heteroaryl or 3-14 membered heterocyclyl;

$R^{C1}$ is $C_{1-6}$-alkyl, halo-$C_{1-6}$-alkyl or oxo; and $R^{C2}$ and $R^{C3}$ are both hydrogen.

In a preferred embodiment, the present invention provides a compound of formula (I) as described herein, or a pharmaceutically acceptable salt thereof, wherein $R^7$ is hydrogen, $C_{1-6}$-alkyl, halo-$C_{1-6}$-alkyl, halogen, $C_{1-6}$-alkoxy, halo-$C_{1-6}$-alkoxy or $SF_5$.

In a particularly preferred embodiment, the present invention provides a compound of formula (I) as described herein, or a pharmaceutically acceptable salt thereof, wherein $R^7$ is hydrogen, fluoro, chloro, $CF_3$, methyl, methoxy, trifluoromethoxy or $SF_5$.

In one embodiment, the present invention provides a compound of formula (I) as described herein, or a pharmaceutically acceptable salt thereof, wherein $R^7$ is hydrogen, $C_{1-6}$-alkyl, halo-$C_{1-6}$-alkyl, halogen, $C_{1-6}$-alkoxy or halo-$C_{1-6}$-alkoxy.

In a preferred embodiment, the present invention provides a compound of formula (I) as described herein, or a pharmaceutically acceptable salt thereof, wherein $R^7$ is hydrogen, fluoro, chloro, $CF_3$, methyl, methoxy or trifluoromethoxy.

In one embodiment, the present invention provides a compound of formula (I) as described herein, or a pharmaceutically acceptable salt thereof, wherein $R^8$ is hydrogen, $C_{1-6}$-alkoxy, halo-$C_{1-6}$-alkyl or halogen.

In a preferred embodiment, the present invention provides a compound of formula (I) as described herein, or a pharmaceutically acceptable salt thereof, wherein $R^8$ is hydrogen, halo-$C_{1-6}$-alkyl or halogen.

In a particularly preferred embodiment, the present invention provides a compound of formula (I) as described herein, or a pharmaceutically acceptable salt thereof, wherein $R^8$ is hydrogen, $CF_3$, chloro or fluoro.

In one embodiment, the present invention provides a compound of formula (I) as described herein, or a pharmaceutically acceptable salt thereof, wherein $R^9$ is hydrogen.

In one embodiment, the present invention provides a compound of formula (I) as described herein, or a pharmaceutically acceptable salt thereof, wherein:

$R^7$ is hydrogen, $C_{1-6}$-alkyl, halo-$C_{1-6}$-alkyl, halogen, $C_{1-6}$-alkoxy or halo-$C_{1-6}$-alkoxy;

$R^8$ is hydrogen, halo-$C_{1-6}$-alkyl or halogen; and $R^9$ is hydrogen.

In one embodiment, the present invention provides a compound of formula (I) as described herein, or a pharmaceutically acceptable salt thereof, wherein $R^{10}$ is halogen or halo-$C_{1-6}$-alkyl.

In a preferred embodiment, the present invention provides a compound of formula (I) as described herein, or a pharmaceutically acceptable salt thereof, wherein $R^{10}$ is halo-$C_{1-6}$-alkyl.

In a particularly preferred embodiment, the present invention provides a compound of formula (I) as described herein, or a pharmaceutically acceptable salt thereof, wherein $R^{10}$ is $CF_3$.

In one embodiment, the present invention provides a compound of formula (I) as described herein, or a pharmaceutically acceptable salt thereof, wherein $R^{11}$ is hydrogen or halo-$C_{1-6}$-alkyl.

In a preferred embodiment, the present invention provides a compound of formula (I) as described herein, or a pharmaceutically acceptable salt thereof, wherein $R^{12}$ is hydrogen or $CF_3$.

In one embodiment, the present invention provides a compound of formula (I) as described herein, or a pharmaceutically acceptable salt thereof, wherein $R^{12}$ is hydrogen.

In one embodiment, the present invention provides a compound of formula (I) as described herein, or a pharmaceutically acceptable salt thereof, wherein:

$R^{10}$ is halo-$C_{1-6}$-alkyl;

$R^{11}$ is hydrogen or halo-$C_{1-6}$-alkyl; and $R^{12}$ is hydrogen.

In a preferred embodiment, the present invention provides a compound of formula (I) as described herein, or a pharmaceutically acceptable salt thereof, wherein A is phenyl or pyridyl.

In one embodiment, the present invention provides a compound of formula (I) as described herein, or a pharmaceutically acceptable salt thereof, wherein:

X is C—$R^5$;

L is a covalent bond, —$(CH_2)_n$—N($C_{1-6}$-alkyl)-, —$(CH_2)_n$—NH—, —$(CH_2)_n$—O—, —$OCH_2$—, —$CH_2$—, —$SO_2$—, —$SO_2$—N($C_{1-6}$-alkyl)- or —$SO_2$—NH—;

n is 0 or 1; and $R^5$ is as defined herein.

In a preferred embodiment, the present invention provides a compound of formula (I) as described herein, or a pharmaceutically acceptable salt thereof, wherein:

X is C—$R^5$;

L is a covalent bond, —$CH_2O$—, —O—, —$OCH_2$—, —$CH_2$— or —$SO_2$—N($C_{1-6}$-alkyl)-; and $R^5$ is as defined herein.

In a particularly preferred embodiment, the present invention provides a compound of formula (I) as described herein, or a pharmaceutically acceptable salt thereof, wherein:

X is C—$R^5$;

L is a covalent bond, —$CH_2O$—, —O—, —$OCH_2$—, —$CH_2$— or —$SO_2$—N(methyl)-; and $R^5$ is as defined herein.

In one embodiment, the present invention provides a compound of formula (I) as described herein, or a pharmaceutically acceptable salt thereof, wherein:

X is C—$R^5$;

L is —$CH_2$—N($C_{1-6}$-alkyl)-, —$CH_2$—NH—, —$(CH_2)_n$—O—, —O—$CH_2$—, —$SO_2$—N($C_{1-6}$-alkyl)- or —$SO_2$—NH—;

n is 0 or 1; and $R^5$ is as defined herein.

In one embodiment, the present invention provides a compound of formula (I) as described herein, or a pharmaceutically acceptable salt thereof, wherein:

X is C—$R^5$;

L is —$CH_2$—N($C_{1-6}$-alkyl)-, —$CH_2$—NH—, —$(CH_2)_n$—O—, —O—$CH_2$—, —$SO_2$—N($C_{1-6}$-alkyl)- or —$SO_2$—NH—;

n is 0 or 1; and $R^5$ is hydrogen.

In a preferred embodiment, the present invention provides a compound of formula (I) as described herein, or a pharmaceutically acceptable salt thereof, wherein:

X is C—$R^5$;

L is —$(CH_2)_n$—O—, —O—$CH_2$— or —$SO_2$—N($C_{1-6}$-alkyl)-;

n is 0 or 1; and $R^5$ is hydrogen.

In a particularly preferred embodiment, the present invention provides a compound of formula (I) as described herein, or a pharmaceutically acceptable salt thereof, wherein:

X is C—$R^5$;

L is —$(CH_2)_n$—O—, —O—$CH_2$— or —$SO_2$—N(methyl)-;

n is 0 or 1; and $R^5$ is hydrogen.

In one embodiment, the present invention provides a compound of formula (I) as described herein, or a pharmaceutically acceptable salt thereof, wherein:

X is N;

L is a covalent bond, —$CH_2$—, —$CHR^6$— or —$SO_2$—; and $R^6$ is as defined herein.

In a preferred embodiment, the present invention provides a compound of formula (I) as described herein, or a pharmaceutically acceptable salt thereof, wherein:

X is N; and

L is —$CH_2$— or —$SO_2$—.

In one embodiment, the present invention provides a compound of formula (I) as described herein, or a pharmaceutically acceptable salt thereof, wherein:

X is N;

L is —$(CH_2)_n$—, —$CHR^6$— or —$SO_2$—; and n is 1; and $R^6$ is as defined herein.

In one embodiment, the present invention provides a compound of formula (I) as described herein, or a pharmaceutically acceptable salt thereof, wherein:

X is N;

L is —$(CH_2)_n$—, —$CHR^6$— or —$SO_2$—; and n is 1; and $R^6$ is $C_{6-14}$-aryl.

In a preferred embodiment, the present invention provides a compound of formula (I) as described herein, or a pharmaceutically acceptable salt thereof, wherein:

X is N;

L is —$(CH_2)_n$— or —$SO_2$—; and n is 1.

In one embodiment, the present invention provides a compound of formula (I) as described herein, or a pharmaceutically acceptable salt thereof, wherein B is a bicyclic spirocycle having formula (II):

(II)

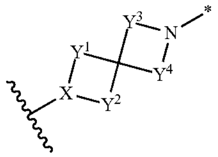

wherein:

X is as defined herein;

$Y^1$, $Y^2$, $Y^3$ and $Y^4$ are each independently $-(CH_2)_m-$, $-(CH_2)_mO-$, $-O(CH_2)_m-$, $-(CH_2)_mNH-$ or $-NH(CH_2)_m-$;

each occurrence of m is independently 1, 2 or 3;

the wavy line indicates the point of attachment of bicyclic spirocycle B to L in formula (I); and the asterisk indicates the point of attachment of bicyclic spirocycle B to the remainder of formula (I).

In one embodiment, the present invention provides a compound of formula (I) as described herein, or a pharmaceutically acceptable salt thereof, wherein B is a bicyclic spirocycle having formula (II):

(II)

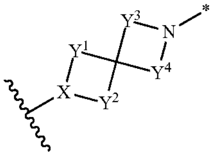

wherein:

X is as defined herein;

$Y^1$ is $-(CH_2)_m-$ or $-(CH_2)_mO-$, wherein m is 1 or 2;

$Y^2$ is $-CH_2-$ or $-CH_2O-$;

$Y^3$ and $Y^4$ are each independently $-(CH_2)_m-$, wherein m is 1 or 2;

the wavy line indicates the point of attachment of bicyclic spirocycle B to L in formula (I); and the asterisk indicates the point of attachment of bicyclic spirocycle B to the remainder of formula (I).

In a preferred embodiment, the present invention provides a compound of formula (I) as described herein, or a pharmaceutically acceptable salt thereof, wherein B is a bicyclic spirocycle having formula (II):

(II)

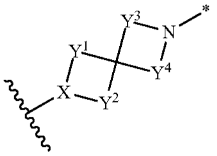

wherein:

X is as defined herein;

$Y^1$ is $-CH_2-$;

$Y^2$ is $-CH_2-$ or $-CH_2O-$;

$Y^3$ and $Y^4$ are each independently $-(CH_2)_m-$, wherein m is 1 or 2;

the wavy line indicates the point of attachment of bicyclic spirocycle B to L in formula (I); and the asterisk indicates the point of attachment of bicyclic spirocycle B to the remainder of formula (I).

In a further preferred embodiment, the present invention provides a compound of formula (I) as described herein, or a pharmaceutically acceptable salt thereof, wherein B is a bicyclic spirocycle selected from the group consisting of:

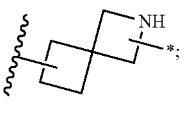

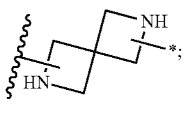

-continued

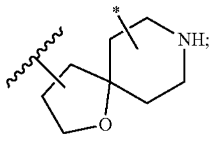

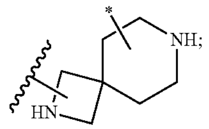

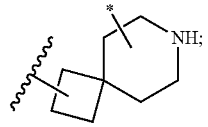

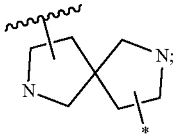

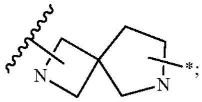

and

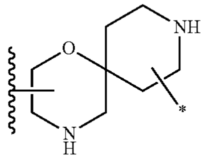

wherein:

(i) a wavy line indicates the point of attachment of bicyclic spirocycle B to L in formula (I); and an asterisk indicates the point of attachment of bicyclic spirocycle B to the remainder of formula (I); or (ii) a wavy line indicates the point of attachment of bicyclic spirocycle B to the remainder of formula (I); and an asterisk indicates the point of attachment of bicyclic spirocycle B to L in formula (I).

In a particularly preferred embodiment, the present invention provides a compound of formula (I) as described herein, or a pharmaceutically acceptable salt thereof, wherein B is a bicyclic spirocycle selected from the group consisting of:

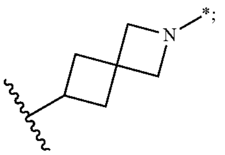

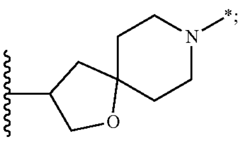

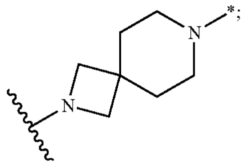

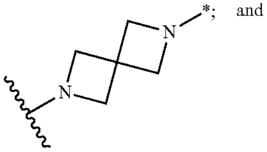

and

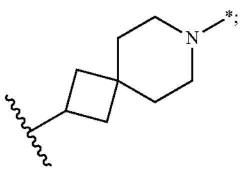

wherein a wavy line indicates the point of attachment of bicyclic spirocycle B to L in formula (I); and an asterisk indicates the point of attachment of bicyclic spirocycle B to the remainder of formula (I).

In one embodiment, the present invention provides a compound of formula (I) as described herein, or a pharmaceutically acceptable salt thereof, wherein:

(i) X is $C-R^5$;

L is a covalent bond, $-CH_2-N(C_{1-6}\text{-alkyl})-$, $-CH_2-NH-$, $-O-$, $-CH_2O-$, $-OCH_2-$, $-CH_2-$, $-SO_2-$, $-SO_2-N(C_{1-6}\text{-alkyl})-$ or $-SO_2-NH-$; and A is:

(i) $C_{6-14}$-aryl substituted with $R^7$, $R^8$ and $R^9$; or (ii) 5-14 membered heteroaryl substituted with $R^{10}$, $R^{11}$ and $R^{12}$; or (ii) X is N;

L is a covalent bond, —$CH_2$—, —$CHR^6$— or —$SO_2$—; and

A is $C_{6-14}$-aryl substituted with $R^7$, $R^8$ and $R^9$; or (iii) X is N;

L is $C_{1-6}$-alkoxycarbonyl; and

A is absent;

B is a bicyclic spirocycle having formula (II):

(II)

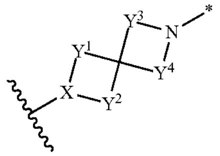

wherein:

$Y^1$ is —$(CH_2)_m$— or —$(CH_2)_m$O—, wherein m is 1 or 2;

$Y^2$ is —$CH_2$— or —$CH_2$O—;

$Y^3$ and $Y^4$ are each independently —$(CH_2)_m$—, wherein m is 1 or 2;

the wavy line indicates the point of attachment of bicyclic spirocycle B to L in formula (I); and the asterisk indicates the point of attachment of bicyclic spirocycle B to the remainder of formula (I);

each of $R^1$, $R^2$, $R^3$, $R^4$, $R^9$ and $R^{12}$ is hydrogen;

$R^5$ is hydrogen or $C_{1-6}$-alkyl;

$R^6$ is $C_{6-14}$-aryl;

$R^7$ is hydrogen, hydroxy, $C_{1-6}$-alkyl, halo-$C_{1-6}$-alkyl, halogen, $C_{1-6}$-alkoxy or halo-$C_{1-6}$-alkoxy, $SF_5$ or a group

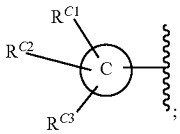;

$R^8$ is hydrogen, $C_{1-6}$-alkoxy, halo-$C_{1-6}$-alkyl or halogen;

$R^{10}$ is halogen or halo-$C_{1-6}$-alkyl;

$R^{11}$ is hydrogen or halo-$C_{1-6}$-alkyl;

$R^{C1}$ is $C_{1-6}$-alkyl, halo-$C_{1-6}$-alkyl or oxo;

$R^{C2}$ and $R^{C3}$ are both hydrogen; and

C is 5-14 membered heteroaryl or 3-14 membered heterocyclyl.

In a preferred embodiment, the present invention provides a compound of formula (I) as described herein, or a pharmaceutically acceptable salt thereof, wherein:

(i) X is C—$R^5$;

L is —$CH_2$O—, —$OCH_2$—, —O—, —$CH_2$— or —$SO_2$—N($C_{1-6}$-alkyl)-; and

A is:

(i) $C_{6-14}$-aryl substituted with $R^7$, $R^8$ and $R^9$; or (ii) 5-14 membered heteroaryl substituted with $R^{10}$, $R^{11}$ and $R^{12}$; or (ii) X is N;

L is —$CH_2$— or —$SO_2$—; and

A is $C_{6-14}$-aryl substituted with $R^7$, $R^8$ and $R^9$; or

B is a bicyclic spirocycle having formula (II):

(II)

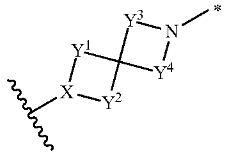

wherein:

$Y^1$ is —$CH_2$—;

$Y^2$ is —$CH_2$— or —$CH_2$O—;

$Y^3$ and $Y^4$ are each independently —$(CH_2)_m$—, wherein m is 1 or 2;

the wavy line indicates the point of attachment of bicyclic spirocycle B to L in formula (I); and the asterisk indicates the point of attachment of bicyclic spirocycle B to the remainder of formula (I);

each of $R^1$, $R^2$, $R^3$, $R^4$, $R^5$, $R^9$, and $R^{12}$ is hydrogen;

$R^7$ is hydrogen, $C_{1-6}$-alkyl, halo-$C_{1-6}$-alkyl, halogen, $C_{1-6}$-alkoxy, halo-$C_{1-6}$-alkoxy or $SF_5$;

$R^8$ is hydrogen, halo-$C_{1-6}$-alkyl or halogen;

$R^{10}$ is halo-$C_{1-6}$-alkyl; and $R^{11}$ is hydrogen or halo-$C_{1-6}$-alkyl.

In a particularly preferred embodiment, the present invention provides a compound of formula (I) as described herein, or a pharmaceutically acceptable salt thereof, wherein:

(i) X is C—$R^5$;

L is —$CH_2$O—, —$OCH_2$—, —O—, —$CH_2$— or —$SO_2$—N(methyl)-; and

A is:

(i) phenyl substituted with $R^7$, $R^8$ and $R^9$; or (ii) pyridyl substituted with $R^{10}$, $R^{11}$ and $R^{12}$; or (ii) X is N;

L is —$CH_2$— or —$SO_2$—; and

A is phenyl substituted with $R^7$, $R^8$ and $R^9$; or

B is a bicyclic spirocycle selected from the group consisting of:

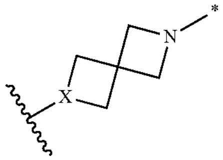

;

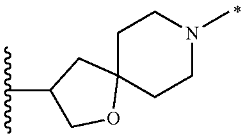

and

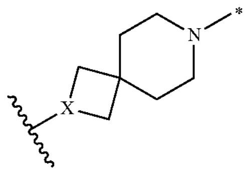

wherein the wavy line indicates the point of attachment of bicyclic spirocycle B to L in formula (I); and the asterisk indicates the point of attachment of bicyclic spirocycle B to the remainder of formula (I);

each of $R^1$, $R^2$, $R^3$, $R^4$, $R^5$, $R^9$, and $R^{12}$ is hydrogen;

$R^7$ is hydrogen, fluoro, chloro, $CF_3$, methyl, methoxy, trifluoromethoxy or $SF_5$;

$R^8$ is hydrogen, $CF_3$, chloro or fluoro;

$R^{10}$ is $CF_3$; and $R^{11}$ is hydrogen or $CF_3$.

In one embodiment, the present invention provides a compound of formula (I) as described herein, or a pharmaceutically acceptable salt thereof, wherein:

(i) X is C—$R^5$;

L is —$CH_2$—N($C_{1-6}$-alkyl)-, —$CH_2$—NH—, —$(CH_2)_n$—O—, —O—$CH_2$—, —$SO_2$—N($C_{1-6}$-alkyl)- or —$SO_2$—NH—; and A is:

(i) $C_{6-14}$-aryl substituted with $R^7$, $R^8$ and $R^9$; or (ii) 5-14 membered heteroaryl substituted with $R^{10}$, $R^{11}$ and $R^{12}$; or (ii) X is N;

L is —$CH_2$—, —$CHR^6$— or —$SO_2$—; and

A is $C_{6-14}$-aryl substituted with $R^7$, $R^8$ and $R^9$; or (iii) X is N;

L is $C_{1-6}$-alkoxycarbonyl; and

A is absent;

B is a bicyclic spirocycle having formula (II):

(II)

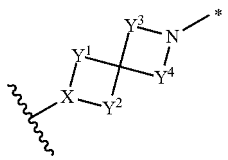

wherein:

$Y^1$ is —$(CH_2)_m$— or —$(CH_2)_m$O—, wherein m is 1 or 2;

$Y^2$ is —$CH_2$— or —$CH_2$O—;

$Y^3$ and $Y^4$ are each independently —$(CH_2)_m$—, wherein m is 1 or 2;

the wavy line indicates the point of attachment of bicyclic spirocycle B to L in formula (I); and the asterisk indicates the point of attachment of bicyclic spirocycle B to the remainder of formula (I);

each of $R^1$, $R^2$, $R^3$, $R^4$, $R^5$, $R^9$ and $R^{12}$ is hydrogen;

$R^6$ is $C_{6-14}$-aryl;

$R^7$ is hydrogen, $C_{1-6}$-alkyl, halo-$C_{1-6}$-alkyl, halogen, $C_{1-6}$-alkoxy or halo-$C_{1-6}$-alkoxy;

$R^8$ is hydrogen, halo-$C_{1-6}$-alkyl or halogen;

$R^{10}$ is halo-$C_{1-6}$-alkyl;

$R^{11}$ is hydrogen or halo-$C_{1-6}$-alkyl; and n is 0 or 1.

In a preferred embodiment, the present invention provides a compound of formula (I) as described herein, or a pharmaceutically acceptable salt thereof, wherein:

(i) X is C—$R^5$;

L is —$(CH_2)_n$—O—, —O—$CH_2$— or —$SO_2$—N($C_{1-6}$-alkyl)-; and

A is:

(i) $C_{6-14}$-aryl substituted with $R^7$, $R^8$ and $R^9$; or (ii) 5-14 membered heteroaryl substituted with $R^{10}$, $R^{11}$ and $R^{12}$; or (ii) X is N;

L is —$CH_2$— or —$SO_2$—; and

A is $C_{6-14}$-aryl substituted with $R^7$, $R^8$ and $R^9$; or

B is a bicyclic spirocycle having formula (II):

(II)

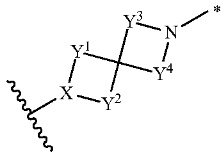

wherein:

$Y^1$ is —$CH_2$—;

$Y^2$ is —$CH_2$— or —$CH_2$O—;

$Y^3$ and $Y^4$ are each independently —$(CH_2)_m$—, wherein m is 1 or 2;

the wavy line indicates the point of attachment of bicyclic spirocycle B to L in formula (I); and the asterisk indicates the point of attachment of bicyclic spirocycle B to the remainder of formula (I);

each of $R^1$, $R^2$, $R^3$, $R^4$, $R^5$, $R^9$, and $R^{12}$ is hydrogen;

$R^7$ is hydrogen, $C_{1-6}$-alkyl, halo-$C_{1-6}$-alkyl, halogen, $C_{1-6}$-alkoxy or halo-$C_{1-6}$-alkoxy;

$R^8$ is hydrogen, halo-$C_{1-6}$-alkyl or halogen;

$R^{10}$ is halo-$C_{1-6}$-alkyl;

$R^{11}$ is hydrogen or halo-$C_{1-6}$-alkyl; and n is 0 or 1.

In a particularly preferred embodiment, the present invention provides a compound of formula (I) as described herein, or a pharmaceutically acceptable salt thereof, wherein:

(i) X is C—$R^5$;

L is —$(CH_2)_n$—O—, —O—$CH_2$— or —$SO_2$—N(methyl)-; and

A is:

(i) phenyl substituted with $R^7$, $R^8$ and $R^9$; or (ii) pyridyl substituted with $R^{10}$, $R^{11}$ and $R^{12}$; or (ii) X is N;

L is —$CH_2$— or —$SO_2$—; and

A is phenyl substituted with $R^7$, $R^8$ and $R^9$; or

B is a bicyclic spirocycle selected from the group consisting of:

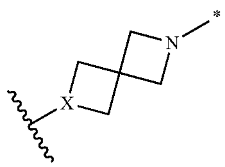

;

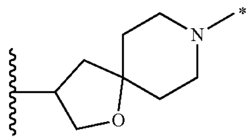

and

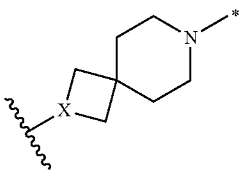

wherein the wavy line indicates the point of attachment of bicyclic spirocycle B to L in formula (I); and the asterisk indicates the point of attachment of bicyclic spirocycle B to the remainder of formula (I);

each of $R^1$, $R^2$, $R^3$, $R^4$, $R^5$, $R^9$, and $R^{12}$ is hydrogen;

$R^7$ is hydrogen, fluoro, chloro, $CF_3$, methyl, methoxy or trifluoromethoxy;

$R^8$ is hydrogen, $CF_3$, chloro or fluoro;

$R^{10}$ is $CF_3$;

$R^{11}$ is hydrogen or $CF_3$; and n is 0 or 1.

In one embodiment, the present invention provides a compound of formula (I) as described herein, or a pharmaceutically acceptable salt thereof, wherein said compound of formula (I) is selected from the group consisting of:

(4aR,8aS)-6-(6-(2-Chloro-4-(trifluoromethoxy)phenoxy)-2-azaspiro[3.3]heptane-2-carbonyl)hexahydro-2H-pyrido[4,3-b][1,4]oxazin-3(4H)-one;

(4aR,8aS)-6-(2-(2-Fluoro-4-(trifluoromethyl)phenoxy)-7-azaspiro[3.5]nonane-7-carbonyl)hexahydro-2H-pyrido[4,3-b][1,4]oxazin-3(4H)-one;

(4aR,8aS)-6-(6-(2-Fluoro-4-(trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(2-Methoxy-5-(trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(2-Fluoro-4-(trifluoromethoxy)phenoxy)-2-azaspiro[3.3]heptane-2-carbonyl)hexahydro-2H-pyrido[4,3-b][1,4]oxazin-3(4H)-one;

(4aR,8aS)-6-(6-(2-Chloro-4-fluorophenoxy)-2-azaspiro[3.3]heptane-2-carbonyl)hexahydro-2H-pyrido[4,3-b][1,4]oxazin-3(4H)-one;

(4aR,8aS)-6-(6-(4-(Trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(4-Chloro-2-(trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(2,4-Difluorophenoxy)-2-azaspiro[3.3]heptane-2-carbonyl)hexahydro-2H-pyrido[4,3-b][1,4]oxazin-3(4H)-one;

(4aR,8aS)-6-(6-(3-Fluoro-5-(trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(2-Fluoro-4-(trifluoromethyl)benzyl)-2,6-diazaspiro[3.3]heptane-2-carbonyl)hexahydro-2H-pyrido[4,3-b][1,4]oxazin-3(4H)-one;

(4aR,8aS)-6-(6-(2-Chloro-4-fluorobenzyl)-2,6-diazaspiro[3.3]heptane-2-carbonyl)hexahydro-2H-pyrido[4,3-b][1,4]oxazin-3(4H)-one;

(4aR,8aS)-6-(2-(2-Fluoro-4-(trifluoromethyl)benzyl)-2,7-diazaspiro[3.5]nonane-7-carbonyl)hexahydro-2H-pyrido[4,3-b][1,4]oxazin-3(4H)-one;

(4aR,8aS)-6-(6-((2-Chloro-4-fluorophenyl)sulfonyl)-2,6-diazaspiro[3.3]heptane-2-carbonyl)hexahydro-2H-pyrido[4,3-b][1,4]oxazin-3(4H)-one;

(4aR,8aS)-6-(7-(2-Fluoro-4-(trifluoromethyl)benzyl)-2,7-diazaspiro[4.4]nonane-2-carbonyl)hexahydro-2H-pyrido[4,3-b][1,4]oxazin-3(4H)-one;

(4aR,8aS)-6-(6-((2-Fluoro-4-(trifluoromethyl)phenyl)sulfonyl)-2,6-diazaspiro[3.3]heptane-2-carbonyl)hexahydro-2H-pyrido[4,3-b][1,4]oxazin-3(4H)-one;

(4aR,8aS)-6-(2-(2-Fluoro-4-(trifluoromethyl)benzyl)-2,6-diazaspiro[3.4]octane-6-carbonyl)hexahydro-2H-pyrido[4,3-b][1,4]oxazin-3(4H)-one;

rac-(4aR,8aS)—N—((R)-8-(3-Oxooctahydro-2H-pyrido[4,3-b][1,4]oxazine-6-carbonyl)-1-oxa-8-azaspiro[4.5]decan-3-yl)benzenesulfonamide;

rac-(4aR,8aS)—N—((S)-8-(3-Oxooctahydro-2H-pyrido[4,3-b][1,4]oxazine-6-carbonyl)-1-oxa-8-azaspiro[4.5]decan-3-yl)benzenesulfonamide;

rac-(4aR,8aS)-6-(2-Benzhydryl-2,6-diazaspiro[3.4]octane-6-carbonyl)hexahydro-2H-pyrido[4,3-b][1,4]oxazin-3(4H)-one;

rac-(4aR,8aS)-6-(4-((4-Fluorophenyl)sulfonyl)-1-oxa-4,9-diazaspiro[5.5]undecane-9-carbonyl)hexahydro-2H-pyrido[4,3-b][1,4]oxazin-3(4H)-one;

(4aR,8aS)-6-(6-((4,5-bis(trifluoromethyl)pyridin-2-yl)oxy)-2-azaspiro[3.3]heptane-2-carbonyl)hexahydro-2H-pyrido[4,3-b][1,4]oxazin-3(4H)-one;

(4aR,8aS)-6-(6-((5,6-Bis(trifluoromethyl)pyridin-2-yl)oxy)-2-azaspiro[3.3]heptane-2-carbonyl)hexahydro-2H-pyrido[4,3-b][1,4]oxazin-3(4H)-one;

2-Chloro-4-fluoro-N-methyl-N—((R)-8-((4aR,8aS)-3-oxooctahydro-2H-pyrido[4,3-b][1,4]oxazine-6-carbonyl)-1-oxa-8-azaspiro[4.5]decan-3-yl)benzenesulfonamide;

(4aR,8aS)-6-(6-((5-(Trifluoromethyl)pyridin-2-yl)oxy)-2-azaspiro[3.3]heptane-2-carbonyl)hexahydro-2H-pyrido[4,3-b][1,4]oxazin-3(4H)-one;

(4aR,8aS)-6-(6-((4-Methyl-3-(trifluoromethyl)benzyl)oxy)-2-azaspiro[3.3]heptane-2-carbonyl)hexahydro-2H-pyrido[4,3-b][1,4]oxazin-3(4H)-one;

(4aR,8aS)-6-(2-((2-Chloro-4-fluorophenyl)sulfonyl)-2,7-diazaspiro[3.5]nonane-7-carbonyl)hexahydro-2H-pyrido[4,3-b][1,4]oxazin-3(4H)-one;

(4aR,8aS)-6-(6-((2-Fluoro-4-(trifluoromethyl)benzyl)oxy)-2-azaspiro[3.3]heptane-2-carbonyl)hexahydro-2H-pyrido[4,3-b][1,4]oxazin-3(4H)-one;

N—((S)-8-((4aR,8aS)-3-Oxooctahydro-2H-pyrido[4,3-b][1,4]oxazine-6-carbonyl)-1-oxa-8-azaspiro[4.5]decan-3-yl)-4-(trifluoromethyl)benzenesulfonamide;

N-Methyl-N—((R)-8-((4aR,8aS)-3-oxooctahydro-2H-pyrido[4,3-b][1,4]oxazine-6-carbonyl)-1-oxa-8-azaspiro[4.5]decan-3-yl)benzenesulfonamide;

2-Chloro-4-fluoro-N—((S)-8-((4aR,8aS)-3-oxooctahydro-2H-pyrido[4,3-b][1,4]oxazine-6-carbonyl)-1-oxa-8-azaspiro[4.5]decan-3-yl)benzenesulfonamide;

N—((S)-8-((4aR,8aS)-3-Oxooctahydro-2H-pyrido[4,3-b][1,4]oxazine-6-carbonyl)-1-oxa-8-azaspiro[4.5]decan-3-yl)-3-(trifluoromethyl)benzenesulfonamide;

(4aR,8aS)-6-(3-((2-Chloro-4-fluorobenzyl)(methyl)amino)-1-oxa-8-azaspiro[4.5]decane-8-carbonyl)hexahydro-2H-pyrido[4,3-b][1,4]oxazin-3(4H)-one;

(4aR,8aS)-6-(3-((2-Chloro-4-fluorobenzyl)(methyl)amino)-1-oxa-8-azaspiro[4.5]decane-8-carbonyl)hexahydro-2H-pyrido[4,3-b][1,4]oxazin-3(4H)-one;

(4aR,8aS)-6-(3-((2-Chloro-4-fluorobenzyl)amino)-1-oxa-8-azaspiro[4.5]decane-8-carbonyl)hexahydro-2H-pyrido[4,3-b][1,4]oxazin-3(4H)-one;

(4aR,8aS)-6-(3-((2-Chloro-4-fluorobenzyl)amino)-1-oxa-8-azaspiro[4.5]decane-8-carbonyl)hexahydro-2H-pyrido[4,3-b][1,4]oxazin-3(4H)-one;

(4aR,8aS)-6-(2-((4-(Trifluoromethyl)phenyl)sulfonyl)-2,7-diazaspiro[3.5]nonane-7-carbonyl)hexahydro-2H-pyrido[4,3-b][1,4]oxazin-3(4H)-one;

rac-(4aR,8aS)-6-(3-((2-Chloro-4-fluorobenzyl)amino)-1-oxa-8-azaspiro[4.5]decane-8-carbonyl)hexahydro-2H-pyrido[4,3-b][1,4]oxazin-3(4H)-one;

(4aR,8aS)-6-(2-(Phenylsulfonyl)-2,7-diazaspiro[3.5]nonane-7-carbonyl)hexahydro-2H-pyrido[4,3-b][1,4]oxazin-3(4H)-one;

rac-tert-butyl 6-((4aR,8aS)-3-oxooctahydro-2H-pyrido[4,3-b][1,4]oxazine-6-carbonyl)-2,6-diazaspiro[3.4]octane-2-carboxylate;

(4aR,8aS)-6-(6-(4-(1-methyl-1H-pyrazol-5-yl)phenyl)-2-azaspiro[3.3]heptane-2-carbonyl)hexahydro-2H-pyrido[4,3-b][1,4]oxazin-3(4H)-one;

(4aR,8aS)-6-(6-(2-fluoro-6-hydroxybenzyl)-2-azaspiro[3.3]heptane-2-carbonyl)hexahydro-2H-pyrido[4,3-b][1,4]oxazin-3(4H)-one;
(4aR,8aS)-6-(6-(2-hydroxybenzyl)-2-azaspiro[3.3]heptane-2-carbonyl)hexahydro-2H-pyrido[4,3-b][1,4]oxazin-3(4H)-one;
(4aR,8aS)-6-(2-(4-(2-oxopyrrolidin-1-yl)phenyl)-2,6-diazaspiro[3.4]octane-6-carbonyl)hexahydro-2H-pyrido[4,3-b][1,4]oxazin-3(4H)-one;
(4aR,8aS)-6-(6-(2-fluoro-6-methoxybenzyl)-2-azaspiro[3.3]heptane-2-carbonyl)hexahydro-2H-pyrido[4,3-b][1,4]oxazin-3(4H)-one;
(4aR,8aS)-6-(6-(4-(pentafluoro-16-sulfaneyl)phenyl)-2-azaspiro[3.3]heptane-2-carbonyl)hexahydro-2H-pyrido[4,3-b][1,4]oxazin-3(4H)-one;
(4aR,8aS)-6-(6-(2-fluoro-4-(trifluoromethyl)benzyl)-2-azaspiro[3.3]heptane-2-carbonyl)hexahydro-2H-pyrido[4,3-b][1,4]oxazin-3(4H)-one;
(4aR,8aS)-6-(6-(2,4-difluorobenzyl)-2-azaspiro[3.3]heptane-2-carbonyl)hexahydro-2H-pyrido[4,3-b][1,4]oxazin-3(4H)-one;
(4aR,8aS)-6-(6-(2-methoxy-4-(trifluoromethyl)benzyl)-2-azaspiro[3.3]heptane-2-carbonyl)hexahydro-2H-pyrido[4,3-b][1,4]oxazin-3(4H)-one;
(4aR,8aS)-6-(6-((2-chloro-4-fluorophenoxy)methyl)-2-azaspiro[3.3]heptane-2-carbonyl)hexahydro-2H-pyrido[4,3-b][1,4]oxazin-3(4H)-one;
(4aR,8aS)-6-(6-((2-fluoro-4-(trifluoromethyl)benzyl)oxy)-6-(trifluoromethyl)-2-azaspiro[3.3]heptane-2-carbonyl)hexahydro-2H-pyrido[4,3-b][1,4]oxazin-3(4H)-one;
(4aR,8aS)-6-(6-(2-fluoro-4-(trifluoromethyl)phenyl)-2-azaspiro[3.3]heptane-2-carbonyl)hexahydro-2H-pyrido[4,3-b][1,4]oxazin-3(4H)-one;
(4aR,8aS)-6-(6-(4-(2-(trifluoromethyl)pyrrolidin-1-yl)phenyl)-2-azaspiro[3.3]heptane-2-carbonyl)hexahydro-2H-pyrido[4,3-b][1,4]oxazin-3(4H)-one;
(4aR,8aS)-6-(6-(2-chloro-4-fluorobenzyl)-2-azaspiro[3.3]heptane-2-carbonyl)hexahydro-2H-pyrido[4,3-b][1,4]oxazin-3(4H)-one;
(4aR,8aS)-6-(6-(2-fluoro-6-(trifluoromethyl)benzyl)-2-azaspiro[3.3]heptane-2-carbonyl)hexahydro-2H-pyrido[4,3-b][1,4]oxazin-3(4H)-one;
(4aR,8aS)-6-(6-(4-(trifluoromethyl)phenyl)-2,6-diazaspiro[3.3]heptane-2-carbonyl)hexahydro-2H-pyrido[4,3-b][1,4]oxazin-3(4H)-one;
(4aR,8aS)-6-(6-(3-(trifluoromethyl)phenyl)-2,6-diazaspiro[3.3]heptane-2-carbonyl)hexahydro-2H-pyrido[4,3-b][1,4]oxazin-3(4H)-one;
(4aR,8aS)-6-(2-(4-(trifluoromethyl)phenyl)-2,6-diazaspiro[3.4]octane-6-carbonyl)hexahydro-2H-pyrido[4,3-b][1,4]oxazin-3(4H)-one;
(4aR,8aS)-6-(2-(3-(trifluoromethyl)phenyl)-2,6-diazaspiro[3.4]octane-6-carbonyl)hexahydro-2H-pyrido[4,3-b][1,4]oxazin-3(4H)-one;
(4aR,8aS)-6-(2-(4-isopropoxyphenyl)-2,6-diazaspiro[3.4]octane-6-carbonyl)hexahydro-2H-pyrido[4,3-b][1,4]oxazin-3(4H)-one;
(4aR,8aS)-6-(6-(4-isopropoxyphenyl)-2,6-diazaspiro[3.3]heptane-2-carbonyl)hexahydro-2H-pyrido[4,3-b][1,4]oxazin-3(4H)-one;
(4aR,8aS)-6-(2-(4-methoxy-3-methylphenyl)-2,6-diazaspiro[3.4]octane-6-carbonyl)hexahydro-2H-pyrido[4,3-b][1,4]oxazin-3(4H)-one;
(4aR,8aS)-6-(2-(4-chloro-3-(trifluoromethyl)phenyl)-2,6-diazaspiro[3.4]octane-6-carbonyl)hexahydro-2H-pyrido[4,3-b][1,4]oxazin-3(4H)-one;
(4aR,8aS)-6-(2-(2-fluoropyridin-4-yl)-2,6-diazaspiro[3.4]octane-6-carbonyl)hexahydro-2H-pyrido[4,3-b][1,4]oxazin-3(4H)-one;
(4aR,8aS)-6-(6-(2,5-bis(trifluoromethyl)phenyl)-2,6-diazaspiro[3.3]heptane-2-carbonyl)hexahydro-2H-pyrido[4,3-b][1,4]oxazin-3(4H)-one;
(4aR,8aS)-6-(6-((4-fluoro-2-(trifluoromethyl)phenyl)sulfonyl)-2,6-diazaspiro[3.3]heptane-2-carbonyl)hexahydro-2H-pyrido[4,3-b][1,4]oxazin-3(4H)-one;
(4aR,8aS)-6-(6-((2-chloro-4-fluorophenyl)sulfonyl)-2-azaspiro[3.3]heptane-2-carbonyl)hexahydro-2H-pyrido[4,3-b][1,4]oxazin-3(4H)-one;
(4aR,8aS)-6-(6-((3-chloro-4-(trifluoromethyl)phenyl)sulfonyl)-2,6-diazaspiro[3.3]heptane-2-carbonyl)hexahydro-2H-pyrido[4,3-b][1,4]oxazin-3(4H)-one;
(4aR,8aS)-6-(6-((2,4-bis(trifluoromethyl)phenyl)sulfonyl)-2,6-diazaspiro[3.3]heptane-2-carbonyl)hexahydro-2H-pyrido[4,3-b][1,4]oxazin-3(4H)-one;
(4aR,8aS)-6-(6-(2,6-difluorobenzyl)-2-azaspiro[3.3]heptane-2-carbonyl)hexahydro-2H-pyrido[4,3-b][1,4]oxazin-3(4H)-one; and
(4aR,8aS)-6-(6-(2-methoxybenzyl)-2-azaspiro[3.3]heptane-2-carbonyl)hexahydro-2H-pyrido[4,3-b][1,4]oxazin-3(4H)-one.

In a preferred embodiment, the present invention provides a compound of formula (I) as described herein, or a pharmaceutically acceptable salt thereof, wherein said compound of formula (I) is selected from the group consisting of:
(4aR,8aS)-6-(6-(2-Chloro-4-(trifluoromethoxy)phenoxy)-2-azaspiro[3.3]heptane-2-carbonyl)hexahydro-2H-pyrido[4,3-b][1,4]oxazin-3(4H)-one;
(4aR,8aS)-6-(2-(2-Fluoro-4-(trifluoromethyl)phenoxy)-7-azaspiro[3.5]nonane-7-carbonyl)hexahydro-2H-pyrido[4,3-b][1,4]oxazin-3(4H)-one;
(4aR,8aS)-6-(6-(2-Fluoro-4-(trifluoromethyl)phenoxy)-2-azaspiro[3.3]heptane-2-carbonyl)hexahydro-2H-pyrido[4,3-b][1,4]oxazin-3(4H)-one;
(4aR,8aS)-6-(6-(2-Methoxy-5-(trifluoromethyl)phenoxy)-2-azaspiro[3.3]heptane-2-carbonyl)hexahydro-2H-pyrido[4,3-b][1,4]oxazin-3(4H)-one;
(4aR,8aS)-6-(6-(2-Fluoro-4-(trifluoromethoxy)phenoxy)-2-azaspiro[3.3]heptane-2-carbonyl)hexahydro-2H-pyrido[4,3-b][1,4]oxazin-3(4H)-one;
(4aR,8aS)-6-(6-(2-Chloro-4-fluorophenoxy)-2-azaspiro[3.3]heptane-2-carbonyl)hexahydro-2H-pyrido[4,3-b][1,4]oxazin-3(4H)-one;
(4aR,8aS)-6-(6-(4-(Trifluoromethyl)phenoxy)-2-azaspiro[3.3]heptane-2-carbonyl)hexahydro-2H-pyrido[4,3-b][1,4]oxazin-3(4H)-one;
(4aR,8aS)-6-(6-(4-Chloro-2-(trifluoromethyl)phenoxy)-2-azaspiro[3.3]heptane-2-carbonyl)hexahydro-2H-pyrido[4,3-b][1,4]oxazin-3(4H)-one;
(4aR,8aS)-6-(6-(2,4-Difluorophenoxy)-2-azaspiro[3.3]heptane-2-carbonyl)hexahydro-2H-pyrido[4,3-b][1,4]oxazin-3(4H)-one;
(4aR,8aS)-6-(6-(2-Fluoro-4-(trifluoromethyl)benzyl)-2,6-diazaspiro[3.3]heptane-2-carbonyl)hexahydro-2H-pyrido[4,3-b][1,4]oxazin-3(4H)-one;
(4aR,8aS)-6-(6-((4,5-bis(trifluoromethyl)pyridin-2-yl)oxy)-2-azaspiro[3.3]heptane-2-carbonyl)hexahydro-2H-pyrido[4,3-b][1,4]oxazin-3(4H)-one;
(4aR,8aS)-6-(6-(4-(pentafluoro-16-sulfaneyl)phenyl)-2-azaspiro[3.3]heptane-2-carbonyl)hexahydro-2H-pyrido[4,3-b][1,4]oxazin-3(4H)-one;

(4aR,8aS)-6-(6-(2-fluoro-4-(trifluoromethyl)benzyl)-2-azaspiro[3.3]heptane-2-carbonyl)hexahydro-2H-pyrido[4,3-b][1,4]oxazin-3(4H)-one;
(4aR,8aS)-6-(6-(2,4-difluorobenzyl)-2-azaspiro[3.3]heptane-2-carbonyl)hexahydro-2H-pyrido[4,3-b][1,4]oxazin-3(4H)-one;
(4aR,8aS)-6-(6-(2-methoxy-4-(trifluoromethyl)benzyl)-2-azaspiro[3.3]heptane-2-carbonyl)hexahydro-2H-pyrido[4,3-b][1,4]oxazin-3(4H)-one; and
(4aR,8aS)-6-(6-((2-chloro-4-fluorophenoxy)methyl)-2-azaspiro[3.3]heptane-2-carbonyl)hexahydro-2H-pyrido[4,3-b][1,4]oxazin-3(4H)-one.

In one embodiment, the present invention provides a compound of formula (I) as described herein, or a pharmaceutically acceptable salt thereof, wherein said compound of formula (I) is selected from the group consisting of:

(4aR,8aS)-6-(6-(2-Chloro-4-(trifluoromethoxy)phenoxy)-2-azaspiro[3.3]heptane-2-carbonyl)hexahydro-2H-pyrido[4,3-b][1,4]oxazin-3(4H)-one;
(4aR,8aS)-6-(2-(2-Fluoro-4-(trifluoromethyl)phenoxy)-7-azaspiro[3.5]nonane-7-carbonyl)hexahydro-2H-pyrido[4,3-b][1,4]oxazin-3(4H)-one;
(4aR,8aS)-6-(6-(2-Fluoro-4-(trifluoromethyl)phenoxy)-2-azaspiro[3.3]heptane-2-carbonyl)hexahydro-2H-pyrido[4,3-b][1,4]oxazin-3(4H)-one;
(4aR,8aS)-6-(6-(2-Methoxy-5-(trifluoromethyl)phenoxy)-2-azaspiro[3.3]heptane-2-carbonyl)hexahydro-2H-pyrido[4,3-b][1,4]oxazin-3(4H)-one;
(4aR,8aS)-6-(6-(2-Fluoro-4-(trifluoromethoxy)phenoxy)-2-azaspiro[3.3]heptane-2-carbonyl)hexahydro-2H-pyrido[4,3-b][1,4]oxazin-3(4H)-one;
(4aR,8aS)-6-(6-(2-Chloro-4-fluorophenoxy)-2-azaspiro[3.3]heptane-2-carbonyl)hexahydro-2H-pyrido[4,3-b][1,4]oxazin-3(4H)-one;
(4aR,8aS)-6-(6-(4-(Trifluoromethyl)phenoxy)-2-azaspiro[3.3]heptane-2-carbonyl)hexahydro-2H-pyrido[4,3-b][1,4]oxazin-3(4H)-one;
(4aR,8aS)-6-(6-(4-Chloro-2-(trifluoromethyl)phenoxy)-2-azaspiro[3.3]heptane-2-carbonyl)hexahydro-2H-pyrido[4,3-b][1,4]oxazin-3(4H)-one;
(4aR,8aS)-6-(6-(2,4-Difluorophenoxy)-2-azaspiro[3.3]heptane-2-carbonyl)hexahydro-2H-pyrido[4,3-b][1,4]oxazin-3(4H)-one;
(4aR,8aS)-6-(6-(3-Fluoro-5-(trifluoromethyl)phenoxy)-2-azaspiro[3.3]heptane-2-carbonyl)hexahydro-2H-pyrido[4,3-b][1,4]oxazin-3(4H)-one;
(4aR,8aS)-6-(6-(2-Fluoro-4-(trifluoromethyl)benzyl)-2,6-diazaspiro[3.3]heptane-2-carbonyl)hexahydro-2H-pyrido[4,3-b][1,4]oxazin-3(4H)-one;
(4aR,8aS)-6-(6-(2-Chloro-4-fluorobenzyl)-2,6-diazaspiro[3.3]heptane-2-carbonyl)hexahydro-2H-pyrido[4,3-b][1,4]oxazin-3(4H)-one;
(4aR,8aS)-6-(2-(2-Fluoro-4-(trifluoromethyl)benzyl)-2,7-diazaspiro[3.5]nonane-7-carbonyl)hexahydro-2H-pyrido[4,3-b][1,4]oxazin-3(4H)-one;
(4aR,8aS)-6-(6-((2-Chloro-4-fluorophenyl)sulfonyl)-2,6-diazaspiro[3.3]heptane-2-carbonyl)hexahydro-2H-pyrido[4,3-b][1,4]oxazin-3(4H)-one;
(4aR,8aS)-6-(7-(2-Fluoro-4-(trifluoromethyl)benzyl)-2,7-diazaspiro[4.4]nonane-2-carbonyl)hexahydro-2H-pyrido[4,3-b][1,4]oxazin-3(4H)-one;
(4aR,8aS)-6-(6-((2-Fluoro-4-(trifluoromethyl)phenyl)sulfonyl)-2,6-diazaspiro[3.3]heptane-2-carbonyl)hexahydro-2H-pyrido[4,3-b][1,4]oxazin-3(4H)-one;
(4aR,8aS)-6-(2-(2-Fluoro-4-(trifluoromethyl)benzyl)-2,6-diazaspiro[3.4]octane-6-carbonyl)hexahydro-2H-pyrido[4,3-b][1,4]oxazin-3(4H)-one;
rac-(4aR,8aS)—N—((R)-8-(3-Oxooctahydro-2H-pyrido[4,3-b][1,4]oxazine-6-carbonyl)-1-oxa-8-azaspiro[4.5]decan-3-yl)benzenesulfonamide;
rac-(4aR,8aS)—N—((S)-8-(3-Oxooctahydro-2H-pyrido[4,3-b][1,4]oxazine-6-carbonyl)-1-oxa-8-azaspiro[4.5]decan-3-yl)benzenesulfonamide;
rac-(4aR,8aS)-6-(2-Benzhydryl-2,6-diazaspiro[3.4]octane-6-carbonyl)hexahydro-2H-pyrido[4,3-b][1,4]oxazin-3(4H)-one;
rac-(4aR,8aS)-6-(4-((4-Fluorophenyl)sulfonyl)-1-oxa-4,9-diazaspiro[5.5]undecane-9-carbonyl)hexahydro-2H-pyrido[4,3-b][1,4]oxazin-3(4H)-one;
(4aR,8aS)-6-(6-((4,5-Bis(trifluoromethyl)pyridin-2-yl)oxy)-2-azaspiro[3.3]heptane-2-carbonyl)hexahydro-2H-pyrido[4,3-b][1,4]oxazin-3(4H)-one;
(4aR,8aS)-6-(6-((5,6-Bis(trifluoromethyl)pyridin-2-yl)oxy)-2-azaspiro[3.3]heptane-2-carbonyl)hexahydro-2H-pyrido[4,3-b][1,4]oxazin-3(4H)-one;
2-Chloro-4-fluoro-N-methyl-N—((R)-8-((4aR,8aS)-3-oxooctahydro-2H-pyrido[4,3-b][1,4]oxazine-6-carbonyl)-1-oxa-8-azaspiro[4.5]decan-3-yl)benzenesulfonamide;
(4aR,8aS)-6-(6-((5-(Trifluoromethyl)pyridin-2-yl)oxy)-2-azaspiro[3.3]heptane-2-carbonyl)hexahydro-2H-pyrido[4,3-b][1,4]oxazin-3(4H)-one;
(4aR,8aS)-6-(6-((4-Methyl-3-(trifluoromethyl)benzyl)oxy)-2-azaspiro[3.3]heptane-2-carbonyl)hexahydro-2H-pyrido[4,3-b][1,4]oxazin-3(4H)-one;
(4aR,8aS)-6-(2-((2-Chloro-4-fluorophenyl)sulfonyl)-2,7-diazaspiro[3.5]nonane-7-carbonyl)hexahydro-2H-pyrido[4,3-b][1,4]oxazin-3(4H)-one;
(4aR,8aS)-6-(6-((2-Fluoro-4-(trifluoromethyl)benzyl)oxy)-2-azaspiro[3.3]heptane-2-carbonyl)hexahydro-2H-pyrido[4,3-b][1,4]oxazin-3(4H)-one;
N—((S)-8-((4aR,8aS)-3-Oxooctahydro-2H-pyrido[4,3-b][1,4]oxazine-6-carbonyl)-1-oxa-8-azaspiro[4.5]decan-3-yl)-4-(trifluoromethyl)benzenesulfonamide;
N-Methyl-N—((R)-8-((4aR,8aS)-3-oxooctahydro-2H-pyrido[4,3-b][1,4]oxazine-6-carbonyl)-1-oxa-8-azaspiro[4.5]decan-3-yl)benzenesulfonamide;
2-Chloro-4-fluoro-N—((S)-8-((4aR,8aS)-3-oxooctahydro-2H-pyrido[4,3-b][1,4]oxazine-6-carbonyl)-1-oxa-8-azaspiro[4.5]decan-3-yl)benzenesulfonamide;
N—((S)-8-((4aR,8aS)-3-Oxooctahydro-2H-pyrido[4,3-b][1,4]oxazine-6-carbonyl)-1-oxa-8-azaspiro[4.5]decan-3-yl)-3-(trifluoromethyl)benzenesulfonamide;
(4aR,8aS)-6-(3-((2-Chloro-4-fluorobenzyl)(methyl)amino)-1-oxa-8-azaspiro[4.5]decane-8-carbonyl)hexahydro-2H-pyrido[4,3-b][1,4]oxazin-3(4H)-one;
(4aR,8aS)-6-(3-((2-Chloro-4-fluorobenzyl)(methyl)amino)-1-oxa-8-azaspiro[4.5]decane-8-carbonyl)hexahydro-2H-pyrido[4,3-b][1,4]oxazin-3(4H)-one;
(4aR,8aS)-6-(3-((2-Chloro-4-fluorobenzyl)amino)-1-oxa-8-azaspiro[4.5]decane-8-carbonyl)hexahydro-2H-pyrido[4,3-b][1,4]oxazin-3(4H)-one;
(4aR,8aS)-6-(3-((2-Chloro-4-fluorobenzyl)amino)-1-oxa-8-azaspiro[4.5]decane-8-carbonyl)hexahydro-2H-pyrido[4,3-b][1,4]oxazin-3(4H)-one;
(4aR,8aS)-6-(2-((4-(Trifluoromethyl)phenyl)sulfonyl)-2,7-diazaspiro[3.5]nonane-7-carbonyl)hexahydro-2H-pyrido[4,3-b][1,4]oxazin-3(4H)-one;
rac-(4aR,8aS)-6-(3-((2-Chloro-4-fluorobenzyl)amino)-1-oxa-8-azaspiro[4.5]decane-8-carbonyl)hexahydro-2H-pyrido[4,3-b][1,4]oxazin-3(4H)-one;
(4aR,8aS)-6-(2-(Phenylsulfonyl)-2,7-diazaspiro[3.5]nonane-7-carbonyl)hexahydro-2H-pyrido[4,3-b][1,4]oxazin-3(4H)-one; and rac-tert-Butyl 6-((4aR,8aS)-3-oxooctahydro-2H-pyrido[4,3-b][1,4]oxazine-6-carbonyl)-2,6-diazaspiro[3.4]octane-2-carboxylate.

In a preferred embodiment, the present invention provides a compound of formula (I) as described herein, or a pharmaceutically acceptable salt thereof, wherein said compound of formula (I) is selected from the group consisting of:

(4aR,8aS)-6-(6-(2-Chloro-4-(trifluoromethoxy)phenoxy)-2-azaspiro[3.3]heptane-2-carbonyl)hexahydro-2H-pyrido[4,3-b][1,4]oxazin-3(4H)-one;

(4aR,8aS)-6-(2-(2-Fluoro-4-(trifluoromethyl)phenoxy)-7-azaspiro[3.5]nonane-7-carbonyl)hexahydro-2H-pyrido[4,3-b][1,4]oxazin-3(4H)-one;

(4aR,8aS)-6-(6-(2-Fluoro-4-(trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(2-Methoxy-5-(trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(2-Fluoro-4-(trifluoromethoxy)phenoxy)-2-azaspiro[3.3]heptane-2-carbonyl)hexahydro-2H-pyrido[4,3-b][1,4]oxazin-3(4H)-one;

(4aR,8aS)-6-(6-(2-Chloro-4-fluorophenoxy)-2-azaspiro[3.3]heptane-2-carbonyl)hexahydro-2H-pyrido[4,3-b][1,4]oxazin-3(4H)-one;

(4aR,8aS)-6-(6-(4-(Trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(4-Chloro-2-(trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(2,4-Difluorophenoxy)-2-azaspiro[3.3]heptane-2-carbonyl)hexahydro-2H-pyrido[4,3-b][1,4]oxazin-3(4H)-one;

(4aR,8aS)-6-(6-(2-Fluoro-4-(trifluoromethyl)benzyl)-2,6-diazaspiro[3.3]heptane-2-carbonyl)hexahydro-2H-pyrido[4,3-b][1,4]oxazin-3(4H)-one; and (4aR,8aS)-6-(6-((4,5-Bis(trifluoromethyl)pyridin-2-yl)oxy)-2-azaspiro[3.3]heptane-2-carbonyl)hexahydro-2H-pyrido[4,3-b][1,4]oxazin-3(4H)-one.

In one embodiment, the present invention provides a compound of formula (I) as described herein, or a pharmaceutically acceptable salt thereof, wherein said compound of formula (I) is not (4aR,8aS)-6-(6-(2-fluoro-6-methoxybenzyl)-2-azaspiro[3.3]heptane-2-carbonyl)hexahydro-2H-pyrido[4,3-b][1,4]oxazin-3(4H)-one.

In a particular embodiment, the present invention provides pharmaceutically acceptable salts of the compounds according to formula (I) as described herein, especially hydrochloride salts. In a further particular embodiment, the present invention provides compounds according to formula (I) as described herein.

In some embodiments, the compounds of formula (I) are isotopically-labeled by having one or more atoms therein replaced by an atom having a different atomic mass or mass number.

Such isotopically-labeled (i.e., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{33}S$, $^{18}F$, $^{36}Cl$, $^{123}I$, and $^{125}I$, respectively. Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Processes of Manufacturing

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. The substituents and indices used in the following description of the processes have the significance given herein, unless indicated to the contrary.

If one of the starting materials, intermediates or compounds of formula (I) contain one or more functional groups which are not stable or are reactive under the reaction conditions of one or more reaction steps, appropriate protective groups (as described e.g., in "Protective Groups in Organic Chemistry" by T. W. Greene and P. G. M. Wutts, 5th Ed., 2014, John Wiley & Sons, N.Y.) can be introduced before the critical step applying methods well known in the art. Such protective groups can be removed at a later stage of the synthesis using standard methods described in the literature.

If starting materials or intermediates contain stereogenic centers, compounds of formula (I) can be obtained as mixtures of diastereomers or enantiomers, which can be separated by methods well known in the art e.g., chiral HPLC, chiral SFC or chiral crystallization. Racemic compounds can e.g., be separated into their antipodes via diastereomeric salts by crystallization with optically pure acids or by separation of the antipodes by specific chromatographic methods using either a chiral adsorbent or a chiral eluent. It is equally possible to separate starting materials and intermediates containing stereogenic centers to afford diastereomerically/enantiomerically enriched starting materials and intermediates. Using such diastereomerically/enantiomerically enriched starting materials and intermediates in the synthesis of compounds of formula (I) will typically lead to the respective diastereomerically/enantiomerically enriched compounds of formula (I).

A person skilled in the art will acknowledge that in the synthesis of compounds of formula (I)—insofar not desired otherwise—an "orthogonal protection group strategy" will be applied, allowing the cleavage of several protective groups one at a time each without affecting other protective groups in the molecule. The principle of orthogonal protection is well known in the art and has also been described in literature (e.g. Barany and R B. Merrifield, J. Am. Chem. Soc. 1977, 99, 7363; H. Waldmann et al., *Angew. Chem. Int. Ed. Engl.* 1996, 35, 2056).

A person skilled in the art will acknowledge that the sequence of reactions may be varied depending on reactivity and nature of the intermediates.

In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations. 2nd Edition*. Richard C. Larock. John Wiley & Sons, New York, N.Y. 1999). It was found convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 hours to several days will usually suffice to yield the described intermediates and compounds. The reaction sequence is not limited to the one displayed in the schemes, however, depending on the starting materials and their respective reactivity, the sequence of reaction steps can be freely altered.

If starting materials or intermediates are not commercially available or their synthesis not described in literature, they can be prepared in analogy to existing procedures for close analogues or as outlined in the experimental section.

The following abbreviations are used in the present text: AcOH=acetic acid, ACN=acetonitrile, Bn=benzyl, Boc=tert-butyloxycarbonyl, CAS RN=chemical abstracts registration number, Cbz=benzyloxycarbonyl, $Cs_2CO_3$=cesium carbonate, CO=carbon monoxide, CuC=copper(I) chloride, CuCN=copper(I) cyanide, CuI=copper(I) iodide, DAST=(diethylamino)sulfur trifluoride, DBU=1,8-diazabicyclo[5,4,0]undec-7-ene, DCM=dichloromethane, DEAD=diethyl azodicarboxylate, DIAD=diisopropyl azodicarboxylate, DMAP=4-dimethylaminopyridine, DME=dimethoxyethane, DMEDA=N,N'-dimethylethylenediamine, DMF=N,N-dimethylformamide, DIPEA=N,N-diisopropylethylamine, dppf=1,1 bis(diphenyl phosphino)ferrocene, EDC.HCl=N-(3-dimethylaminopropyl)-N'-ethylcarbodiimide hydrochloride, EI=electron impact, ESI=electrospray ionization, EtOAc=ethyl acetate, EtOH=ethanol, h=hour(s), FA=formic acid, $H_2O$=water, $H_2SO_4$=sulfuric acid, HATU=1-[bis(dimethylamino)methylene]-1H-1,2,3-triazolo[4,5-b]pyridinium-3-oxide hexafluorophosphate, HBTU=O-benzotriazole-N,N,N',N'-tetramethyl-uronium-hexafluoro-phosphate, HCl=hydrogen chloride, HOBt=1-hydroxy-1H-benzotriazole; HPLC=high performance liquid chromatography, iPrMgCl=isopropylmagnesium chloride, 12=iodine, IPA=2-propanol, ISP=ion spray positive (mode), ISN=ion spray negative (mode), $K_2CO_3$=potassium carbonate, $KHCO_3$=potassium bicarbonate, KI=potassium iodide, KOH=potassium hydroxide, $K_3PO_4$=potassium phosphate tribasic, $LiAlH_4$ or LAH=lithium aluminium hydride, LiHMDS=lithium bis(trimethylsilyl)amide, LiOH=lithium hydroxide, $MgSO_4$=magnesium sulfate, min=minute(s), mL=milliliter, MPLC=medium pressure liquid chromatography, MS=mass spectrum, MTBE=Methyl tert-butyl ether, nBuLi=n-butyllithium, $NaBH_3CN$=sodium cyanoborohydride, NaH=sodium hydride, $NaHCO_3$=sodium hydrogen carbonate, NaNO2=sodium nitrite, $NaBH(OAc)_3$=sodium triacetoxyborohydride, NaOH=sodium hydroxide, $Na_2CO_3$=sodium carbonate, $Na_2SO_4$=sodium sulfate, $Na_2S_2O_3$=sodium thiosulfate, NBS=N-bromosuccinimide, nBuLi=n-butyllithium, $NEt_3$=triethylamine (TEA), $NH_4Cl$=ammonium chloride, NMP=N-methyl-2-pyrrolidone, OAc=Acetoxy, $T_3P$=propylphosphonic anhydride, PE=petroleum ether, PG=protective group, Pd—C=palladium on activated carbon, $PdCl_2(dppf)$-$CH_2Cl_2$=1,1'-bis(diphenylphosphino)ferrocene-palladium (II)dichloride dichloromethane complex, $Pd_2(dba)_3$=tris (dibenzylideneacetone)dipalladium(0), $Pd(OAc)_2$=palladium(II) acetate, $Pd(OH)_2$=palladium hydroxide, $Pd(PPh_3)_4$=tetrakis(triphenylphosphine)palladium(0), PTSA=p-toluenesulfonic acid, R=any group, RT=room temperature, SFC=Supercritical Fluid Chromatography, S-PHOS=2-dicyclohexylphosphino-2',6'-dimethoxybiphenyl, TBAI=tetra butyl ammonium iodine, TEA=triethylamine, TFA=trifluoroacetic acid, THF=tetrahydrofuran, TMEDA=N,N,N',N'-tetramethylethylenediamine, $ZnCl_2$=zinc chloride, Hal=halogen.

Compounds of formula I wherein A, L, X, $R^1$, $R^2$, $R^3$ and $R^4$ are as described herein can be synthesized in analogy to literature procedures and/or as depicted for example in Scheme 1a.

Scheme 1a

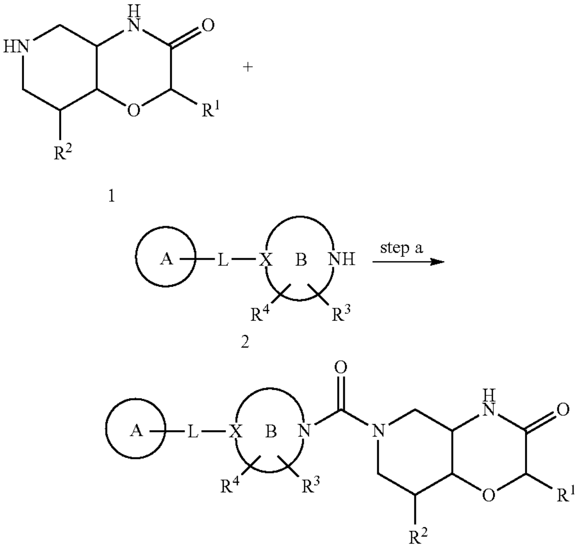

1

2

I

Accordingly, 4a,5,6,7,8,8a-hexahydro-4H-pyrido[4,3-b][1,4]oxazin-3-ones 1 are reacted with intermediates 2 in the presence of a urea forming reagent such as bis(trichloromethyl) carbonate using a suitable base and solvent such as, e.g. sodium bicarbonate in DCM, to give compounds of formula I (step a). Further urea forming reagents include but are not limited to phosgene, trichloromethyl chloroformate, (4-nitrophenyl)carbonate, 1,1'-carbonyldiimidazole or 1,1'-carbonyl-di-(1,2,4-triazole). Reactions of this type and the use of these reagents are widely described in literature (e.g. G. Sartori et al., *Green Chemistry* 2000, 2, 140). A person skilled in the art will acknowledge that the order of the addition of the reagents can be important in this type of reactions due to the reactivity and stability of the intermediary formed carbamoyl chlorides, as well as for avoiding formation of undesired symmetrical urea by-products.

Compounds of formula (I) wherein $R^1$, $R^2$, $R^3$ and $R^4$ are as defined herein and wherein $R^7$ is Cl or Br, can be further modified according to the general procedure outlined in Scheme 1b.

Scheme 1b

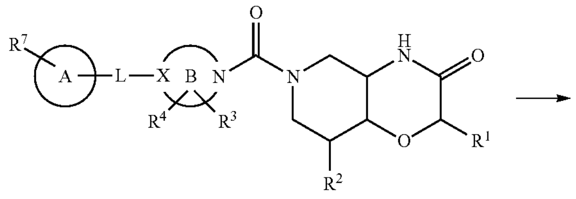

I $R^7$ = Cl, Br

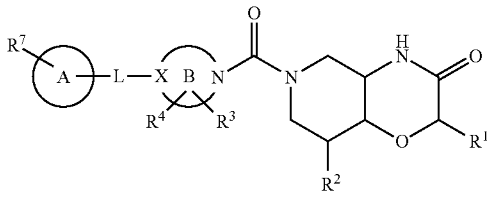

I $R^7$ = alkyl, heterocyclyl, cycloalkyl, heteroaryl

Treatment of compounds of formula I, containing a bromo- or chloroaryl as A under typical conditions of a Suzuki-Miyaura reaction, a Buchwald-Hartwig reaction, or other organometallic C—C or C—N cross couplings known in the art lead to substituted compounds of formula I where the bromine has been replaced with an alkyl, heterocyclyl, cycloalkyl or heteroaryl moiety. This typically requires a suitable reaction partner such as a boronic acid, a potassium trifluoroborate, a pinacol boronate, an amine or an organozinc compound, a suitable catalyst for example tetrakis(triphenylphosphine)palladium (0), PdCl2(DPPF)-CH2Cl2, Pd2(dba)3+Xantphos, cataCXium A Pd G2, RuPhos Pd G2, an organic or inorganic base such as sodium carbonate, TEA, TMEDA or cesium carbonate in a solvent system such as Dioxane/Water, DMF or toluene/water. Reactions are typically carried out at elevated temperatures between 100 and 120° C. under inert atmosphere (argon).

Intermediates 1 may be synthesized as depicted for example in Scheme 2 and/or in analogy to methods described in literature.

Scheme 2

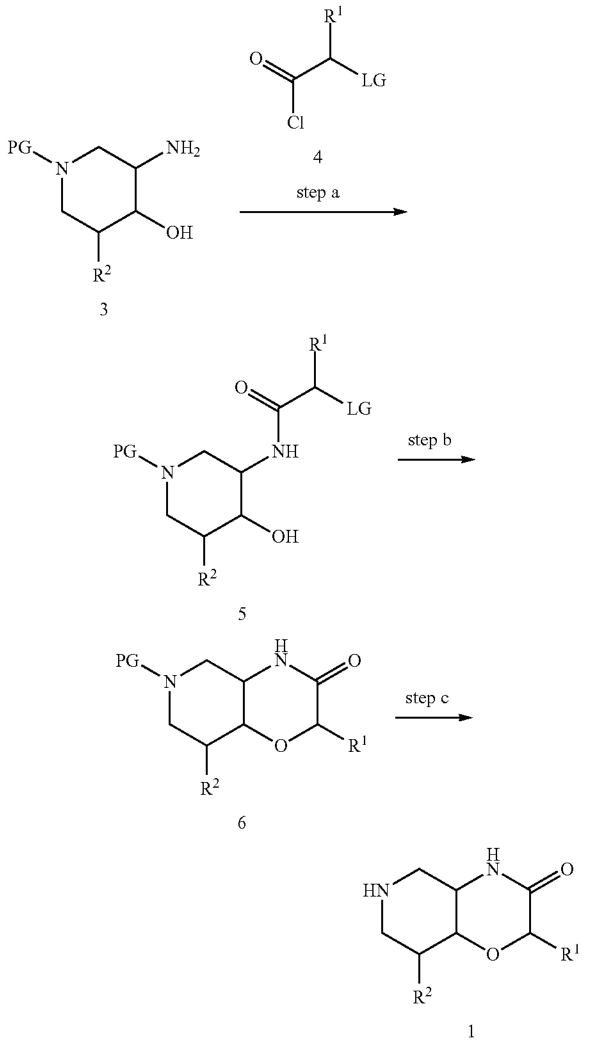

Thus, 3-aminopiperidin-4-ol derivatives 3 in which "PG" signifies a suitable protective group such as a Cbz or Boc protective group, and $R^2$ is as defined herein can be acylated for example with acyl chlorides 4 in which $R^1$ is as defined herein and "LG" signifies a suitable leaving group (e.g., Cl or Br), using a suitable base such as sodium or potassium carbonate, sodium hydroxide or sodium acetate in an appropriate solvent such as THF, water, acetone or mixtures thereof, to provide intermediates 5 (step a). Intermediates 4 are either commercially available or can be prepared according to literature methods in achiral ($R^1$=H) racemic ($R^1$ not H) or enantiomerically pure form ($R^1$ not H).

Intermediates 5 can be cyclized to intermediates 6 using methods well known in the art, for example by treatment of 5 with sodium hydride in THF or potassium tert-butoxide in IPA and water (step b). Reactions of that type are described in literature (e.g. Z. Rafinski et al., *J.* Org. Chem. 2015, 80, 7468; S. Dugar et al., *Synthesis* 2015, 47(5), 712; WO2005/066187).

Removal of the protective group in intermediates 6, applying methods known in the art (e.g., a Boc group using TFA in DCM at temperatures between 0° C. and room temperature, a Cbz group using hydrogen in the presence of a suitable catalyst such as Pd or $Pd(OH)_2$ on charcoal in a suitable solvent such as MeOH, EtOH, EtOAc or mixtures thereof and as described for example in "Protective Groups in Organic Chemistry" by T. W. Greene and P. G. M. Wuts, 4th Ed., 2006, Wiley N.Y.), furnishes intermediates 1 (step c).

Intermediates 1 can be obtained as mixtures of diastereomers and enantiomers, respectively, or as single stereoisomers depending on whether racemic mixtures or enantiomerically pure forms of cis- or trans-3-aminopiperidin-4-ol derivatives 3 and acid chlorides 4 (when $R^1$ is not H) are employed in their syntheses. In case racemization occurs at a stereocentre bearing $R^1$ during the conversion of 3 to 5 (step a) and/or of 5 to 6 (step b), the resulting diastereoisomers may be separated by chromatography (e.g. HPLC, chiral HPLC) or other methods known in the art. Intermediates 3 are commercially available and their synthesis has also been described in literature (e.g. WO2005/066187; WO2011/0059118; WO2016/185279). Optically pure cis-configured intermediates 1B and 1C can be obtained for example according to Scheme 3 by chiral separation of commercially available rac-(4aR,8aS)-4a,5,6,7,8,8a-hexahydro-4H-pyrido[4,3-b][1,4]oxazin-3-one (1A) (optionally in form of a salt such as, e.g. a hydrochloride salt) using methods known in the art, e.g. by diastereomeric salt crystallization or by chiral chromatography (step a).

Scheme 3

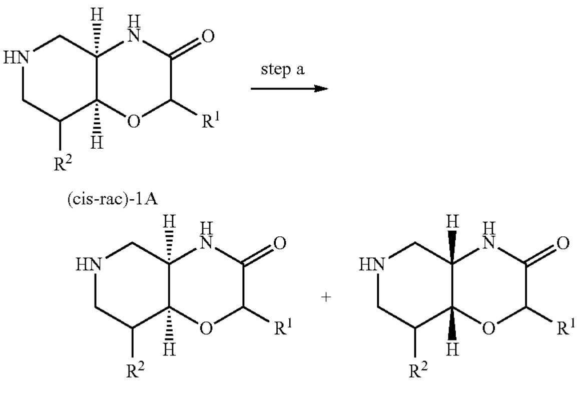

(cis-rac)-1A

1B

1C

In some embodiments, intermediates 2 are intermediates of type A. Intermediates of type A in which A, B, $R^3$ and $R^4$ are as described herein and $R^5$ is hydrogen, $C_{1-6}$-alkyl or halo-$C_{1-6}$-alkyl, can be prepared by methods well known by a person skilled in the art and as exemplified by the general synthetic procedure outlined in Scheme 4.

Scheme 4

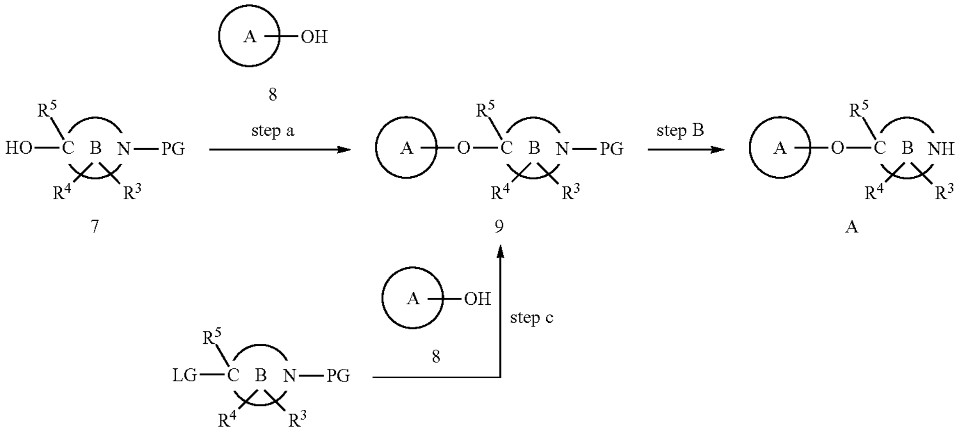

8

7

9

A

8

10

PG = Protecting group LG = Leaving group

Spirocyclic compounds 7 in which PG signifies a suitable protective group such as a Boc, Cbz or Bn protecting group (either commercially available or prepared as described in literature, e.g. in *Eur. J. Org. Chem.* 2017, 36, 5316; *Topics in Het. Chem.* 2014, 35, 189; *World Journal of Pharmacy and Pharmaceutical Sciences* 2014, 3(12), 536; *Chem. Rev.* 2014, 114(16), 8257-8322) can be subjected to a Mitsunobu reaction with alcohol derivatives 8 using an appropriate phosphine such as triphenylphosphine and a dialkyl azodicarboxylate such as DEAD or DIAD in a suitable solvent such as THF to give intermediates 9 (step a). Mitsunobu reactions of that type are broadly described in literature (e.g. *Org. Chem. Front.* 2015, 2, 739; *Chem. Rev.* 2009, 109 (6), 2551).

Removal of the protective group from intermediates 9, applying methods known in the art, e.g., a Boc group using TFA in DCM or 4M HCl in dioxane at temperatures between 0° C. and room temperature, a Bn or Cbz group using hydrogen in the presence of a suitable catalyst such as Pd or $Pd(OH)_2$ on charcoal in a suitable solvent such as MeOH, EtOH, EtOAc or mixtures thereof and as described for example in "Protective Groups in Organic Chemistry" by T. W. Greene and P. G. M. Wuts, 4th Ed., 2006, Wiley N.Y.), furnishes intermediates A (step b).

Intermediates 9 may alternatively be prepared by alkylation of compounds 8 with spirocyclic derivatives 10 (either commercially available or prepared by methods known in the art) in which LG signifies a suitable leaving group such as chlorine, bromine, iodine, $OSO_2$alkyl (e.g. mesylate (methanesulfonate), $OSO_2$fluoroalkyl (e.g. triflate (trifluoromethanesulfonate) or $OSO_2$aryl (e.g. tosylate (p-toluenesulfonate) using a suitable base and an appropriate solvent (e.g. sodium hydride in DMF) at temperatures between 0° C. and the boiling temperature of the solvent (step c).

In some embodiments, intermediates 2 are intermediates of type B. Intermediates of type B in which A, B, $R^3$ and $R^4$ are as described herein can be prepared by methods well known by a person skilled in the art and as exemplified by the general synthetic procedure outlined in Scheme 5.

Compounds of type 11 either commercially available or prepared by methods known in the art and in which PG signifies a suitable protecting group such as, e.g. a Boc, Cbz or Bn protecting group, can be subjected to a reductive amination reaction with aldehydes of type 12 using a suitable reducing agent and solvent such as $NaBH_3CN$ in MeOH, AcOH or mixtures thereof, or $NaBH(OAc)_3$ in DCE, DCM or THF to give intermediates 13 (step a).

Removal of the protective group from intermediates 13, applying methods known in the art and for example described under Scheme 4, step b, furnishes intermediates B (step b).

Intermediates 13 may alternatively prepared by alkylation of compounds 11 with compounds 15 (either commercially available or prepared by methods known in the art) in which LG is a suitable leaving group such as chlorine, bromine, iodine, $OSO_2$alkyl (e.g. methanesulfonate), $OSO_2$fluoroalkyl (e.g. trifluoromethanesulfonate) or $OSO_2$aryl (e.g. p-toluenesulfonate using a suitable base in an appropriate solvent (e.g. $NEt_3$ or DIPEA in ACN) at temperatures between 0° C. and the boiling temperature of the solvent (step c). Reactions of that type are known in the art and broadly described in literature (e.g. ARKIVOC 2005 (vi) 287-292).

In some embodiments, intermediates 2 are intermediates of type C, D or E. Intermediates of type C, D or E in which A, B, $R^3$ and $R^4$ are as described herein, can be prepared by methods well known by a person skilled in the art and as exemplified by the general synthetic procedure outlined in Scheme 6.

Scheme 5

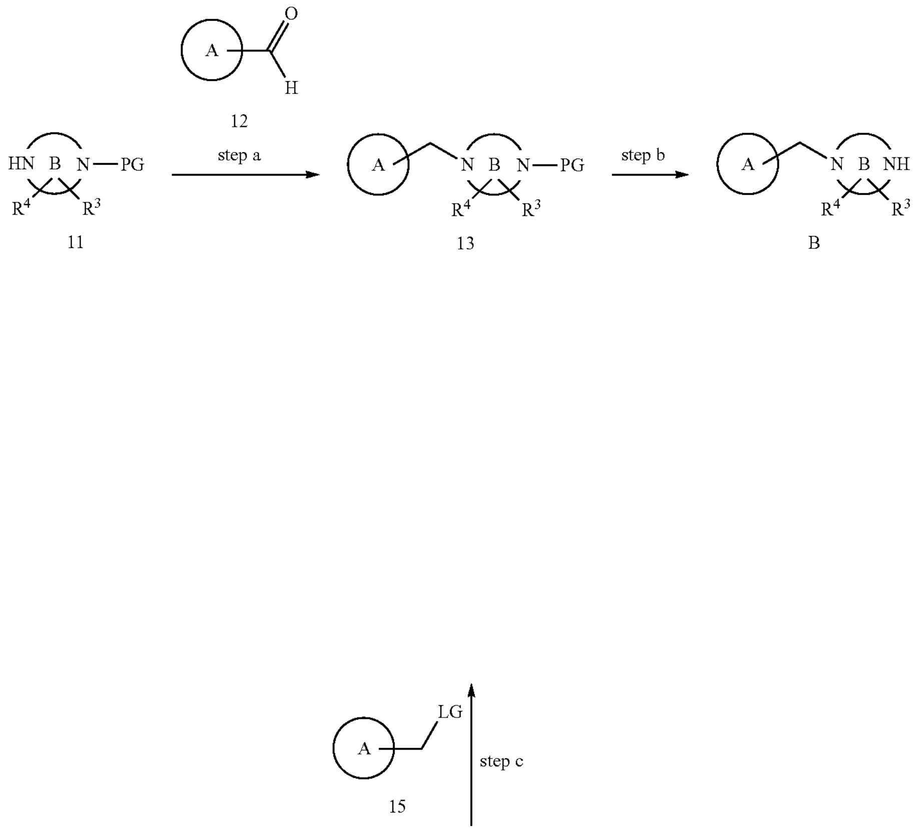

PG = Protecting group LG = Leaving group

Scheme 6

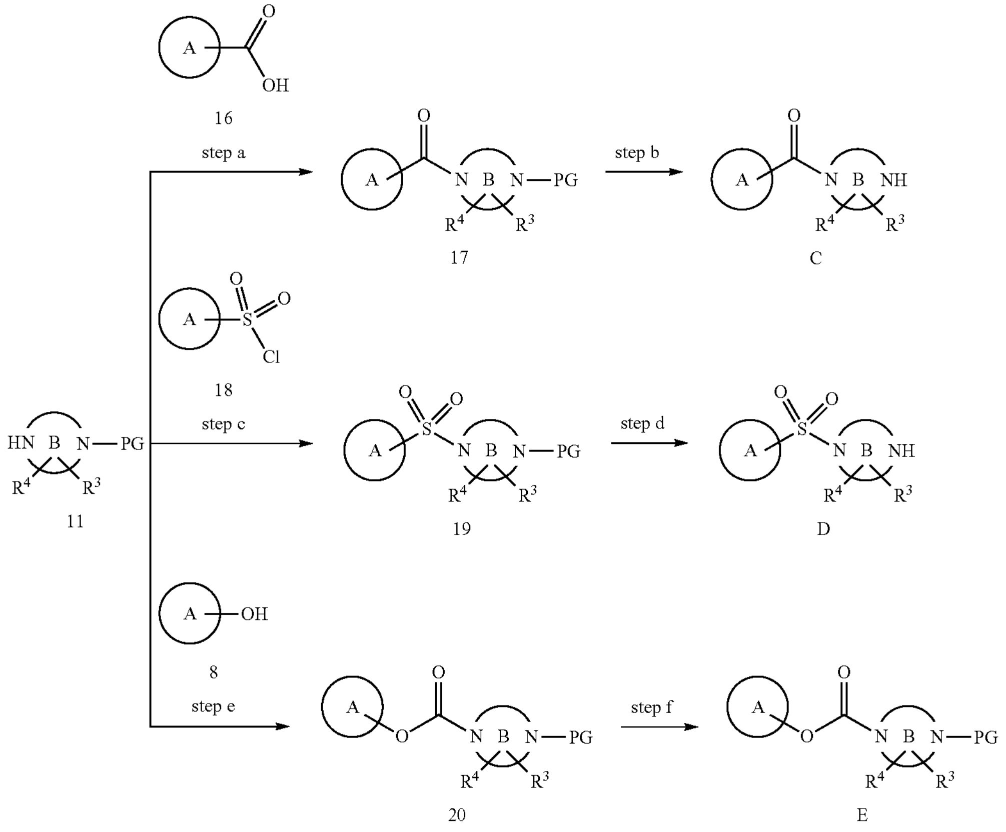

PG = Protecting group

Compounds of type 11 either commercially available or prepared by methods known in the art and in which PG signifies a suitable protecting group such as, e.g. a Boc, Cbz or Bn protecting group, can be acylated with carboxylic acids 16 to give intermediates 17 (step a). Amide couplings of this type are widely described in the literature and can be accomplished by the usage of coupling reagents such as CDI, DCC, HATU, HBTU, HOBT, TBTU, T3P or Mukaiyama reagent (e.g. *Angew. Chem., Int. Ed. Engl.* 1979, 18, 707) in a suitable solvent such as DMF, DMA, DCM or dioxane, optionally in the presence of a base, e.g. $NEt_3$, DIPEA (Huenig's base) or DMAP.

Alternatively, carboxylic acids 16 can be converted into their acid chlorides by treatment with, e.g. thionyl chloride or oxalyl chloride, neat or optionally in a solvent such as DCM. Reaction of the acid chloride with intermediates 11 in an appropriate solvent such as DCM or DMF and a base, e.g. NEt3, Huenig's base, pyridine, DMAP or lithium bis(trimethylsilyl)amide at temperatures ranging from 0° C. to the reflux temperature of the solvent or solvent mixture, yields intermediates 17 (step a).

Removal of the protective group from intermediates 17, applying methods known in the art and for example described under Scheme 4, step b, furnishes intermediates C (step b). Compounds of type 11 can be sulphonylated for example by treatment with sulfonyl chlorides 18 (either commercially available of prepared my methods known in the art or described in literature) using a suitable base and solvent such as NEt3 or pyridine in DCM to provide intermediates 19 (step c).

Removal of the protective group from intermediates 19, applying methods known in the art and for example described under Scheme 4, step b, furnishes intermediates D (step d).

Compounds of type 11 can be converted into the corresponding carbamates 20 for example by first reacting 11 with an activating and carbonylating reagent such as bis (trichloromethyl) carbonate using a suitable base and solvent such as, e.g. sodium bicarbonate in DCM, followed by reaction of the intermediately formed carbamoylchloride with alcohols of type 8 in the presence of a suitable base such as pyridine or NEt3, optionally at elevated temperatures (step e). Further activating agents include but are not limited to phosgene, trichloromethyl chloroformate, (4-nitrophenyl)carbonate or 1,1'-carbonyldiimidazole. The synthesis of carbamates is well known in the art and is broadly described in literature (e.g. J. Med. Chem. 2015, 58(7), 2895).

Removal of the protective group from intermediates 20, applying methods known in the art and for example described under Scheme 4, step b, furnishes intermediates E (step f).

In some embodiments, intermediates 2 are intermediates of type F, G, and H. Intermediates of type F, G, and H in which A, B, $R^3$ and $R^4$ are as described herein and $R^5$ is hydrogen; $C_{1-6}$-alkyl, halo-$C_{1-6}$-alkyl, can be prepared by methods known in the art and as exemplified by the general synthetic procedure outlined in Scheme 7.

Scheme 7

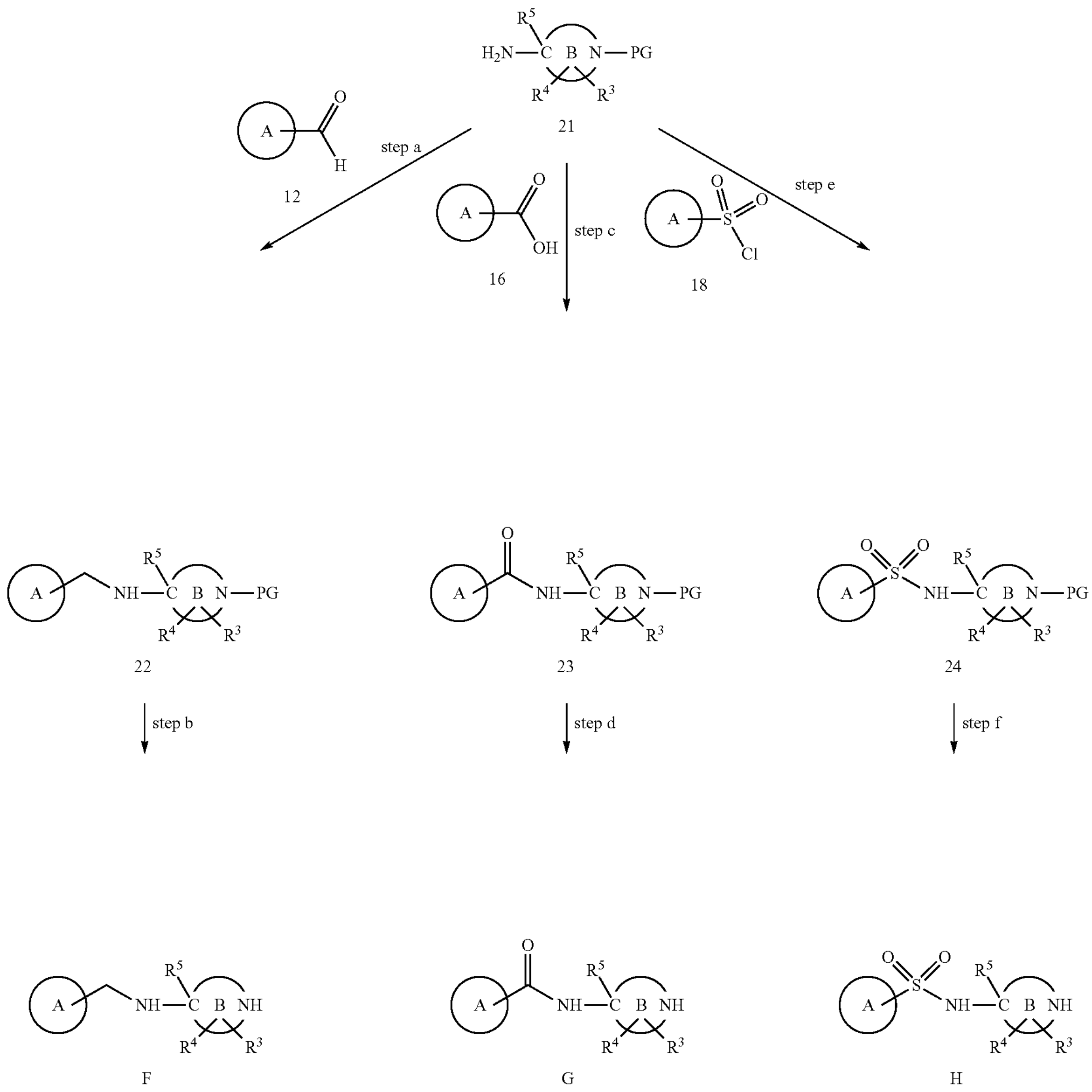

12, 16, 18, 21, 22, 23, 24, F, G, H

PG = Protecting group LG = Leaving group

Intermediates 21, either commercially available or prepared by literature methods, can be converted to intermediates 22 for example by reductive amination using aldehydes 12 and applying the conditions described under Scheme 5, (step a).

Removal of the protective group from intermediates 22, applying methods known in the art and for example described under Scheme 4, step b, furnishes intermediates F (step b).

Intermediates 21 can be reacted with carboxylic acids 16 using for example the conditions described under Scheme 6, step a to provide intermediates 23 (step c).

Removal of the protective group from intermediates 23, applying methods known in the art and for example described under Scheme 4, step b, furnishes intermediates G (step d).

Intermediates 21 can be sulphonylated for example by treatment with sulfonyl chlorides 18 (either commercially available of prepared my methods known in the art or described in literature) using for example the reaction conditions described under Scheme 6 step c, to yield intermediates 24 (step e).

Removal of the protective group from intermediates 24, applying methods known in the art and for example described under Scheme 4, step b, furnishes intermediates H (step f).

In some embodiments, intermediates 2 are intermediates of type J, K, and L. Intermediates of type J, K, and L in which A, B, $R^3$ and $R^4$ are as described herein, $R^5$ is hydrogen, $C_{1-6}$-alkyl or halo-$C_{1-6}$-alkyl, and $R^{19}$ is hydrogen or $C_{1-6}$-alkyl can be prepared by methods known in the art and as exemplified by the general synthetic procedure outlined in Scheme 8.

Scheme 8

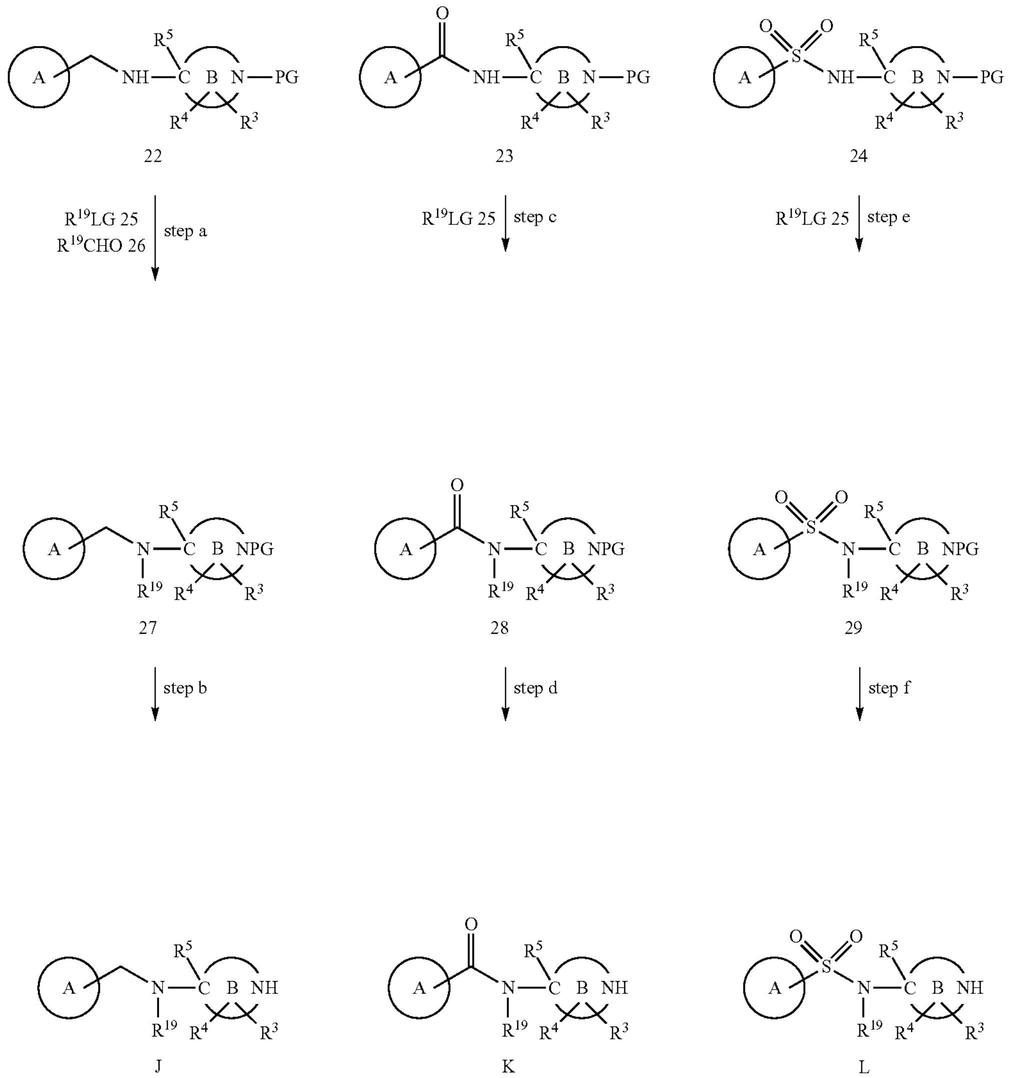

PG = Protecting group LG = Leaving group

Intermediates 22 can be converted to intermediates 27 for example by reductive amination using aldehydes 26 and applying the conditions described under Scheme 5, step a (step a).

Alternatively, intermediates 22 can be alkylated with compounds 25 of type $R^{20}LG$ in which LG is a suitable leaving group such as chlorine, bromine, iodine, methanesulfonate, trifluoromethanesulfonate or p-toluenesulfonate using for example the conditions described under Scheme 4, step c, to provide intermediates 27 (step a).

Removal of the protective group from intermediates 27, applying methods known in the art and for example described under Scheme 4, step b, furnishes intermediates J (step b).

Intermediates 22 can be alkylated with compounds 25 of type $R^{20}LG$ in which LG is a suitable leaving group such as chlorine, bromine, iodine, methanesulfonate, trifluoromethanesulfonate or p-toluenesulfonate using for example the conditions described under Scheme 4, step c, to provide intermediates 28 (step c).

Removal of the protective group from intermediates 28, applying methods known in the art and for example described under Scheme 4, step b, furnishes intermediates K (step d).

Intermediates 24 can be alkylated with compounds 25 of type $R^{20}LG$ in which LG is a suitable leaving group such as chlorine, bromine, iodine, methanesulfonate, trifluoromethanesulfonate or p-toluenesulfonate using for example the conditions described under Scheme 4, step c, to provide intermediates 29 (step e).

Removal of the protective group from intermediates 29, applying methods known in the art and for example described under Scheme 4, step b, furnishes intermediates L (step d).

In some embodiments, intermediates 2 are intermediates of type M. Intermediates of type M in which A, B, $R^3$ and $R^4$ are as described herein and $R^5$ is hydrogen; $C_{1-6}$-alkyl or halo-$C_{1-6}$-alkyl can be prepared by methods well known in the art and as exemplified by the general synthetic procedures outlined in Scheme 9.

Scheme 9

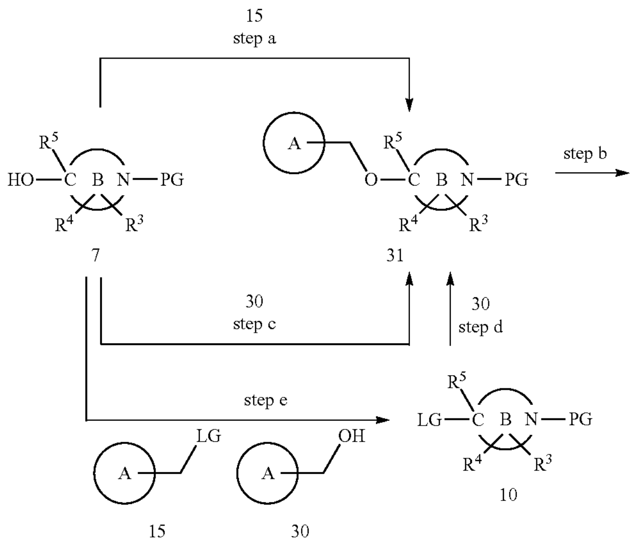

PG = Protecting group LG = Leaving group

Spirocyclic compounds 7 in which PG is a suitable protective group can be alkylated with compounds 15 in which LG is a suitable leaving group such as chlorine, bromine, iodine, methanesulfonate, trifluoromethanesulfonate or p-toluenesulfonate (prepared by literature methods for example from compounds 30) using for example the conditions described under Scheme 4 step c, to provide intermediates 31 (step a).

Removal of the protective group from intermediates 31, applying methods known in the art and for example described under Scheme 4, step b, furnishes intermediates M (step b).

Alternatively, intermediates 31 may be prepared from intermediates 7 and compounds 30 via Mitsunobu reaction, applying for example the conditions described under Scheme 4, step a (step c).

Furthermore, intermediates 31 may be also prepared by alkylation of compounds 7 with compounds 10 and using for example the conditions described under Scheme 4, step (step d).

Intermediates 10 in turn may be synthesized from compounds 7 converting the hydroxy function into a suitable leaving group such as an alkyl halide (e.g. bromine by using of $PBr_3$, chlorine through the use of $SOCl_2$) or alkyl- or aryl-sulfonate such as methanesulfonate (using mesyl chloride) or p-toluenesulfonate (using tosyl chloride). Reactions of that type are broadly described in literature and are well known in the art.

In some embodiments, intermediates 2 are intermediates of type N. Intermediates of type N in which A, B, $R^3$, $R^4$ and $R^5$ are as described herein, can be prepared by methods well known in the art and as exemplified by the general synthetic procedures outlined in Scheme 10.

Scheme 10

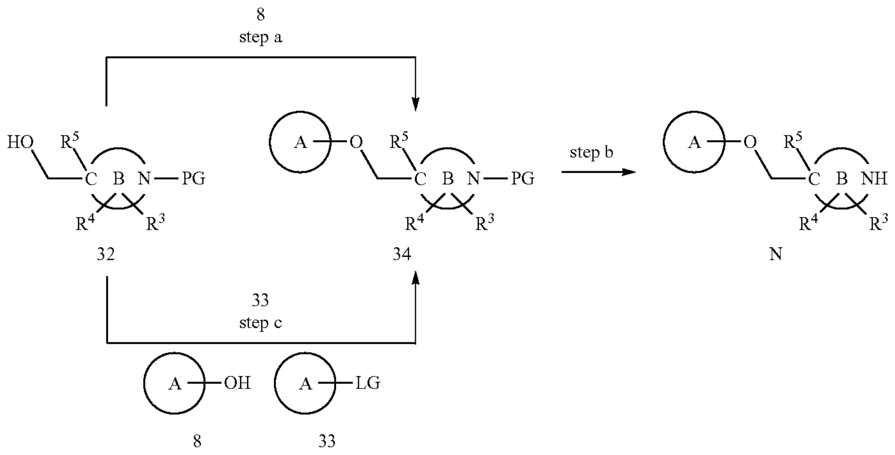

PG = Protecting group LG = Leaving group

Compounds of type 32, either commercially available or prepared by methods known in the art, can be subjected to a Mitsunobu reaction with compounds 8, applying for example the conditions described under Scheme 4, step a, to provide intermediates 34 (step a).

Removal of the protective group from intermediates 34, applying methods known in the art and for example described under Scheme 4, step b, furnishes intermediates N (step b).

Alternatively, intermediates 34 may be prepared by alkylation of compounds 32 with compounds 33 in which LG is a suitable leaving group applying the conditions outlined for example under Scheme 4, step c (step c).

Intermediates N may alternatively be prepared as exemplified by the general synthetic procedures outlined in Scheme 11.

Scheme 12

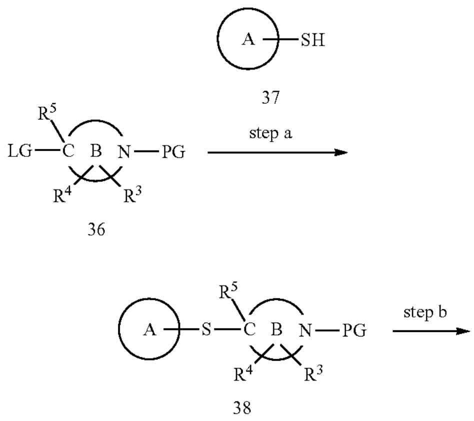

Scheme 11

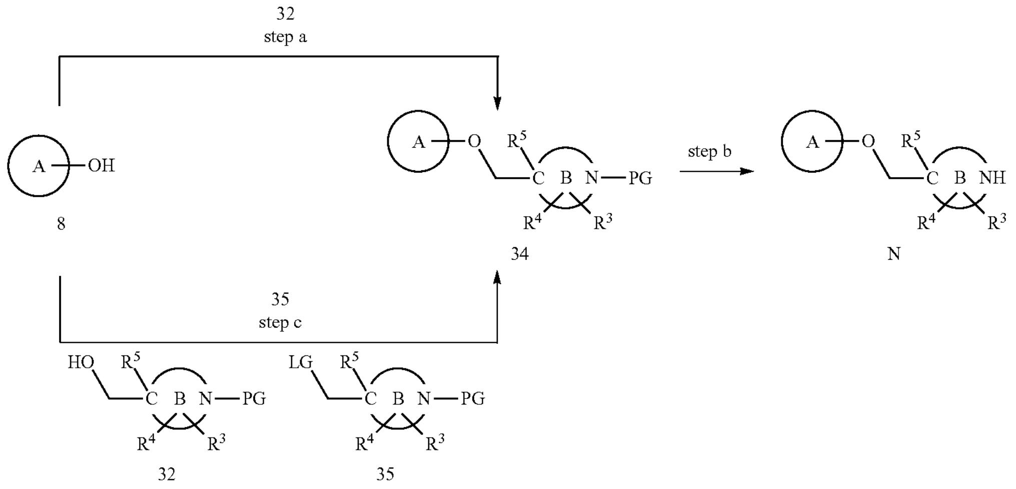

PG = Protecting group LG = Leaving group

Compounds 8 can be subjected to a Mitsunobu reaction with compounds 32 using the conditions described under Scheme 4, step a, to provide intermediates 34 (step a).

Removal of the protective group from intermediates 34, applying methods known in the art and for example described under Scheme 4, step b, furnishes intermediates N (step b).

Alternatively, compounds 8 may be alkylated with compounds 35 in which LG signifies a suitable leaving group such as chlorine, bromine, iodine, methanesulfonate, trifluoromethanesulfonate or p-toluenesulfonate, using for example the conditions described under Scheme 4, step c, to provide intermediates 34 (step c).

In some embodiments, intermediates 2 are intermediates of type P. Intermediates of type P in which A, B, $R^3$ and $R^4$ are as described herein and $R^5$ is hydrogen, Cia-alkyl or halo-$C_{1-6}$-alkyl, can be prepared by methods well known by a person skilled in the art and as exemplified by the general synthetic procedure outlined in Scheme 12.

-continued

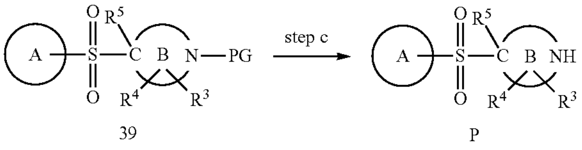

PG = Protecting group LG = Leaving group

Spirocyclic compounds 38 in which PG signifies a suitable protective group such as a Boc, Cbz or Bn protecting group (either commercially available or prepared as described in literature, e.g. in *Eur. J. Org. Chem.* 2017, 36, 5316; *Topics in Het. Chem.* 2014, 35, 189; *World Journal of Pharmacy and Pharmaceutical Sciences* 2014, 3(12), 536; *Chem. Rev.* 2014, 114(16), 8257-8322) can be prepared by alkylation of thiol 37 with spirocyclic derivatives 36 (either commercially available or prepared by methods known in the art) in which LG signifies a suitable leaving group such as chlorine, bromine, iodine, $OSO_2$alkyl (e.g. mesylate (methanesulfonate), $OSO_2$fluoroalkyl (e.g. triflate (trifluoromethanesulfonate) or $OSO_2$aryl (e.g. tosylate (p-toluenesulfonate) using a suitable base and an appropriate solvent (e.g. $K_2CO_3$ in DMF) at temperatures between 0° C. and the boiling temperature of the solvent (step a).

Intermediates 38 can be oxidized to intermediates 39, using a suitable oxidizing reagent, such as mCPBA, in an appropriate solvent (e.g. in DCM) at temperatures between 0° C. and the boiling temperature of the solvent (step b).

Removal of the protective group from intermediates 39, applying methods known in the art, e.g., a Boc group using TFA in DCM or 4M HCl in dioxane at temperatures between 0° C. and room temperature, a Bn or Cbz group using hydrogen in the presence of a suitable catalyst such as Pd or $Pd(OH)_2$ on charcoal in a suitable solvent such as MeOH, EtOH, EtOAc or mixtures thereof and as described for example in "Protective Groups in Organic Chemistry" by T. W. Greene and P. G. M. Wuts, 4th Ed., 2006, Wiley N.Y.), furnishes intermediates P (step c).

In some embodiments, intermediates 2 are intermediates of type Q. Intermediates of type Q in which A, B, $R^3$ and $R^4$ are as described herein and $R^5$ is hydrogen, $C_{1-6}$-alkyl or halo-$C_{1-6}$-alkyl, can be prepared by methods well known by a person skilled in the art and as exemplified by the general synthetic procedure outlined in Scheme 13.

Scheme 13

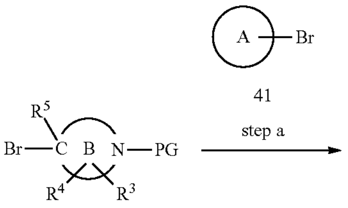

41

40

-continued

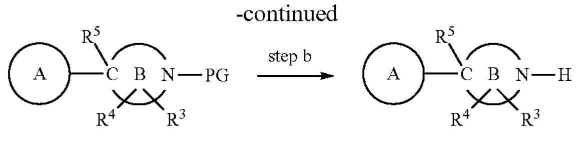

42

Q

PG = Protecting group

Alternatively, compounds 40, functionalized with a bromide, can be subjected to a cross-electrophile coupling with aryl- or heteroarylbromides 41 under irradiation with a 420 nm blue light lamp using an appropriate photo catalyst such as $[Ir\{dF(CF_3)ppy\}2(dtbpy)]PF_6$ ([4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate), a Nickel catalyst like $NiCl_2$ glyme (dichloro (dimethoxyethane)nickel), 4,4'-di-tert-butyl-2,2'-dipyridyl and tris(trimethylsilyl)silane, in the presence of a suitable base such as anhydrous sodium carbonate in a solvent like DME. Reactions of this type are described in literature, e.g. *J. Am. Chem. Soc.* 2016, 138, 8084. (step a).

Removal of the protective group from intermediates 42 applying methods well known in the art and as described for example under Scheme 12, step c, furnishes intermediates Q (step b).

In some embodiments, intermediates 2 are intermediates of type R and S. Intermediates of type R and S in which A, B, $R^3$ and $R^4$ are as described herein and $R^5$ is hydrogen, can be prepared by methods well known by a person skilled in the art and as exemplified by the general synthetic procedure outlined in Scheme 14.

Scheme 14

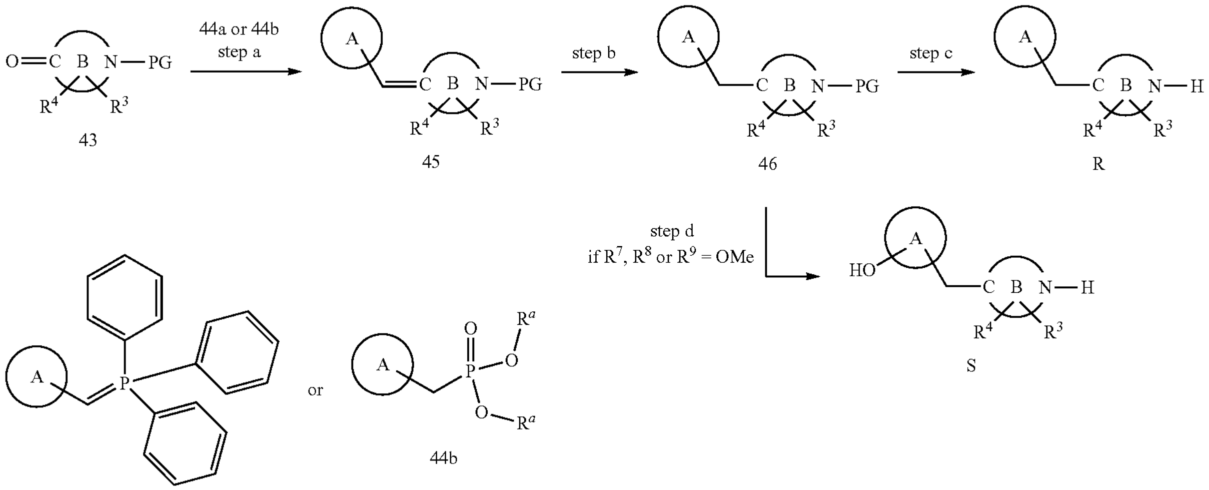

43 45 46 R S 44a 44b

PG = Protecting group

Ketones 43, either commercially available or prepared by methods known in the art, can be subjected for example to a Wittig reaction with alkylidene triphenylphosphoranes of type 44a in a suitable solvent such as, e.g. THF, Methyl-THF or DMSO to give intermediates 45 (step a). Phosphoranes 44a can be formed by treating the corresponding phosphonium salts with a suitable base such as BuLi, NaH, or KOtBu in a suitable solvent such as THF, dioxane or Methyl-THF and may be isolated or used in situ. Phosphonium salts in turn are readily available from an aryl/heteroaryl % heterocyclic-substituted alkylhalide (with halide being Cl, Br and iodo) and triphenylphosphine in a suitable solvent such as toluene. Heating may be applied to accelerate the reaction or drive the reaction to completion (e.g. H. J. Cristau, F. Plénat in PATAI'S Chemistry of Functional Groups, Editor(s): Frank R Hartley, 7 Aug. 2006, Series Editor(s): Prof. Saul Patai).

Alternatively, intermediates 45 can be obtained using a Homer-Wadsworth-Emmons (HWE) reaction using ketones 43 and phosphonates 44b, wherein Ra is alkyl, for example methyl or ethyl. Phosphonates 44b are in situ α-metalated using a suitable base and solvent such as NaH, nBuLi or KOtBu in THF (step a). Phosphonates 44b are readily prepared using for example the Arbuzov reaction by alkylation of an aryl/heteroaryl/heterocyclic halide (with halide being Cl, Br and iodo) with commercially available trialkyl phosphite (e.g. *Chem. Rev.* 1984, 84, 577).

Olefination reactions of both types are broadly described in literature (e.g. *Current Org. Chem.* 2015, 19(9), page 744; *Chem. Rev.* 1989, 89(4), 863; *Org. React.* 1977, 25, 73; *Liebigs Ann./Recueil* 1997, 1283; *Acc. Chem. Res.* 1983, 16, 411).

Reduction of the double bond in intermediates 45 using, e.g. hydrogen in the presence of a suitable catalyst such as palladium on charcoal in an appropriate solvent or solvent mixture such as EtOAc, MeOH or AcOH yields compounds 46 (step b).

Removal of the protective group from intermediates 45 applying methods known in the art (e.g., a Boc group using TFA in DCM or 4M HCl in dioxane at temperatures between 0° C. and room temperature, a Cbz group using hydrogen in the presence of a suitable catalyst such as Pd or $Pd(OH)_2$ on charcoal in a suitable solvent such as MeOH, EtOH, EtOAc or mixtures thereof and as described for example in "Protective Groups in Organic Chemistry" by T. W. Greene and P. G. M. Wuts, 4th Ed., 2006, Wiley N.Y.), furnishes intermediates R (step c).

If methoxy is among the substituents of A ($R^7$, $R^8$ or $R^9$), demethylation can lead to hydroxy-substituted intermediates S. This requires a reagent such as BBr3 in a suitable solvent such as DCM, at temperatures between 0° C. and the boiling temperature of the solvent. A Boc protecting group will also be cleaved under the reaction conditions, directly leading to intermediates S (step d).

In some embodiments, intermediates 2 are intermediates of type T. Intermediates of type T in which A, B, $R^3$ and $R^4$ are as described herein and X is nitrogen, can be prepared by methods by methods well known by a person skilled in the art and as exemplified by the general synthetic procedure outlined in Scheme 15.

Scheme 15

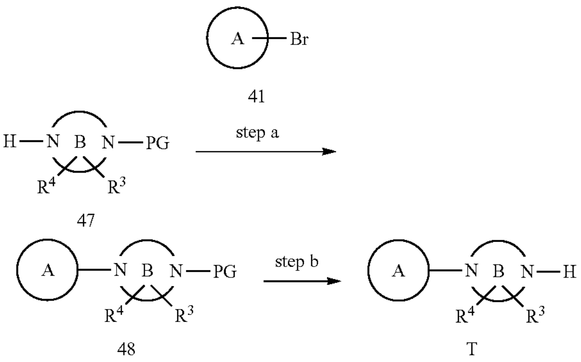

PG = Protecting group

Treatment of amines 47, with a bromo-aryl or bromo-heteroaryl 41 under typical conditions of a Buchwald-Hartwig reaction, or other organometallic C—N cross couplings known in the art, leads to intermediates 48. This typically requires a suitable catalyst system for example, $PdCl_2(DPPF)$-$CH_2Cl_2$, $Pd_2(dba)_3$+Xantphos, cataCXium A Pd G2, RuPhos Pd G2, an organic or inorganic base such as cesium carbonate or sodium tert-butoxide in a solvent such as Dioxane or toluene. Reactions are typically carried out at elevated temperatures between 70 and 120° C. under inert atmosphere (step a).

Removal of the protective group from intermediates 48 applying methods well known in the art and as described for example under Scheme 12, step c, furnishes intermediates T (step b).

In one aspect, the present invention provides a process of manufacturing the urea compounds of formula (I) described herein, and pharmaceutically acceptable salts thereof, comprising:

(c) reacting a first amine of formula 1, wherein $R^1$ and $R^2$ are as described herein, preferably wherein $R^1$ and $R^2$ are hydrogen,

1

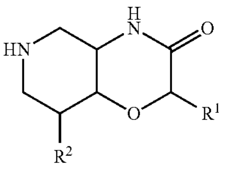

with a second amine 2, wherein A, B, L, X, $R^3$ and $R^4$ are as described herein

2

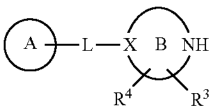

in the presence of a base and a urea forming reagent, to form said compound of formula (I); and optionally (d) transforming said compound of formula (I) to a pharmaceutically acceptable salts thereof.

In one embodiment, there is provided a process according to the invention, wherein said base is sodium bicarbonate.

In one embodiment, there is provided a process according to the invention, wherein said urea forming reagent is selected from bis(trichloromethyl) carbonate, phosgene, trichloromethyl chloroformate, (4-nitrophenyl)carbonate and 1,1'-carbonyldiimidazole, preferably wherein said urea forming reagent is bis(trichloromethyl) carbonate.

In one aspect, the present invention provides a compound of formula (I) as described herein, when manufactured according to any one of the processes described herein.

MAGL Inhibitory Activity

Compounds of the present invention are MAGL inhibitors. Thus, in one aspect, the present invention provides the use of compounds of formula (I) as described herein for inhibiting MAGL in a mammal.

In a further aspect, the present invention provides compounds of formula (I) as described herein for use in a method of inhibiting MAGL in a mammal.

In a further aspect, the present invention provides the use of compounds of formula (I) as described herein for the preparation of a medicament for inhibiting MAGL in a mammal.

In a further aspect, the present invention provides a method for inhibiting MAGL in a mammal, which method comprises administering an effective amount of a compound of formula (I) as described herein to the mammal.

Compounds were profiled for MAGL inhibitory activity by measuring the enzymatic activity of MAGL by following the hydrolysis of 4-nitrophenylacetate resulting in 4-nitrophenol, which absorbs at 405-412 nm (G. G. Muccioli, G. Labar, D. M. Lambert, *Chem. Bio. Chem.* 2008, 9, 2704-2710). This assay is hereinafter abbreviated "4-NPA assay".

The 4-NPA assay was carried out in 384 well assay plates (black with clear bottom, non-binding surface treated, Corning Ref. 3655) in a total volume of 40 μL. Compound dilutions were made in 100% DMSO (VWR Chemicals 23500.297) in a polypropylene plate in 3-fold dilution steps to give a final concentration range in the assay from 25 μM to 1.7 nM. 1 μL compound dilutions (100% DMSO) were added to 19 μL MAGL (recombinant wild-type) in assay buffer (50 mM TRIS (GIBCO, 15567-027), 1 mM EDTA (Fluka, 03690-100 ml)). The plate was shaked for 1 min at 2000 rpm (Variomag Teleshake) and then incubated for 15 min at RT. To start the reaction, 20 μL 4-Nitrophenylacetate (Sigma N-8130) in assay buffer with 6% EtOH was added. The final concentrations in the assay were 1 nM MAGL and 300 μM 4-Nitrophenylacetate. After shaking (1 min, 2000 rpm) and 5 min incubation at RT, the absorbance at 405 nm was measured for a first time (Molecular Devices, SpectraMax Paradigm). A second measurement was then done after incubation for 80 min at RT. From the two measurements, the slope was calculated by subtracting the first from the second measurement.

Alternatively, compounds were profiled for MAGL inhibitory activity by determining the enzymatic activity by following the hydrolysis of the natural substrate 2-arachidonoylglycerol resulting in arachidonic acid, which can be followed by mass spectrometry. This assay is hereinafter abbreviated "2-AG assay".

The 2-AG assay was carried out in 384 well assay plates (PP, Greiner Cat #784201) in a total volume of 20 μL. Compound dilutions were made in 100% DMSO (VWR Chemicals 23500.297) in a polypropylene plate in 3-fold dilution steps to give a final concentration range in the assay from 12.5 μM to 0.8 μM. 0.25 μL compound dilutions (100% DMSO) were added to 9 μL MAGL in assay buffer (50 mM TRIS (GIBCO, 15567-027), 1 mM EDTA (Fluka, 03690-100 ml), 0.01% (v/v) Tween. After shaking, the plate was incubated for 15 min at RT. To start the reaction, 10 μL 2-arachidonoylglycerol in assay buffer was added. The final concentrations in the assay was 50 μM MAGL and 8 μM 2-arachidonoylglycerol. After shaking and 30 min incubation at RT, the reaction was quenched by the addition of 40 μL of acetonitrile containing 4 μM of d8-arachidonic acid. The amount of arachidonic acid was traced by an online SPE system (Agilent Rapidfire) coupled to a triple quadrupole mass spectrometer (Agilent 6460). A C18 SPE cartridge (G9205A) was used in an acetonitrile/water liquid setup. The mass spectrometer was operated in negative electrospray mode following the mass transitions 303.1→259.1 for arachidonic acid and 311.1→267.0 for d8-arachidonic acid. The activity of the compounds was calculated based on the ratio of intensities [arachidonic acid/d8-arachidonic acid].

TABLE 1

| Example | Name | Structure | $IC_{50}$ MAGL [nM] |
|---|---|---|---|
| 1 | (4aR,8aS)-6-(6-(2-Chloro-4-fluorophenoxy)-2-azaspiro[3.3]heptane-2-carbonyl)hexahdyro-2H-pyrido[4,3-b][1,4]oxazin-3(4H)-one | 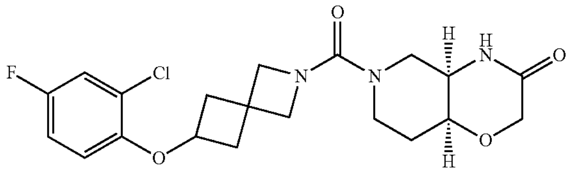 | 4.5[a] |
| 2 | (4aR,8aS)-6-(6-(4-(Trifluoromethyl)phenoxy)-2-azaspiro[3.3]heptane-2-carbonyl)hexahydro-2H-pyrido[4,3-b][1,4]oxazin-3(4H)-one | 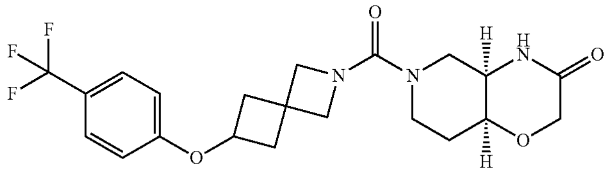 [SMILES: O=C1CO[C@H]2CCN(C(=O)N3CC4(CC(Oc5ccc(C(F)(F)F)cc5)C4)C3)C[C@H]2N1] | 5.0[a] |

TABLE 1-continued

| Ex-ample | Name | Structure | IC$_{50}$ MAGL [nM] |
|---|---|---|---|
| 3 | (4aR,8aS)-6-(6-(2-Fluoro-4-(trifluoromethyl)phenoxy)-2-azaspiro[3.3]heptane-2-carbonyl)hexahydro-2H-pyrido[4,3-b][1,4]oxazin-3(4H)-one | 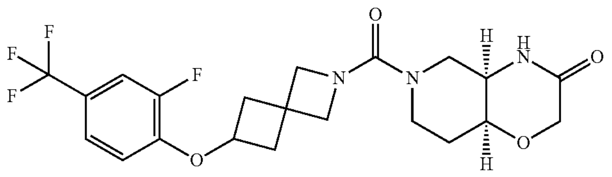 [SMILES: O=C1CO[C@H]2CCN(C(=O)N3CC4(CC(Oc5ccc(C(F)(F)F)cc5F)C4)C3)C[C@H]2N1] | 2.3[a] |
| 4 | (4aR,8aS)-6-(6-(2-Fluoro-4-(trifluoromethoxy)phenoxy)-2-azaspiro[3.3]heptane-2-carbonyl)hexahydro-2H-pyrido[4,3-b][1,4]oxazin-3(4H)-one | 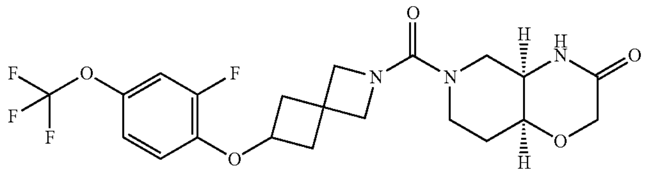 [SMILES: O=C1CO[C@H]2CCN(C(=O)N3CC4(CC(Oc5ccc(OC(F)(F)F)cc5F)C4)C3)C[C@H]2N1] | 3.0[a] |
| 5 | (4aR,8aS)-6-(6-(2-Chloro-4-(trifluoromethoxy)phenoxy)-2-azaspiro[3.3]heptane-2-carbonyl)hexahydro-2H-pyrido[4,3-b][1,4]oxazin-3(4H)-one | 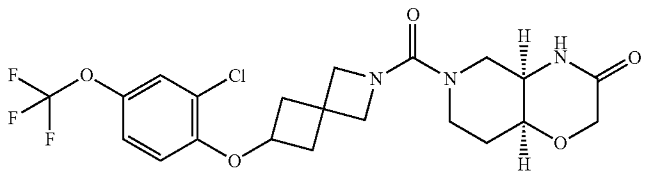 [SMILES: O=C1CO[C@H]2CCN(C(=O)N3CC4(CC(Oc5ccc(OC(F)(F)F)cc5Cl)C4)C3)C[C@H]2N1] | 0.6[a] |
| 6 | (4aR,8aS)-6-(6-(2-Methoxy-5-(trifluoromethyl)phenoxy)-2-azaspiro[3.3]heptane-2-carbonyl)hexahydro-2H-pyrido[4,3-b][1,4]oxazin-3(4H)-one | 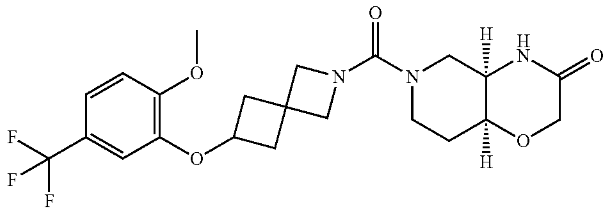 [SMILES: COc1ccc(C(F)(F)F)cc1OC1CC2(C1)CN(C(=O)N1CC[C@@H]3OCC(=O)N[C@@H]3C1)C2] | 2.8[a] |
| 7 | (4aR,8aS)-6-(6-(4-Chloro-2-(trifluoromethyl)phenoxy)-2-azaspiro[3.3]heptane-2-carbonyl)hexahydro-2H-pyrido[4,3-b][1,4]oxazin-3(4H)-one | 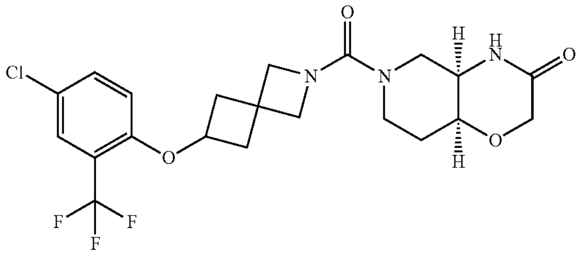 [SMILES: O=C1CO[C@H]2CCN(C(=O)N3CC4(CC(Oc5ccc(Cl)cc5C(F)(F)F)C4)C3)C[C@H]2N1] | 8.5[a] |
| 8 | (4aR,8aS)-6-(6-(2,4-Difluorophenoxy)-2-azaspiro[3.3]heptane-2-carbonyl)hexahydro-2H-pyrido[4,3-b][1,4]oxazin-3(4H)-one | 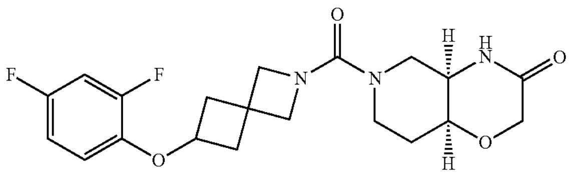 | 10.7[a] |
| 9 | (4aR,8aS)-6-(6-(3-Fluoro-5-(trifluoromethyl)phenoxy)-2-azaspiro[3.3]heptane-2-carbonyl)hexahydro-2H-pyrido[4,3-b][1,4]oxazin-3(4H)-one | 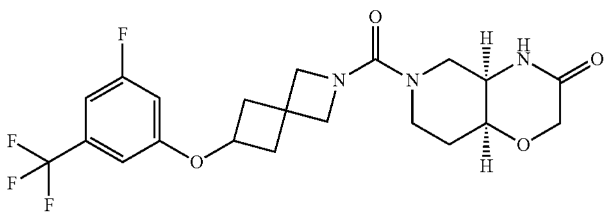 [SMILES: O=C1CO[C@H]2CCN(C(=O)N3CC4(CC(Oc5cc(F)cc(C(F)(F)F)c5)C4)C3)C[C@H]2N1] | 12.5[a] |

TABLE 1-continued

| Example | Name | Structure | IC50 MAGL [nM] |
|---|---|---|---|
| 10 | (4aR,8aS)-6-(2-(2-Fluoro-4-(trifluoromethyl)phenoxy)-7-azaspiro[3.5]nonane-7-carbonyl)hexahydro-2H-pyrido[4,3-b][1,4]oxazin-3(4)-one | 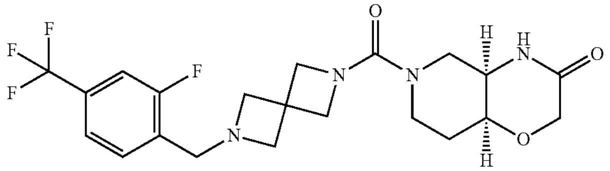 [SMILES: O=C1CO[C@H]2CCN(C(=O)N3CC4(CN(Cc5ccc(C(F)(F)F)cc5F)C4)C3)C[C@H]2N1] | 0.8[a] |
| 11 | (4aR,8aS)-6-(6-(2-Chloro-4-fluorobenzyl)-2,6-diazaspiro[3.3]heptane-2-carbonyl)hexahydro-2H-pyrido[4,3-b][1,4]oxazin-3(4H)-one | 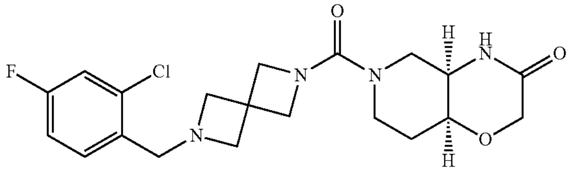 | 19.8[a] |
| 12 | (4aR,8aS)-6-(6-(2-Fluoro-4-(trifluoromethyl)benzyl)-2,6-diazaspiro[3.3]heptane-2-carbonyl)hexahydro-2H-pyrido[4,3-b][1,4]oxazin-3(4H)-one | 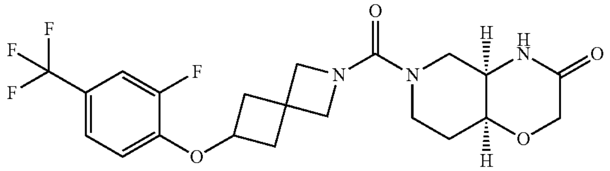 [SMILES: O=C1CO[C@H]2CCN(C(=O)N3CC4(CC(Oc5ccc(C(F)(F)F)cc5F)C4)C3)C[C@H]2N1] | 15.7[a] |
| 13 | (4aR,8aS)-6-(2-(2-Fluoro-4-(trifluoromethyl)benzyl)-2,7-diazaspiro[3.5]nonane-7-carbonyl)hexahydro-2H-pyrido[4,3-b][1,4]oxazin-3(4H)-one | 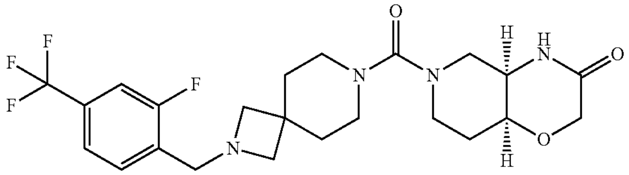 [SMILES: O=C1CO[C@H]2CCN(C(=O)N3CCC4(CC3)CN(Cc3ccc(C(F)(F)F)cc3F)C4)C[C@H]2N1] | 76.4[a] |
| 14 | (4aR,8aS)-6-(7-(2-Fluoro-4-(trifluoromethyl)benzyl)-2,7-diazaspiro[4.4]nonane-2-carbonyl)hexahydro-2H-pyrido[4,3-b][1,4]oxazin-3(4H)-one | 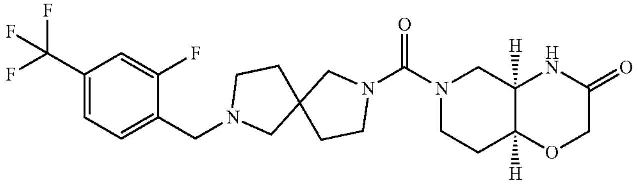 [SMILES: O=C1CO[C@H]2CCN(C(=O)N3CCC4(CCN(Cc5ccc(C(F)(F)F)cc5F)C4)C3)C[C@H]2N1] | 268[a] |
| 15 | (4aR,8aS)-6-(2-(2-Fluoro-4-(trifluoromethyl)benzyl)-2,6-diazaspiro[3.4]octane-6-carbonyl)hexahydro-2H-pyrido[4,3-b][1,4]oxazin-3(4H)-one | 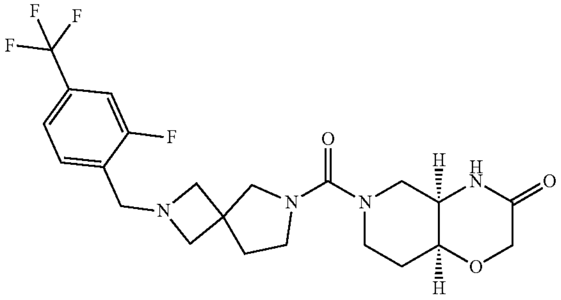 [SMILES: O=C1CO[C@H]2CCN(C(=O)N3CCC4(CN(Cc5ccc(C(F)(F)F)cc5F)C4)C3)C[C@H]2N1] | 2032[a] |
| 16 | (4aR,8aS)-6-(6-((2-Chloro-4-fluorophenyl)sulfonyl)-2,6-diazaspiro[3.3]heptane-2-carbonyl)hexahydro-2H-pyrido[4,3-b][1,4]oxazin-3(4H)-one | 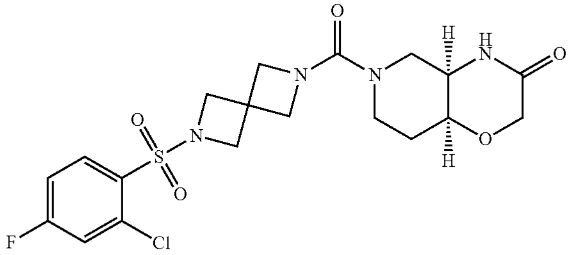 [SMILES: O=C1CO[C@H]2CCN(C(=O)N3CC4(C3)CN(S(=O)(=O)c3ccc(F)cc3Cl)C4)C[C@H]2N1] | 228[a] |

TABLE 1-continued

| Example | Name | Structure | IC50 MAGL [nM] |
|---|---|---|---|
| 17 | (4aR,8aS)-6-(6-((2-Fluoro-4-(trifluoromethyl)phenyl)sulfonyl)-2,6-diazaspiro[3.3]heptane-2-carbonyl)hexahydro-2H-pyrido[4,3-b][1,4]oxazin-3(4H)-one | 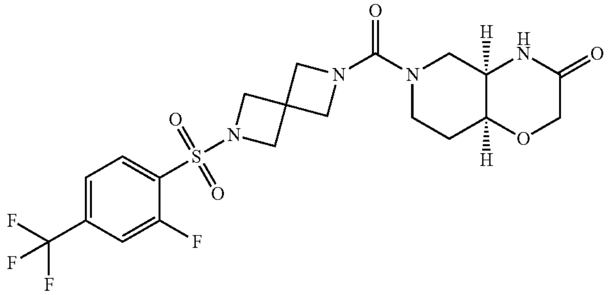 [SMILES: O=C1CO[C@H]2CCN(C(=O)N3CC4(C3)CN(S(=O)(=O)c3ccc(C(F)(F)F)cc3F)C4)C[C@H]2N1] | 768[a] |
| 18 | rac-(4aR,8aS)-N-((R)-8-(3-oxooctahydro-2H-pyrido[4,3-b][1,4]oxazine-6-carbonyl)-1-oxa-8-azaspiro[4.5]decan-3-yl)benzenesulfonamide | 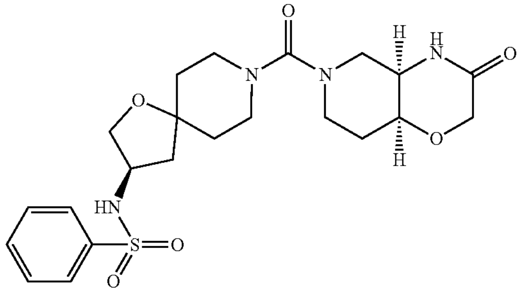 [SMILES: O=C1CO[C@H]2CCN(C(=O)N3CCC4(CC3)C[C@@H](NS(=O)(=O)c3ccccc3)CO4)C[C@H]2N1] | 316[a] |
| 19 | rac-(4aR,8aS)-N-((S)-8-(3-oxooctahydro-2H-pyrido[4,3-b][1,4]oxazine-6-carbonyl)-1-oxa-8-azaspiro[4.5]decan-3-yl)benzenesulfonamide | 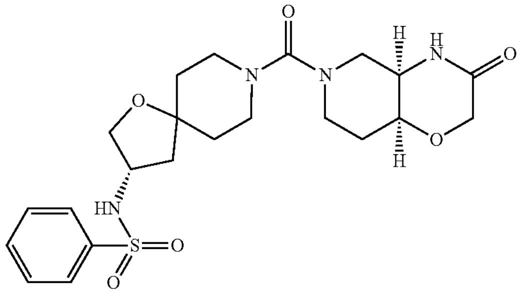 [SMILES: O=C1CO[C@H]2CCN(C(=O)N3CCC4(CC3)C[C@H](NS(=O)(=O)c3ccccc3)CO4)C[C@H]2N1] | 821[a] |
| 20 | rac-(4aR,8aS)-6-(2-Benzhydryl-2,6-diazaspiro[3.4]octane-6-carbonyl)hexahydro-2H-pyrido[4,3-b][1,4]oxazin-3(4H)-one | 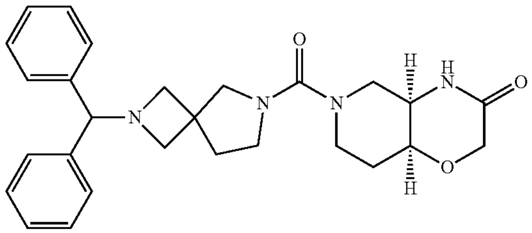 [SMILES: O=C1CO[C@H]2CCN(C(=O)N3CCC4(C3)CN(C(c3ccccc3)c3ccccc3)C4)C[C@H]2N1] | 2689[b] |
| 21 | rac-(4aR,8aS)-6-(4-((4-Fluorophenyl)sulfonyl)-1-oxa-4,9-diazaspiro[5.5]undecane-9-carbonyl)hexahydro-2H-pyrido[4,3-b][1,4]oxazin-3(4H)-one | 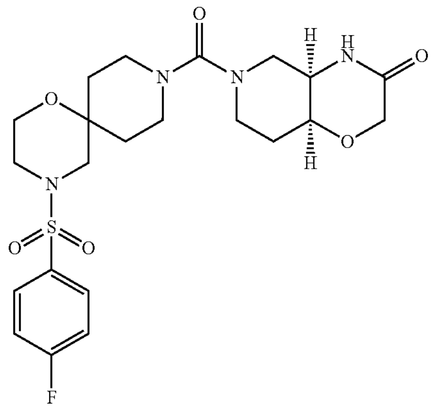 [SMILES: O=C1CO[C@H]2CCN(C(=O)N3CCC4(CC3)CN(S(=O)(=O)c3ccc(F)cc3)CCO4)C[C@H]2N1] | 836[b] |

TABLE 1-continued

| Example | Name | Structure | $IC_{50}$ MAGL [nM] |
|---|---|---|---|
| Int-1 | rac-tert-Butyl 6-((4aR,8aS)-3-oxooctahydro-2H-pyrido[4,3-b][1,4]oxazine-6-carbonyl)-2,6-diazaspiro[3.4]octane-2-carboxylate | 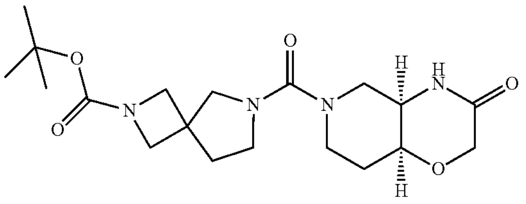 [SMILES: CC(C)(C)OC(=O)N1CC2(CCN(C(=O)N3CC[C@@H]4OCC(=O)N[C@@H]4C3)C2)C1] | 539[b] |
| 22 | (4aR,8aS)-6-(6-((4,5-Bis(trifluoromethyl)pyridin-2-yl)oxy)-2-azaspiro[3.3]heptane-2-carbonyl)hexahydro-2H-pyrido[4,3-b][1,4]oxazin-3(4H)-one | Chiral 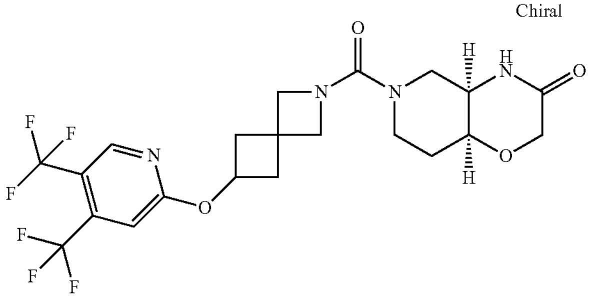 [SMILES: O=C1CO[C@H]2CCN(C(=O)N3CC4(CC(Oc5cc(C(F)(F)F)c(C(F)(F)F)cn5)C4)C3)C[C@H]2N1] | 3.8[a] |
| 23 | (4aR,8aS)-6-(6-((5,6-Bis(trifluoromethyl)pyridin-2-yl)oxy)-2-azaspiro[3.3]heptane-2-carbonyl)hexahydro-2H-pyrido[4,3-b][1,4]oxazin-3(4H)-one | Chiral 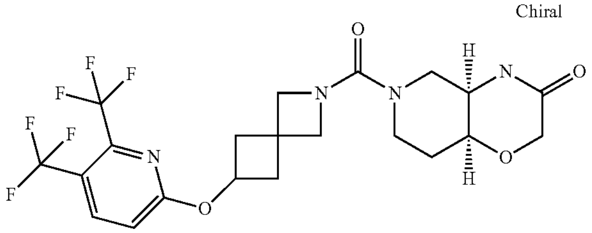 [SMILES: O=C1CO[C@H]2CCN(C(=O)N3CC4(CC(Oc5ccc(C(F)(F)F)c(C(F)(F)F)n5)C4)C3)C[C@H]2N1] | 4.8[a] |
| 24 | 2-Chloro-4-fluoro-N-methyl-N-((R)-8-((4aR,8aS)-3-oxooctahydro-2H-pyrido[4,3-b][1,4]oxazine-6-carbonyl)-1-oxa-8-azaspiro[4.5]decan-3-yl)benzenesulfonamide | Chiral 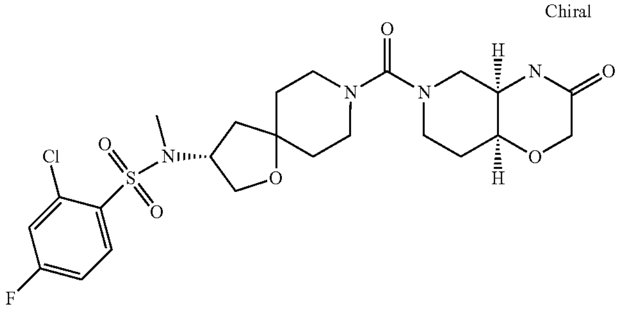 [SMILES: CN([C@H]1COC2(CCN(C(=O)N3CC[C@@H]4OCC(=O)N[C@@H]4C3)CC2)C1)S(=O)(=O)c1ccc(F)cc1Cl] | 20.9[a] |
| 25 | (4aR,8aS)-6-(6-((5-(Trifluoromethyl)pyridin-2-yl)oxy)-2-azaspiro[3.3]heptane-2-carbonyl)hexahydro-2H-pyrido[4,3-b][1,4]oxazin-3(4H)-one | Chiral 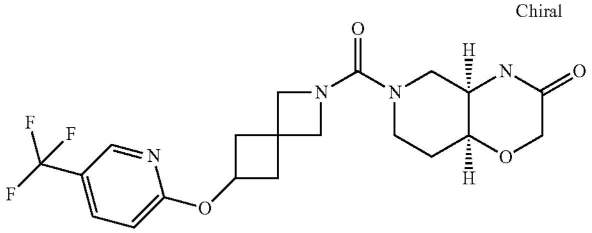 [SMILES: O=C1CO[C@H]2CCN(C(=O)N3CC4(CC(Oc5ccc(C(F)(F)F)cn5)C4)C3)C[C@H]2N1] | 28.9[a] |

TABLE 1-continued

| Example | Name | Structure | $IC_{50}$ MAGL [nM] |
| --- | --- | --- | --- |
| 26 | (4aR,8aS)-6-(6-((4-Methyl-3-(trifluoromethyl)benzyl)oxy)-2-azaspiro[3.3]heptane-2-carbonyl)hexahydro-2H-pyrido[4,3-b][1,4]oxazin-3(4H)-one | Chiral 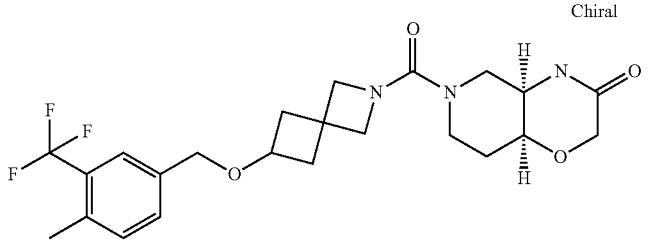 [SMILES: Cc1ccc(COC2CC3(C2)CN(C(=O)N2CC[C@@H]4OCC(=O)N[C@@H]4C2)C3)cc1C(F)(F)F] | 31.0[a] |
| 27 | (4aR,8aS)-6-(2-((2-Chloro-4-fluorophenyl)sulfonyl)-2,7-diazaspiro[3.5]nonane-7-carbonyl)hexahydro-2H-pyrido[4,3-b][1,4]oxazin-3(4H)-one | Chiral 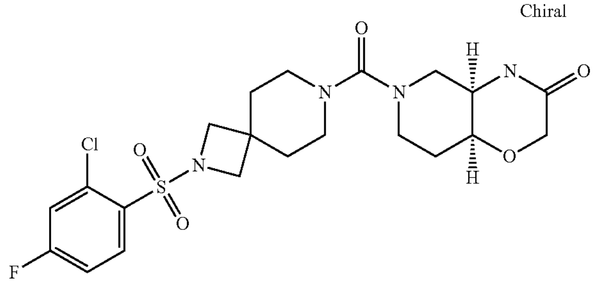 [SMILES: O=C1CO[C@H]2CCN(C(=O)N3CCC4(CC3)CN(S(=O)(=O)c3ccc(F)cc3Cl)C4)C[C@H]2N1] | 33.1[a] |
| 28 | (4aR,8aS)-6-(6-((2-Fluoro-4-(trifluoromethyl)benzyl)oxy)-2-azaspiro[3.3]heptane-2-carbonyl)hexahydro-2H-pyrido[4,3-b][1,4]oxazin-3(4H)-one | Chiral 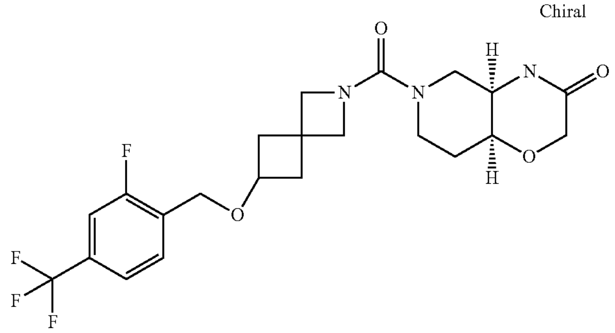 [SMILES: O=C1CO[C@H]2CCN(C(=O)N3CC4(CC(OCc5ccc(C(F)(F)F)cc5F)C4)C3)C[C@H]2N1] | 36.4[a] |
| 29 | N-((S)-8-((4aR,8aS)-3-Oxooctahydro-2H-pyrido[4,3-b][1,4]oxazine-6-carbonyl)-1-oxa-8-azaspiro[4.5]decan-3-yl)-4-(trifluoromethyl)benzenesulfonamide | Chiral 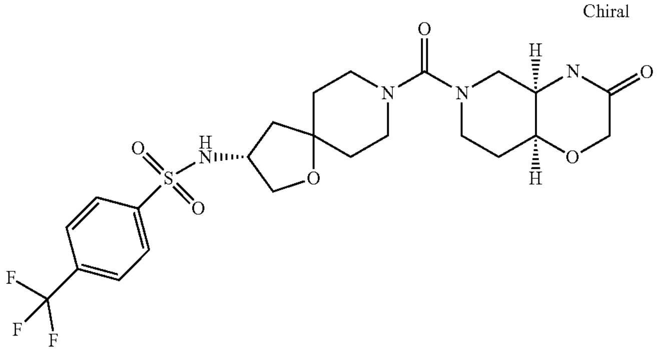 [SMILES: O=C1CO[C@H]2CCN(C(=O)N3CCC4(CC3)C[C@@H](NS(=O)(=O)c3ccc(C(F)(F)F)cc3)CO4)C[C@H]2N1] | 47.5[a] |
| 30 | N-Methyl-N-((R)-8-((4aR,8aS)-3-oxooctahydro-2H-pyrido[4,3-b][1,4]oxazine-6-carbonyl)-1-oxa-8-azaspiro[4.5]decan-3-yl)benzenesulfonamide | Chiral 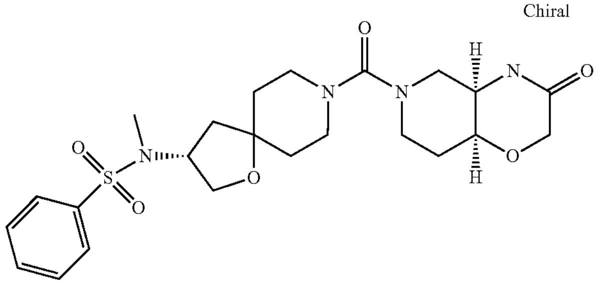 [SMILES: CN([C@H]1COC2(CCN(C(=O)N3CC[C@@H]4OCC(=O)N[C@@H]4C3)CC2)C1)S(=O)(=O)c1ccccc1] | 49.3[a] |

TABLE 1-continued

| Example | Name | Structure | IC50 MAGL [nM] |
|---|---|---|---|
| 31 | 2-Chloro-4-fluoro-N-((S)-8-((4aR,8aS)-3-oxooctahydro-2H-pyrido[4,3-b][1,4]oxazine-6-carbonyl)-1-oxa-8-azaspiro[4.5]decan-3-yl)benzenesulfonamide | Chiral 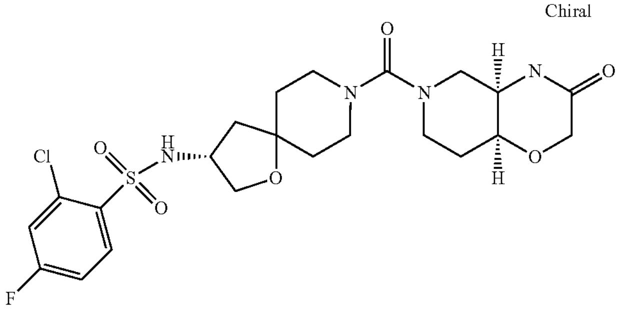 [SMILES: O=C1CO[C@H]2CCN(C(=O)N3CCC4(CC3)C[C@@H](NS(=O)(=O)c3ccc(F)cc3Cl)CO4)C[C@H]2N1] | 51.3[a] |
| 32 | N-((S)-8-((4aR,8aS)-3-Oxooctahydro-2H-pyrido[4,3-b][1,4]oxazine-6-carbonyl)-1-oxa-8-azaspiro[4.5]decan-3-yl)-3-(trifluoromethyl) benzenesulfonamide | Chiral 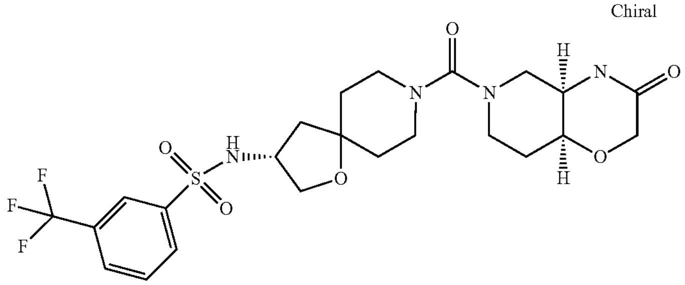 [SMILES: O=C1CO[C@H]2CCN(C(=O)N3CCC4(CC3)C[C@@H](NS(=O)(=O)c3cccc(C(F)(F)F)c3)CO4)C[C@H]2N1] | 123.6[a] |
| 33 | (4aR,8aS)-6-(3-((2-Chloro-4-fluorobenzyl)(methyl)amino)-1-oxa-8-azaspiro[4.5]decane-8-carbonyl)hexahydro-2H-pyrido[4,3-b][1,4]oxazin-3(4H)-one | 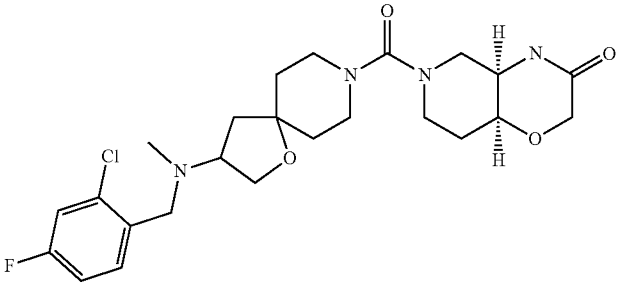 [SMILES: CN(Cc1ccc(F)cc1Cl)C1COC2(CCN(C(=O)N3CC[C@@H]4OCC(=O)N[C@@H]4C3)CC2)C1] | 129.3[a] |
| 34 | (4aR,8aS)-6-(3-((2-Chloro-4-fluorobenzyl)(methyl)amino)-1-oxa-8-azaspiro[4.5]decane-8-carbonyl)hexahydro-2H-pyrido[4,3-b][1,4]oxazin-3(4H)-one | Chiral 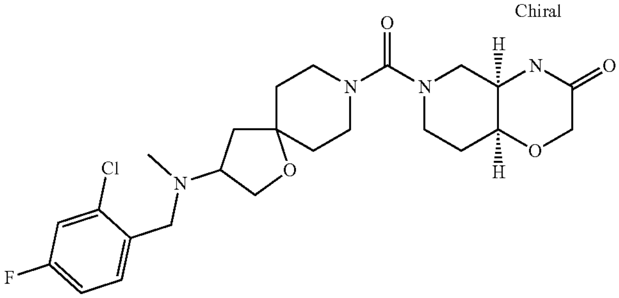 [SMILES: CN(Cc1ccc(F)cc1Cl)C1COC2(CCN(C(=O)N3CC[C@@H]4OCC(=O)N[C@@H]4C3)CC2)C1] | 132.6[a] |
| 35 | (4aR,8aS)-6-(3-((2-Chloro-4-fluorobenzyl)amino)-1-oxa-8-azaspiro[4.5]decane-8-carbonyl)hexahydro-2H-pyrido[4,3-b][1,4]oxazin-3(4H)-one | Chiral 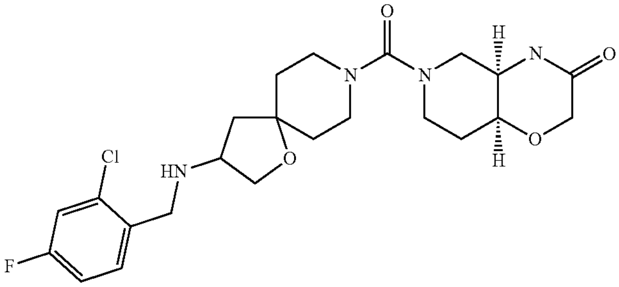 | 182.1[a] |

TABLE 1-continued

| Example | Name | Structure | $IC_{50}$ MAGL [nM] |
|---|---|---|---|
| 36 | (4aR,8aS)-6-(3-((2-Chloro-4-fluorobenzyl)amino)-1-oxa-8-azaspiro[4.5]decane-8-carbonyl)hexahydro-2H-pyrido[4,3-b][1,4]oxazin-3(4H)-one | Chiral 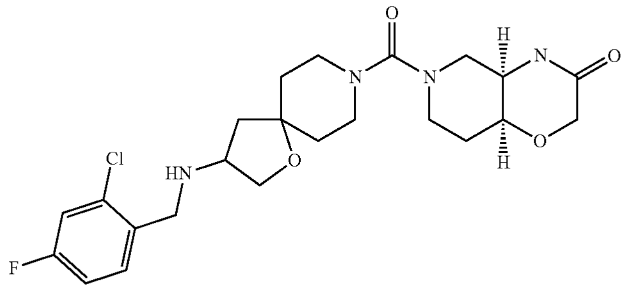 [SMILES: O=C1CO[C@H]2CCN(C(=O)N3CCC4(CC3)CC(NCc3ccc(F)cc3Cl)CO4)C[C@H]2N1] | 279.3[a] |
| 37 | (4aR,8aS)-6-(2-((4-(Trifluoromethyl)phenyl)sulfonyl)-2,7-diazaspiro[3.5]nonane-7-carbonyl)hexahydro-2H-pyrido[4,3-b][1,4]oxazin-3(4H)-one | Chiral 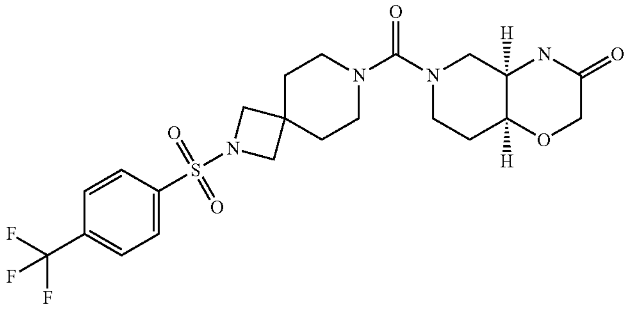 | 389.1[a] |
| 38 | rac-(4aR,8aS)-6-(3-((2-Chloro-4-fluorobenzyl)amino)-1-oxa-8-azaspiro[4.5]decane-8-carbonyl)hexahydro-2H-pyrido[4,3-b][1,4]oxazin-3(4H)-one | 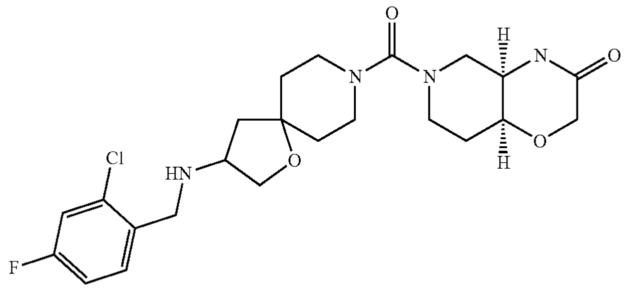 | 415.6[a] |
| 39 | (4aR,8aS)-6-(2-(Phenylsulfonyl)-2,7-diazaspiro[3.5]nonane-7-carbonyl)hexahydro-2H-pyrido[4,3-b][1,4]oxazin-3(4H)-one | Chiral 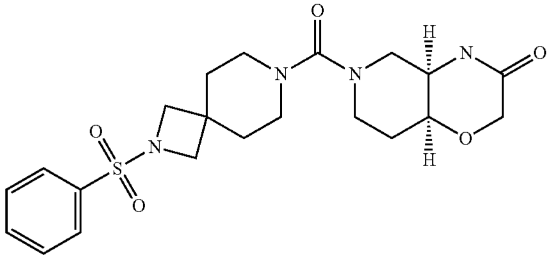 | 598.6[b] |
| 40 | (4aR,8aS)-6-[2-(2,4-Difluorophenoxy)-7-azaspiro[3.5]nonane-7-carbonyl]-4,4a,5,7,8,8a-hexahydropyrido[4,3-b][1,4]oxazin-3-one | Chiral 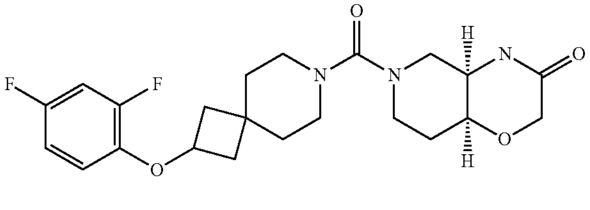 | 11.3[a] |

TABLE 1-continued

| Example | Name | Structure | $IC_{50}$ MAGL [nM] |
| --- | --- | --- | --- |
| 41 | (4aR,8aS)-6-(6-(2-Chloro-4-fluorophenoxy)-2-azaspiro[3.3]heptane-2-carbonyl)hexahydro-2H-pyrido[4,3-b][1,4]oxazin-3(4H)-one | Chiral 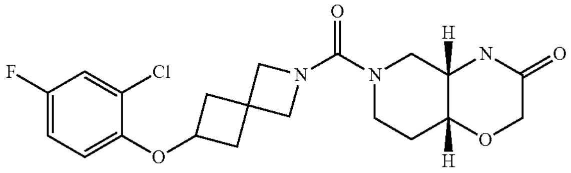 | 466.0[a] |
| 42 | (4aR,8aS)-6-[2-(2-Chloro-4-fluoro-phenoxy)-7-azaspiro[3.5]nonane-7-carbonyl]-4,4a,5,7,8,8a-hexahydropyrido[4,3-b][1,4]oxazin-3-one | Chiral 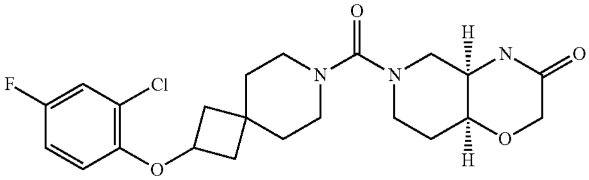 | 2.1[a] |
| 43 | (4aR,8aS)-6-[6-[[2-Fluoro-4-(trifluoromethyl)phenoxy]methyl]-2-azaspiro[3.3]heptane-2-carbonyl]-4,4a,5,7,8,8a-hexahydropyrido[4,3-b][1,4]oxazin-3-one | Chiral 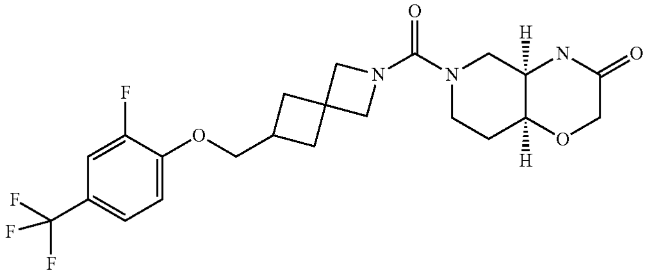 | 1.0[a] |
| 44 | (4aR,8aS)-6-(6-((2-fluoro-4-(trifluoromethyl)benzyl)oxy)-6-(trifluoromethyl)-2-azaspiro[3.3]heptane-2-carbonyl)hexahydro-2H-pyrido[4,3-b][1,4]oxazin-3(4H)-one | Chiral 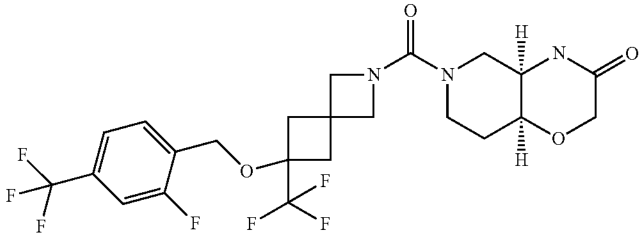 | 185.3 |
| 45 | (4aR,8aS)-6-(6-(2-fluoro-4-(trifluoromethyl)phenyl)-2-azaspiro[3.3]heptane-2-carbonyl)hexahydro-2H-pyrido[4,3-b][1,4]oxazin-3(4H)-one | Chiral 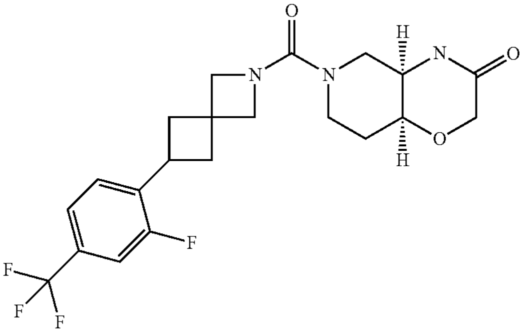 | 37.0 |

TABLE 1-continued

| Example | Name | Structure | $IC_{50}$ MAGL [nM] |
|---|---|---|---|
| 46 | (4aR,8aS)-6-(6-(4-(pentafluoro-l6-sulfaneyl)phenyl)-2-azaspiro[3.3]heptane-2-carbonyl)hexahydro-2H-pyrido[4,3-b][1,4]oxazin-3(4H)-one | Chiral 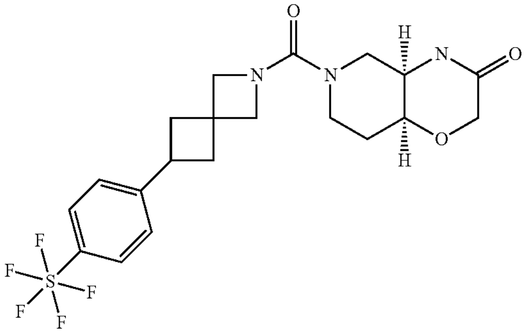 | 14.5 |
| 47 | (4aR,8aS)-6-(6-(4-(2-(trifluoromethyl)pyrrolidin-1-yl)phenyl)-2-azaspiro[3.3]heptane-2-carbonyl)hexahydro-2H-pyrido[4,3-b][1,4]oxazin-3(4H)-one | 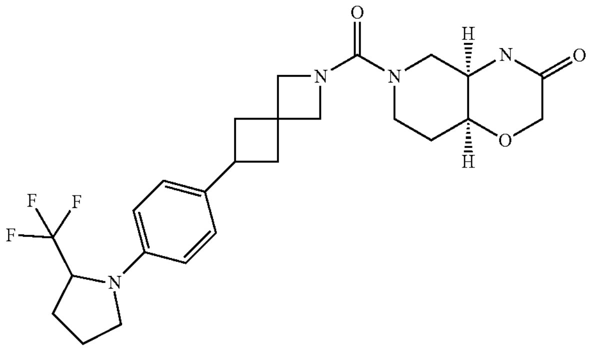 | 39.8 |
| 48 | (4aR,8aS)-6-(6-(4-(1-methyl-1H-pyrazol-5-yl)phenyl)-2-azaspiro[3.3]heptane-2-carbonyl)hexahydro-2H-pyrido[4,3-b][1,4]oxazin-3(4H)-one | Chiral 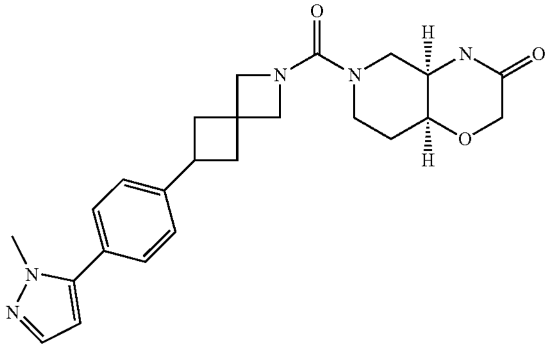 | 222.9 |
| 49 | (4aR,8aS)-6-(6-(2-fluoro-4-(trifluoromethyl)benzyl)-2-azaspiro[3.3]heptane-2-carbonyl)hexahydro-2H-pyrido[4,3-b][1,4]oxazin-3(4H)-one | Chiral 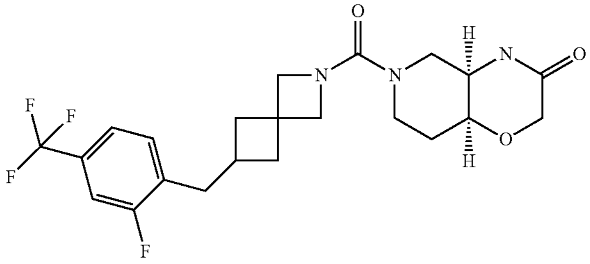 | 0.03 |

TABLE 1-continued

| Example | Name | Structure | $IC_{50}$ MAGL [nM] |
|---|---|---|---|
| 50 | (4aR,8aS)-6-(6-(2-chloro-4-fluorobenzyl)-2-azaspiro[3.3]heptane-2-carbonyl)hexahydro-2H-pyrido[4,3-b][1,4]oxazin-3(4H)-one | Chiral 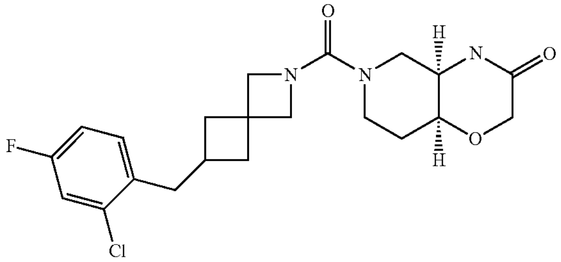 | 0.04 |
| 51 | (4aR,8aS)-6-(6-(2,4-difluorobenzyl)-2-azaspiro[3.3]heptane-2-carbonyl)hexahdyro-2H-pyrido[4,3-b][1,4]oxazin-3(4H)-one | Chiral 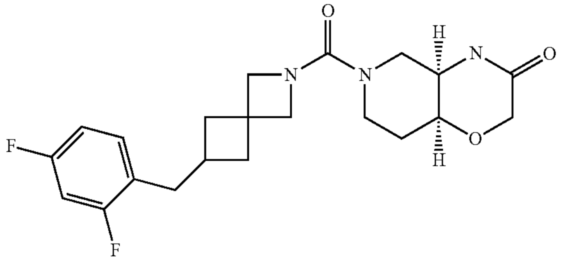 | 0.17 |
| 52 | (4aR,8aS)-6-(6-(2-methoxy-4-(trifluoromethyl)benzyl)-2-azaspiro[3.3]heptane-2-carbonyl)hexahydro-2H-pyrido[4,3-b][1,4]oxazin-3(4H)-one | Chiral 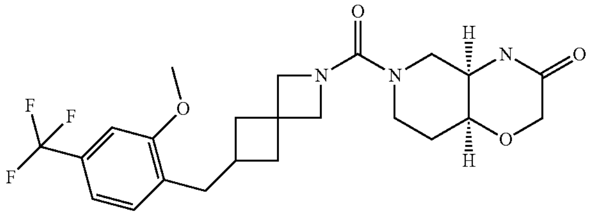 | 0.03 |
| 53 | (4aR,8aS)-6-(6-(2-fluoro-6-(trifluoromethyl)benzyl)-2-azaspiro[3.3]heptane-2-carbonyl)hexahydro-2H-pyrido[4,3-b][1,4]oxazin-3(4H)-one | Chiral 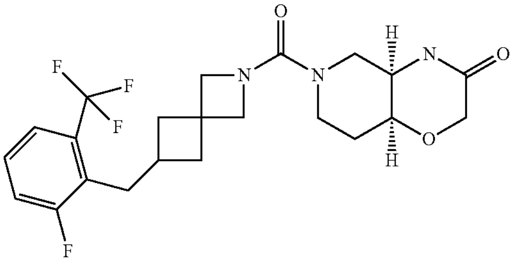 | 0.05 |
| 54 | (4aR,8aS)-6-(6-((2-chloro-4-fluorophenoxy)methyl)-2-azaspiro[3.3]heptane-2-carbonyl)hexahydro-2H-pyrido[4,3-b][1,4]oxazin-3(4H)-one | Chiral 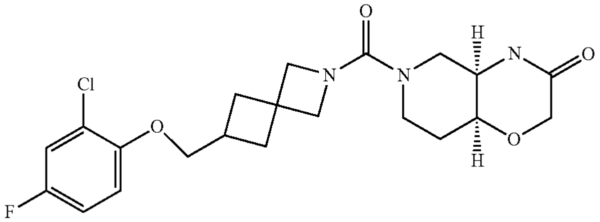 | 1.46 |

TABLE 1-continued

| Ex-ample | Name | Structure | $IC_{50}$ MAGL [nM] |
|---|---|---|---|
| 55 | (4aR,8aS)-6-(6-(4-(trifluoromethyl)phenyl)-2,6-diazaspiro[3.3]heptane-2-carbonyl)hexahydro-2H-pyrido[4,3-b][1,4]oxazin-3(4H)-one | Chiral 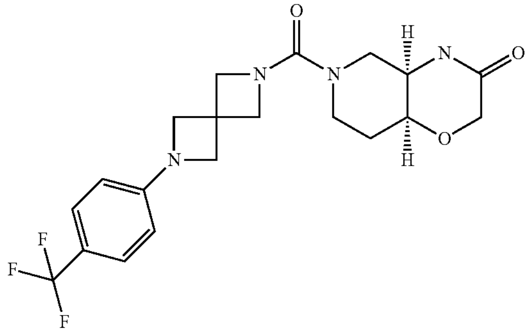 | 1038 |
| 56 | (4aR,8aS)-6-(6-(3-(trifluoromethyl)phenyl)-2,6-diazaspiro[3.3]heptane-2-carbonyl)hexahydro-2H-pyrido[4,3-b][1,4]oxazin-3(4H)-one | Chiral 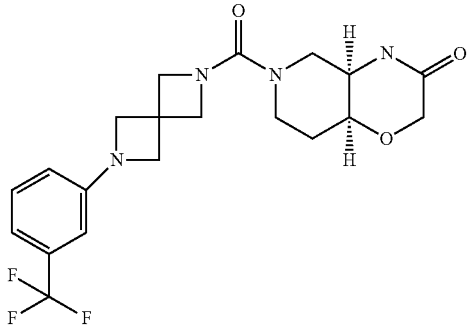 | 361 |
| 57 | (4aR,8aS)-6-(2-(4-(trifluoromethyl)phenyl)-2,6-diazaspiro[3.4]octane-6-carbonyl)hexahydro-2H-pyrido[4,3-b][1,4]oxazin-3(4H)-one | Chiral 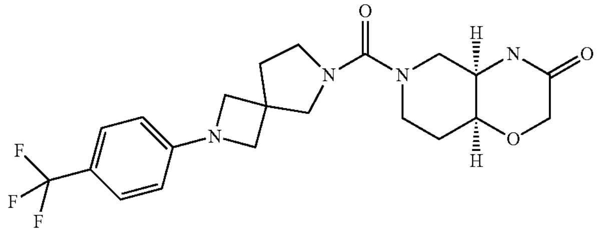 | 175 |
| 58 | (4aR,8aS)-6-(2-(3-(trifluoromethyl)phenyl)-2,6-diazaspiro[3.4]octane-6-carbonyl)hexahydro-2H-pyrido[4,3-b][1,4]oxazin-3(4H)-one | Chiral 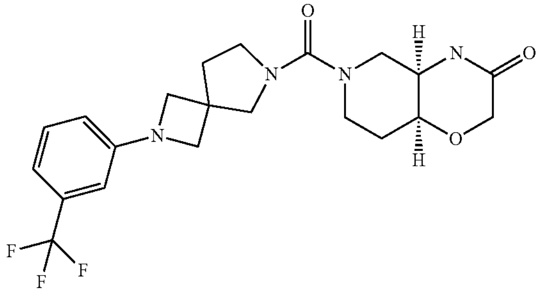 | 70.7 |
| 59 | (4aR,8aS)-6-(2-(4-isopropoxyphenyl)-2,6-diazaspiro[3.4]octane-6-carbonyl)hexahydro-2H-pyrido[4,3-b][1,4]oxazin-3(4H)-one | Chiral 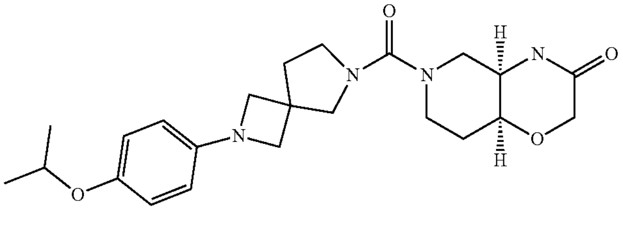 | 297 |

TABLE 1-continued

| Example | Name | Structure | $IC_{50}$ MAGL [nM] |
|---|---|---|---|
| 60 | (4aR,8aS)-6-(6-(4-isopropoxyphenyl)-2,6-diazaspiro[3.3]heptane-2-carbonyl)hexahydro-2H-pyrido[4,3-b][1,4]oxazin-3(4H)-one | Chiral 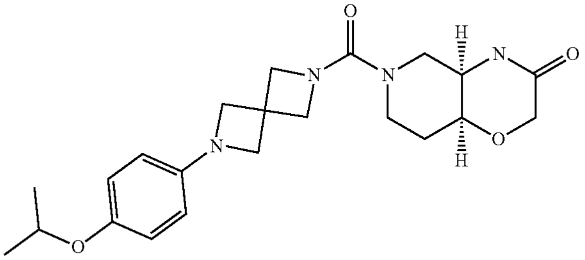 | 1587 |
| 61 | (4aR,8aS)-6-(2-(4-(2-oxopyrrolidin-1-yl)phenyl)-2,6-diazaspiro[3.4]octane-6-carbonyl)hexahydro-2H-pyrido[4,3-b][1,4]oxazin-3(4H)-one | Chiral 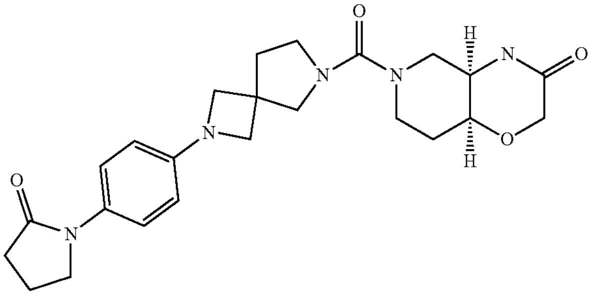 | 2296 |
| 62 | (4aR,8aS)-6-(2-(4-methoxy-3-methylphenyl)-2,6-diazaspiro[3.4]octane-6-carbonyl)hexahydro-2H-pyrido[4,3-b][1,4]oxazin-3(4H)-one | Chiral 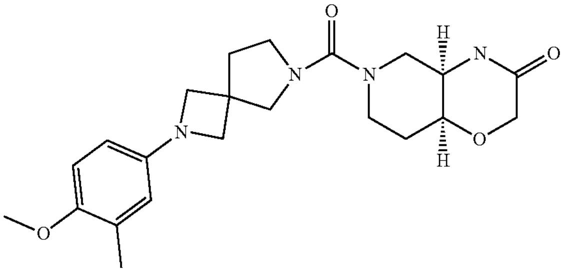 | 58.8 |
| 63 | (4aR,8aS)-6-(2-(4-chloro-3-(trifluoromethyl)phenyl)-2,6-diazaspiro[3.4]octane-6-carbonyl)hexahydro-2H-pyrido[4,3-b][1,4]oxazin-3(4H)-one | Chiral 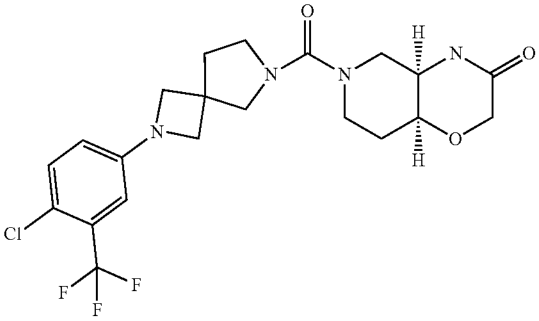 | 15.9 |
| 64 | (4aR,8aS)-6-(2-(2-fluoropyridin-4-yl)-2,6-diazaspiro[3.4]octane-6-carbonyl)hexahydro-2H-pyrido[4,3-b][1,4]oxazin-3(4H)-one | Chiral 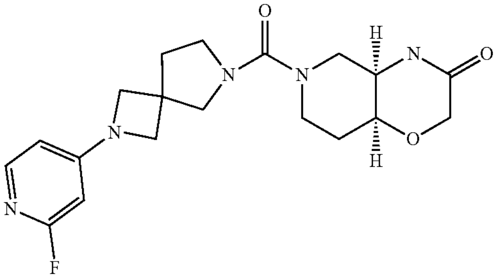 | 4968 |

TABLE 1-continued

| Ex-ample | Name | Structure | $IC_{50}$ MAGL [nM] |
|---|---|---|---|
| 65 | (4aR,8aS)-6-(6-(2,5-bis(trifluoromethyl)phenyl)-2,6-diazaspiro[3.3]heptane-2-carbonyl)hexahydro-2H-pyrido[4,3-b][1,4]oxazin-3(4H)-one | Chiral 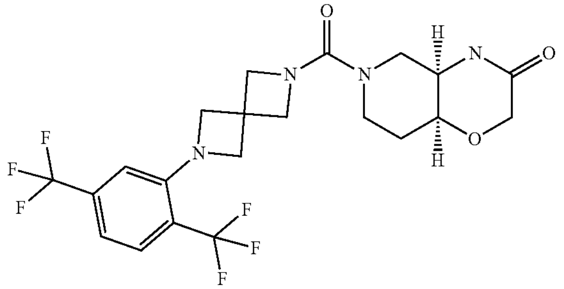 | 1100 |
| 66 | (4aR,8aS)-6-(6-((4-fluoro-2-(trifluoromethyl)phenyl) sulfonyl)-2,6-diazaspiro[3.3]heptane-2-carbonyl)hexahydro-2H-pyrido[4,3-b][1,4]oxazin-3(4H)-one | Chiral 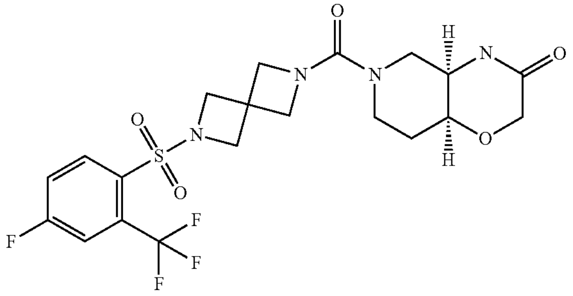 | 194.9 |
| 67 | (4aR,8aS)-6-(6-((2-chloro-4-fluorophenyl)sulfonyl)-2-azaspiro[3.3]heptane-2-carbonyl)hexahydro-2H-pyrido[4,3-b][1,4]oxazin-3(4H)-one | Chiral 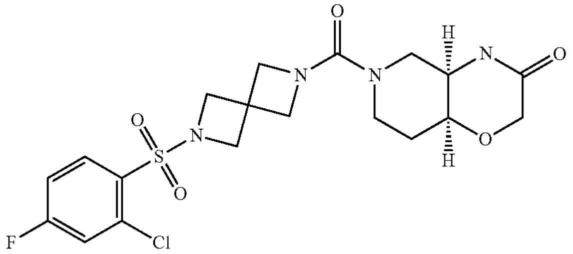 | 67.1 |
| 68 | (4aR,8aS)-6-(6-((3-chloro-4-(trifluoromethyl)phenyl) sulfonyl)-2,6-diazaspiro[3.3]heptane-2-carbonyl)hexahydro-2H-pyrido[4,3-b][1,4]oxazin-3(4H)-one | Chiral 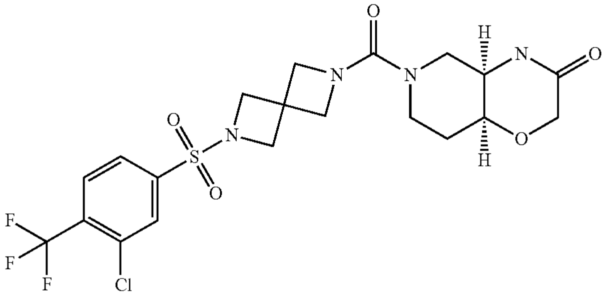 | 357.1 |

TABLE 1-continued

| Example | Name | Structure | IC50 MAGL [nM] |
|---|---|---|---|
| 69 | (4aR,8aS)-6-(6-((2,4-bis(trifluoromethyl)phenyl)sulfonyl)-2,6-diazaspiro[3.3]heptane-2-carbonyl)hexahydro-2H-pyrido[4,3-b][1,4]oxazin-3(4H)-one | Chiral 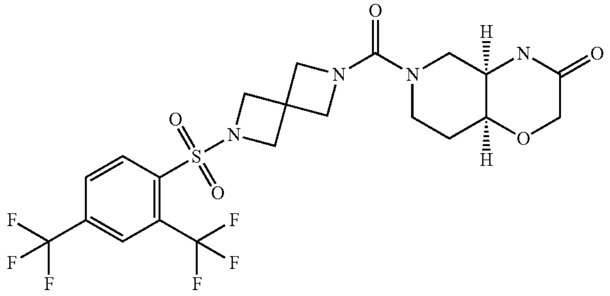 | 213.9 |
| 70 | (4aR,8aS)-6-(6-(2,6-difluorobenzyl)-2-azaspiro[3.3]heptane-2-carbonyl)hexahydro-2H-pyrido[4,3-b][1,4]oxazin-3(4H)-one | Chiral 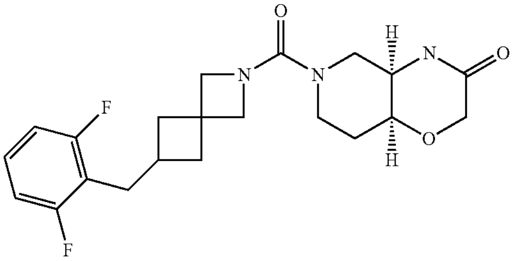 | 0.1 |
| 71 | (4aR,8aS)-6-(6-(2-fluoro-6-methoxybenzyl)-2-azaspiro[3.3]heptane-2-carbonyl)hexahydro-2H-pyrido[4,3-b][1,4]oxazin-3(4H)-one | Chiral 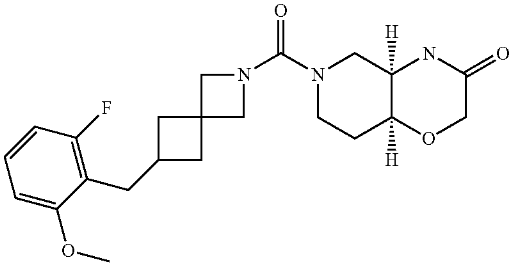 | 0.1 |
| 72 | (4aR,8aS)-6-(6-(2-methoxybenzyl)-2-azaspiro[3.3]heptane-2-carbonyl)hexahydro-2H-pyrido[4,3-b][1,4]oxazin-3(4H)-one | Chiral 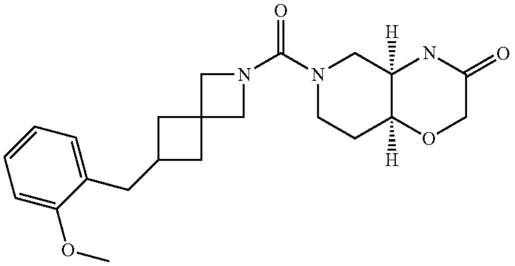 | 0.2 |
| 73 | (4aR,8aS)-6-(6-(2-fluoro-6-hydroxybenzyl)-2-azaspiro[3.3]heptane-2-carbonyl)hexahydro-2H-pyrido[4,3-b][1,4]oxazin-3(4H)-one | Chiral 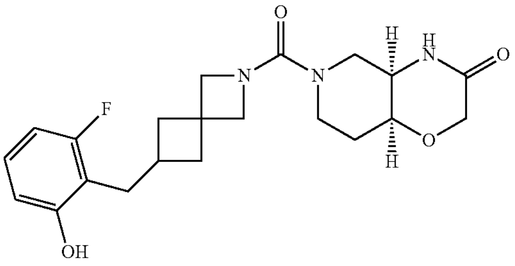 | 0.1 |

TABLE 1-continued

| Example | Name | Structure | $IC_{50}$ MAGL [nM] |
| --- | --- | --- | --- |
| 74 | (4aR,8aS)-6-(6-(2-hydroxybenzyl)-2-azaspiro[3.3]heptane-2-carbonyl)hexahydro-2H-pyrido[4,3-b][1,4]oxazin-3(4H)-one | Chiral 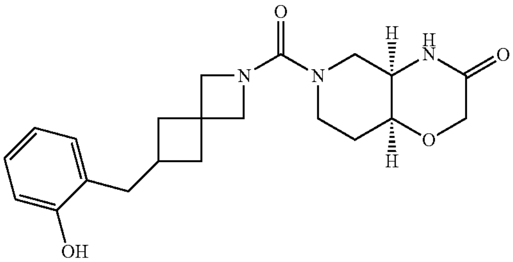 | 0.5 |

[a]measured in 2-AG assay; [b]measured in 4-NPA assay; n/a: not available.

In one aspect, the present invention provides compounds of formula (I) and their pharmaceutically acceptable salts or esters as described herein, wherein said compounds of formula (I) and their pharmaceutically acceptable salts or esters have $IC_{50}$'s for MAGL inhibition below 25 μM, preferably below 10 μM, more preferably below 5 μM as measured in the MAGL assays described herein.

In one embodiment, compounds of formula (I) and their pharmaceutically acceptable salts or esters as described herein have $IC_{50}$ (MAGL inhibition) values between 0.000001 μM and 25 μM, particular compounds have $IC_{50}$ values between 0.000005 μM and 10 μM, further particular compounds have $IC_{50}$ values between 0.00005 μM and 5 μM, as measured in the MAGL assays described herein.

In one embodiment, the present invention provides compounds of formula (I) and their pharmaceutically acceptable salts or esters as described herein, wherein said compounds of formula (I) and their pharmaceutically acceptable salts or esters have an $IC_{50}$ for MAGL below 25 μM, preferably below 10 μM, more preferably below 5 μM as measured in an assay comprising the steps of:

a) providing a solution of a compound formula (I), or a pharmaceutically acceptable salt or ester thereof, in DMSO;
b) providing a solution of MAGL (recombinant wild-type) in assay buffer (50 mM tris(hydroxymethyl) aminomethane; 1 mM ethylenediaminetetraacetic acid);
c) adding 1 μL of compound solution from step a) to 19 μL of MAGL solution from step b);
d) shaking the mixture for 1 min at 2000 rpm;
e) incubating for 15 min at RT;
f) adding 20 μL of a solution of 4-nitrophenylacetate in assay buffer (50 mM tris(hydroxymethyl)aminomethane; 1 mM ethylenediaminetetraacetic acid, 6% EtOH);
g) shaking the mixture for 1 min at 2000 rpm;
h) incubating for 5 min at RT;
i) measuring the absorbance of the mixture at 405 nm a first time;
j) incubating a further 80 min at RT;
k) measuring the absorbance of the mixture at 405 nm a second time;
l) subtracting the absorbance measured under i) from the absorbance measured under k) and calculating the slope of absorbance;

wherein:

i) the concentration of the compound of formula (I), or the pharmaceutically acceptable salt or ester thereof in the assay after step f) is in the range of 25 μM to 1.7 nM;
ii) the concentration of MAGL in the assay after step f) is 1 nM;
iii) the concentration of 4-nitrophenylacetate in the assay after step f) is 300 μM; and
iv) steps a) to 1) are repeated for at least 3 times, each time with a different concentration of the compound of formula (I), or the pharmaceutically acceptable salt or ester thereof.

Using the Compounds of the Invention

In one aspect, the present invention provides compounds of formula (I) as described herein for use as therapeutically active substance.

In a further aspect, the present invention provides the use of compounds of formula (I) as described herein for the treatment or prophylaxis of neuroinflammation, neurodegenerative diseases, pain, cancer and/or mental disorders in a mammal.

In one embodiment, the present invention provides the use of compounds of formula (I) as described herein for the treatment or prophylaxis of neuroinflammation and/or neurodegenerative diseases in a mammal.

In one embodiment, the present invention provides the use of compounds of formula (I) as described herein for the treatment or prophylaxis of neurodegenerative diseases in a mammal.

In one embodiment, the present invention provides the use of compounds of formula (I) as described herein for the treatment or prophylaxis of cancer in a mammal.

In one aspect, the present invention provides the use of compounds of formula (I) as described herein for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a preferred embodiment, the present invention provides the use of compounds of formula (I) as described herein for the treatment or prophylaxis of multiple sclerosis, Alzheimer's disease and/or Parkinson's disease in a mammal.

In a particularly preferred embodiment, the present invention provides the use of compounds of formula (I) as described herein for the treatment or prophylaxis of multiple sclerosis in a mammal.

In one aspect, the present invention provides compounds of formula (I) as described herein for use in the treatment or prophylaxis of neuroinflammation, neurodegenerative diseases, pain, cancer and/or mental disorders in a mammal.

In one embodiment, the present invention provides compounds of formula (I) as described herein for use in the treatment or prophylaxis of neuroinflammation and/or neurodegenerative diseases in a mammal.

In one embodiment, the present invention provides compounds of formula (I) as described herein for use in the treatment or prophylaxis of cancer in a mammal.

In one embodiment, the present invention provides compounds of formula (I) as described herein for use in the treatment or prophylaxis of neurodegenerative diseases in a mammal.

In one aspect, the present invention provides compounds of formula (I) as described herein for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a preferred embodiment, the present invention provides compounds of formula (I) as described herein for use in the treatment or prophylaxis of multiple sclerosis, Alzheimer's disease and/or Parkinson's disease in a mammal.

In a particularly preferred embodiment, the present invention provides compounds of formula (I) as described herein for use in the treatment or prophylaxis of multiple sclerosis in a mammal.

In one aspect, the present invention provides the use of compounds of formula (I) as described herein for the preparation of a medicament for the treatment or prophylaxis of neuroinflammation, neurodegenerative diseases, pain, cancer and/or mental disorders in a mammal.

In one embodiment, the present invention provides the use of compounds of formula (I) as described herein for the preparation of a medicament for the treatment or prophylaxis of neuroinflammation and/or neurodegenerative diseases in a mammal.

In one embodiment, the present invention provides the use of compounds of formula (I) as described herein for the preparation of a medicament for the treatment or prophylaxis of neurodegenerative diseases in a mammal.

In one embodiment, the present invention provides the use of compounds of formula (I) as described herein for the preparation of a medicament for the treatment or prophylaxis of cancer in a mammal.

In a further aspect, the present invention provides the use of compounds of formula (I) as described herein for the preparation of a medicament for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a preferred embodiment, the present invention provides the use of compounds of formula (I) as described herein for the preparation of a medicament for the treatment or prophylaxis of multiple sclerosis, Alzheimer's disease and/or Parkinson's disease in a mammal.

In a particularly preferred embodiment, the present invention provides the use of compounds of formula (I) as described herein for the preparation of a medicament for the treatment or prophylaxis of multiple sclerosis in a mammal.

In one aspect, the present invention provides a method for the treatment or prophylaxis of neuroinflammation, neurodegenerative diseases, pain, cancer and/or mental disorders in a mammal, which method comprises administering an effective amount of a compound of formula (I) as described herein to the mammal.

In one embodiment, the present invention provides a method for the treatment or prophylaxis of neuroinflammation and/or neurodegenerative diseases in a mammal, which method comprises administering an effective amount of a compound of formula (I) as described herein to the mammal.

In one embodiment, the present invention provides a method for the treatment or prophylaxis of neurodegenerative diseases in a mammal, which method comprises administering an effective amount of a compound of formula (I) as described herein to the mammal.

In one aspect, the present invention provides a method for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression and/or pain in a mammal, which method comprises administering an effective amount of a compound of formula (I) as described herein to the mammal.

In a preferred embodiment, the present invention provides a method for the treatment or prophylaxis of multiple sclerosis, Alzheimer's disease and/or Parkinson's disease in a mammal, which method comprises administering an effective amount of a compound of formula (I) as described herein to the mammal.

In a particularly preferred embodiment, the present invention provides a method for the treatment or prophylaxis of multiple sclerosis in a mammal, which method comprises administering an effective amount of a compound of formula (I) as described herein to the mammal.

Pharmaceutical Compositions and Administration

In one aspect, the present invention provides a pharmaceutical composition comprising a compound of formula (I) as described herein and a therapeutically inert carrier.

The compounds of formula (I) and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

Method A1

Example 4

(4aR,8aS)-6-(6-(2-Fluoro-4-(trifluoromethoxy)phenoxy)-2-azaspiro[3.3]heptane-2-carbonyl)hexahydro-2H-pyrido[4,3-b][1,4]oxazin-3(4H)-one

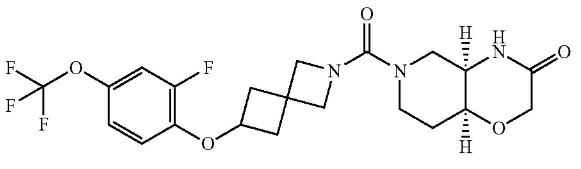 [SMILES: O=C1CO[C@H]2CCN(C(=O)N3CC4(CC(Oc5ccc(OC(F)(F)F)cc5F)C4)C3)C[C@H]2N1]

To a solution of BB9 (143.7 mg, 284 μmol) in ACN (1.42 mL) was added DIPEA (110 mg, 149 μl, 851 μmol) and 4-nitrophenyl (4aR,8aS)-3-oxohexahydro-2H-pyrido[4,3-b][1,4]oxazine-6(5H)-carboxylate (91.1 mg, 284 μmol, BB2a). The reaction vial was stirred at 80° C. for 4 h. The crude material was purified by reversed-phase HPLC to yield the title compound (66.8 mg, 134 μmol, 47.3%) as a white solid. MS (ESI): m/z=474.3 $[M+H]^+$.

Method A2

Example 1

(4aR,8aS)-6-(6-(2-Chloro-4-fluorophenoxy)-2-azaspiro[3.3]heptane-2-carbonyl)hexahydro-2H-pyrido[4,3-b][1,4]oxazin-3(4H)-one

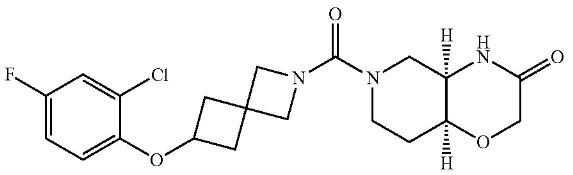 [SMILES: O=C1CO[C@H]2CCN(C(=O)N3CC4(CC(Oc5ccc(F)cc5Cl)C4)C3)C[C@H]2N1]

To a solution of 6-(2-chloro-4-fluorophenoxy)-2-azaspiro[3.3]heptane trifluoroacetate (1026 mg, 2.31 mmol, BB6) in ACN (11.5 mL) was added DIPEA (895 mg, 1.21 mL, 6.92 mmol) and 4-nitrophenyl (4aR,8aS)-3-oxohexahydro-2H-pyrido[4,3-b][1,4]oxazine-6(5H)-carboxylate (816 mg, 2.54 mmol, BB2a). The reaction vial was stirred at 80° C. for 2.5 h. The solution was evaporated. The residue was dissolved in saturated aqueous $NaHCO_3$ solution (30 mL) and EtOAc (30 mL) and the layers were separated. The organic layer was washed once with saturated aqueous $NaHCO_3$ solution (30 mL). The combined aqueous layers were extracted once with EtOAc (100 mL). The organic layers were washed once with saturated aqueous $NaHCO_3$ solution (100 mL) and brine, dried over $MgSO_4$, filtered, treated with silica gel and evaporated. The compound was purified by silica gel chromatography on a 40 g column using a MPLC system eluting with a gradient of n-heptane:EtOAc/EtOH 3/1 (70:30 to 0:100) and evaporated to afford the title compound as a white foam (841.2 mg, 1.94 mmol, 84.3%). MS (ESI): m/z=424.4 $[M+H]^+$.

Method A3

Example 18 rac-(4aR,8aS)—N—((R)-8-(3-oxooctahydro-2H-pyrido[4,3-b][1,4]oxazine-6-carbonyl)-1-oxa-8-azaspiro[4.5]decan-3-yl)benzenesulfonamide

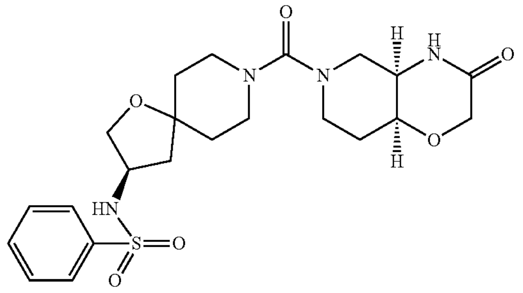 [SMILES: O=C1CO[C@H]2CCN(C(=O)N3CCC4(CC3)C[C@@H](NS(=O)(=O)c3ccccc3)CO4)C[C@H]2N1]

To an ice-cold suspension of bis(trichloromethyl) carbonate (45.3 mg, 153 μmol) and $NaHCO_3$ (73.3 mg, 873 μmol) in DCM (1 mL) was added (R)—N-(1-oxa-8-azaspiro[4.5]decan-3-yl)benzenesulfonamide 2,2,2-trifluoroacetate (89.6 mg, 218 μmol, prepared as described in US20170029390) in one portion and the mixture was stirred at RT overnight. It was cooled down in an-ice bath and rac-(4aR,8aS)-hexahydro-2H-pyrido[4,3-b][1,4]oxazin-3(4H)-one dihydrochloride (50 mg, 218 μmol, BB1) and DIPEA (113 mg, 152

µL, 873 µmol) were added. The suspension was stirred at RT for 4 h. The reaction mixture was poured on water and DCM and the layers were separated. The aqueous layer was extracted twice with DCM. The organic layers were dried over $MgSO_4$, filtered, treated with silica gel and evaporated. The product was purified on a preparative HPLC (Gemini NX column) using a gradient of ACN:water (containing 0.1% formic acid) (20:80 to 98:2) to yield the desired compound as a colorless gum (0.025 g; 23.9%). MS (ESI): m/z=479.2 $[M+H]^+$.

Method A4

Example 22

A round-bottom flask was heat gun-dried under HV, back filled with argon and charged with bis(trichloromethyl) carbonate (39.9 mg, 134 µmol) and sodium bicarbonate (64.5 mg, 768 µmol). DCM (2 mL) was added to give a suspension. (4aR,8aS)-hexahydro-2H-pyrido[4,3-b][1,4]oxazin-3(4H)-one (30 mg, 192 µmol) was added to the suspension at 0° C. The mixture was stirred at 0° C. for 5 min and at RT for 20 hours. BB22 (84.6 mg, 192 µmol) and DIPEA (99.3 mg, 134 µL, 768 µmol) were added. The resulting off-white suspension was stirred at RT for 1 hour. The reaction mixture was poured into 5 mL $H_2O$ and extracted with DCM (2×10 mL). The organic layers were combined, washed with brine, dried over $Na_2SO_4$ and concentrated in vacuo. The crude material was purified by flash chromatography (silica gel, 10 g, 0% to 10% MeOH in DCM). Fractions were combined and evaporated to yield the product as white foam, 69 mg, 70% yield.

Method A5

Chiral Separation of Stereoisomers with NR Column

The two stereoisomers of rac-(4aR,8aS)-6-(3-((2-chloro-4-fluorobenzyl)(methyl)amino)-1-oxa-8-azaspiro[4.5]decane-8-carbonyl)hexahydro-2H-pyrido[4,3-b][1,4]oxazin-3(4H)-one (Examples 33 and 34) were separated by preparative chiral HPLC (Reprosil Chiral NR column) using an isocratic mixture of EtOH (containing 0.05% of $NH_4OAc$):n-heptane (40:60). Absolute stereochemistry of isomers not determined.

Method A6

Chiral Separation of Stereoisomers with OD Column

The two stereoisomers of rac-(4aR,8aS)-6-(3-((2-Chloro-4-fluorobenzyl)amino)-1-oxa-8-azaspiro[4.5]decane-8-carbonyl)hexahydro-2H-pyrido[4,3-b][1,4]oxazin-3(4H)-one (Example 38) were separated by preparative chiral HPLC (Reprosil Chiral OD column) using an isocratic mixture of EtOH (containing 0.05% of $NH_4OAc$):n-heptane (40:60). Absolute stereochemistry of isomers not determined.

Method A7

Preparative HPLC: Gemini NX, 12 nm, 5 µm, 100×30 mm column, 15 min run time, gradient 25-45-60-100% ACN in water+0.1% HCOOH Method A5

Preparative HPLC: YMC-Triart C18, 12 nm, 5 µm, 100×30 mm column, 11 min run time, gradient 30-50-60-100% ACN in water+0.1% HCOOH Method A9

Preparative HPLC: Gemini NX, 12 nm, 5 µm, 100×30 mm column, gradient ACN in water+0.1% TEA Method A10

Preparative HPLC: YMC-Triart C18, 12 nm, 5 µm, 100×30 mm column, 11 min run time, gradient 20-40-60-100% ACN in water+0.1% TEA Method A11

Preparative HPLC: YMC-Triart C18, 12 nm, 5 µm, 100×30 mm column, 11 min run time, gradient 15-35-50-100% ACN in water+0.1% HCOOH The following examples were prepared from the corresponding building blocks and methods as outlined in Table 2.

TABLE 2

| Ex. | Systematic Name/Structure | Building block(s) | MS, m/z | Method |
|---|---|---|---|---|
| 2 | (4aR,8aS)-6-(6-(4-(Trifluoromethyl)phenoxy)-2-azaspiro[3.3]heptane-2-carbonyl)hexahydro-2H-pyrido[4,3-b][1,4]oxazin-3(4H)-one 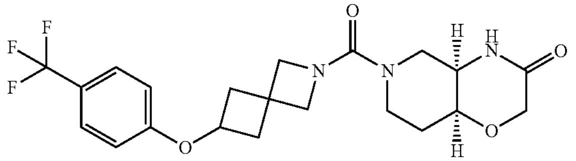 | BB2a and BB6 | 440.3 $[M + H]^+$ | A1 |
| 3 | (4aR,8aS)-6-(6-(2-Fluoro-4-(trifluoromethyl)phenoxy)-2-azaspiro[3.3]-heptane-2-carbonyl)hexahydro-2H-pyrido-[4,3-b][1,4]oxazin-3(4H)-one 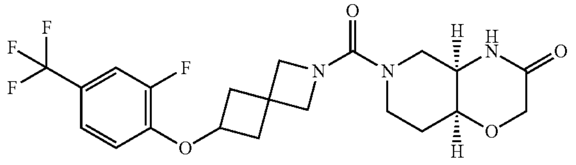 | BB2a and BB7 | 458.4 $[M + H]^+$ | A2 |

TABLE 2-continued

| Ex. | Systematic Name/Structure | Building block(s) | MS, m/z | Method |
|---|---|---|---|---|
| 5 | (4aR,8aS)-6-(6-(2-Chloro-4-(trifluoromethoxy)phenoxy)-2-azaspiro[3.3]-heptane-2-carbonyl)hexahydro-2H-pyrido[4,3-b][1,4]oxazin-3(4H)-one 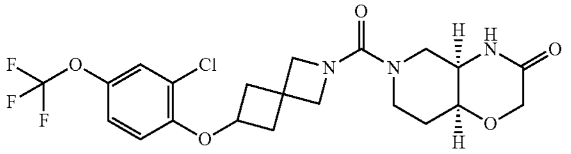 | BB2a and BB9 | 490.4 [M + H]$^+$ | A1 |
| 6 | (4aR,8aS)-6-(6-(2-Methoxy-5-(trifluoromethyl)phenoxy)-2-azaspiro[3.3] heptane-2-carbonyl)hexahydro-2H-pyrido[4,3-b][1,4]oxazin-3(4H)-one 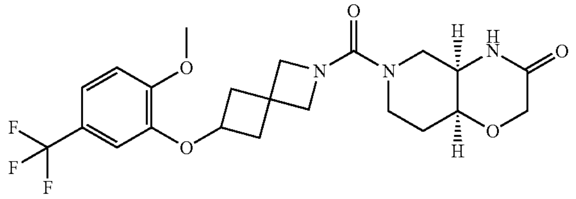 | BB2a and BB10 | 470.3 [M + H]$^+$ | A1 |
| 7 | (4aR,8aS)-6-(6-(4-Chloro-2-(trifluoromethyl)phenoxy)-2-azaspiro[3.3]-heptane-2-carbonyl)hexahydro-2H-pyrido[4,3-b][1,4]oxazin-3(4H)-one 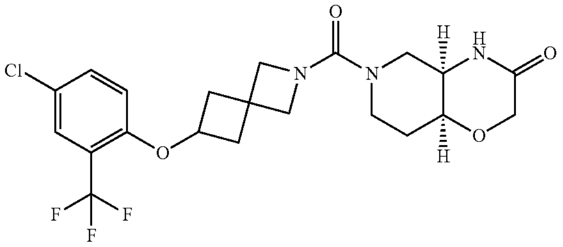 | BB2a and BB11 | 474.3 [M + H]$^+$ | A1 |
| 8 | (4aR,8aS)-6-(6-(2,4-Difluorophenoxy)-2-azaspiro[3.3]heptane-2-carbonyl)hexahydro-2H-pyrido[4,3-b][1,4]oxazin-3(4H)-one 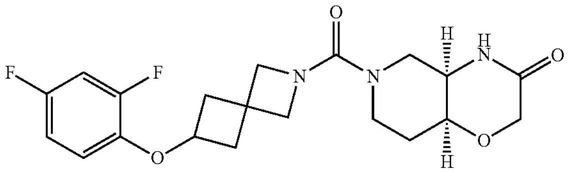 | BB2a and BB12 | 408.3 [M + H]$^+$ | A1 |
| 9 | (4aR,8aS)-6-(6-(3-Fluoro-5-(trifluoromethyl)phenoxy)-2-azaspiro[3.3]-heptane-2-carbonyl)hexahydro-2H-pyrido[4,3-b][1,4]oxazin-3(4H)-one 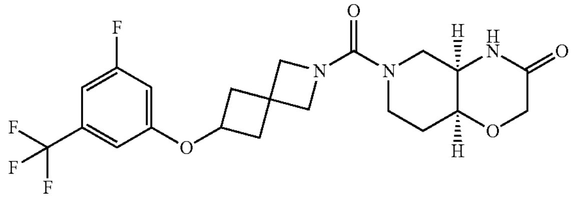 | BB2a and BB13 | 458.4 [M + H]$^+$ | A1 |
| 10 | (4aR,8aS)-6-(2-(2-Fluoro-4-(trifluoromethyl)phenoxy)-7-azaspiro[3.5]-nonane-7-carbonyl)hexahydro-2H-pyrido[4,3-b][1,4]oxazin-3(4H)-one 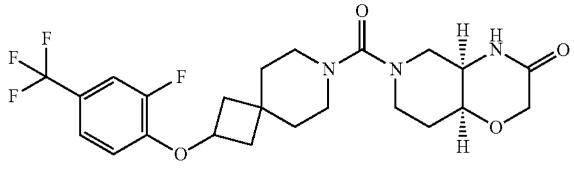 | BB2a and BB14 | 486.4 [M + H]$^+$ | A1 Heat for 14 h |

TABLE 2-continued

| Ex. | Systematic Name/Structure | Building block(s) | MS, m/z | Method |
|---|---|---|---|---|
| 11 | (4aR,8aS)-6-(6-(2-Chloro-4-fluorobenzyl)-2,6-diazaspiro[3.3]heptane-2-carbonyl)hexahydro-2H-pyrido[4,3-b][1,4]oxazin-3(4H)-one 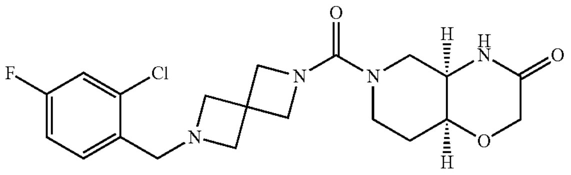 | BB2a and BB15 | 423.3 $[M + H]^+$ | A1 |
| 12 | (4aR,8aS)-6-(6-(2-Fluoro-4-(trifluoromethyl)benzyl)-2,6-diazaspiro[3.3]-heptane-2-carbonyl)hexahydro-2H-pyrido[4,3-b][1,4]oxazin-3(4H)-one 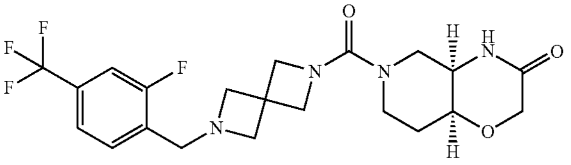 | BB2a and BB16 | 457.3 $[M + H]^+$ | A1 |
| 13 | (4aR,8aS)-6-(2-(2-Fluoro-4-(trifluoromethyl)benzyl)-2,7-diazaspiro[3.5]-nonane-7-carbonyl)hexahydro-2H-pyrido[4,3-b][1,4]oxazin-3(4H)-one 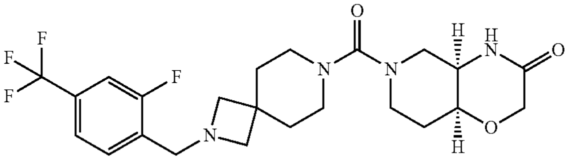 | BB2a and BB17 | 485.4 $[M + H]^+$ | A1 |
| 14 | (4aR,8aS)-6-(7-(2-Fluoro-4-(trifluoromethyl)benzyl)-2,7-diazaspiro[4.4]-nonane-2-carbonyl)hexahydro-2H-pyrido[4,3-b][1,4]oxazin-3(4H)-one 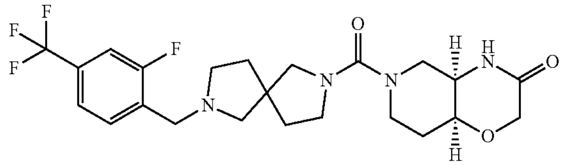 | BB2a and BB18 | 485.4 $[M + H]^+$ | A1 |
| 15 | (4aR,8aS)-6-(2-(2-Fluoro-4-(trifluoromethyl)benzyl)-2,6-diazaspiro[3.4]-octane-6-carbonyl)hexahydro-2H-pyrido[4,3-b][1,4]oxazin-3(4H)-one 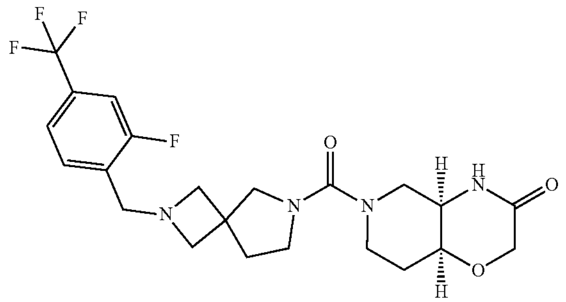 | BB2a and BB19 | 471.4 $[M + H]^+$ | A1 |

TABLE 2-continued

| Ex. | Systematic Name/Structure | Building block(s) | MS, m/z | Method |
| --- | --- | --- | --- | --- |
| 16 | (4aR,8aS)-6-(6-((2-Chloro-4-fluorophenyl)sulfonyl)-2,6-diazaspiro[3.3]-heptane-2-carbonyl)hexahydro-2H-pyrido[4,3-b][1,4]oxazin-3(4H)-one 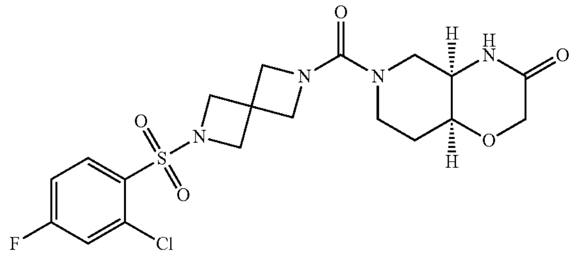 | BB2a and BB20 | 473.3 [M + H]+ | A1 |
| 17 | (4aR,8aS)-6-(6-((2-Fluoro-4-(trifluoromethyl)phenyl)sulfonyl)-2,6-diazaspiro[3.3]heptane-2-carbonyl)hexahydro-2H-pyrido[4,3-b][1,4]-oxazin-3(4H)-one 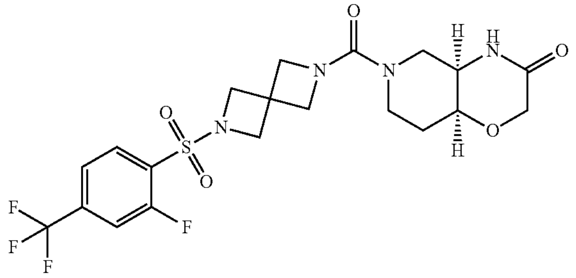 | BB2a and BB21 | 507.3 [M + H]+ | A1 |
| 19 | rac-(4aR,8aS)-N-((S)-8-(3-oxooctahydro-2H-pyrido[4,3-b][1,4]-oxazine-6-carbonyl)-1-oxa-8-azaspiro[4.5]decan-3-yl)benzene-sulfonamide 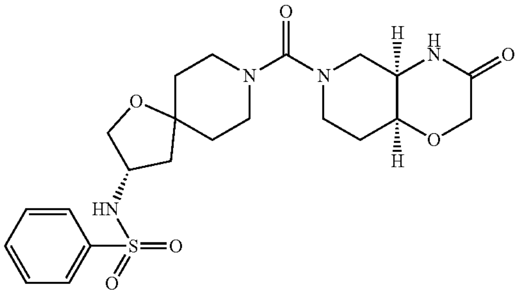 | BB1 and (S)-N-(1-oxa-8-azaspiro-[4.5]decan-3-yl)-benzene-sulfonamide 2,2,2-trifluoro-acetate (prepared as described in US20170029390) | 479.2 [M + H]+ | A3 |
| 20 | rac-(4aR,8aS)-6-(2-Benzhydryl-2,6-diazaspiro[3.4]octane-6-carbon-yl)hexahydro-2H-pyrido[4,3-b][1,4]oxazin-3(4H)-one 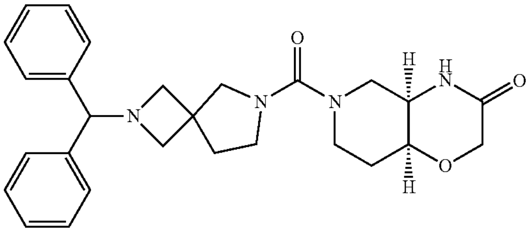 | BB1 and 2-Benzhydryl-2,6-diazaspiro-[3.4]octane (CAS RN 1250443-61-8) | 461.3 [M + H]+ | A3 |

TABLE 2-continued

| Ex. | Systematic Name/Structure | Building block(s) | MS, m/z | Method |
|---|---|---|---|---|
| 21 | rac-(4aR,8aS)-6-(4-((4-Fluorophenyl)sulfonyl)-1-oxa-4,9-diazaspiro[5.5]undecane-9-carbonyl)hexahydro-2H-pyrido[4,3-b][1,4]oxazin-3(4H)-one 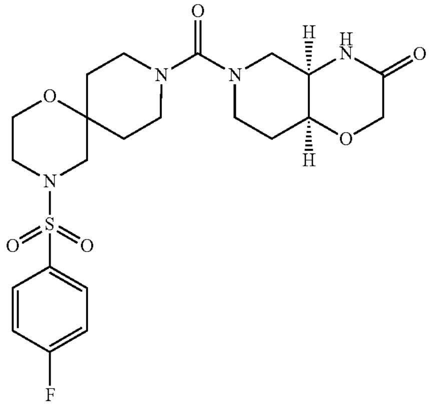 | BB1 and 4-((4-Fluorophenyl)-sulfonyl)-1-oxa-4,9-diazaspiro[5.5]-undecane 2,2,2-trifluoroacetate (prepared as described in U.S. Pat. Appl. Publ., 20170029390) | 497.2 [M + H]+ | A3 |
| Int-1 | rac-tert-Butyl 6-((4aR,8aS)-3-oxooctahydro-2H-pyrido[4,3-b][1,4]-oxazine-6-carbonyl)-2,6-diazaspiro[3.4]octane-2-carboxylate 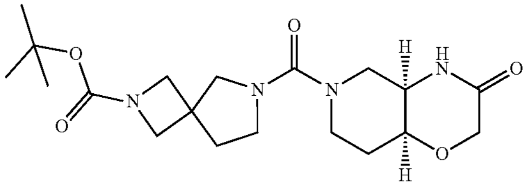 | BB1 and tert-Butyl 2,6-diazaspiro-[3.4]octane-2-carboxylate (CAS RN 885270-84-8) | 395.2 [M + H]+ | A3 |
| 23 | (4aR,8aS)-6-(6-((5,6-Bis(trifluoromethyl)pyridin-2-yl)oxy)-2-azaspiro-[3.3]heptane-2-carbonyl)hexahydro-2H-pyrido[4,3-b][1,4]oxazin-3(4H)-one Chiral 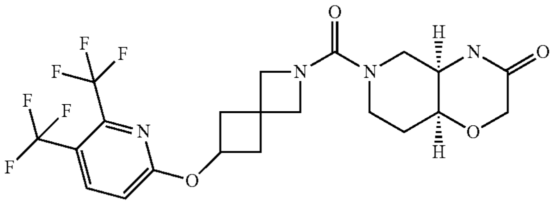 | BB1a and BB23 | 509.16 [M + H]+ | A4 |
| 24 | 2-Chloro-4-fluoro-N-methyl-N-((R)-8-((4aR,8aS)-3-oxooctahydro-2H-pyrido[4,3-b][1,4]oxazine-6-carbonyl)-1-oxa-8-azaspiro[4.5]decan-3-yl)benzenesulfonamide Chiral 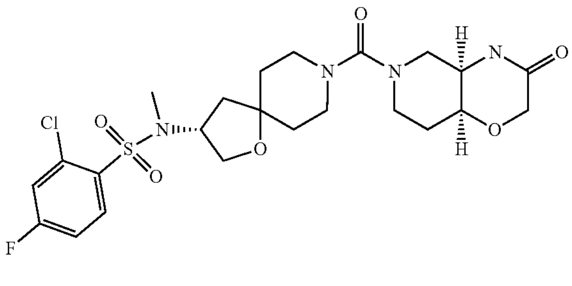 | BB1a and BB24 | 545.2 [M + H]+ | A4 |

TABLE 2-continued

| Ex. | Systematic Name/Structure | Building block(s) | MS, m/z | Method |
|---|---|---|---|---|
| 25 | (4aR,8aS)-6-(6-((5-Trifluoromethyl)pyridin-2-yl)oxy)-2-azaspiro[3.3]-heptane-2-carbonyl)hexahydro-2H-pyrido[4,3-b][1,4]oxazin-3(4H)-one<br>Chiral<br>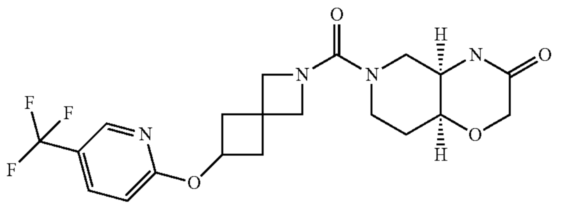 | BB1a and BB25 | 441.18 [M + H]+ | A4 |
| 26 | (4aR,8aS)-6-(6-((4-Methyl-3-(trifluoromethyl)benzyl)oxy)-2-azaspiro-[3.3]heptane-2-carbonyl)hexahydro-2H-pyrido[4,3-b][1,4]oxazin-3(4H)-one<br>Chiral<br>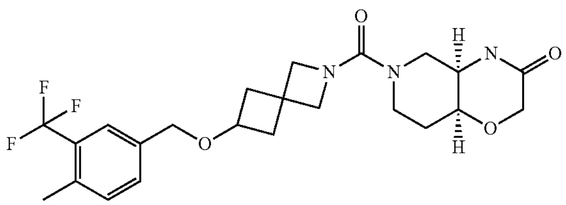 | BB1a and BB26 | 468.20 [M + H]+ | A4 |
| 27 | (4aR,8aS)-6-(2-((2-Chloro-4-fluorophenyl)sulfonyl)-2,7-diazaspiro[3.5]-nonane-7-carbonyl)hexahydro-2H-pyrido[4,3-b][1,4]oxazin-3(4H)-one<br>Chiral<br>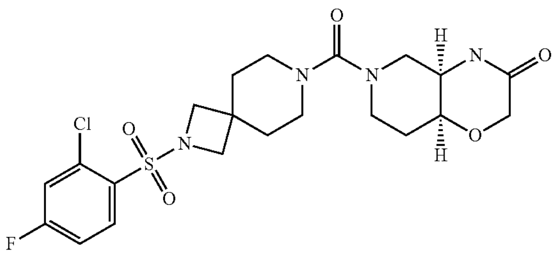 | BB1a and BB27 | 501.1 [M + H]+ | A4 |
| 28 | (4aR,8aS)-6-(6-((2-Fluoro-4-(trifluoromethyl)benzyl)oxy)-2-azaspiro[3.3]-heptane-2-carbonyl)hexahydro-2H-pyrido[4,3-b][1,4]oxazin-3(4H)-one<br>Chiral<br>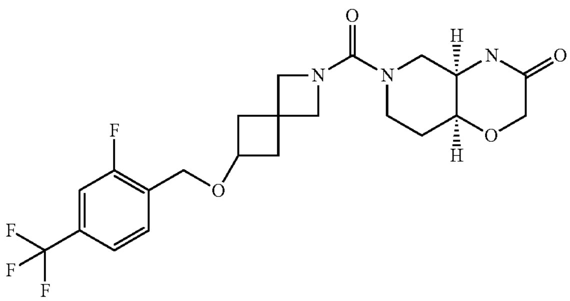 | BB1a and BB28 | 472.2 [M + H]+ | A4 |

TABLE 2-continued

| Ex. | Systematic Name/Structure | Building block(s) | MS, m/z | Method |
|---|---|---|---|---|
| 29 | N-((S)-8-((4aR,8aS)-3-Oxooctahydro-2H-pyrido[4,3-b][1,4]oxazine-6-carbonyl)-1-oxa-8-azaspiro[4.5]decan-3-yl)-4-(trifluoromethyl)-benzenesulfonamide<br>Chiral<br>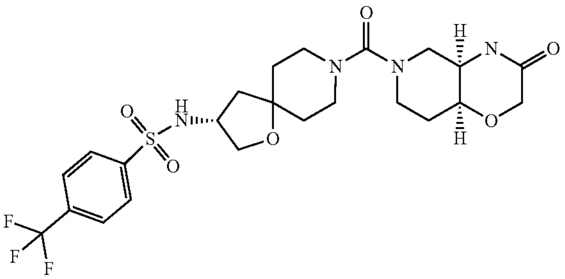 | BB1a and BB29 | 547.2 $[M + H]^+$ | A4 |
| 30 | N-Methyl-N-((R)-8-((4aR,8aS)-3-oxooctahydro-2H-pyrido[4,3-b]-[1,4]oxazine-6-carbonyl)-1-oxa-8-azaspiro[4.5]decan-3-yl)-benzenesulfonamide<br>Chiral<br>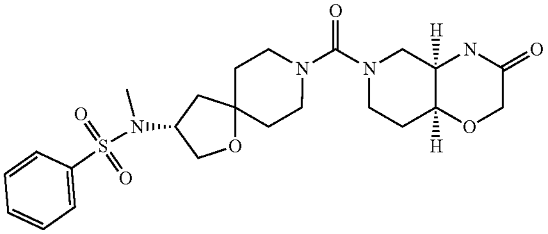 | BB1a and BB30 | 493.2 $[M + H]^+$ | A4 |
| 31 | 2-Chloro-4-fluoro-N-((S)-8-((4aR,8aS)-3-oxooctahydro-2H-pyrido[4,3-b]-[1,4]oxazine-6-carbonyl)-1-oxa-8-azaspiro[4.5]decan-3-yl)benzene-sulfonamide<br>Chiral<br>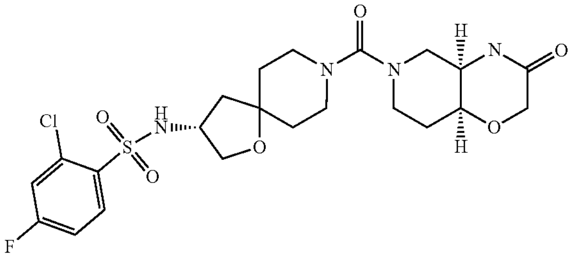 | BB1a and BB31 | 531.2 $[M + H]^+$ | A4 |
| 32 | N-((S)-8-((4aR,8aS)-3-Oxooctahydro-2H-pyrido[4,3-b][1,4]oxazine-6-carbonyl)-1-oxa-8-azaspiro[4.5]decan-3-yl)-3-(trifluoromethyl)-benzenesulfonamide<br>Chiral<br>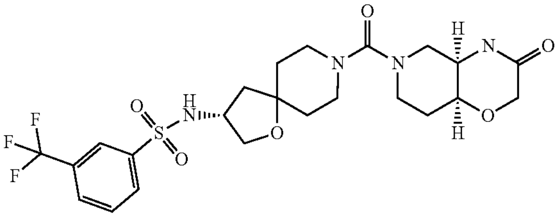 | BB1a and BB32 | 547.3 $[M + H]^+$ | A4 |

TABLE 2-continued

| Ex. | Systematic Name/Structure | Building block(s) | MS, m/z | Method |
|---|---|---|---|---|
| 33 | (4aR,8aS)-6-(3-((2-Chloro-4-fluorobenzyl)(methyl)amino)-1-oxa-8-azaspiro[4.5]decane-8-carbonyl)hexahydro-2H-pyrido[4,3-b][1,4]-oxazin-3(4H)-one (Epimer A)<br>Chiral<br>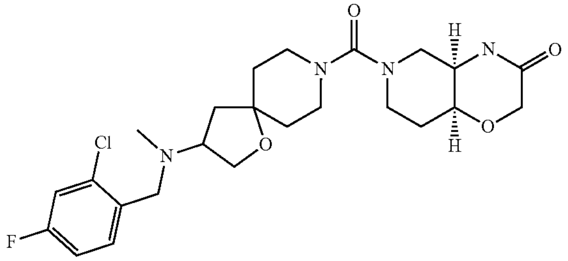 | BB1a and BB33 | 495.22 [M + H]+ | A4, then chiral HPLC; Method A5 |
| 34 | (4aR,8aS)-6-(3-((2-Chloro-4-fluorobenzyl)(methyl)amino)-1-oxa-8-azaspiro[4.5]decane-8-carbonyl)hexahydro-2H-pyrido[4,3-b][1,4]-oxazin-3(4H)-one (Epimer B)<br>Chiral<br>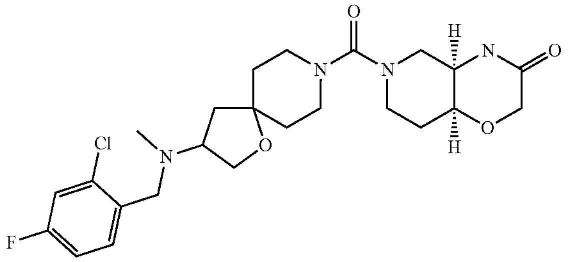 | BB1a and BB33 | 495.22 [M + H]+ | A4, then chiral HPLC: Method A5 |
| 35 | (4aR,8aS)-6-(3-((2-Chloro-4-fluorobenzyl)amino)-1-oxa-8-azaspiro[4.5]-decane-8-carbonyl)hexahydro-2H-pyrido[4,3-b][1,4]oxazin-3(4H)-one Epimer A<br>Chiral<br>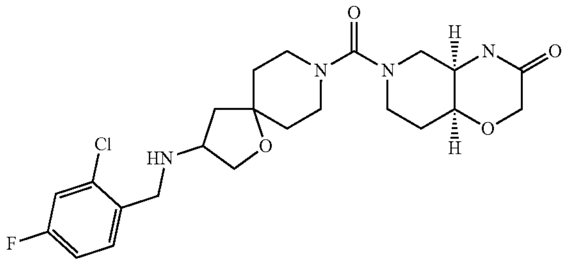 | BB1a and BB34 | 481.2 [M + H]+ | A4, then chiral HPLC: Method A6 |
| 36 | (4aR,8aS)-6-(3-((2-Chloro-4-fluorobenzyl)amino)-1-oxa-8-azaspiro[4.5]-decane-8-carbonyl)hexahydro-2H-pyrido[4,3-b][1,4]oxazin-3(4H)-one Epimer B<br>Chiral<br>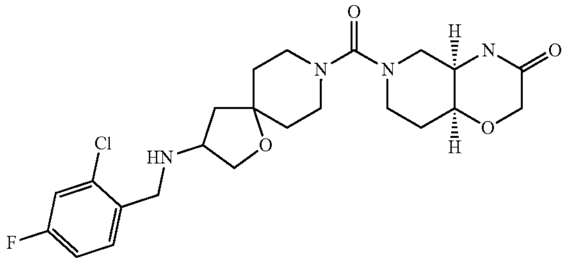 | BB1a and BB34 | 481.2 [M + H]+ | A4, then chiral HPLC: Method A6 |

TABLE 2-continued

| Ex. | Systematic Name/Structure | Building block(s) | MS, m/z | Method |
|---|---|---|---|---|
| 37 | (4aR,8aS)-6-(2-((4-(Trifluoromethyl)phenyl)sulfonyl)-2,7-diazaspiro[3.5]-nonane-7-carbonyl)hexahydro-2H-pyrido[4,3-b][1,4]oxazin-3(4H)-one<br>Chiral<br>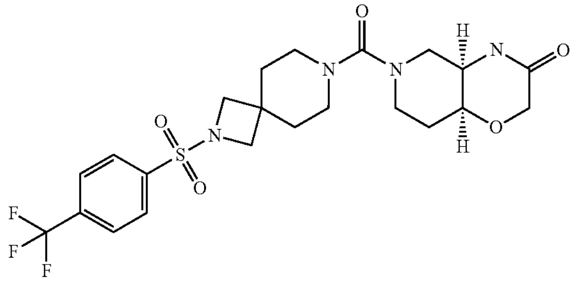 | BB1a and BB35 | 517.1 [M + H]$^+$ | A4 |
| 38 | rac-(4aR,8aS)-6-(3-((2-Chloro-4-fluorobenzyl)amino)-1-oxa-8-azaspiro-[4.5]decane-8-carbonyl)hexahydro-2H-pyrido[4,3-b][1,4]oxazin-3(4H)-one<br>Chiral<br>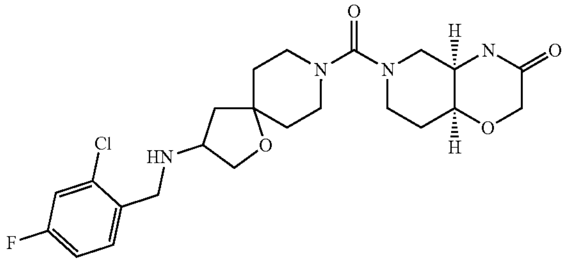 | BB1a and BB34 | 481.2 [M + H]$^+$ | A4 |
| 39 | (4aR,8aS)-6-(2-(Phenylsulfonyl)-2,7-diazaspiro[3.5]nonane-7-carbonyl)-hexahydro-2H-pyrido[4,3-b][1,4]oxazin-3(4H)-one<br>Chiral<br>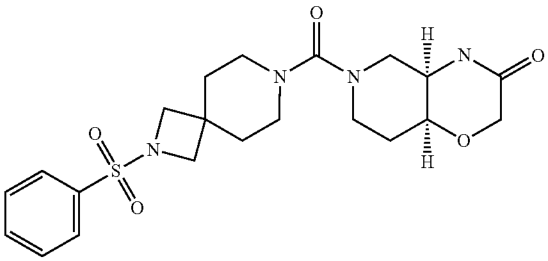 | BB1 and BB36 | 449.1 [M + H]$^+$ | A4 |
| 40 | (4aR,8aS)-6-[2-(2,4-difluorophenoxy)-7-azaspiro[3.5]nonane-7-carbon-yl]-4,4a,5,7,8,8a-hexahydropyrido[4,3-b][1,4]oxazin-3-one<br>Chiral<br>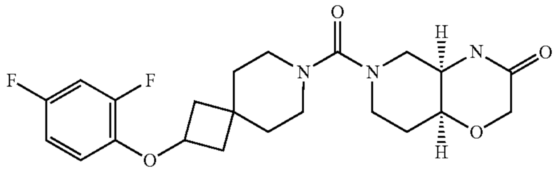 | BB1a and BB37 | 436.3 [M + H]$^+$ | A4 |

TABLE 2-continued

| Ex. | Systematic Name/Structure | Building block(s) | MS, m/z | Method |
|---|---|---|---|---|
| 41 | (4aS,8aR)-6-(6-(2-Chloro-4-fluorophenoxy)-2-azaspiro[3.3]heptane-2-carbonyl)hexahydro-2H-pyrido[4,3-b][1,4]oxazin-3(4H)-one<br>Chiral<br>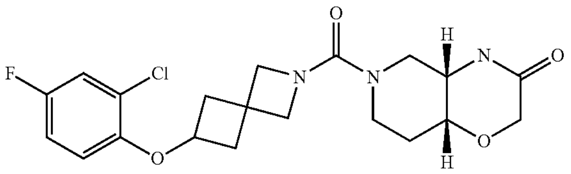 | BB1b and BB5 | 424.2 [M + H]$^+$ | A2 |
| 42 | (4aR,8aS)-6-[2-(2-chloro-4-fluoro-phenoxy)-7-azaspiro[3.5]nonane-7-carbonyl]-4,4a,5,7,8,8a-hexadropyrido[4,3-b][1,4]oxazin-3-one<br>Chiral<br>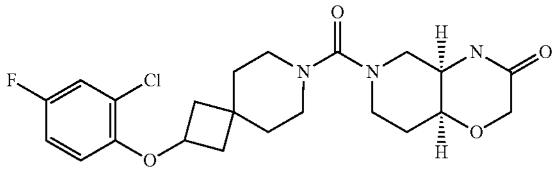 | BB1a and BB38 | 452.8 [M + H]$^+$ | A4 |
| 43 | (4aR,8aS)-6-[6-[[2-Fluoro-4-(trifluoromethyl)phenoxy]methyl]-2-azaspiro-[3.3]heptane-2-carbonyl]-4,4a,5,7,8,8a-hexahydropyrido[4,3-b][1,4]oxazin-3-one<br>Chiral<br>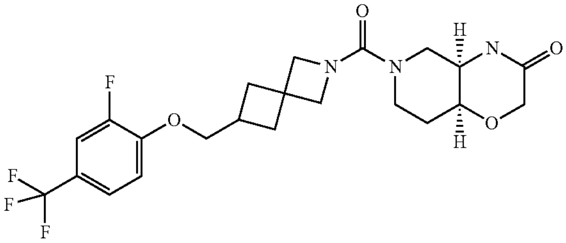 | BB1a and BB39 | 472.19 [M + H]$^+$ | A4 |
| 44 | (4aR,8aS)-6-(6-((2-fluoro-4-(trifluoromethyl)benzyl)oxy)-6-(trifluoro-methyl)-2-azaspiro[3.3]heptane-2-carbonyl)hexahydro-2H-pyrido[4,3-b][1,4]oxazin-3(4H)-one<br>Chiral<br>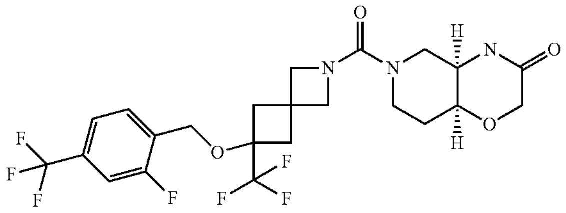 | BB1a and BB40 | 540.17 [M + H]$^+$ | A3 |

TABLE 2-continued

| Ex. | Systematic Name/Structure | Building block(s) | MS, m/z | Method |
|---|---|---|---|---|
| 45 | (4aR,8aS)-6-(6-(2-fluoro-4-(trifluoromethyl)phenyl)-2-azaspiro-[3.3]heptane-2-carbonyl)hexahydro-2H-pyrido[4,3-b][1,4]oxazin-3(4H)-one Chiral 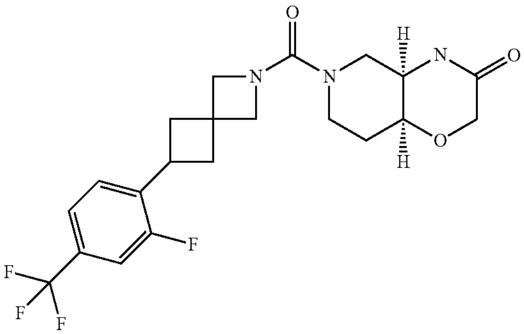 | Bb1a and BB41 | 442.17 $[M + H]^+$ | A4 + A7 |
| 46 | (4aR,8aS)-6-(6-(4-(pentafluoro-16-sulfaneyl)phenyl)-2-azaspiro-[3.3]heptane-2-carbonyl)hexahydro-2H-pyrido[4,3-b][1,4]oxazin-3(4H)-one Chiral 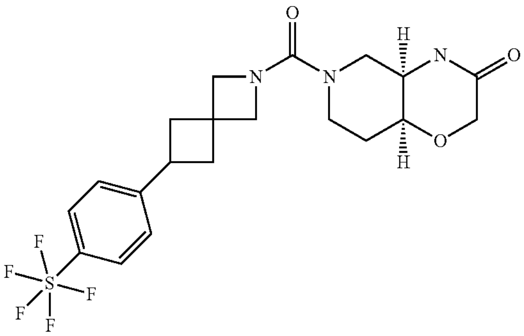 | BB1a and CAS 2059985-86-1 | 482.15 $[M + H]^+$ | A3 + A8 |
| 49 | (4aR,8aS)-6-(6-(2-fluoro-4-(trifluoromethyl)benzyl)-2-azaspiro[3.3]-heptane-2-carbonyl)hexahydro-2H-pyrido[4,3-b][1,4]oxazin-3(4H)-one Chiral 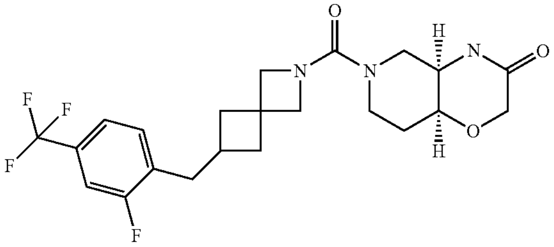 | BB1a and BB42 | 456.19 $[M + H]^+$ | A4 |

TABLE 2-continued

| Ex. | Systematic Name/Structure | Building block(s) | MS, m/z | Method |
|---|---|---|---|---|
| 50 | (4aR,8aS)-6-(6-(2-chloro-4-fluorobenzyl)-2-azaspiro[3.3]heptane-2-carbonyl)hexahydro-2H-pyrido[4,3-b][1,4]oxazin-3(4H)-one<br>Chiral<br>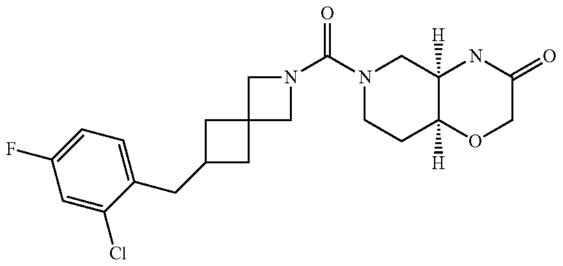 | BB1 and BB43 | 422.16 [M + H]+ | A4 |
| 51 | (4aR,8aS)-6-(6-(2,4-difluorobenzyl)-2-azaspiro[3.3]heptane-2-carbonyl)hexahydro-2H-pyrido[4,3-b][1,4]oxazin-3(4H)-one<br>Chiral<br>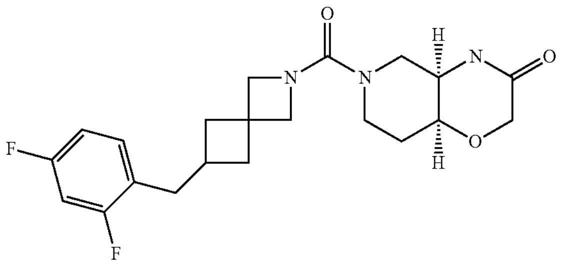 | BB1a and BB44 | 406.19 [M + H]+ | A4 |
| 52 | (4aR,8aS)-6-(6-(2-methoxy-4-(trifluoromethyl)benzyl)-2-azaspiro[3.3]-heptane-2-carbonyl)hexahydro-2H-pyrido[4,3-b][1,4]oxazin-3(4H)-one<br>Chiral<br>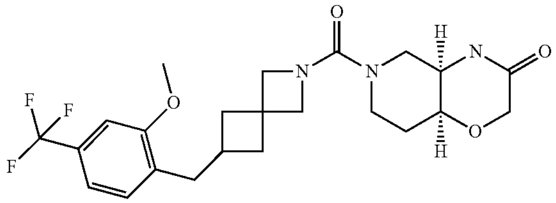 | BB1a and BB45 | 468.21 [M + H]+ | A4 |
| 53 | (4aR,8aS)-6-(6-(2-fluoro-6-(trifluoromethyl)benzyl)-2-azaspiro-[3.3]heptane-2-carbonyl)hexahydro-2H-pyrido[4,3-b][1,4]-oxazin-3(4H)-one<br>Chiral<br>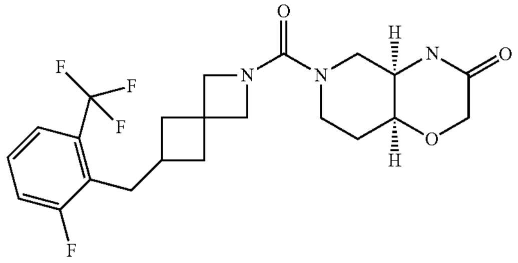 | BB1a and BB46 | 456.19 [M + H]+ | A4 |

TABLE 2-continued

| Ex. | Systematic Name/Structure | Building block(s) | MS, m/z | Method |
|---|---|---|---|---|
| 54 | (4aR,8aS)-6-(6-((2-chloro-4-fluorophenyl)methyl)-2-azaspiro[3.3]-heptane-2-carbonyl)hexahydro-2H-pyrido[4,3-b][1,4]oxazin-3(4H)-one<br>Chiral<br>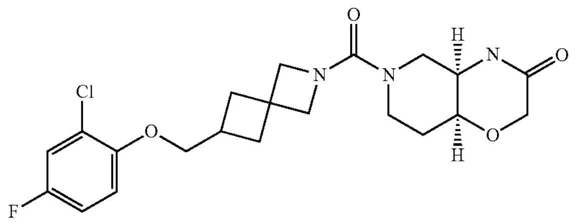 | BB1a and BB47 | 438.2 [M + H]$^+$ | A4 + A9 |
| 55 | (4aR,8aS)-6-(6-(4-(trifluoromethyl)phenyl)-2,6-diazaspiro[3.3]-heptane-2-carbonyl)hexahydro-2H-pyrido[4,3-b][1,4]oxazin-3(4H)-one<br>Chiral<br>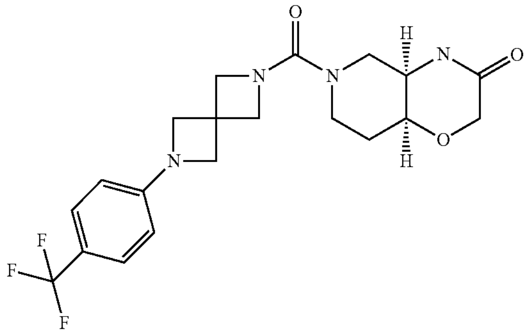 | BB1a and CAS 1609024-22-7 | 425.1 [M + H]$^+$ | A4 + A10 |
| 56 | (4aR,8aS)-6-(6-(3-(trifluoromethyl)phenyl)-2,6-diazaspiro-[3.3]heptane-2-carbonyl)hexahydro-2H-pyrido[4,3-b][1,4]-oxazin-3(4H)-one<br>Chiral<br>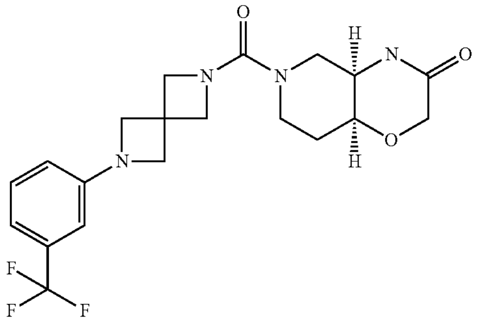 | BB1a + BB48 | 425.1 [M + H]$^+$ | A4 + A8 |
| 57 | (4aR,8aS)-6-(2-(4-trifluoromethyl)phenyl)-2,6-diazaspiro[3.4]octane-6-carbonyl)hexahydro-2H-pyrido[4,3-b][1,4]oxazin-3(4H)-one<br>Chiral<br>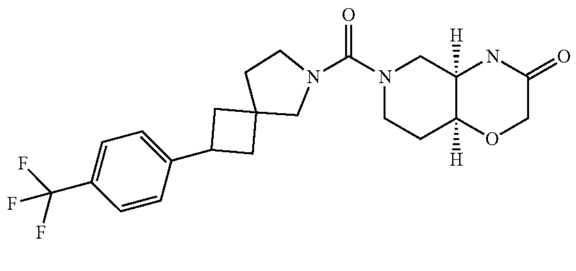 | BBa + CAS 1785600-00-1 | 439.3 [M + H]$^+$ | A4 + A9 |

TABLE 2-continued

| Ex. | Systematic Name/Structure | Building block(s) | MS, m/z | Method |
|---|---|---|---|---|
| 58 | (4aR,8aS)-6-(2-(3-(trifluoromethyl)phenyl)-2,6-diazaspiro[3.4]-octane-6-carbonyl)hexahydro-2H-pyrido[4,3-b][1,4]oxazin-3(4H)-one<br>Chiral<br>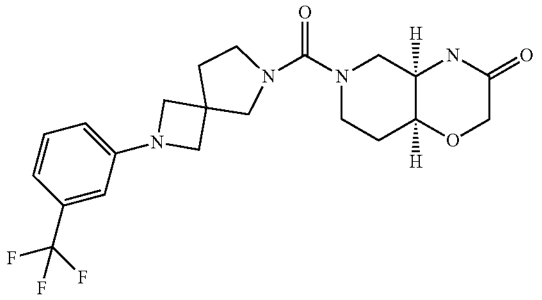 | BB1a + CAS 1782337-64-7 | 439.3 $[M + H]^+$ | A4 + A9 |
| 59 | (4aR,8aS)-6-(2-(4-isopropoxyphenyl)-2,6-diazaspiro[3.4]octane-6-carbonyl)hexahydro-2H-pyrido[4,3-b][1.4]oxazin-3(4H)-one<br>Chiral<br>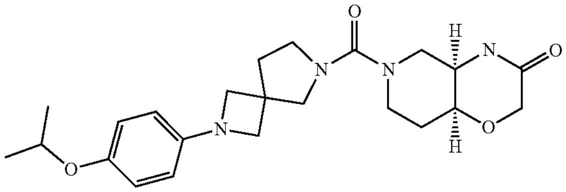 | BB1a + CAS 1785235-75-7 | 429.3 $[M + H]^+$ | A4 + A11 |
| 60 | (4aR,8aS)-6-(6-(4-isopropoxyphenyl)-2,6-diazaspiro[3.3]heptane-2-carbonyl)hexahydro-2H-pyrido[4,3-b][1,4]oxazin-3(4H)-one<br>Chiral<br>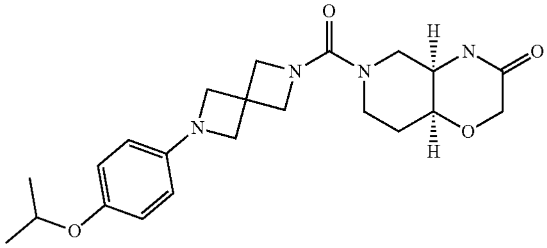 | BB2a + BB49 | 415.3 $[M + H]^+$ | A1 + A10 |
| 61 | (4aR,8aS)-6-(2-(4-(2-oxopyrrolidin-1-yl)phenyl)-2,6-diazaspiro[3.4]-octane-6-carbonyl)hexahydro-2H-pyrido[4,3-b][1,4]oxazin-3(4H)-one<br>Chiral<br>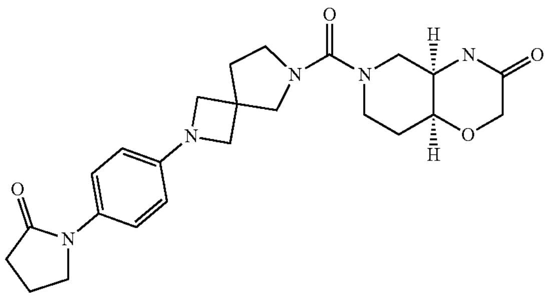 | BB2a + BB50 | 454.3 $[M + H]^+$ | A1 + A7 |

TABLE 2-continued

| Ex. | Systematic Name/Structure | Building block(s) | MS, m/z | Method |
|---|---|---|---|---|
| 62 | (4aR,8aS)-6-(2-(4-methoxy-3-methylphenyl)-2,6-diazaspiro[3.4]octane-6-carbonyl)hexahydro-2H-pyrido[4,3-b][1,4]oxazin-3(4H)-one<br>Chiral<br>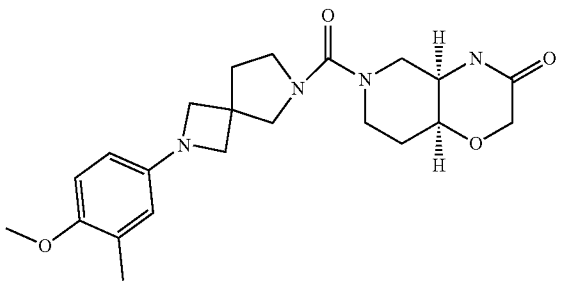 | BB2a + BB51 | 415.3 [M + H]$^+$ | A1 + A10 |
| 63 | (4aR,8aS)-6-(2-(4-chloro-3-(trifluoromethyl)phenyl)-2,6-diazaspiro-[3.4]octane-6-carbonyl)hexahydro-2H-pyrido[4,3-b][1,4]oxazin-3(4H)-one<br>Chiral<br>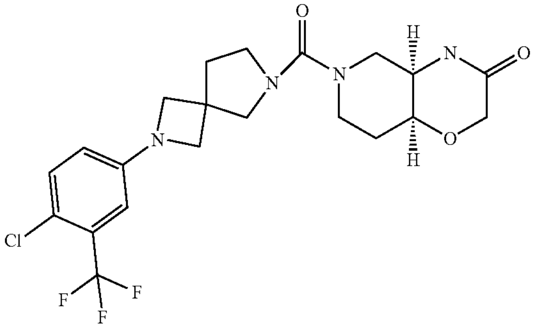 | BB2a + BB52 | 473.2 [M + H]$^+$ | A1 + A7 |
| 64 | (4aR,8aS)-6-(2-(2-fluoropyridin-4-yl)-2,6-diazaspiro[3.4]octane-6-carbonyl)hexahydro-2H-pyrido[4,3-b][1,4]oxazin-3(4H)-one<br>Chiral<br>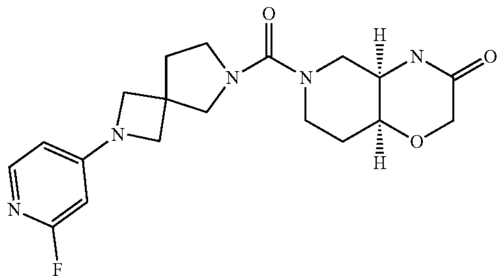 | BB2a + BB53 | 390.2 [M + H]$^+$ | A1 + A10 |
| 65 | (4aR,8aS)-6-(6-(2,5-bis(trifluoromethyl)phenyl)-2,6-diazaspiro[3.3]-heptane-2-carbonyl)hexahydro-2H-pyrido[4,3-b][1,4]oxazin-3(4H)-one<br>Chiral<br>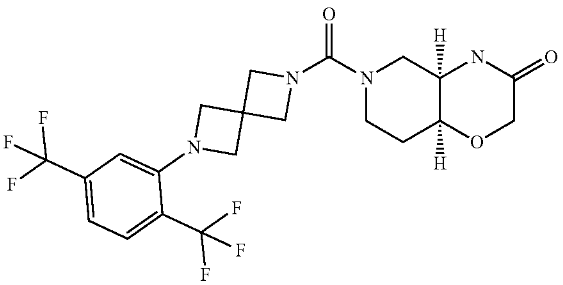 | BB2a + BB54 | 493.3 [M + H]$^+$ | A1 + A10 |

TABLE 2-continued

| Ex. | Systematic Name/Structure | Building block(s) | MS, m/z | Method |
|---|---|---|---|---|
| 66 | (4aR,8aS)-6-(6-((4-fluoro-2-(trifluoromethyl)phenyl)sulfonyl)-2,6-diazaspiro[3.3]heptane-2-carbonyl)hexahydro-2H-pyrido[4,3-b][1,4]-oxazin-3(4H)-one<br>Chiral<br>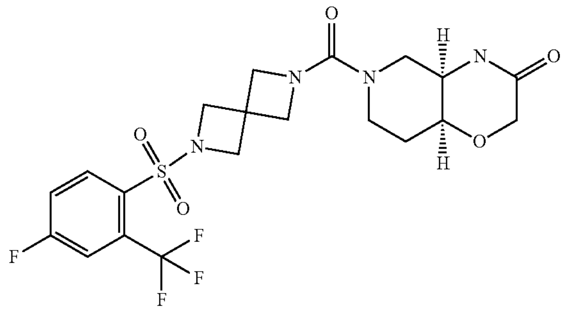 | BB2a + BB55 | 507.2 [M + H]$^+$ | A1 + A9 |
| 67 | (4aR,8aS)-6-(6-((2-chloro-4-fluorophenyl)sulfonyl)-2-azaspiro[3.3]-heptane-2-carbonyl)hexahydro-2H-pyrido[4,3-b][1,4]oxazin-3(4H)-one<br>Chiral<br>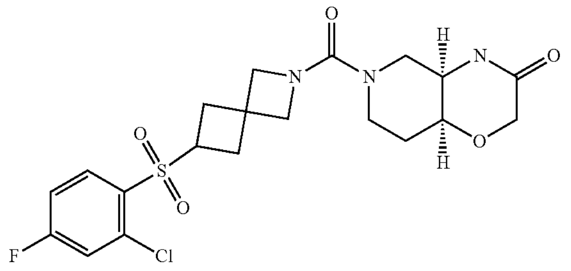 | BB2a + BB56 | 472.1 [M + H]$^+$ | A1 + A9 |
| 68 | (4aR,8aS)-6-(6-((3-chloro-4-(trifluoromethyl)phenyl)sulfonyl)-2,6-diazaspiro[3.3]heptane-2-carbonyl)hexahydro-2H-pyrido[4,3-b][1,4]-oxazin-3(4H)-one<br>Chiral<br>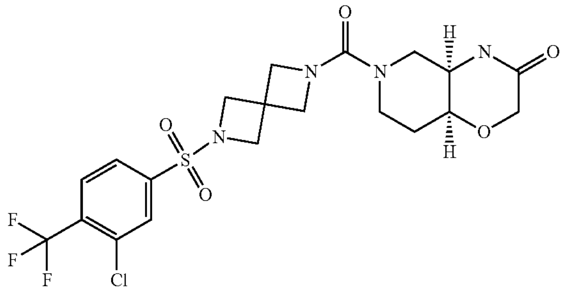 | BB2a + BB57 | 523.2 [M + H]$^+$ | A1 + A7 |

TABLE 2-continued

| Ex. | Systematic Name/Structure | Building block(s) | MS, m/z | Method |
|---|---|---|---|---|
| 69 | (4aR,8aS)-6-(6-((2,4-bis(trifluoromethyl)phenyl)sulfonyl)-2,6-diazaspiro-[3.3]heptane-2-carbonyl)hexahydro-2H-pyrido[4,3-b][1,4]oxazin-3(4H)-one<br>Chiral<br>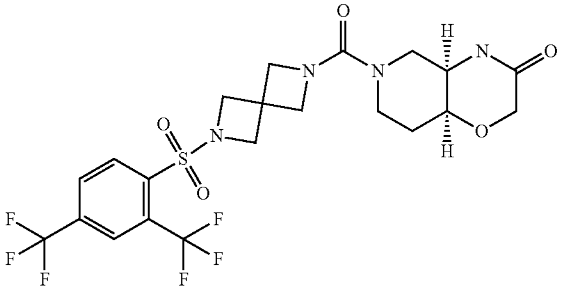 | BB2a + BB58 | 557.2 [M + H]$^+$ | A1 + A7 |
| 70 | (4aR,8aS)-6-(6-(2,6-difluorobenzyl)-2-azaspiro[3.3]heptane-2-carbonyl)hexahydro-2H-pyrido[4,3-b][1,4]oxazin-3(4H)-one<br>Chiral<br>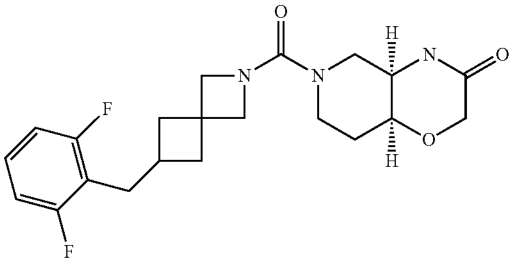 | BB1a + BB59 | 406.19 [M + H]$^+$ | A4 |
| 71 | (4aR,8aS)-6-(6-(2-fluoro-6-methoxybenzyl)-2-azaspiro[3.3]-heptane-2-carbonyl)hexahydro-2H-pyrido[4,3-b][1,4]oxazin-3(4H)-one<br>Chiral<br>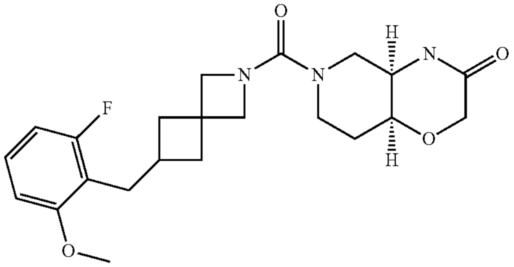 | BB1a + BB60 | 418.24 [M + H]$^+$ | A4 |
| 72 | (4aR,8aS)-6-(6-(2-methoxybenzyl)-2-azaspiro[3.3]heptane-2-carbonyl)hexahydro-2H-pyrido[4,3-b][1,4]oxazin-3(4H)-one<br>Chiral<br>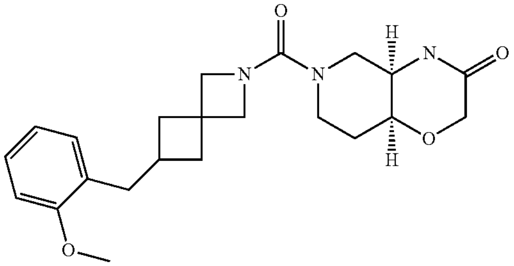 | BB1a + BB61 | 400.2 [M + H]$^+$ | A4 |

TABLE 2-continued

| Ex. | Systematic Name/Structure | Building block(s) | MS, m/z | Method |
|---|---|---|---|---|
| 73 | (4aR,8aS)-6-(6-(2-fluoro-6-hydroxybenzyl)-2-azaspiro[3.3]-heptane-2-carbonyl)hexahydro-2H-pyrido[4,3-b][1,4]oxazin-3(4H)-one<br>Chiral<br>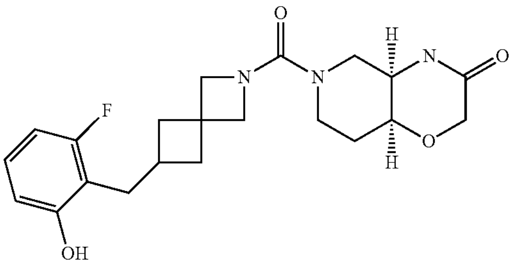 | BB1a + BB62 | 404.19 [M + H]+ | A4 |
| 74 | (4aR,8aS)-6-(6-(2-hydroxybenzyl)-2-azaspiro[3.3]heptane-2-carbonyl)hexahydro-2H-pyrido[4,3-b][1,4]oxazin-3(4H)-one<br>Chiral<br>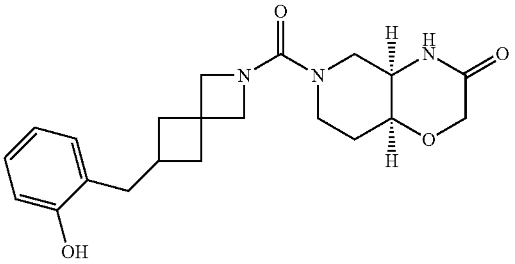 | BB1a + BB63 | 386.20 [M + H]+ | A4 |

Example 47

(4aR,8aS)-6-(6-(4-(2-(trifluoromethyl)pyrrolidin-1-yl)phenyl)-2-azaspiro[3.3]heptane-2-carbonyl)hexahydro-2H-pyrido[4,3-b][1,4]oxazin-3(4H)-one

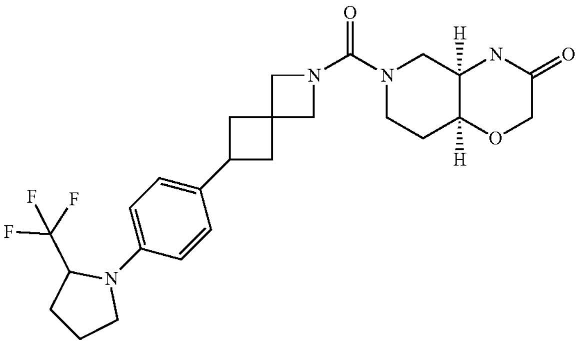

To a suspension of (4aR,8aS)-6-(6-(4-bromophenyl)-2-azaspiro[3.3]heptane-2-carbonyl)hexahydro-2H-pyrido[4,3-b][1,4]oxazin-3(4H)-one (0.050 g, 115 μmol) and 2-(trifluoromethyl)pyrrolidine (16 mg, 115 μmol) in tert-Butanol (1 ml) under argon were added XPhos (4.94 mg, 10.4 μmol, Eq: 0.09), Pd2(dba)3·$CHCl_3$ (3.57 mg, 3.45 μmol) and cesium carbonate (150 mg, 460 μmol) and the mixture was heated in a microwave to 100° C. for 30 min. The mixture was filtered, the filtrate was evaporated. The product was purified by prep HPLC (Gemini NX, 12 nm, 5 μm, 100×30 mm, gradient of acetonitrile/water+0.1% TEA)yielding the desired product as 2.1 mg of a yellow oil. MS (ESI): m/z=493.4 $[M+H]^+$.

Step a) 6-(4-bromophenyl)-2-azaspiro[3.3]heptane trifluoroacetate was obtained in analogy to BB41 from tert-butyl 6-bromo-2-azaspiro[3.3]heptane-2-carboxylate (1 eq) and 1,4-dibromobenzene (2 eq). MS (ESI): m/z=298.1 $[M-56-H]^+$.

Step b) (4aR,8aS)-6-(6-(4-bromophenyl)-2-azaspiro[3.3]heptane-2-carbonyl)hexahydro-2H-pyrido[4,3-b][1,4]oxazin-3(4H)-one Synthesized in analogy to general method A4 from 6-(4-bromophenyl)-2-azaspiro[3.3]heptane trifluoroacetate and BB1a, purified by flash chromatography (silica gel, 0% to 10% MeOH in DCM). MS (ESI): m/z=434.2 $[M+H]^+$.

Example 48

(4aR,8aS)-6-(6-(4-(1-methyl-1H-pyrazol-5-yl)phenyl)-2-azaspiro[3.3]heptane-2-carbonyl)hexahydro-2H-pyrido[4,3-b][1,4]oxazin-3(4H)-one

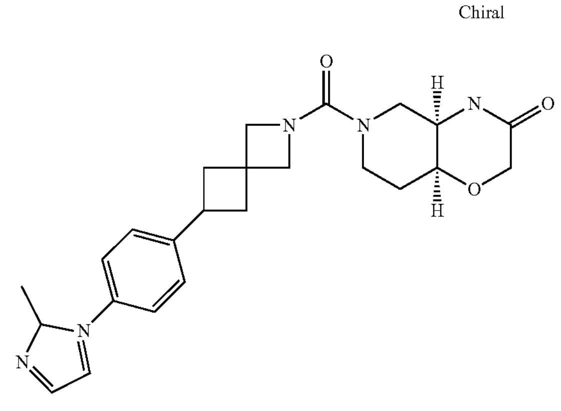

(4aR,8aS)-6-(6-(4-bromophenyl)-2-azaspiro[3.3]heptane-2-carbonyl)hexahydro-2H-pyrido[4,3-b][1,4]oxazin-3(4H)-one (0.050 g, 115 μmol), (1-methyl-1H-pyrazol-5-yl)boronic acid (14.5 mg, 115 μmol), potassium carbonate (79.5 mg, 576 μmol) and tetrakis(triphenylphosphine)palladium(0) (6.65 mg, 5.76 μmol) were dissolved in THF (1.5 ml)/water (0.150 ml) under argon, and stirred at 80° C. for 2 days. The reaction mixture was poured into 10 mL $H_2O$ and extracted with EtOAc (2×20 mL). The organic layers were combined, washed with brine, dried over $Na_2SO_4$ and concentrated in vacuo. The crude material was purified by preparative HPLC (YMC-Triart C18, 12 nm, 5 μm, 100×30 mm, mins run time, gradient 15-35-50-100 ACN in water+0.1% HCOOH). The product was obtained as a white lyophilized powder (15.6 mg, 31%). MS (ESI): m/z=436.4 $[M+H]^+$.

Synthesis of Building Blocks

BB1a & BB1b (+)-(4aR,8aS)-4a,5,6,7,8,8a-Hexahydro-4H-pyrido[4,3-b][1,4]oxazin-3-one (BB1a)

and (−)-(4aS,8aR)-4a,5,6,7,8,8a-Hexahydro-4H-pyrido[4,3-b][1,4]oxazin-3-one (BB1b)

The enantiomers of rac-(4aR,8aS)-hexahydro-2H-pyrido[4,3-b][1,4]oxazin-3(4H)-one dihydrochloride (BB1, 500 mg, 2.18 mmol, ChemBridge Corporation) were separated by preparative chiral HPLC (ReprosilChiral NR column) using an isocratic mixture of EtOH (containing 0.05% of $NH_4OAc$):n-heptane (30:70).

First eluting enantiomer: (+)-cis-4a,5,6,7,8,8a-Hexahydro-4H-pyrido[4,3-b][1,4]oxazin-3-one (BB1a). Yellow solid (0.150 g; 44.0%). MS (ESI): m/z=157.1 $[M+H]^+$.

Second eluting enantiomer: (−)-cis-4a,5,6,7,8,8a-Hexahydro-4H-pyrido[4,3-b][1,4]oxazin-3-one. (BB1b). Yellow solid (0.152 g; 44.6%). MS (ESI): m/z=157.1 $[M+H]^+$.

BB2a and BB2b (+)-4-Nitrophenyl (4aR,8aS)-3-oxohexahydro-2H-pyrido[4,3-b][1,4]oxazine-6(5H)-carboxylate (BB2a)

and (−)-4-Nitrophenyl (4aS,8aR)-3-oxohexahydro-2H-pyrido[4,3-b][1,4]oxazine-6(5H)-carboxylate (BB2b)

To a suspension of rac-(4aR,8aS)-hexahydro-2H-pyrido[4,3-b][1,4]oxazin-3(4H)-one; dihydrochloride salt (4.5 g, 19.6 mmol, BB1) in dry DCM (125 mL) at 0° C. was added DIPEA (6.35 g, 8.58 mL, 49.1 mmol) followed by 4-nitrophenyl carbonochloridate (4.35 g, 21.6 mmol). The reaction mixture was stirred at 0° C. for 10 min and at RT for 2 h. The crude reaction was diluted with DCM and transferred into a separating funnel for extraction with sat. aq. $Na_2CO_3$ solution. The organic phase was collected and the aqueous phase was back-extracted with DCM. The combined organic phases were dried over $Na_2SO_4$ and evaporated down to dryness to yield 6.62 g of a crude racemic product (BB2) as a yellow solid. The crude material was directly submitted for a chiral SFC separation to yield enantiomer BB2b (2.72 g, second eluting enantiomer) as a yellow solid and enantiomer BB2a (3.25 g, first eluting enantiomer) as a light beige solid but contaminated with BB2b. A further SFC chiral separation was carried out to yield 2.71 g of BB2a. MS (ESI): m/z=322.2 $[M+H]^+$ for both enantiomers.

BB3

(2R,4aR,8aS)-2-Methyl-4a,5,6,7,8,8a-hexahydro-4H-pyrido[4,3-b][1,4]oxazin-3-one

To a solution of 6-benzyl-2-methyl-5,6,7,8-tetrahydro-2H-pyrido[4,3-b][1,4]oxazin-3(4H)-one (Isomer A, 1.10 g, 4.26 mmol) in EtOAc (16 mL) and MeOH (16 mL) was added under argon Pd—C (227 mg, 213 μmol) and the suspension was stirred under a hydrogen atmosphere (balloon) at 1 bar for 24 h. The suspension was filtered over a microglass filter and washed with 20 mL EtOAc under inert gas. The filtrate was evaporated to give BB4 as a colorless solid (715 mg). MS (ESI): m/z=170.8 $[M+H]^+$. Note: Only the single enantiomer formed during the reduction. Relative conformation confirmed by proton NMR.

Step a) 2-Methyl-4H-pyrido[4,3-b][1,4]oxazin-3-one

To a solution of 3-aminopyridin-4-ol (2.5 g, 22.7 mmol) in DMF (100 mL) was added dropwise 2-chloropropanoyl chloride (3.03 g, 2.31 mL, 23.8 mmol) and the mixture was stirred at RT for 30 min. After addition of $K_2CO_3$ (7.84 g, 56.8 mmol), the suspension was heated to 100° C. (oil bath) for 20 h. The DMF was removed in vacuo, then 100 mL EtOAc were added and stirred at RT for 10 min, and it was washed with 50 mL $H_2O$, extracted 3 times with EtOAc. The organic phases were combined, dried with $MgSO_4$ and concentrated under vacuo to yield 3.72 g of 2-methyl-4H-pyrido[4,3-b][1,4]oxazin-3-one which was used in the next step without further purification.

Step b) 6-Benzyl-2-methyl-3-oxo-3,4-dihydro-2H-pyrido[4,3-b][1.4]oxazin-6-ium bromide A suspension of 2-methyl-2H-pyrido[4,3-b][1,4]oxazin-3(4H)-one (3.72 g, 22.7 mmol) in DCM (32 mL) and MeOH (8 mL) was treated with (bromomethyl)benzene (4.65 g, 3.23 mL, 27.2 mmol) and the mixture was stirred at RT for 60 h. A suspension formed, which was cooled down to 0° C., 20 mL n-hexane were added and then the precipitate was filtered. The residue was washed with 15 mL of cold DCM/n-hexan to yield the compound as an off-white solid (5.2 g). MS (ESI): m/z=255 $[M+H]^+$.

Step c) (rac)-6-Benzyl-2-methyl-5,6,7,8-tetrahydro-2H-pyrido[4,3-b][1,4]oxazin-3(4H)-one To a suspension of 6-benzyl-2-methyl-3-oxo-3,4-dihydro-2H-pyrido[4,3-b][1,4]oxazin-6-ium bromide (5.2 g, 15.5 mmol) in EtOH (38 mL) was added in portions $NaBH_4$ (763 mg, 20.2 mmol) (exothermic, 22° C. to 30° C., yellow suspension). After the exothermic reaction faded out the mixture was stirred at room temperature for 3 h, then at 60° C. for 1 h and at 22° C. for 1 h. The reaction mixture was evaporated, partitioned between $H_2O$ and EtOAc and the layers were separated. The aqueous layer was extracted once with EtOAc. The organic layers were washed twice with $H_2O$, dried over $MgSO_4$, filtered, treated with silica gel and evaporated. The compound was purified by silica gel chromatography on a 120 g column using an MPLC system eluting with a gradient of n-heptane:EtOAc (50 to 100 in 30 min.) to provide the compound as a light yellow solid (2.48 g) which could be used in the following step without further purification.

Step d) 6-Benzyl-2-methyl-5,6,7,8-tetrahydro-2H-pyrido[4,3-b][1,4]oxazin-3(4H)-one The enantiomers were separated by preparative chiral HPLC (Chiralcel OD column) using an isocratic mixture of EtOH (containing 0.05% of $NH_4OAc$):n-heptane (10:90). The fractions were evaporated to provide the desired compounds as light yellow solids (Isomer A 1.17 g, Isomer B 1.10 g).

BB4 rac-(4aS,8aS)-Hexahydro-2H-pyrido[4,3-b][1,4]oxazin-3(4H)-one rac-Benzyl (4aS,8aS)-3-oxohexahydro-2H-pyrido[4,3-b][1,4]oxazine-6(5H)-carboxylate (125 mg, 431 μmol) was dissolved in MeOH (5 mL). The reaction solution was degassed in vacuo and backfilled with argon. Pd—C (20 mg, 188 μmol) was added under an argon atmosphere. Argon was evacuated from the reaction mixture and backfilled with hydrogen. The reaction mixture was stirred at RT for 15 h under a hydrogen atmosphere. The reaction mixture was filtered through a syringe filter and concentrated in vacuo to afford the desired product as a colorless solid (62 mg, 92.2%). MS (ESI): m/z=157.098 $[M+H]^+$.

Step a) rac-Benzyl (3S,4S)-3-(2-chloroacetamido)-4-hydroxypiperidine-1-carboxylate To a stirred suspension of rac-benzyl (3S,4S)-3-amino-4-hydroxypiperidine-1-carboxylate (317 mg, 1.27 mmol, synthesized according to patent US 2011/59118 A1) and sodium acetate (208 mg, 2.53 mmol, CAS RN 127-09-3) in a mixture of acetone (4 mL)/$H_2O$ (0.5 mL) was added dropwise a solution of chloroacetyl chloride (150 mg, 107 μL, 1.33 mmol, CAS RN 79-04-9) in acetone (3 mL) between 0-5° C. After the addition the reaction mixture was stirred at RT for 1 h and subsequently evaporated to dryness giving a yellow gum. The crude product was purified by silica gel chromatography to afford the desired product as a yellow solid (385 mg, 93%). MS (ESI): m/z=325.2 $[M-H]^-$.

Step b) Benzyl rac-(4aS,8aS)-3-oxohexahydro-2H-pyrido[4,3-b][1,4]oxazine-6(5H)-carboxylate To a stirred solution of rac-benzyl (3S,4S)-3-(2-chloroacetamido)-4-hydroxypiperidine-1-carboxylate (385 mg, 1.18 mmol) in dry THF (4 mL) was added NaH (67.9 mg, 1.7 mmol) at 0° C. The mixture was allowed to reach RT and then stirred for 90 min under an argon atmosphere. $H_2O$ (5 mL) was added and stirring was continued for 10 min at RT. THF was removed in vacuo from the reaction mixture. The residue was treated with DCM and the organic phase was washed with $H_2O$ and brine, dried over $Na_2SO_4$, filtered and then concentrated in vacuo. The residue was purified by flash chromatography (12 g reversed phase column, gradient 0-100% ACN in $H_2O$ (containing 0.1% FA) to afford the desired product as a colorless solid (133 mg, 38.9%). MS (ESI): m/z=291.3 $[M+H]^+$.

BB5

6-(2-Chloro-4-fluorophenoxy)-2-azaspiro[3.3]heptane; trifluoroacetate salt

To a solution of tert-butyl 6-(2-chloro-4-fluorophenoxy)-2-azaspiro[3.3]heptane-2-carboxylate (1.5065 g, 4.41 mmol) in DCM (22 mL) was added TFA (4.02 g, 2.72 mL, 35.3 mmol) and the reaction was stirred at RT for 3.5 h. The reaction mixture was concentrated to afford the title compound as a yellow oil (2.015 g, 4.42 mmol, 100%) which was used in the next step without further purification. MS (ESI): m/z=242.2 $[M+H]^+$.

Step a) tert-Butyl 6-(2-chloro-4-fluorophenoxy)-2-azaspiro[3.3]heptane-2-carboxylate To a solution of 2-chloro-4-fluorophenol (756 mg, 562 μL, 5.16 mmol, CAS RN 1996-41-4), tert-butyl 6-hydroxy-2-azaspiro[3.3]heptane-2-carboxylate (1000 mg, 4.69 mmol, CAS RN 1147557-97-8) and triphenylphosphine (1.48 g, 5.63 mmol, CAS RN 603-35-0) in THF (23.4 mL) was added DIAD (1.14 g, 1.09 mL, 5.63 mmol, CAS RN 2446-83-5) dropwise at 0° C. and the reaction was stirred at RT for 18 h. Triphenylphosphine (738 mg, 2.81 mmol), followed by DIAD (569 mg, 547 μL, 2.81 mmol) were added and the reaction was stirred at RT for 6 h. The reaction mixture was poured into sat. aq. $NaHCO_3$ solution (50 mL) and EtOAc (30 mL) was added. The phases were separated and the aq. phase was extracted with EtOAc. The combined organic layers were washed with brine, dried over sodium sulfate, filtered and concentrated to give an orange oil. The crude product was immobilized on Isolute and purified by column chromatography (40 gr, 0 to 30% EtOAc in heptane) to afford the title compound as a yellow solid (1.51 g, 4.19 mmol, 89.3%). MS (ESI): m/z=286.2 $[M-56+H]^+$.

In analogy to BB5 and BB5 step a), intermediates 1B16-BB13 of the following table were prepared from the commercially available phenols.

| BB No. | Systematic Name | Starting material | MS, m/z |
|---|---|---|---|
| BB6 | 6-(4-(Trifluoromethyl)phenoxy)-2-azaspiro[3.3]heptane; trifluoroacetate salt | 4-(Trifluoromethyl)phenol (CAS: 402-45-9) | 258.2 $[M + H]^+$ |
| BB7 | 6-(2-Fluoro-4-(trifluoromethyl)phenoxy)-2-azaspiro[3.3]heptane; trifluoroacetate salt | 2-Fluoro-4-(trifluoromethyl)phenol (CAS: 77227-78-2) | 276.2 $[M + H]^+$ |
| BB8 | 6-(2-Fluoro-4-(trifluoromethoxy)phenoxy)-2-azaspiro[3.3]heptane; trifluoroacetate salt | 2-Fluoro-4-(trifluoromethoxy)phenol (CAS: 77227-78-2) | 292.2 $[M + H]^+$ |
| BB9 | 6-(2-Chloro-4-(trifluoromethoxy)phenoxy)-2-azaspiro[3.3]heptane; trifluoroacetate salt | 2-Chloro-4-(trifluoromethoxy)phenol (CAS: 70783-75-4) | 308.2 $[M + H]^+$ |
| BB10 | 6-(2-Methoxy-5-(trifluoromethyl)phenoxy)-2-azaspiro[3.3]heptane; trifluoroacetate salt | 2-Methoxy-5-(trifluoromethyl)phenol (CAS: 349-67-7) | 288.2 $[M + H]^+$ |
| BB11 | 6-(4-Chloro-2-(trifluoromethyl)phenoxy)-2-azaspiro[3.3]heptane; trifluoroacetate salt | 4-Chloro-2-(trifluoromethyl)phenol (CAS: 53903-51-8) | 292.2 $[M + H]^+$ |
| BB12 | 6-(2,4-Difluorophenoxy)-2-azaspiro[3.3]heptane; trifluoroacetate salt | 2,4-Difluorophenol (CAS: 367-27-1) | 226.2 $[M + H]^+$ |
| BB13 | 6-(3-Fluoro-5-(trifluoromethyl)phenoxy)-2-azaspiro[3.3]heptane; trifluoroacetate salt | 3-Fluoro-5-(trifluoromethyl) phenol (CAS: 172333-87-8) | 276.2 $[M + H]^+$ |

BB14

2-(2-Fluoro-4-trifluoromethyl)phenoxy)-7-azaspiro[3.5]nonane; trifluoroacetate salt To a solution of tert-butyl 2-(2-fluoro-4-(trifluoromethyl) phenoxy)-7-azaspiro[3.5]nonane-7-carboxylate (21.3 mg, 52.8 μmol) in DCM (520 μL) was added trifluoroacetic acid (48.2 mg, 32.5 μL, 422 μmol) and the reaction was stirred at RT for 19 h. The reaction mixture was concentrated to afford the title compound as an off-white solid (23.2 mg, 52.8 μmol, 100%) which was used in the next step without further purification. MS (ESI): m/z=304.2 $[M+H]^+$.

Step a) tert-Butyl 2-(2-fluoro-4-(trifluoromethyl) phenoxy)-7-azaspiro[3.5]nonane-7-carboxylate To a solution of 2-fluoro-4-(trifluoromethyl)phenol (41 mg, 28.7 μL, 228 μmol, CAS RN 77227-78-2), tert-butyl 2-hydroxy-7-azaspiro[3.5]nonane-7-carboxylate (50 mg, 207 μmol, CAS RN 240401-28-9) and triphenylphosphine (59.8 mg, 228 μmol, CAS RN 603-35-0) in THF (1.04 mL) was added DIAD (46.1 mg, 44.3 μL, 228 μmol, CAS RN 2446-83-5) dropwise and the reaction was stirred at rt for 23 h. The reaction mixture was quenched by addition of sat. aq. $NaHCO_3$ solution. The phases were separated and the aq. phase was extracted with EtOAc. The combined organic layers were dried over sodium sulfate, filtered and concentrated to afford a colorless oil. The crude product was immobilized on Isolute and purified by column chromatography (12 gr, 0 to 30% EtOAc in n-heptane) to afford the title compound as a colorless oil (21.3 mg, 50.2 μmol, 24.2%). MS (ESI): m/z=348.2 $[M-56+H]^+$.

BB15

2-(2-Chloro-4-fluorobenzyl)-2,6-diazaspiro[3.3]heptane; trifluoroacetate salt

To a solution of tert-butyl 6-(2-chloro-4-fluorobenzyl)-2,6-diazaspiro[3.3]heptane-2-carboxylate (65.5 mg, 192 μmol) in DCM (961 μL) was added TFA (175 mg, 118 μL, 1.54 mmol) and the reaction was stirred at RT for 7 h. The reaction mixture was concentrated to afford the title compound as a yellow oil that crystallized upon standing (116.8 mg, 191 μmol, 99.4%) which was used in the next step without further purification. MS (ESI): m/z=241.1 $[M+H]^+$.

Step a) tert-Butyl 6-(2-chloro-4-fluorobenzyl)-2,6-diazaspiro[3.3]heptane-2-carboxylate To a suspension of tert-butyl 2,6-diazaspiro[3.3]heptane-2-carboxylate hemioxalate (50 mg, 204 μmol, CAS RN 1041026-71-4) and 2-chloro-4-fluorobenzaldehyde (32.4 mg, 204 μmol, CAS RN 84194-36-5) in DCE (1.02 mL) was added sodium triacetoxyborohydride (64.9 mg, 306 μmol, CAS RN 56553-60-7), and the mixture was stirred at RT for 2.5 h. The solution was diluted with EtOAc. The combined organic layers were and washed with aq. sat. $NaHCO_3$ solution. The phases were separated and the aq. layer was extracted with EtOAc washed with brine, filtered over $MgSO_4$ and evaporated to dryness to afford the title compound as a light-yellow oil (65.5 mg, 84.7%) which was used in the next step without further purification. MS (ESI): m/z=341.1 $[M+H]^+$.

BB16

2-(2-Fluoro-4-(trifluoromethyl)benzyl)-2,6-diazaspiro[3.3]heptane; trifluoroacetate salt To a solution of tert-butyl 6-(2-fluoro-4-(trifluoromethyl) benzyl)-2,6-diazaspiro[3.3]heptane-2-carboxylate (71.0 mg, 190 μmol) in DCM (948 μL) was added trifluoroacetic acid (173 mg, 117 μL, 1.52 mmol) and the reaction was stirred at RT for 17 h. The reaction mixture was concentrated to afford the title compound as a yellow oil (119.5 mg, 188 μmol, 99%) which was used without further purification in the next step. MS (ESI): m/z=275.2 $[M+H]^+$.

Step a) tert-Butyl 2-(2-fluoro-4-(trifluoromethyl) benzyl)-2,7-diazaspiro[3.5]nonane-7-carboxylate To a suspension of tert-butyl 2,6-diazaspiro[3.3]heptane-2-carboxylate hemioxalate (50 mg, 204 μmol, CAS RN 1041026-71-4) and 2-fluoro-4-(trifluoromethyl)benzaldehyde (39.2 mg, 27.8 μL, 204 μmol, CAS RN 89763-93-9) in DCE (1.0 mL) was added sodium triacetoxyborohydride (64.9 mg, 306 μmol, CAS RN 56553-60-7), and the mixture was stirred at rt for 19 h. The solution was diluted with EtOAc and washed with aq. sat. $NaHCO_3$solution. The phases were separated and the aq. layer was extracted with EtOAc. The combined organic layers were washed with brine, filtered over $MgSO_4$ and evaporated to dryness. The residue was immobilized on Isolute and purified by column chromatography (4 gr, 0 to 40% 3:1 EtOAc/EtOH in n-heptane) to afford to afford the title compound as a light-yellow oil (71.0 mg, 180 μmol, 88.2%). MS (ESI): m/z=375.3 $[M+H]^+$.

BB17

2-(2-Fluoro-4-(trifluoromethyl)benzyl)-2,7-diazaspiro[3.5]nonane

To a solution of tert-butyl 2-(2-fluoro-4-(trifluoromethyl) benzyl)-2,7-diazaspiro[3.5]nonane-7-carboxylate (79 mg, 196 μmol) in DCM (982 μL) was added trifluoroacetic acid (179 mg, 121 μL, 1.57 mmol) and the reaction was stirred at rt for 7 h. The reaction mixture was concentrated and the resulting residue was dissolved in EtOAc, washed with sat. aq. $NaHCO_3$solution and the aqueous phase was back-extracted with EtOAc three times. The combined organic layers were washed with brine, dried over sodium sulfate and concentrated to afford the title compound as a yellow oil (57.3 mg, 91.7%) which was used in the next step without further purification. MS (ESI): m/z=303.3 $[M+H]^+$.

Step a) tert-Butyl 2-(2-fluoro-4-(trifluoromethyl) benzyl)-2,7-diazaspiro[3.5]nonane-7-carboxylate To a suspension of tert-butyl 2,7-diazaspiro[3.5]nonane-7-carboxylate (50 mg, 221 μmol, CAS RN 896464-16-7) and 2-fluoro-4-(trifluoromethyl)benzaldehyde (42.4 mg, 30.1 μL, 221 μmol, CAS RN 89763-93-9) in DCE (1.1 mL) was added sodium triacetoxyborohydride (70.2 mg, 331 μmol, CAS RN 56553-60-7), and the mixture was stirred at RT for 4 h. The solution was diluted with EtOAc and washed with aq. sat. $NaHCO_3$ solution. The phases were separated and the aq. layer was extracted with EtOAc. The combined organic layers were washed with brine, filtered over $MgSO_4$ and evaporated to dryness to afford to afford the title compound as an off-white oil (79.0 mg, 80%) which was used without further purification in the next step. MS (ESI): m/z=403.4 $[M+H]^+$.

BB18

2-(2-Fluoro-4-(trifluoromethyl)benzyl)-2,7-diazaspiro[4.4]nonane

To a solution of tert-butyl 7-(2-fluoro-4-(trifluoromethyl) benzyl)-2,7-diazaspiro[4.4]nonane-2-carboxylate (123 mg, 275 μmol) in DCM (1.38 mL) was added trifluoroacetic acid (251 mg, 170 μL, 2.2 mmol) and the reaction was stirred at rt for 7 h. The reaction mixture was concentrated and the resulting residue was dissolved in EtOAc, washed with sat. aq. $NaHCO_3$solution and the aqueous phase was back-extracted with EtOAc three times. The combined organic layers were washed with brine, dried over sodium sulfate and concentrated to afford the title compound as a yellow oil (107.7 mg, 99.7%) which was used in the next step without further purification. MS (ESI): m/z=303.3 $[M+H]^+$.

Step a) tert-Butyl 7-(2-fluoro-4-(trifluoromethyl) benzyl)-2,7-diazaspiro[4.4]nonane-2-carboxylate To a suspension of tert-butyl tert-butyl 2,7-diazaspiro[4.4] nonane-2-carboxylate (83.1 mg, 367 μmol, CAS RN 236406-49-8) and 2-fluoro-4-(trifluoromethyl)benzaldehyde (70.5 mg, 0.05 mL, 367 μmol, CAS RN 89763-93-9) in DCE (1.1 mL) was added sodium triacetoxyborohydride (117 mg, 550 μmol, CAS RN 56553-60-7), and the mixture was stirred at rt for 1 h. The solution was diluted with EtOAc and washed with aq. sat. $NaHCO_3$ solution. The phases were separated and the aq. layer was extracted with EtOAc. The combined organic layers were washed with brine, filtered over $MgSO_4$ and evaporated to dryness to afford to afford the title compound as a light-yellow oil (123.0 mg, 75%) which was used in the next step without further purification. MS (ESI): m/z=403.4 $[M+H]^+$.

BB19

2-(2-Fluoro-4-(trifluoromethyl)benzyl)-2,6-diazaspiro[3.4]octane

To a solution of tert-butyl 2-(2-fluoro-4-(trifluoromethyl) benzyl)-2,6-diazaspiro[3.4]octane-6-carboxylate (147.6 mg, 361 μmol) in DCM (1.8 mL) was added trifluoroacetic acid (329 mg, 223 μL, 2.89 mmol) and the reaction was stirred at rt for 7 h. The reaction mixture was concentrated and the resulting residue was dissolved in EtOAc, washed with sat. aq. $NaHCO_3$solution and the aqueous phase was back-extracted with EWtOAc three times. The combined organic layers were washed with brine, dried over sodium sulfate and concentrated to afford the title compound as a yellow oil (84.7 mg, 77.3%) which was used without further purification in the next step. MS (ESI): m/z=289.2 $[M+H]^+$.

Step a) tert-Butyl 2-(2-fluoro-4-(trifluoromethyl) benzyl)-2,6-diazaspiro[3.4]octane-6-carboxylate To a suspension of tert-butyl 2,6-diazaspiro[3.4]octane-6-carboxylate (85.6 mg, 403 μmol, CAS RN 885270-86-0) and 2-fluoro-4-(trifluoromethyl)benzaldehyde (77.5 mg, 55 μL, 403 μmol, CAS RN 89763-93-9) in DCE (2.0 mL) was added sodium triacetoxyborohydride (128 mg, 605 μmol, CAS RN 56553-60-7), and the mixture was stirred at rt for 1 h. The solution was diluted with EtOAc and washed with aq. sat. $NaHCO_3$ solution. The phases were separated and the aq. layer was extracted with EtOAc. The combined organic layers were washed with brine, filtered over $MgSO_4$ and evaporated to dryness to afford to afford the title compound as a light-yellow oil (147.6 mg, 361 μmol, 89.5% yield) which was used in the next step without further purification. MS (ESI): m/z=389.3 $[M+H]^+$.

BB20

2-((2-Chloro-4-fluorophenyl)sulfonyl)-2,6-diazaspiro[3.3]heptane; trifluoroacetate salt To a solution of tert-butyl 6-((2-chloro-4-fluorophenyl) sulfonyl)-2,6-diazaspiro[3.3]heptane-2-carboxylate (54.7 mg, 140 μmol) in DCM (700 L) was added trifluoroacetic acid (128 mg, 86.3 μL, 1.12 mmol) and the reaction was stirred at RT for 22 h. The reaction mixture was concentrated to afford the title compound as an off-white oil (75.7 mg, 140 μmol, 100%) which was used without further purification in the next step. MS (ESI): m/z=291.2 $[M+H]^+$.

Step a) tert-Butyl 6-((2-chloro-4-fluorophenyl)sulfonyl)-2,6-diazaspiro[3.3]heptane-2-carboxylate To a suspension of tert-butyl 2,6-diazaspiro[3.3]heptane-2-carboxylate hemioxalate (50 mg, 204 μmol, CAS RN 885270-86-0) was added TEA (31 mg, 43 μL, 306 μmol), followed by 2-chloro-4-fluorobenzenesulfonyl chloride (58.5 mg, 37 μL, 255 μmol, CAS RN 85958-57-2) and the resulting clear solution was stirred at RT for 17.5 h. The reaction mixture diluted with DCM and quenched with water. The phases were separated and the aq. phase was extracted with DCM. The combined organic layers were washed with brine, dried over sodium sulfate, filtered and concentrated to afford the title compound as a white solid (54.7 mg, 65.1%) which was used in the next step without further purification. MS (ESI): m/z=335.1 $[M+H]^+$.

BB21

2-((2-Fluoro-4-(trifluoromethyl)phenyl)sulfonyl)-2,6-diazaspiro[3.3]heptane; trifluoroacetate salt To a solution of tert-butyl 6-((2-fluoro-4-(trifluoromethyl)phenyl)sulfonyl)-2,6-diazaspiro[3.3]heptane-2-carboxylate (67.6 mg, 159 μmol) in DCM (796 μL) was added TFA (145 mg, 98.2 μL, 1.27 mmol) and the reaction was stirred at RT for 20 h. The reaction mixture was concentrated to afford the title compound as a yellow oil (90 mg, 99.3%) which was used in the next step without further purification. MS (ESI): m/z=325.2 $[M+H]^+$.

Step a) tert-Butyl 6-((2-fluoro-4-(trifluoromethyl)phenyl)sulfonyl)-2,6-diazaspiro[3.3]heptane-2-carboxylate To a suspension of tert-butyl 2,6-diazaspiro[3.3]heptane-2-carboxylate hemioxalate (50 mg, 204 μmol, CAS RN 885270-86-0) in DCM was added TEA (31 mg, 42.7 μL, 306 μmol), followed by 2-fluoro-4-(trifluoromethyl)benzenesulfonyl chloride (59 mg, 225 μmol, CAS 1177009-38-9) and the resulting clear solution was stirred at RT for 18 h. The reaction mixture diluted with DCM and quenched with water. The phases were separated and the aq. phase was extracted with DCM. The combined organic layers were washed with brine, dried over sodium sulfate, filtered and concentrated to afford the title compound as a white solid (67.6 mg, 74.1%) which was used in the next step without further purification. MS (ESI): m/z=369.2 $[M+H]^+$.

BB22

6-[[4,5-bis(Trifluoromethyl)-2-pyridyl]oxy]-2-azaspiro[3.3]heptane trifluoroacetate salt To a solution of tert-butyl 6-((4,5-bis(trifluoromethyl)pyridin-2-yl)oxy)-2-azaspiro[3.3]heptane-2-carboxylate (0.334 g, 783 μmol) in $CH_2Cl2$ (5 mL) was added TFA (893 mg, 604 μl, 7.83 mmol). The resulting reaction mixture was stirred at RT for 1 hour. The reaction mixture was concentrated on high vacuum to yield 366 mg of the desired product as a light yellow oil. MS (ESI): m/z=327.2 $[M+H]^+$.

Step a) tert-Butyl 6-((4,5-bis(trifluoromethyl)pyridin-2-yl)oxy)-2-azaspiro[3.3]heptane-2-carboxylate To a solution of tert-butyl 6-hydroxy-2-azaspiro[3.3]heptane-2-carboxylate (0.2 g, 938 μmol) in dry THF (3 mL) was added potassium tert-butoxide 1M solution in THF (985 μl, 985 μmol) and the turbid reaction mixture was stirred at RT for 15 min followed by addition of 2-chloro-4,5-bis(trifluoromethyl)pyridine (234 mg, 938 μmol). The reaction mixture was then stirred at RT for 19 hours. The crude reaction was diluted with EtOAc and extracted with water, the organic phase was collected and the aqueous phase was back-extracted with EtOAc. The combined organic phases were dried over sodium sulfate and evaporated down to dryness. The crude material was purified by flash chromatography (silica gel, 20 g, 0% to 100% EtOAc in heptane). The desired product was obtained as a white solid, 334 mg. MS (ESI): m/z=371.2 [M−56+H]+

BB23

6-[[5,6-bis(trifluoromethyl)-2-pyridyl]oxy]-2-azaspiro[3.3]heptane trifluoroacetate salt To a solution of tert-butyl 6-((5,6-bis(trifluoromethyl)pyridin-2-yl)oxy)-2-azaspiro[3.3]heptane-2-carboxylate (0.376 g, 882 μmol) in $CH_2Cl_2$ (5 mL) was added TFA (1.01 g, 679 μl, 8.82 mmol). The resultant reaction mixture was stirred at RT for 1 hour. The reaction mixture was concentrated on high vacuum to yield 398 mg of the desired product as a light yellow oil. MS (ESI): m/z=327.2 $[M+H]^+$.

Step a) tert-Butyl 6-((5,6-bis(trifluoromethyl)pyridin-2-yl)oxy)-2-azaspiro[3.3]heptane-2-carboxylate To a solution of tert-butyl 6-hydroxy-2-azaspiro[3.3]heptane-2-carboxylate (0.2 g, 938 μmol) in dry THF (3 mL) was added potassium tert-butoxide 1M solution in THF (985 μl, 985 μmol) and the turbid reaction mixture was stirred at RT for 15 min followed by addition of 6-chloro-2,3-bis(trifluoromethyl)pyridine (234 mg, 938 μmol). The reaction mixture was then stirred at RT for 19 hours. The crude reaction was diluted with EtOAc and extracted with water, the organic phase was collected and the aqueous phase was back-extracted with EtOAc. The combined organic phases were dried over sodium sulfate and evaporated down to dryness. The crude material was purified by flash chromatography (silica gel, 20 g, 0% to 100% EtOAc in heptane). The desired product was obtained as a white solid, 376 mg. MS (ESI): m/z=371.2 $[M-56+H]^+$.

BB24

2-Chloro-4-fluoro-N-methyl-N-[(3R)-1-oxa-8-azaspiro[4.5]decan-3-yl]benzenesulfonamide hydrochloride salt In a 10 mL tube, tert-butyl (R)-3-((2-chloro-4-fluoro-N-methylphenyl)sulfonamido)-1-oxa-8-azaspiro[4.5]decane-8-carboxylate (87 mg, 188 μmol) was dissolved in DCM (3.61 mL) and HCl in diethylether 2M (752 μL, 1.5 mmol) was added. The reaction was stirred at RT for 6 hr. The solvent was removed in vacuum, the product was used in the next step without purification. MS (ESI): m/z=363.1 $[M+H]^+$.

Step a) tert-Butyl (R)-3-((2-chloro-4-fluorophenyl)sulfonamido)-1-oxa-8-azaspiro[4.5]decane-8-carboxylate In a 20 mL tube purged with argon, tert-butyl (R)-3-amino-1-oxa-8-azaspiro[4.5]decane-8-carboxylate (80 mg, 312 μmol) was dissolved in DCM (2.67 mL). TEA (69.5 mg, 687 μmol) and 2-chloro-4-fluorobenzenesulfonyl chloride (75.1 mg, 328 μmol) were added, and the reaction mixture was stirred for 2 h at RT. The reaction mixture was extracted with DCM/water, dried with $Na_2SO_4$, the solvent removed in vacuo, and the residue was purified by preparative HPLC (Gemini NX column, ACN/water+0.1% TEA gradient). The product was obtained as a white solid (83 mg). MS (ESI): m/z=448.9 $[M-H]^-$.

Step b) tert-Butyl (R)-3-((2-chloro-4-fluoro-N-methylphenyl)sulfonamido)-1-oxa-8-azaspiro[4.5]decane-8-carboxylate To a solution of tert-butyl (R)-3-((2-chloro-4-fluorophenyl)sulfonamido)-1-oxa-8-azaspiro[4.5]decane-8-carboxylate (110 mg, 245 μmol) in DMF (2 mL) at 0° C. was added NaH in mineral oil 60% (14.7 mg, 368 μmol.). The reaction mixture was stirred at RT for 30 minutes, whereupon iodomethane (104 mg, 46 μL, 735 μmol) was added, and stirring was continued for 1 hour.

Saturated aqueous ammonium chloride solution was added, and the aqueous layer was extracted three times with EtOAc. The combined organic layers were dried over magnesium sulfate, filtered, and concentrated in vacuo to provide the crude product, which was purified by preparative HPLC HPLC (Gemini NX column, ACN/water+0.1% HCOOH gradient). 87 mg of product were obtained as a white solid. MS (ESI): m/z=407.2 $[M-56+H]^+$.

BB25

6-[[5-(Trifluoromethyl)-2-pyridyl]oxy]-2-azaspiro[3.3]heptane trifluoroacetate salt tert-butyl 6-((5-(trifluoromethyl)pyridin-2-yl)oxy)-2-azaspiro[3.3]heptane-2-carboxylate (0.314 g, 876 μmol) was dissolved in $CH_2Cl_2$ (3 mL) and TFA (799 mg, 540 μL, 7.01 mmol) was added. The reaction mixture was stirred at RT for 2 hours. The solvent was removed in vacuum, the product was used in the next step without purification. MS (ESI): m/z=259.2 $[M+H]^+$.

Step a) tert-Butyl 6-((S-(trifluoromethyl)pyridin-2-yl)oxy)-2-azaspiro[3.3]heptane-2-carboxylate To a solution of tert-butyl 6-hydroxy-2-azaspiro[3.3]heptane-2-carboxylate (0.200 g, 938 μmol) in dry THF (3 mL) was added potassium tert-butoxide 1M solution in THF (985 μl, 985 μmol) and the turbid reaction mixture was stirred at RT for 15 min followed by addition of 2-bromo-5-(trifluoromethyl)pyridine (212 mg, 938 μmol). The reaction mixture was then stirred at RT for 19 hours. The crude reaction was diluted with EtOAc and extracted with water, the organic phase was collected and the aqueous phase was back-extracted with EtOAc. The combined organic phases were dried over sodium sulfate and evaporated down to dryness. Purification: The crude material was purified by flash chromatography (silica gel, 20 g, 0% to 100% EtOAc in heptane). The product was obtained as a light yellow solid (314 mg). MS (ESI): m/z=303.2 $[M-56+H]^+$.

BB26

6-[[4-Methyl-3-(trifluoromethyl)phenyl]methoxy]-2-azaspiro[3.3]heptane tert-Butyl 6-((4-methyl-3-(trifluoromethyl)benzyl)oxy)-2-azaspiro[3.3]heptane-2-carboxylate (170 mg, 441 μmol) was dissolved in DCM (2 mL) and TFA (302 mg, 204 μL, 2.65 mmol) was added. The reaction mixture was stirred at RT for 8 hours. The solvent was removed in vacuum, the product was used in the next step without purification. MS (ESI): m/z=286.3 $[M+H]^+$.

Step a) tert-Butyl 6-((4-methyl-3-(trifluoromethyl)benzyl)oxy)-2-azaspiro[3.3]heptane-2-carboxylate In a 20 ml tube under argon, tert-butyl 6-hydroxy-2-azaspiro[3.3]heptane-2-carboxylate (142 mg, 664 μmol) was dissolved in DMF (2.5 mL) and cooled to 2-4° C. NaH (31.9 mg, 797 μmol) was added and the mixture stirred for 20 min. The cooling bath was removed and 4-(bromomethyl)-1-methyl-2-(trifluoromethyl)benzene (168 mg, 664 μmol) was added, then stirred at 22° C. for 3 hr. 3 mL sat. $NH_4Cl$-solution were added, extracted with water/EtOAc/sat.NaCl, dried over $MgSO_4$. The solvent was removed and the crude product was purified by flash chromatography (20 g silica with Heptane/EtOAc 0 to 40% in 30 min at UV 265 nm). MS (ESI): m/z=330.2 $[M-56+H]^+$.

BB27

2-((2-Chloro-4-fluorophenyl)sulfonyl)-2,7-diazaspiro[3.5]nonane hydrochloride

In a 10 mL tube, tert-butyl 2-((2-chloro-4-fluorophenyl)sulfonyl)-2,7-diazaspiro[3.5]nonane-7-carboxylate (140 mg, 334 μmol) was dissolved in DCM (4 mL) and HCl in diethylether 2M (1 mL, 2 mmol) was added. The reaction was stirred at RT for 6 hr. The solvent was removed in vacuum, the product was used in the next step without purification. MS (ESI): m/z=319.1 $[M+H]^+$.

Step a) tert-Butyl 2-((2-chloro-4-fluorophenyl)sulfonyl)-2,7-diazaspiro[3.5]nonane-7-carboxylate In a 20 mL tube purged with argon, tert-butyl 2,7-diazaspiro[3.5]nonane-7-carboxylate (80 mg, 353 μmol) was dissolved in DCM (3.3 mL). TEA (78.7 mg, 108 μL, 778 μmol) and 2-chloro-4-fluorobenzenesulfonyl chloride (89.1 mg, 389 μmol) were added, the mixture stirred 2 h at RT. The reaction was extracted with DCM/water, organic fraction were combined and dried over $Na_2SO_4$, solvent was removed in vacuo, the residue was purified by preparative HPLC (YMC-Triart C18, 12 nm, 5 μm, 100×30 mm, 9 min gradient ACN/Water+0.1% TEA). Product was obtained as a white foam. MS (ESI): m/z=363.1 $[M-56+H]^+$.

BB28

6-((2-Fluoro-4-(trifluoromethyl)benzyl)oxy)-2-azaspiro[3.3]heptane 2,2,2-trifluoroacetate tert-Butyl 6-((2-fluoro-4-(trifluoromethyl)benzyl)oxy)-2-azaspiro[3.3]heptane-2-carboxylate (235 mg, 604 μmol) was dissolved in DCM (3 mL) and TFA (344 mg, 232 μL, 3.02 mmol) was added. The reaction mixture was stirred at RT for 8 hours and concentrated in vacuo (azeotrop with toluol, EE+Hep). Used directly for next step. MS (ESI): m/z=290.2 $[M+H]^+$.

Step a) tert-Butyl 6-((2-fluoro-4-(trifluoromethyl)benzyl)oxy)-2-azaspiro[3.3]heptane-2-carboxylate To an ice-cold solution of tert-butyl 6-hydroxy-2-azaspiro[3.3]heptane-2-carboxylate (250 mg, 1.17 mmol) in DMF (3 mL) was added NaH 60% in mineral oil (51.6 mg, 1.29 mmol) in portions and the mixture was stirred at ice-bath temperature for 5 minutes followed by stirring at RT for 40 minutes. A solution of 2-fluoro-4-(trifluoromethyl)benzyl methanesulfonate (383 mg, 1.41 mmol) was dissolved in DMF (1 mL) and added dropwise to the mixture at RT. Stirring of the slurry was continued at RT for 16 hours. The reaction mixture was poured on saturated aqueous $NH_4Cl$ solution (10 mL) and EtOAc (20 mL) and the layers were separated. The aqueous layer was extracted once with EtOAc (50 mL). The organic layers were washed twice with water, dried over $MgSO_4$, filtered, treated with silica gel and evaporated. The compound was purified by silica gel chromatography on a 20 g column using an MPLC system eluting with a gradient of n-heptane:EtOAc (100:0 to 50:40) to get the desired compound as a light yellow solid (235 mg). MS (ESI): m/z=334.2 $[M-56+H]^+$.

BB29

(R)—N-(1-oxa-8-azaspiro[4.5]decan-3-yl)-4-(trifluoromethyl)benzenesulfonamide hydrochloride In a 10 mL tube, tert-butyl (R)-3-((4-(trifluoromethyl)phenyl)sulfonamido)-1-oxa-8-azaspiro[4.5]decane-8-carboxylate (63 mg, 136 μmol) was dissolved in DCM (1 mL) and HCl in diethylether 2M (678 uL, 1.36 mmol) was added. The reaction was stirred at RT for 4 hr. The solvent was removed in vacuum, the product was used in the next step without purification. MS (ESI): m/z=365.1 $[M+H]^+$.

Step a) tert-Butyl (R)-3-((4-(trifluoromethyl)phenyl)sulfonamido)-1-oxa-8-azaspiro[4.5]decane-8-carboxylate In a 20 mL tube purged with argon, tert-butyl (R)-3-amino-1-oxa-8-azaspiro[4.5]decane-8-carboxylate (60 mg, 234 μmol) was dissolved in DCM (2 mL). TEA (52.1 mg, 515 μmol) and 4-(trifluoromethyl)benzenesulfonyl chloride (68.7 mg, 281 μmol) were added, the mixture stirred 2 h at RT. The reaction was extracted with DCM/water, organic fraction were combined and dried over $Na_2SO_4$, solvent was removed in vacuo, the residue was purified by preparative HPLC (Gemini NX, 12 nm, 5 μm, 100×30 mm, gradient ACN/Water+0.1% TEA). Product was obtained as a white solid (63 mg). MS (ESI): m/z=463.3 $[M-H]^-$.

BB30

(R)—N-methyl-N-(1-oxa-8-azaspiro[4.5]decan-3-yl)benzenesulfonamide hydrochloride In a 10 mL tube, tert-butyl (R)-3-(N-methylphenylsulfonamido)-1-oxa-8-azaspiro[4.5]decane-8-carboxylate (96 mg, 234 μmol) was dissolved in DCM (1 mL) and HCl in diethylether 2M (1.75 mL, 3.51 mmol) was added. The reaction was stirred at RT for 4 hr. The solvent was removed in vacuum, the product was used in the next step without purification. MS (ESI): m/z=311.2 $[M+H]^+$.

Step a) tert-Butyl (R)-3-(phenylsulfonamido)-1-oxa-8-azaspiro[4.5]decane-8-carboxylate In a 20 mL tube purged with argon, tert-butyl (R)-3-amino-1-oxa-8-azaspiro[4.5]decane-8-carboxylate (60 mg, 234 μmol) was dissolved in DCM (2 mL). TEA (52.1 mg, 515 μmol) and benzenesulfonyl chloride (49.6 mg, 281 μmol) were added, the mixture stirred 2 h at RT. The reaction was extracted with DCM/water, organic fraction were combined and dried over $Na_2SO_4$, solvent was removed in vacuo, the residue was purified by preparative HPLC (Gemini NX, 12 nm, 5 μm, 100×30 mm, gradient ACN/Water+0.1% TEA). Product was obtained as a white solid (63 mg). MS (ESI): m/z=395.3 $[M-H]^-$.

Step b) tert-Butyl (R)-3-(N-methylphenylsulfonamido)-1-oxa-8-azaspiro[4.5]decane-8-carboxylate To a solution of tert-butyl (R)-3-(phenylsulfonamido)-1-oxa-8-azaspiro[4.5]decane-8-carboxylate (110 mg, 277 μmol) in DMF (1.2 mL) at 0° C. was added NaH in mineral oil 60% (16.6 mg, 416 μmol) The reaction mixture was stirred at RT for 30 minutes, whereupon iodomethane (118 mg, 52 μL, 832 μmol) was added, and stirring was continued for 1 hour. Saturated aqueous $NH_4Cl$ solution was added, and the aqueous layer was extracted three times with EtOAc. The combined organic layers were dried over magnesium sulfate, filtered, and concentrated in vacuo to provide the crude product which was purified by preparative HPLC. (Gemini NX, 12 nm, 5 μm, 100×30 mm, gradient ACN/Water+0.1% TEA). Product was obtained as a colorless oil (96 mg). MS (ESI): m/z=355.1 $[M-56+H]^+$.

BB31

(R)-2-Chloro-4-fluoro-N-(1-oxa-8-azaspiro[4.5]decan-3-yl)benzenesulfonamide hydrochloride In a 10 mL tube, tert-butyl (R)-3-((2-chloro-4-fluorophenyl)sulfonamido)-1-oxa-8-azaspiro[4.5]decane-8-carboxylate (64 mg, 143 μmol) was dissolved in DCM (2 mL) and HCl in diethyl ether 2M (1070 μL, 2.14 mmol) was added. The reaction was stirred at RT for 6 h. The solvent was removed in vacuum, the product was used in the next step without purification. MS (ESI): m/z=349.1 $[M+H]^+$.

Step a) tert-butyl (R)-3-((2-chloro-4-fluorophenyl)sulfonamido)-1-oxa-8-azaspiro[4.5]decane-8-carboxylate Synthesis described under BB24.

BB32

(R)—N-(1-oxa-8-azaspiro[4.5]decan-3-yl)-3-(trifluoromethyl)benzenesulfonamide hydrochloride Synthesized as described for BB29, starting from tert-butyl (R)-3-amino-1-oxa-8-azaspiro[4.5]decane-8-carboxylate (60 mg, 234 umol), and 3-(trifluoromethyl)benzenesulfonyl chloride (68.7 mg, 281 μmol). 53 mg of product obtained as a light yellow oil. MS (ESI): m/z=365.1 $[M+H]^+$.

BB33

N-(2-chloro-4-fluorobenzyl)-N-methyl-1-oxa-8-azaspiro[4.5]decan-3-amine trifluoroacetate To a solution of tert-butyl 3-((2-chloro-4-fluorobenzyl)(methyl)amino)-1-oxa-8-azaspiro[4.5]decane-8-carboxylate (0.107 g, 259 μmol) in DCM (2 mL) was added trifluoroacetic acid (236 mg, 160 μL, 2.07 mmol) and the reaction was stirred at RT for 19 h. The reaction mixture was concentrated to afford the title compound as light yellow oil (111 mg) which was used in the next step without further purification. MS (ESI): m/z=313.2 $[M+H]^+$.

Step a) tert-Butyl 3-((2-chloro-4-fluorobenzyl)amino)-1-oxa-8-azaspiro[4.5]decane-8-carboxylate To a solution of tert-butyl 3-amino-1-oxa-8-azaspiro[4.5]decane-8-carboxylate (0.5 g, 1.95 mmol) and 2-chloro-4- fluorobenzaldehyde (309 mg, 1.95 mmol) in MeOH (12 mL) was added sodium cyanoborohydride (613 mg, 9.75 mmol). the reaction mixture was stirred at RT for 2 hours—For work up, the reaction mixture was poured into sat. $NaHCO_3$ and extracted with EtOAc. The organic layers were combined, washed with brine, dried over $Na_2SO_4$ and concentrated in vacuo. The crude material was purified by flash chromatography (silica gel, 20 g, 0% to 100% EtOAc in heptane) to obtain 231 mg of product as a colorless oil. MS (ESI): m/z=399.2 $[M+H]^+$.

Step b) tert-Butyl 3-((2-chloro-4-fluorobenzyl)(methyl)amino)-1-oxa-8-azaspiro[4.5]decane-8-carboxylate To a solution of tert-butyl 3-((2-chloro-4-fluorobenzyl)amino)-1-oxa-8-azaspiro[4.5]decane-8-carboxylate (0.100 g, 251 μmol) in DMF (1.5 mL) at 0° C. was added NaH 60% in mineral oil (15 mg, 376 μmol). The reaction mixture was stirred at RT for 30 minutes, and then iodomethane (107 mg, 47 μl, 752 μmol) was added, and stirring was continued for 1 hour. Saturated aqueous ammonium chloride solution was added, and the aqueous layer was extracted three times with EtOAc. The combined organic layers were dried over magnesium sulfate, filtered, and concentrated in vacuo to provide the desired product as a yellow oil (104 mg), which was used directly for the next step. MS (ESI): m/z=413.4 $[M+H]^+$.

BB34

N-(2-chloro-4-fluorobenzyl)-1-oxa-8-azaspiro[4.5]decan-3-amine trifluoroacetate

To a solution of tert-butyl 3-((2-chloro-4-fluorobenzyl)amino)-1-oxa-8-azaspiro[4.5]decane-8-carboxylate (0.088 g, 221 μmol) in DCM (1 mL) was added trifluoroacetic acid (201 mg, 136 μL, 1.76 mmol) and the reaction was stirred at RT for 2 h. The reaction mixture was concentrated to afford the title compound as colorless oil (91 mg) which was used in the next step without further purification.

Step a) tert-Butyl 3-((2-chloro-4-fluorobenzyl)amino)-1-oxa-8-azaspiro[4.5]decane-8-carboxylate tert-Butyl 3-((2-chloro-4-fluorobenzyl)amino)-1-oxa-8-azaspiro[4.5]decane-8-carboxylate was synthesized as described for BB33.

BB35

2-((4-(Trifluoromethyl)phenyl)sulfonyl)-2,7-diazaspiro[3.5]nonane hydrochloride

In a 10 mL tube tert-butyl 2-((4-(trifluoromethyl)phenyl)sulfonyl)-2,7-diazaspiro[3.5]nonane-7-carboxylate (124 mg, 285 μmol) was dissolved in DCM (4 mL) and HCl in diethylether 2M (856 μl, 1.71 mmol) was added. The reaction was stirred at RT for 3 hr. The solvent was removed in vacuum, the product was obtained as a white solid (105 mg) and was used in the next step without purification. MS (ESI): m/z=335.1 $[M+H]^+$.

Step a) tert-Butyl 2-((4-(trifluoromethyl)phenyl)sulfonyl)-2,7-diazaspiro[3.5]nonane-7-carboxylate In a 20 mL tube purged with argon, tert-butyl 2,7-diazaspiro[3.5]nonane-7-carboxylate (80 mg, 353 μmol, Eq: 1) was dissolved in DCM (3.3 mL). TEA (78.7 mg, 108 μL, 778 μmol) and 4-(trifluoromethyl)benzenesulfonyl chloride (95.1 mg, 389 μmol) were added, the mixture stirred 2 h at RT. The reaction was extracted with DCM/water, organic fraction were combined and dried over $Na_2SO_4$, solvent was removed in vacuo, the residue was purified by preparative HPLC (YMC-Triart C18, 12 nm, 5 μm, 100×30 mm, 9 min gradient ACN/Water+0.1% TEA). Product was obtained as a white foam. MS (ESI): m/z=379.1 $[M-56+H]^+$.

BB36

2-(Phenylsulfonyl)-2,7-diazaspiro[3.5]nonane hydrochloride

BB36 was obtained from tert-butyl 2,7-diazaspiro[3.5]nonane-7-carboxylate (80 mg, 353 μmol) and benzenesulfonyl chloride (74.9 mg, 424 μmol), as described for BB35. MS (ESI): m/z=267.2 $[M+H]^+$.

BB37

2-(2,4-Difluorophenoxy)-7-azaspiro[3.5]nonane trifluoroacetate

To a solution of tert-butyl 2-(2,4-difluorophenoxy)-7-azaspiro[3.5]nonane-7-carboxylate (510 mg, 1.44 mmol) in DCM (3 mL) was added trifluoroacetic acid (823 mg, 556 μL, 7.22 mmol) and the reaction was stirred at RT for 3 h. The reaction mixture was concentrated to afford the title compound as a white solid (510 mg) which was used in the next step without further purification. MS (ESI): m/z=254.2 [M+H]+

Step a) tert-Butyl 2-(2,4-difluorophenoxy)-7-azaspiro[3.5]nonane-7-carboxylate

In a 25 mL four-necked sulphonation flask under argon, tert-butyl 2-hydroxy-7-azaspiro[3.5]nonane-7-carboxylate (401 mg, 1.66 mmol, CAS RN 240401-28-9) was dissolved in THF (6 mL), 2,4-difluorophenol (216 mg, 159 μL, 1.66 mmol) and triphenylphosphine (479 mg, 1.83 mmol) were added. The clear solution was stirred at RT for 5, then cooled to 0-2° C. and DEAD (318 mg, 289 μL, 1.83 mmol) was added slowly within 10 min, stirring was continued for 1 hr at 2-4° C., then the cooling bath was removed and it was stirred over night at RT. 20 mL diethylether were added, the mixture was washed with water, 1M NaOH and brine. The organic layer was dried over $Na_2SO_4$ and concentrated in vacuo. The crude material was purified by flash chromatography (silica gel, 50 g, 0% to 40% EtOAc in heptane) to obtain 511 mg of product as a colorless oil. MS (ESI): m/z=298.3 $[M-56+H]^+$.

BB38

2-(2-Chloro-4-fluorophenoxy)-7-azaspiro[3.5]nonane trifluoroacetate

BB38 was obtained from tert-butyl 2-hydroxy-7-azaspiro[3.5]nonane-7-carboxylate (412 mg, 1.71 mmol) and 2-chloro-4-fluorophenol (250 mg, 1.71 mmol), as described for BB37. MS (ESI): m/z=270.2 $[M+H]^+$.

BB39

6-[[2-Fluoro-4-(trifluoromethyl)phenoxy]methyl]-2-azaspiro[3.3]heptane trifluoro acetate BB39 was obtained in analogy to BB37 from tert-butyl 6-[[2-fluoro-4-(trifluoromethyl)phenoxy]methyl]-2- azaspiro[3.3]heptane-2-carboxylate and was used in the next step without further purification. MS (ESI): m/z=290.2 $[M+H]^+$.

Step a) tert-Butyl 6-[[2-fluoro-4-(trifluoromethyl) phenoxy]methyl]-2-azaspiro[3.3]heptane-2-carboxylate The compound was obtained in analogy to example 37, step a, from tert-butyl 6-(hydroxymethyl)-2-azaspiro[3.3] heptane-2-carboxylate (CAS RN 1363381-93-4) and 2-fluoro-4-(trifluoromethyl)phenol (CAS RN 77227-78-2). After extraction the material was used in the next step without further purification. MS (ESI): m/z=334.1 $[M-56-H]^+$.

BB40

6-((2-fluoro-4-(trifluoromethyl)benzyl)oxy)-6-(trifluoromethyl)-2-azaspiro[3.3]heptane trifluoroacetate BB40 was obtained in analogy to BB25 from tert-butyl 6-hydroxy-6-(trifluoromethyl)-2-azaspiro[3.3]heptane-2-carboxylate (CAS 1251923-04-2) and 1-(bromomethyl)-2-fluoro-4-(trifluoromethyl)benzene. MS (ESI): m/z=358.1 $[M-56-H]^+$.

BB41

6-(2-fluoro-4-(trifluoromethyl)phenyl)-2-azaspiro [3.3]heptane trifluoroacetate

To a solution of tert-butyl 6-(2-fluoro-4-(trifluoromethyl) phenyl)-2-azaspiro[3.3]heptane-2-carboxylate (0.151 g, 420 µmol) in DCM (4 ml) was added TFA (240 mg, 162 µl, 2.1 mmol). The resultant reaction mixture was stirred at RT for 1 hour and was then concentrated in vacuo (azeotrop with toluene) yielding 143 mg of colorless oil, used in the next step without further purification. MS (ESI): m/z=260.2 $[M+H]^+$.

Step a) tert-butyl 6-(2-fluoro-4-(trifluoromethyl) phenyl)-2-azaspiro[3.3]heptane-2-carboxylate To an 20 mL vial equipped with a stir bar was added photocatalyst $(Ir[dF(CF_3)ppy]_2(dtbpy))PF_6$ (6.09 mg, 5.43 µmol), 1-bromo-2-fluoro-4-(trifluoromethyl)benzene (198 mg, 137 µl, 815 µmol), tert-butyl 6-bromo-2-azaspiro[3.3] heptane-2-carboxylate (0.150 g, 543 µmol), Tris(trimethylsilyl)silane (135 mg, 168 µl, 543 µmol) and anhydrous sodium carbonate (115 mg, 1.09 mmol). The vial was sealed and placed under argon before DME (3 ml) was added. To a separate vial was added Nickel(II) chloride ethylene glycol dimethyl ether complex (1.19 mg, 5.43 µmol) and 4,4'-di-tert-butyl-2,2'-bipyridine (1.46 mg, 5.43 µmol). The precatalyst vial was sealed, purged with argon then to it was added DME (2 ml). The precatalyst vial was sonicated for 5 min, after which, 1 mL (0.5 mol % catalyst, 0.005 eq) was syringed into the reaction vessel. The solution was degassed by sparging with argon. The reaction was stirred and irradiated with a 420 nm lamp for 5 hours. The reaction was quenched by exposure to air and concentrated in vacuo. The crude material was purified by flash chromatography (silica gel, 50 g, 0% to 20% EtOAc in heptane), yielding 151 mg (yield 77%, not pure based on NMR) of a colorless liquid which was used for the next step. MS (ESI): m/z=304.2 $[M-56-H]^+$.

BB42

6-(2-fluoro-4-(trifluoromethyl)benzyl)-2-azaspiro [3.3]heptane trifluoroacetate

To a solution of tert-butyl 6-(2-fluoro-4-(trifluoromethyl) benzyl)-2-azaspiro[3.3]heptane-2-carboxylate (0.102 g, 273 µmol) in DCM (3 ml) was added TFA (156 mg, 105 µl, 1.37 mmol). The resultant reaction mixture was stirred at RT for 2 hour and was then concentrated in vacuo (azeotrop with toluene) yielding 108 mg of colorless oil, used in the next step without further purification. MS (ESI): m/z=274.2 $[M+H]^+$.

Step a) (2-fluoro-4-(trifluoromethyl)benzyl)triphenylphosphonium bromide

Under argon, triphenylphosphine (1.02 g, 3.89 mmol) was dissolved in acetonitrile (10 ml) and 1-(bromomethyl)-2-fluoro-4-(trifluoromethyl)benzene (1 g, 3.89 mmol) was added. The mixture was stirred at 80° C. for 3 hours. The suspension was allowed to cool to RT. It was added 100 mL MTBE and was stirred at RT for 30 min. The solid was filtrated and washed with MTBE. The solid was dried under HV, the product was used directly for the next step. White solid, 2.02 g (98%). MS (ESI): m/z=439.2 $[M+H]^+$.

Step b) tert-butyl 6-(2-fluoro-4-(trifluoromethyl) benzylidene)-2-azaspiro[3.3]heptane-2-carboxylate Under Argon at −78° C., (2-fluoro-4-(trifluoromethyl) benzyl)triphenylphosphonium bromide (0.5 g, 963 µmol) was dissolved in dry THF (5 ml) and LiHMDS (1.93 ml, 1.93 mmol) was added. The reaction mixture was stirred at −78° C. for 2 hours. Then at RT, tert-butyl 6-oxo-2-azaspiro [3.3]heptane-2-carboxylate (407 mg, 1.93 mmol) was added and the mixture was stirred at 85° C. overnight. MTBE was added and the precipitate was filtrated off (Triphenylphoshinoxide). Filtrate was concentrated and directly purified. The crude material was purified by flash chromatography (silica gel, 20 g, 0% to 80% EtOAc in heptane) yielding the product as a yellow solid (119 mg, 33%). MS (ESI): m/z=316.2 $[M-56+H]^+$.

Step c) tert-butyl 6-(2-fluoro-4-(trifluoromethyl) benzyl)-2-azaspiro[3.3]heptane-2-carboxylate tert-butyl 6-(2-fluoro-4-(trifluoromethyl)benzylidene)-2-azaspiro[3.3]heptane-2-carboxylate (0.119 g, 320 µmol) was dissolved in ethyl acetate (2.5 ml). The flask was purged and backfilled with argon (3×). Pd—C (34.1 mg, 32 µmol) was added and the reaction was stirred under $H_2$ (ballon) for 2 hours. The reaction mixture was filtered through a celite pad, washed with EtOAc and dried under vacuum, yielding the product as a colorless oil (108 mg, 90%). MS (ESI): m/z=318.2 $[M-56+H]^+$.

BB43

6-(2-chloro-4-fluorobenzyl)-2-azaspiro[3.3]heptane trifluoroacetate

BB43 was obtained in analogy to BB42 starting from tert-butyl 6-oxo-2-azaspiro[3.3]heptane-2-carboxylate and 1-(bromomethyl)-2-chloro-4-fluorobenzene. MS (ESI): m/z=240.1 $[M+H]^+$.

BB44

6-(2,4-difluorobenzyl)-2-azaspiro[3.3]heptane trifluoroacetate

BB44 was obtained in analogy to BB42 starting from tert-butyl 6-oxo-2-azaspiro[3.3]heptane-2-carboxylate and 1-(bromomethyl)-2,4-difluorobenzene. MS (ESI): m/z=224.1 $[M+H]^+$.

BB45

6-(2-methoxy-4-(trifluoromethyl)benzyl)-2-azaspiro[3.3]heptane trifluoroacetate

BB45 was obtained in analogy to BB42 starting from tert-butyl 6-oxo-2-azaspiro[3.3]heptane-2-carboxylate and 1-(bromomethyl)-2-methoxy-4-(trifluoromethyl)benzene. MS (ESI): m/z=286.2 $[M+H]^+$.

BB46

6-(2-fluoro-6-(trifluoromethyl)benzyl)-2-azaspiro[3.3]heptane trifluoroacetate

BB46 was obtained in analogy to BB42 starting from tert-butyl 6-oxo-2-azaspiro[3.3]heptane-2-carboxylate and 1-(bromomethyl)-2-fluoro-6-(trifluoromethyl)benzene. MS (ESI): m/z=274.2 $[M+H]^+$.

BB47

6-((2-chloro-4-fluorophenoxy)methyl)-2-azaspiro[3.3]heptane trifluoroacetate

BB47 was obtained from tert-butyl 6-(hydroxymethyl)-2-azaspiro[3.3]heptane-2-carboxylate (300 mg, 1.32 mmol) and 2-chloro-4-fluorophenol (193 mg, 1.32 mmol), as described for BB37. MS (ESI): m/z=256.1 $[M+H]^+$.

BB48

2-(3-(trifluoromethyl)phenyl)-2,6-diazaspiro[3.3]heptane trifluoroacetate

To a solution of tert-butyl 6-(3-(trifluoromethyl)phenyl)-2,6-diazaspiro[3.3]heptane-2-carboxylate (230 mg, 672 μmol) in DCM (2 ml) was added TFA (306 mg, 207 μl, 2.69 mmol). The resultant reaction mixture was stirred at RT over night and was then concentrated in vacuo (azeotrop with toluene) yielding 245 mg of colorless oil, used in the next step without further purification. MS (ESI): m/z=243.2 $[M+H]^+$.

Step a) tert-butyl 6-(3-(trifluoromethyl)phenyl)-2,6-diazaspiro[3.3]heptane-2-carboxylate To a flask was added: 1-bromo-3-(trifluoromethyl)benzene (170 mg, 104 μl, 756 μmol), tert-butyl 2,6-diazaspiro[3.3]heptane-2-carboxylate (165 mg, 831 μmol), Cs2CO3 (492 mg, 1.51 mmol) and 1,4-Dioxane (4 ml), the suspension was bubbled with N2 for 5 mins and Chloro(2-dicyclohexylphosphino-2',6'-diisopropoxy-1,1'-biphenyl)[2-(2'-amino-1,1'-biphenyl)]palladium(II) (RuPhos Pd G2, 29.3 mg, 37.8 μmol) was added. The mixture was heated to 100° C. for 2h. The mixture was diluted with 10 mL EA and filtered through celite, the filtrate was concentrated to give a yellow oil. Then it was purified over 20 g silica with Heptane/EA 0-40%, the product-fractions were concentrated to give the desired product as a yellow solid (233 mg, 90%). MS (ESI): m/z=343.2 $[M+H]^+$.

BB49

2-(4-isopropoxyphenyl)-2,6-diazaspiro[3.3]heptane 2,2,2-trifluoroacetate

BB49 was obtained in analogy to BB48 starting from tert-butyl 2,6-diazaspiro[3.3]heptane-2-carboxylate and 1-bromo-4-isopropoxybenzene. Reaction was heated to 120° C. for 4h. MS (ESI): m/z=233.2 $[M+H]^+$.

BB50

1-(4-(2,6-diazaspiro[3.4]octan-2-yl)phenyl)pyrrolidin-2-one 2,2,2-trifluoroacetate BB50 was obtained in analogy to BB48 starting from tert-butyl 2,6-diazaspiro[3.4]octane-6-carboxylate and 1-(4-bromophenyl)pyrrolidin-2-one. Reaction was heated to 125° C. for 18h. MS (ESI): m/z=272.3 $[M+H]^+$.

BB51

2-(4-methoxy-3-methylphenyl)-2,6-diazaspiro[3.4]octane trifluoroacetate

BB51 was obtained in analogy to BB48 starting from tert-butyl 2,6-diazaspiro[3.4]octane-6-carboxylate and 4-bromo-1-methoxy-2-methylbenzene. Reaction was heated to 125° C. for 18h. MS (ESI): m/z=233.2 $[M+H]^+$.

BB52

2-(4-chloro-3-(trifluoromethyl)phenyl)-2,6-diazaspiro[3.4]octane trifluoroacetate BB52 was obtained in analogy to BB48 starting from tert-butyl 2,6-diazaspiro[3.4]octane-6-carboxylate and 4-bromo-1-chloro-2-(trifluoromethyl)benzene. Reaction was heated to 125° C. for 18h. MS (ESI): m/z=291.1 $[M+H]^+$.

BB53

2-(2-fluoropyridin-4-yl)-2,6-diazaspiro[3.4]octane dihydrochloride

BB53 was obtained in analogy to BB48 starting from tert-butyl 2,6-diazaspiro[3.4]octane-6-carboxylate and 4-bromo-2-fluoropyridine. Reaction was heated to 125° C. for 18h. Deprotection was achieved using 2M HCl in diethyl ether (16 hr, RT). MS (ESI): m/z=208.2 $[M+H]^+$.

BB54

2-(2,5-bis(trifluoromethyl)phenyl)-2,6-diazaspiro[3.3]heptane trifluoroacetate

BB54 was obtained in analogy to BB48 starting from tert-butyl 2,6-diazaspiro[3.4]octane-6-carboxylate and 4-bromo-2-fluoropyridine. Reaction was heated to 120° C. for 4h. MS (ESI): m/z=311.4 $[M+H]^+$.

BB55

2-((4-fluoro-2-(trifluoromethyl)phenyl)sulfonyl)-2,6-diazaspiro[3.3]heptane 2,2,2-trifluoroacetate To a solution of tert-butyl 6-((4-fluoro-2-(trifluoromethyl)phenyl)sulfonyl)-2,6-diazaspiro[3.3]heptane-2-carboxylate (269 mg, 634 μmol) in DCM (2 ml) was added TFA (434 mg, 293 μl, 3.8 mmol). The resultant reaction mixture was stirred at RT for 4 hr and was then concentrated in vacuo (azeotrop with toluene) yielding 264 mg of a white solid, used in the next step without further purification. MS (ESI): m/z=325.1 $[M+H]^+$.

Step a) tert-butyl 6-((4-fluoro-2-(trifluoromethyl)phenyl)sulfonyl)-2,6-diazaspiro[3.3]heptane-2-carboxylate In a 20 ml glass tube under argon, tert-butyl 2,6-diazaspiro[3.3]heptane-2-carboxylate (190 mg, 958 μmol) in DCM (3 ml) and TEA (145 mg, 200 μl, 1.44 mmol) was stirred for 5 min at RT, then 4-fluoro-2-(trifluoromethyl)benzenesulfonyl chloride (315 mg, 1.2 mmol) was added (slightly exothermic) and stirred over night at RT. 10 ml DCM was added and silica gel, solvent was removed under vacuum and chromatography over 20 g silica with Heptane/EA (0 to 50% in 35 min) yielded the desired product as a white solid (269 mg, 66%). MS (ESI): m/z=369.1 $[M-56+H]^+$.

BB56

6-((2-chloro-4-fluorophenyl)sulfonyl)-2-azaspiro[3.3]heptane trifluoroacetate

To a solution of tert-butyl 6-((2-chloro-4-fluorophenyl)sulfonyl)-2-azaspiro[3.3]heptane-2-carboxylate (209 mg, 536 μmol) in DCM (2 ml) was added TFA (306 mg, 207 μl, 2.68 mmol). The resultant reaction mixture was stirred at RT for 16 hr and was then concentrated in vacuo (azeotrop with toluene), 5 ml diethyl ether were added and the suspension was put in an ultrasonic bath, filtration yielded the desired product as a white solid (195 mg, 100%), used in the next step without further purification. MS (ESI): m/z=290.1 $[M+H]^+$.

Step a) tert-butyl 6-((2-chloro-4-fluorophenyl)sulfonyl)-2-azaspiro[3.3]heptane-2-carboxylate In a 20 ml glass tube, tert-butyl 6-((methylsulfonyl)oxy)-2-azaspiro[3.3]heptane-2-carboxylate (538 mg, 1.84 mmol), 2-chloro-4-fluorobenzenethiol (250 mg, 1.54 mmol) and $K_2CO_3$ (425 mg, 3.07 mmol) were dissolved in DMF (7 ml) under argon atmosphere. The suspension was heated-up at 80° C. for 4 hr. The reaction mixture was diluted with ethyl acetate (20 ml), washed twice with water (40 ml), then with brine (40 ml). The organic layer was dried over $MgSO_4$, filter off and the solvent was removed under reduced pressure. The crude was purified over 50 g silica with heptane/EA 0 to 40% in 40 min, after removing the solvent under vacuum the product was obtained as a colorless viscous oil (218 mg, 38%). MS (ESI): m/z=302.1 $[M-56+H]^+$.

Step b) tert-butyl 6-((2-chloro-4-fluorophenyl)sulfonyl)-2-azaspiro[3.3]heptane-2-carboxylate In a 25 ml glass tube under argon, tert-butyl 6-((2-chloro-4-fluorophenyl)thio)-2-azaspiro[3.3]heptane-2-carboxylate (218 mg, 609 μmol) was dissolved in DCM (8 ml), mCPBA (315 mg, 1.28 mmol) was added in portions at 10-12° C., and stirred at RT for 3 hr. 10 ml DCM were added, the organic phase was washed with 5% $NaHCO_3$, water and brine, dried with $MgSO_4$ and the solvent was removed under vacuum. Chromatography over 20 g silica with heptane/EA (0 to 50%) yielded the product as 209 mg (88%) of a white solid. MS (ESI): m/z=334.1 $[M-56+H]^+$.

BB57

2-((3-chloro-4-(trifluoromethyl)phenyl)sulfonyl)-2,6-diazaspiro[3.3]heptane trifluoroacetate BB57 was obtained in analogy to BB55 starting from tert-butyl 2,6-diazaspiro[3.3]heptane-2-carboxylate and 3-chloro-4-(trifluoromethyl)benzenesulfonyl chloride. MS (ESI): m/z=341.0 $[M+H]^+$.

BB58

2-((2,4-bis(trifluoromethyl)phenyl)sulfonyl)-2,6-diazaspiro[3.3]heptane trifluoroacetate BB58 was obtained in analogy to BB55 starting from tert-butyl 2,6-diazaspiro[3.3]heptane-2-carboxylate and 2,4-bis(trifluoromethyl)benzenesulfonyl chloride. MS (ESI): m/z=419.1 $[M+H]^+$.

BB59

6-(2,6-difluorobenzyl)-2-azaspiro[3.3]heptane trifluoroacetate

BB59 was obtained in analogy to BB42 starting from tert-butyl 6-oxo-2-azaspiro[3.3]heptane-2-carboxylate and 1-(bromomethyl)-2,6-difluoro-benzene. MS (ESI): m/z=224.1 $[M+H]^+$.

BB60

6-(2-fluoro-6-methoxybenzyl)-2-azaspiro[3.3]heptane trifluoroacetate

BB60 was obtained in analogy to BB42 starting from tert-butyl 6-oxo-2-azaspiro[3.3]heptane-2-carboxylate and 1-(bromomethyl)-2-fluoro-6-methoxybenzene. MS (ESI): m/z=236.2 $[M+H]^+$.

BB61

6-(2-methoxybenzyl)-2-azaspiro[3.3]heptane trifluoroacetate

BB61 was obtained in analogy to BB42 starting from tert-butyl 6-oxo-2-azaspiro[3.3]heptane-2-carboxylate and 1-(bromomethyl)-2-methoxybenzene. MS (ESI): m/z=218.2 $[M+H]^+$.

BB62

2-((2-azaspiro[3.3]heptan-6-yl)methyl)-3-fluorophenol

In a 10 mL round-bottomed flask, tert-butyl 6-(2-fluoro-6-methoxybenzyl)-2-azaspiro[3.3]heptane-2-carboxylate (0.050 g, 149 μmol) was combined with DCM (1 ml) to give a colorless solution. $BBr_3$ (37.3 mg, 14.1 μl, 149 μmol) was added at 0° C. The reaction was stirred at RT for 3 hours. $BBr_3$ (37.3 mg, 14.1 μl, 149 μmol) was added again and the reaction stirred at RT overnight. The reaction mixture was quenched by addition of saturated solution of $NaHCO_3$ and extracted with EtOAc/THF. Organic layers were combined, washed with brine, dried over $Na_2SO_4$ and concentrated in vacuo. MS (ESI): m/z=222.2 $[M+H]^+$.

BB63

2-((2-azaspiro[3.3]heptan-6-yl)methyl)phenol

BB61 was obtained in analogy to BB62 starting from tert-butyl 6-(2-methoxybenzyl)-2-azaspiro[3.3]heptane-2-carboxylate. MS (ESI): m/z=204.2 $[M+H]^+$.

The invention claimed is:

1. A compound of formula (I):

(I)

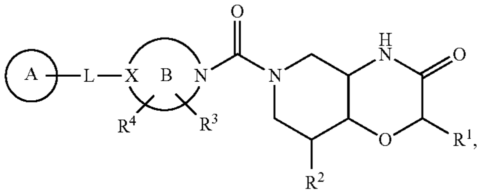

or a pharmaceutically acceptable salt thereof, wherein:

(i) X is C—$R^5$;

L is a covalent bond, —$(CH_2)_n$—N($C_{1-6}$-alkyl)-, —$(CH_2)_n$—NH—, —N($C_{1-6}$-alkyl)-$(CH_2)_p$—, —NH—$(CH_2)_p$—, —($CH_2$)—O—, —O—$(CH_2)_p$—, —$SO_2$—N($C_{1-6}$-alkyl)-, —$SO_2$—NH—, —N($C_{1-6}$-alkyl)-$SO_2$—, —NH—$SO_2$—, carbonyl, —$(CH_2)_n$—, —$CHR^6$—, —$CF_2$—$(CH_2)_n$—, —$(CH_2)_p$—$CF_2$—, —$(CH_2)_n$—S—, —S—$(CH_2)_p$—, —$SO_2$—, —C(O)—NH—, —C(O)—N($C_{1-6}$-alkyl)-, —NH—C(O)— or —N($C_{1-6}$-alkyl)-C(O)—; and A is:

(i) $C_{6-14}$-aryl substituted with $R^7$, $R^8$ and $R^9$; or (ii) 5-14 membered heteroaryl substituted with $R^{10}$, $R^{11}$ and $R^{12}$; or (ii) X is N;

L is a covalent bond, —$(CH_2)_n$-, —$CHR^6$—, —$SO_2$—, carbonyl, —N($C_{1-6}$-alkyl)-$(CH_2)_p$—, —NH—$(CH_2)_p$—, —O—$(CH_2)_p$—, —$CF_2$—$CH_2$—, —N($C_{1-6}$-alkyl)-$SO_2$—, —NH—$SO_2$—, —NH—C(O)— or —N($C_{1-6}$-alkyl)-C(O)—; and A is:

(i) $C_{6-14}$-aryl substituted with $R^7$, $R^8$ and $R^9$; or (ii) 5-14 membered heteroaryl substituted with $R^{10}$, $R^{11}$ and $R^{12}$; or (iii) X is N;

L is $C_{1-6}$-alkoxycarbonyl, $C_{6-14}$-aryloxycarbonyl or 5-14 membered heteroaryloxycarbonyl; and A is absent;

B is a bicyclic spirocycle;

$R^1$, $R^2$, $R^3$, $R^4$ and $R^5$ are independently hydrogen, halogen, hydroxy, $C_{1-6}$-alkyl or halo-$C_{1-6}$-alkyl;

$R^6$ is $C_{6-14}$-aryl or 5-14 membered heteroaryl;

$R^7$, $R^8$, $R^9$, $R^{10}$, $R^{11}$ and $R^{12}$ are each at each occurrence independently hydrogen, hydroxy, $C_{1-6}$-alkyl, halo-$C_{1-6}$-alkyl, halogen, $C_{1-6}$-alkoxy, halo-$C_{1-6}$-alkoxy, $SF_5$, $C_{1-6}$-alkylsulfonyl, cyano or a group

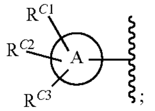

;

C is 5-14 membered heteroaryl, 3-14 membered heterocyclyl or $C_{3-10}$-cycloalkyl;

$R^{C1}$, $R^{C2}$ and $R^{C3}$ are each independently hydrogen, $C_{1-6}$-alkyl, halo-$C_{1-6}$-alkyl, oxo, halogen, hydroxy, $C_{1-6}$-alkoxy or halo-$C_{1-6}$-alkoxy;

each occurrence of n is independently 0, 1, 2 or 3; and each occurrence of p is independently 1, 2 or 3.

2. The compound of formula (I) according to claim 1, (I)

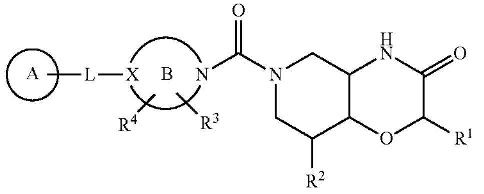

or a pharmaceutically acceptable salt thereof, wherein:

(i) X is C—$R^5$;

L is —$(CH_2)_n$—N($C_{1-6}$-alkyl)-, —$(CH_2)_n$—NH—, —N($C_{1-6}$-alkyl)-$(CH_2)_p$—, —NH—$(CH_2)_p$—, —($CH_2$)~—O—, —O—$(CH_2)_p$—, —$SO_2$—N($C_{1-6}$-alkyl)-, —$SO_2$—NH—, —N($C_{1-6}$-alkyl)-$SO_2$—, —NH—$SO_2$—, carbonyl, —$(CH_2)_n$—, —$CHR^6$—, —$CF_2$—$(CH_2)_n$—, —$(CH_2)_p$—$CF_2$—, —$(CH_2)_n$—S—, —S—$(CH_2)_p$—, —$SO_2$—, —C(O)—NH—, —C(O)—N($C_{1-6}$-alkyl)-, —NH—C(O)— or —N($C_{1-6}$-alkyl)-C(O)—; and A is:

(i) $C_{6-14}$-aryl substituted with $R^7$, $R^8$ and $R^9$; or (ii) 5-14 membered heteroaryl substituted with $R^{10}$, $R^{11}$ and $R^{12}$; or (ii) X is N;

L is —$(CH_2)_n$—, —$CHR^6$—, —$SO_2$—, carbonyl, —N($C_{1-6}$-alkyl)-$(CH_2)_p$—, —NH—$(CH_2)_p$, —O—$(CH_2)_p$—, —$CF_2$—$CH_2$—, —N($C_{1-6}$-alkyl)-$SO_2$—, —NH—$SO_2$—, —NH—C(O)— or —N($C_{1-6}$-alkyl)-C(O)—; and A is:

(i) $C_{6-14}$-aryl substituted with $R^7$, $R^8$ and $R^9$; or (ii) 5-14 membered heteroaryl substituted with $R^{10}$, $R^{11}$ and $R^{12}$; or (iii) X is N;

L is $C_{1-6}$-alkoxycarbonyl, $C_{6-14}$-aryloxycarbonyl or 5-14 membered heteroaryloxycarbonyl; and A is absent;

B is a bicyclic spirocycle;

$R^1$ is hydrogen or $C_{1-6}$-alkyl;

$R^2$ is hydrogen or $C_{1-6}$-alkyl;

$R^3$ is hydrogen, $C_{1-6}$-alkyl, halo-$C_{1-6}$-alkyl, halogen or hydroxy;

$R^4$ is hydrogen, $C_{1-6}$-alkyl, halo-$C_{1-6}$-alkyl, halogen or hydroxy;

$R^5$ is hydrogen, $C_{1-6}$-alkyl, halo-$C_{1-6}$-alkyl, halogen or hydroxy;

$R^6$ is $C_{6-14}$-aryl or 5-14 membered heteroaryl;

$R^7$, $R^8$, $R^9$, $R^{10}$, $R^{11}$ and $R^{12}$ are each at each occurrence independently hydrogen, $C_{1-6}$-alkyl, halo-$C_{1-6}$-alkyl, halogen, $C_{1-6}$-alkoxy, halo-$C_{1-6}$-alkoxy, $SF_5$, $SO_2CH_3$, cyano, a group

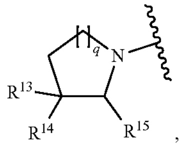

, a group

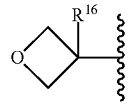

or a group

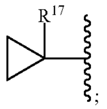;

$R^{13}$ is hydrogen, $C_{1-6}$-alkyl, halo-$C_{1-6}$-alkyl, halogen, hydroxy or $C_{1-6}$-alkoxy; and $R^{14}$ is hydrogen, $C_{1-6}$-alkyl, halo-$C_{1-6}$-alkyl, halogen, hydroxy, $C_{1-6}$-alkoxy;

$R^{15}$ is hydrogen, $C_{1-6}$-alkyl or halo-$C_{1-6}$-alkyl;

$R^{16}$ is hydrogen, hydroxy, $C_{1-6}$-alkyl, or halo-$C_{1-6}$-alkyl;

$R^{17}$ is hydrogen, hydroxy, halo-$C_{1-6}$-alkyl, or $C_{1-6}$-alkyl;

each occurrence of n is independently 0, 1, 2 or 3;

each occurrence of p is independently 1, 2 or 3; and q is 0, 1 or 2.

3. The compound of formula (I) according to claim 1, or a pharmaceutically acceptable salt thereof, wherein $R^1$, $R^2$, $R^3$, and $R^4$ are each hydrogen.

4. The compound of formula (I) according to claim 3, or a pharmaceutically acceptable salt thereof, wherein present, is phenyl or pyridyl.

5. The compound of formula (I) according to claim 1, or a pharmaceutically acceptable salt thereof, wherein:

A is $C_{6-14}$-aryl substituted with $R^7$, $R^8$ and $R^9$, where $R^7$ is hydrogen, hydroxy, $C_{1-6}$-alkyl, halo-$C_{1-6}$-alkyl, halogen, $C_{1-6}$-alkoxy, halo-$C_{1-6}$-alkoxy, $SF_5$ or a group

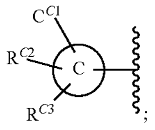;

wherein

C is 5-14 membered heteroaryl or 3-14 membered heterocyclyl;

$R^{C1}$ is $C_{1-6}$-alkyl, halo-$C_{1-6}$-alkyl or oxo; and $R^{C2}$ and $R^{C3}$ are both hydrogen;

$R^8$ is hydrogen, $C_{1-6}$-alkoxy, halo-$C_{1-6}$-alkyl or halogen;

$R^9$ is hydrogen;

or A is 5-14 membered heteroaryl substituted with $R^{10}$, $R^{11}$ and $R^{12}$, where $R^{10}$ is halogen or halo-$C_{1-6}$-alkyl;

$R^{11}$ is hydrogen or halo-$C_{1-6}$-alkyl; and $R^{12}$ is hydrogen.

6. The compound of formula (I) according to claim 5, or a pharmaceutically acceptable salt thereof, wherein:

A is $C_{6-14}$-aryl substituted with $R^7$ and $R^8$, where $R^7$ is hydrogen, $C_{1-6}$-alkyl, halo-$C_{1-6}$-alkyl, halogen, $C_{1-6}$-alkoxy, halo-$C_{1-6}$-alkoxy or $SF_5$; and $R^8$ is hydrogen, halo-$C_{1-6}$-alkyl or halogen;

or A is 5-14 membered heteroaryl substituted with $R^{10}$, where $R^{10}$ is halo-$C_{1-6}$-alkyl.

7. The compound of formula (I) according to claim 6, or a pharmaceutically acceptable salt thereof, wherein:

A is $C_{6-14}$-aryl substituted with $R^7$ and $R^8$, where $R^7$ is hydrogen, fluoro, chloro, $CF_3$, methyl, methoxy, trifluoromethoxy or $SF_5$; and $R^8$ is hydrogen, $CF_3$, chloro or fluoro;

or A is 5-14 membered heteroaryl substituted with $R^{10}$ and $R^{11}$, where $R^{10}$ is $CF_3$; and $R^{11}$ is hydrogen or $CF_3$.

8. The compound of formula (I) according to claim 1, or a pharmaceutically acceptable salt thereof, wherein:

X is C—$R^5$;

L is a covalent bond, —$(CH_2)_n$—N($C_{1-6}$-alkyl)-, —$(CH_2)_n$—NH—, —$(CH_2)_n$—O—, —$OCH_2$—, —$CH_2$—, —$SO_2$—, —$SO_2$—N($C_{1-6}$-alkyl)- or —$SO_2$—NH—;

n is 0 or 1; and $R^5$ is hydrogen or halo-$C_{1-6}$-alkyl;

or

X is N;

L is a covalent bond, —$CH_2$—, —$CHR^6$— or —$SO_2$—; and $R^6$ is $C_{6-14}$-aryl.

9. The compound of formula (I) according to claim 8, or a pharmaceutically acceptable salt thereof, wherein:

X is C—$R^5$;

L is a covalent bond, —$CH_2O$—, —O—, —$OCH_2$—, —$CH_2$— or —$SO_2$—N($C_{1-6}$-alkyl)-; and $R^5$ is hydrogen.

10. The compound of formula (I) according to claim 8, or a pharmaceutically acceptable salt thereof, wherein:

X is C—$R^5$;

L is a covalent bond, —$CH_2O$—, —O—, —$OCH_2$—, —$CH_2$— or —$SO_2$—N(methyl)-; and $R^5$ is hydrogen.

11. The compound of formula (I) according to claim 8, or a pharmaceutically acceptable salt thereof, wherein:

X is N;

L is —$CH_2$— or —$SO_2$—; and $R^6$ is $C_{6-14}$-aryl.

12. The compound of formula (I) according to claim 1, or a pharmaceutically acceptable salt thereof, wherein B is a bicyclic spirocycle having formula (II):

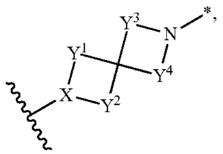, (II)

wherein:

X is as defined in formula (I);

$Y^1$, $Y^2$, $Y^3$ and $Y^4$ are each independently —$(CH_2)_m$—, —$(CH_2)_m$O—, —O$(CH_2)_m$—, —$(CH_2)_m$NH— or —NH$(CH_2)_m$—;

each occurrence of m is independently 1, 2 or 3;

the wavy line indicates the point of attachment of bicyclic spirocycle B to L in formula (I); and the asterisk indicates the point of attachment of bicyclic spirocycle B to the remainder of formula (I).

13. The compound of formula (I) according claim 12, or a pharmaceutically acceptable salt thereof, wherein B is a bicyclic spirocycle having formula (II):

(II)

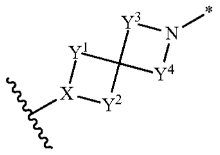

wherein:

X is as defined in formula (I);

$Y^1$ is $—(CH_2)_m—$ or $—(CH_2)_mO—$, wherein m is 1 or 2;

$Y^2$ is $—CH_2—$ or $—CH_2O—$;

$Y^3$ and $Y^4$ are each independently $—(CH_2)_m—$, wherein m is 1 or 2;

the wavy line indicates the point of attachment of bicyclic spirocycle B to L in formula (I); and the asterisk indicates the point of attachment of bicyclic spirocycle B to the remainder of formula (I).

14. The compound of formula (I) according to claim 13, or a pharmaceutically acceptable salt thereof, wherein B is a bicyclic spirocycle having formula (II):

(II)

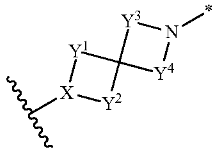

wherein:

X is as defined in formula (I);

$Y^1$ is $—CH_2—$;

$Y^2$ is $—CH_2—$ or $—CH_2O—$;

$Y^3$ and $Y^4$ are each independently $—(CH_2)_m—$, wherein m is 1 or 2;

the wavy line indicates the point of attachment of bicyclic spirocycle B to L in formula (I); and the asterisk indicates the point of attachment of bicyclic spirocycle B to the remainder of formula (I).

15. The compound of formula (I) according to claim 12, or a pharmaceutically acceptable salt thereof, wherein:

$R^1$, $R^2$, $R^3$, and $R^4$ are each hydrogen;

A is phenyl or pyridyl, and

X and L are as defined in formula (I).

16. The compound of formula (I) according to claim 1, or a pharmaceutically acceptable salt thereof, wherein B is a bicyclic spirocycle selected from the group consisting of:

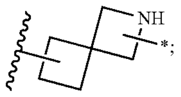
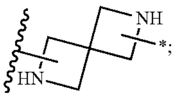
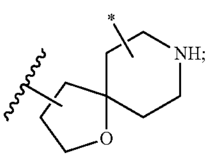
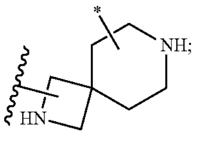
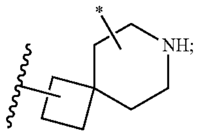

-continued

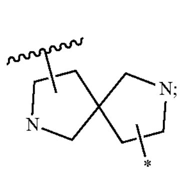
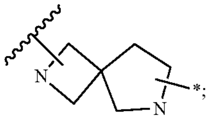
and
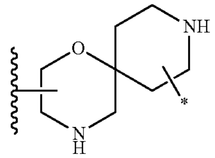

wherein:

(i) a wavy line indicates the point of attachment of bicyclic spirocycle B to L in formula (I); and an asterisk indicates the point of attachment of bicyclic spirocycle B to the remainder of formula (I); or (ii) a wavy line indicates the point of attachment of bicyclic spirocycle B to the remainder of formula (I); and an asterisk indicates the point of attachment of bicyclic spirocycle B to L in formula (I), and wherein X, L, A, $R^1$, and $R^2$ are as defined in formula (I).

17. The compound of formula (I) according to claim 1, or a pharmaceutically acceptable salt thereof, wherein B is a bicyclic spirocycle selected from the group consisting of:

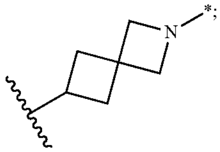
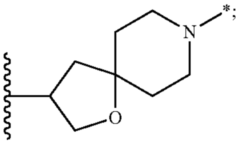
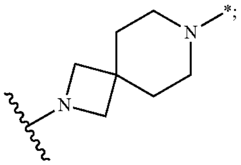
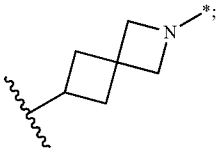
and
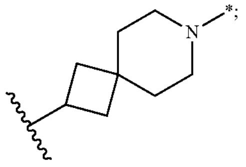

wherein a wavy line indicates the point of attachment of bicyclic spirocycle B to L in formula (I); and an asterisk indicates the point of attachment of bicyclic spirocycle B to the remainder of formula (I), and wherein X, L, A, $R^1$, and $R^2$ are as defined in formula (I).

18. The compound of formula (I) according to claim 1, or a pharmaceutically acceptable salt thereof, wherein:

(i) X is $C—R^5$;

L is a covalent bond, $—CH_2—N(C_{1-6}\text{-alkyl})-$, $—CH_2—NH—$, $—O—$, $—CH_2O—$, $—OCH_2—$, $—CH_2—$, $—SO_2—$, $—SO_2—N(C_{1-6}\text{-alkyl})-$ or $—SO_2—NH—$; and A is:

(i) $C_{6-14}$-aryl substituted with $R^7$, $R^8$ and $R^9$; or (ii) 5-14 membered heteroaryl substituted with $R^{10}$, $R^{11}$ and $R^{12}$; or (ii) X is N;

L is a covalent bond, $—CH_2—$, $—CHR^6—$ or $—SO_2—$; and

A is $C_{6-14}$-aryl substituted with $R^7$, $R^8$ and $R^9$; or (iii) X is N;

L is $C_{1-6}$-alkoxycarbonyl; and

A is absent;

B is a bicyclic spirocycle having formula (II):

(II)

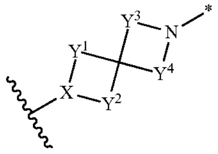

wherein:

$Y^1$ is $—(CH_2)_m—$ or $—(CH_2)_mO—$, wherein m is 1 or 2;

$Y^2$ is $—CH_2—$ or $—CH_2O—$;

$Y^3$ and $Y^4$ are each independently $—(CH_2)_m—$, wherein m is 1 or 2;

the wavy line indicates the point of attachment of bicyclic spirocycle B to L in formula (I); and the asterisk indicates the point of attachment of bicyclic spirocycle B to the remainder of formula (I);

each of $R^1$, $R^2$, $R^3$, $R^4$, $R^9$ and $R^{12}$ is hydrogen;

$R^5$ is hydrogen or $C_{1-6}$-alkyl;

$R^6$ is $C_{6-14}$-aryl;

$R^7$ is hydrogen, hydroxy, $C_{1-6}$-alkyl, halo-$C_{1-6}$-alkyl, halogen, $C_{1-6}$-alkoxy or halo-$C_{1-6}$-alkoxy, $SF_5$ or a group

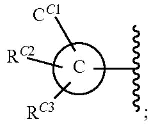

;

$R^8$ is hydrogen, $C_{1-6}$-alkoxy, halo-$C_{1-6}$-alkyl or halogen;

$R^{10}$ is halogen or halo-$C_{1-6}$-alkyl;

$R^{11}$ is hydrogen or halo-$C_{1-6}$-alkyl;

$R^{C1}$ is $C_{1-6}$-alkyl, halo-$C_{1-6}$-alkyl or oxo;

$R^{C2}$ and $R^{C3}$ are both hydrogen; and

C is 5-14 membered heteroaryl or 3-14 membered heterocyclyl.

19. The compound of formula (I) according to claim 1, or a pharmaceutically acceptable salt thereof, wherein:

(i) X is C—$R^5$;

L is $—CH_2O—$, $—OCH_2—$, —O—, $—CH_2—$ or $—SO_2—N(C_{1-6}$-alkyl)-; and

A is:

(i) $C_{6-14}$-aryl substituted with $R^7$, $R^8$ and $R^9$; or (ii) 5-14 membered heteroaryl substituted with $R^{10}$, $R^{11}$ and $R^{12}$; or (ii) X is N;

L is $—CH_2—$ or $—SO_2—$; and

A is $C_{6-14}$-aryl substituted with $R^7$, $R^1$ and $R^9$;

B is a bicyclic spirocycle having formula (II):

(II)

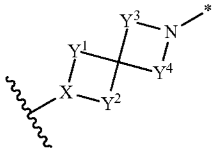

wherein:

$Y^1$ is $—CH_2—$;

$Y^2$ is $—CH_2—$ or $—CH_2O—$;

$Y^3$ and $Y^4$ are each independently $—(CH_2)_m—$, wherein m is 1 or 2;

the wavy line indicates the point of attachment of bicyclic spirocycle B to L in formula (I); and the asterisk indicates the point of attachment of bicyclic spirocycle B to the remainder of formula (I);

each of $R^1$, $R^2$, $R^3$, $R^4$, $R^5$, $R^9$, and $R^{12}$ is hydrogen;

$R^7$ is hydrogen, $C_{1-6}$-alkyl, halo-$C_{1-6}$-alkyl, halogen, $C_{1-6}$-alkoxy, halo-$C_{1-6}$-alkoxy or $SF_5$;

$R^8$ is hydrogen, halo-$C_{1-6}$-alkyl or halogen;

$R^{10}$ is halo-$C_{1-6}$-alkyl; and $R^{11}$ is hydrogen or halo-$C_{1-6}$-alkyl.

20. The compound of formula (I) according to claim 1, or a pharmaceutically acceptable salt thereof, wherein:

(i) X is C—$R^5$;

L is $—CH_2O—$, $—OCH_2—$, —O—, $—CH_2—$ or $—SO_2—$N(methyl)-; and

A is:

(i) phenyl substituted with $R^7$, $R^1$ and $R^9$; or (ii) pyridyl substituted with $R^{10}$, $R^{11}$ and $R^{12}$; or (ii) X is N;

L is $—CH_2—$ or $—SO_2—$; and

A is phenyl substituted with $R^7$, $R^1$ and $R^9$;

B is a bicyclic spirocycle selected from the group consisting of:

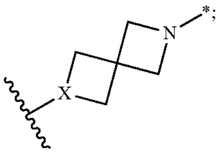

;

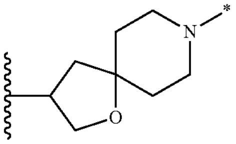

and

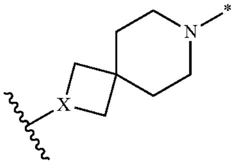

wherein the wavy line indicates the point of attachment of bicyclic spirocycle B to L in formula (I); and the asterisk indicates the point of attachment of bicyclic spirocycle B to the remainder of formula (I);

each of $R^1$, $R^2$, $R^3$, $R^4$, $R^5$, $R^9$, and $R^{12}$ is hydrogen;

$R^7$ is hydrogen, fluoro, chloro, $CF_3$, methyl, methoxy, trifluoromethoxy or $SF_5$;

$R^8$ is hydrogen, $CF_3$, chloro or fluoro;

$R^{10}$ is $CF_3$; and $R^{11}$ is hydrogen or $CF_3$.

21. The compound of formula (I) according to claim 1, wherein said compound is:

(4aR,8aS)-6-(6-(2-Chloro-4-(trifluoromethoxy)phenoxy)-2-azaspiro[3.3]heptane-2-carbonyl)hexahydro-2H-pyrido[4,3-b][1,4]oxazin-3(4H)-one;

(4aR,8aS)-6-(2-(2-Fluoro-4-(trifluoromethyl)phenoxy)-7-azaspiro[3.5]nonane-7-carbonyl)hexahydro-2H-pyrido[4,3-b][1,4]oxazin-3(4H)-one;

(4aR,8aS)-6-(6-(2-Fluoro-4-(trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(2-Methoxy-5-(trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(2-Fluoro-4-(trifluoromethoxy)phenoxy)-2-azaspiro[3.3]heptane-2-carbonyl)hexahydro-2H-pyrido[4,3-b][1,4]oxazin-3(4H)-one;

(4aR,8aS)-6-(6-(2-Chloro-4-fluorophenoxy)-2-azaspiro[3.3]heptane-2-carbonyl)hexahydro-2H-pyrido[4,3-b][1,4]oxazin-3(4H)-one;

(4aR,8aS)-6-(6-(4-(Trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(4-Chloro-2-(trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(2,4-Difluorophenoxy)-2-azaspiro[3.3]heptane-2-carbonyl)hexahydro-2H-pyrido[4,3-b][1,4]oxazin-3(4H)-one;

(4aR,8aS)-6-(6-(3-Fluoro-5-(trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(2-Fluoro-4-(trifluoromethyl)benzyl)-2,6-diazaspiro[3.3]heptane-2-carbonyl)hexahydro-2H-pyrido[4,3-b][1,4]oxazin-3(4H)-one;

(4aR,8aS)-6-(6-(2-Chloro-4-fluorobenzyl)-2,6-diazaspiro[3.3]heptane-2-carbonyl)hexahydro-2H-pyrido[4,3-b][1,4]oxazin-3(4H)-one;

(4aR,8aS)-6-(2-(2-Fluoro-4-(trifluoromethyl)benzyl)-2,7-diazaspiro[3.5]nonane-7-carbonyl)hexahydro-2H-pyrido[4,3-b][1,4]oxazin-3(4H)-one;

(4aR,8aS)-6-(6-((2-Chloro-4-fluorophenyl)sulfonyl)-2,6-diazaspiro[3.3]heptane-2-carbonyl)hexahydro-2H-pyrido[4,3-b][1,4]oxazin-3(4H)-one;

(4aR,8aS)-6-(7-(2-Fluoro-4-(trifluoromethyl)benzyl)-2,7-diazaspiro[4.4]nonane-2-carbonyl)hexahydro-2H-pyrido[4,3-b][1,4]oxazin-3(4H)-one;

(4aR,8aS)-6-(6-((2-Fluoro-4-(trifluoromethyl)phenyl)sulfonyl)-2,6-diazaspiro[3.3]heptane-2-carbonyl)hexahydro-2H-pyrido[4,3-b][1,4]oxazin-3(4H)-one;

(4aR,8aS)-6-(2-(2-Fluoro-4-(trifluoromethyl)benzyl)-2,6-diazaspiro[3.4]octane-6-carbonyl)hexahydro-2H-pyrido[4,3-b][1,4]oxazin-3(4H)-one;

rac-(4aR,8aS)—N—((R)-8-(3-Oxooctahydro-2H-pyrido[4,3-b][1,4]oxazine-6-carbonyl)-1-oxa-8-azaspiro[4.5]decan-3-yl)benzenesulfonamide;

rac-(4aR,8aS)—N—((S)-8-(3-Oxooctahydro-2H-pyrido[4,3-b][1,4]oxazine-6-carbonyl)-1-oxa-8-azaspiro[4.5]decan-3-yl)benzenesulfonamide;

rac-(4aR,8aS)-6-(2-Benzhydryl-2,6-diazaspiro[3.4]octane-6-carbonyl)hexahydro-2H-pyrido[4,3-b][1,4]oxazin-3(4H)-one;

rac-(4aR,8aS)-6-(4-((4-Fluorophenyl)sulfonyl)-1-oxa-4,9-diazaspiro[5.5]undecane-9-carbonyl)hexahydro-2H-pyrido[4,3-b][1,4]oxazin-3(4H)-one;

(4aR,8aS)-6-(6-((4,5-bis(trifluoromethyl)pyridin-2-yl)oxy)-2-azaspiro[3.3]heptane-2-carbonyl)hexahydro-2H-pyrido[4,3-b][1,4]oxazin-3(4H)-one;

(4aR,8aS)-6-(6-((5,6-Bis(trifluoromethyl)pyridin-2-yl)oxy)-2-azaspiro[3.3]heptane-2-carbonyl)hexahydro-2H-pyrido[4,3-b][1,4]oxazin-3(4H)-one;

2-Chloro-4-fluoro-N-methyl-N—((R)-8-((4aR,8aS)-3-oxooctahydro-2H-pyrido[4,3-b][1,4]oxazine-6-carbonyl)-1-oxa-8-azaspiro[4.5]decan-3-yl)benzenesulfonamide;

(4aR,8aS)-6-(6-((5-(Trifluoromethyl)pyridin-2-yl)oxy)-2-azaspiro[3.3]heptane-2-carbonyl)hexahydro-2H-pyrido[4,3-b][1,4]oxazin-3(4H)-one;

(4aR,8aS)-6-(6-((4-Methyl-3-(trifluoromethyl)benzyl)oxy)-2-azaspiro[3.3]heptane-2-carbonyl)hexahydro-2H-pyrido[4,3-b][1,4]oxazin-3(4H)-one;

(4aR,8aS)-6-(2-((2-Chloro-4-fluorophenyl)sulfonyl)-2,7-diazaspiro[3.5]nonane-7-carbonyl)hexahydro-2H-pyrido[4,3-b][1,4]oxazin-3(4H)-one;

(4aR,8aS)-6-(6-((2-Fluoro-4-(trifluoromethyl)benzyl)oxy)-2-azaspiro[3.3]heptane-2-carbonyl)hexahydro-2H-pyrido[4,3-b][1,4]oxazin-3(4H)-one;

N—((S)-8-((4aR,8aS)-3-Oxooctahydro-2H-pyrido[4,3-b][1,4]oxazine-6-carbonyl)-1-oxa-8-azaspiro[4.5]decan-3-yl)-4-(trifluoromethyl)benzenesulfonamide;

N-Methyl-N—((R)-8-((4aR,8aS)-3-oxooctahydro-2H-pyrido[4,3-b][1,4]oxazine-6-carbonyl)-1-oxa-8-azaspiro[4.5]decan-3-yl)benzenesulfonamide;

2-Chloro-4-fluoro-N—((S)-8-((4aR,8aS)-3-oxooctahydro-2H-pyrido[4,3-b][1,4]oxazine-6-carbonyl)-1-oxa-8-azaspiro[4.5]decan-3-yl)benzenesulfonamide;

N—((S)-8-((4aR,8aS)-3-Oxooctahydro-2H-pyrido[4,3-b][1,4]oxazine-6-carbonyl)-1-oxa-8-azaspiro[4.5]decan-3-yl)-3-(trifluoromethyl)benzenesulfonamide;

(4aR,8aS)-6-(3-((2-Chloro-4-fluorobenzyl)(methyl)amino)-1-oxa-8-azaspiro[4.5]decane-8-carbonyl)hexahydro-2H-pyrido[4,3-b][1,4]oxazin-3(4H)-one;

(4aR,8aS)-6-(3-((2-Chloro-4-fluorobenzyl)(methyl)amino)-1-oxa-8-azaspiro[4.5]decane-8-carbonyl)hexahydro-2H-pyrido[4,3-b][1,4]oxazin-3(4H)-one;

(4aR,8aS)-6-(3-((2-Chloro-4-fluorobenzyl)amino)-1-oxa-8-azaspiro[4.5]decane-8-carbonyl)hexahydro-2H-pyrido[4,3-b][1,4]oxazin-3(4H)-one;

(4aR,8aS)-6-(3-((2-Chloro-4-fluorobenzyl)amino)-1-oxa-8-azaspiro[4.5]decane-8-carbonyl)hexahydro-2H-pyrido[4,3-b][1,4]oxazin-3(4H)-one;

(4aR,8aS)-6-(2-((4-(Trifluoromethyl)phenyl)sulfonyl)-2,7-diazaspiro[3.5]nonane-7-carbonyl)hexahydro-2H-pyrido[4,3-b][1,4]oxazin-3(4H)-one;

rac-(4aR,8aS)-6-(3-((2-Chloro-4-fluorobenzyl)amino)-1-oxa-8-azaspiro[4.5]decane-8-carbonyl)hexahydro-2H-pyrido[4,3-b][1,4]oxazin-3(4H)-one;

(4aR,8aS)-6-(2-(Phenylsulfonyl)-2,7-diazaspiro[3.5]nonane-7-carbonyl)hexahydro-2H-pyrido[4,3-b][1,4]oxazin-3(4H)-one;

rac-tert-butyl 6-((4aR,8aS)-3-oxooctahydro-2H-pyrido[4,3-b][1,4]oxazine-6-carbonyl)-2,6-diazaspiro[3.4]octane-2-carboxylate;

(4aR,8aS)-6-(6-(4-(1-methyl-1H-pyrazol-5-yl)phenyl)-2-azaspiro[3.3]heptane-2-carbonyl)hexahydro-2H-pyrido[4,3-b][1,4]oxazin-3(4H)-one;

(4aR,8aS)-6-(6-(2-fluoro-6-hydroxybenzyl)-2-azaspiro[3.3]heptane-2-carbonyl)hexahydro-2H-pyrido[4,3-b][1,4]oxazin-3(4H)-one;

(4aR,8aS)-6-(6-(2-hydroxybenzyl)-2-azaspiro[3.3]heptane-2-carbonyl)hexahydro-2H-pyrido[4,3-b][1,4]oxazin-3(4H)-one;

(4aR,8aS)-6-(2-(4-(2-oxopyrrolidin-1-yl)phenyl)-2,6-diazaspiro[3.4]octane-6-carbonyl)hexahydro-2H-pyrido[4,3-b][1,4]oxazin-3(4H)-one;

(4aR,8aS)-6-(6-(2-fluoro-6-methoxybenzyl)-2-azaspiro[3.3]heptane-2-carbonyl)hexahydro-2H-pyrido[4,3-b][1,4]oxazin-3(4H)-one;

(4aR,8aS)-6-(6-(4-(pentafluoro-16-sulfaneyl)phenyl)-2-azaspiro[3.3]heptane-2-carbonyl)hexahydro-2H-pyrido[4,3-b][1,4]oxazin-3(4H)-one;

(4aR,8aS)-6-(6-(2-fluoro-4-(trifluoromethyl)benzyl)-2-azaspiro[3.3]heptane-2-carbonyl)hexahydro-2H-pyrido[4,3-b][1,4]oxazin-3(4H)-one;

(4aR,8aS)-6-(6-(2,4-difluorobenzyl)-2-azaspiro[3.3]heptane-2-carbonyl)hexahydro-2H-pyrido[4,3-b][1,4]oxazin-3(4H)-one;

(4aR,8aS)-6-(6-(2-methoxy-4-(trifluoromethyl)benzyl)-2-azaspiro[3.3]heptane-2-carbonyl)hexahydro-2H-pyrido[4,3-b][1,4]oxazin-3(4H)-one;

(4aR,8aS)-6-(6-((2-chloro-4-fluorophenoxy)methyl)-2-azaspiro[3.3]heptane-2-carbonyl)hexahydro-2H-pyrido[4,3-b][1,4]oxazin-3(4H)-one;

(4aR,8aS)-6-(6-((2-fluoro-4-(trifluoromethyl)benzyl)oxy)-6-(trifluoromethyl)-2-azaspiro[3.3]heptane-2-carbonyl)hexahydro-2H-pyrido[4,3-b][1,4]oxazin-3(4H)-one;

(4aR,8aS)-6-(6-(2-fluoro-4-(trifluoromethyl)phenyl)-2-azaspiro[3.3]heptane-2-carbonyl)hexahydro-2H-pyrido[4,3-b][1,4]oxazin-3(4H)-one;

(4aR,8aS)-6-(6-(4-(2-(trifluoromethyl)pyrrolidin-1-yl)phenyl)-2-azaspiro[3.3]heptane-2-carbonyl)hexahydro-2H-pyrido[4,3-b][1,4]oxazin-3(4H)-one;

(4aR,8aS)-6-(6-(2-chloro-4-fluorobenzyl)-2-azaspiro[3.3]heptane-2-carbonyl)hexahydro-2H-pyrido[4,3-b][1,4]oxazin-3(4H)-one;

(4aR,8aS)-6-(6-(2-fluoro-6-(trifluoromethyl)benzyl)-2-azaspiro[3.3]heptane-2-carbonyl)hexahydro-2H-pyrido[4,3-b][1,4]oxazin-3(4H)-one;

(4aR,8aS)-6-(6-(4-(trifluoromethyl)phenyl)-2,6-diazaspiro[3.3]heptane-2-carbonyl)hexahydro-2H-pyrido[4,3-b][1,4]oxazin-3(4H)-one;

(4aR,8aS)-6-(6-(3-(trifluoromethyl)phenyl)-2,6-diazaspiro[3.3]heptane-2-carbonyl)hexahydro-2H-pyrido[4,3-b][1,4]oxazin-3(4H)-one;

(4aR,8aS)-6-(2-(4-(trifluoromethyl)phenyl)-2,6-diazaspiro[3.4]octane-6-carbonyl)hexahydro-2H-pyrido[4,3-b][1,4]oxazin-3(4H)-one;

(4aR,8aS)-6-(2-(3-(trifluoromethyl)phenyl)-2,6-diazaspiro[3.4]octane-6-carbonyl)hexahydro-2H-pyrido[4,3-b][1,4]oxazin-3(4H)-one;

(4aR,8aS)-6-(2-(4-isopropoxyphenyl)-2,6-diazaspiro[3.4]octane-6-carbonyl)hexahydro-2H-pyrido[4,3-b][1,4]oxazin-3(4H)-one;

(4aR,8aS)-6-(6-(4-isopropoxyphenyl)-2,6-diazaspiro[3.3]heptane-2-carbonyl)hexahydro-2H-pyrido[4,3-b][1,4]oxazin-3(4H)-one;

(4aR,8aS)-6-(2-(4-methoxy-3-methylphenyl)-2,6-diazaspiro[3.4]octane-6-carbonyl)hexahydro-2H-pyrido[4,3-b][1,4]oxazin-3(4H)-one;

(4aR,8aS)-6-(2-(4-chloro-3-(trifluoromethyl)phenyl)-2,6-diazaspiro[3.4]octane-6-carbonyl)hexahydro-2H-pyrido[4,3-b][1,4]oxazin-3(4H)-one;

(4aR,8aS)-6-(2-(2-fluoropyridin-4-yl)-2,6-diazaspiro[3.4]octane-6-carbonyl)hexahydro-2H-pyrido[4,3-b][1,4]oxazin-3(4H)-one;

(4aR,8aS)-6-(6-(2,5-bis(trifluoromethyl)phenyl)-2,6-diazaspiro[3.3]heptane-2-carbonyl)hexahydro-2H-pyrido[4,3-b][1,4]oxazin-3(4H)-one;

(4aR,8aS)-6-(6-((4-fluoro-2-(trifluoromethyl)phenyl)sulfonyl)-2,6-diazaspiro[3.3]heptane-2-carbonyl)hexahydro-2H-pyrido[4,3-b][1,4]oxazin-3(4H)-one;

(4aR,8aS)-6-(6-((2-chloro-4-fluorophenyl)sulfonyl)-2-azaspiro[3.3]heptane-2-carbonyl)hexahydro-2H-pyrido[4,3-b][1,4]oxazin-3(4H)-one;

(4aR,8aS)-6-(6-((3-chloro-4-(trifluoromethyl)phenyl)sulfonyl)-2,6-diazaspiro[3.3]heptane-2-carbonyl)hexahydro-2H-pyrido[4,3-b][1,4]oxazin-3(4H)-one;

(4aR,8aS)-6-(6-((2,4-bis(trifluoromethyl)phenyl)sulfonyl)-2,6-diazaspiro[3.3]heptane-2-carbonyl)hexahydro-2H-pyrido[4,3-b][1,4]oxazin-3(4H)-one;

(4aR,8aS)-6-(6-(2,6-difluorobenzyl)-2-azaspiro[3.3]heptane-2-carbonyl)hexahydro-2H-pyrido[4,3-b][1,4]oxazin-3(4H)-one; or (4aR,8aS)-6-(6-(2-methoxybenzyl)-2-azaspiro[3.3]heptane-2-carbonyl)hexahydro-2H-pyrido[4,3-b][1,4]oxazin-3(4H)-one, or is a pharmaceutically acceptable salt thereof.

22. A compound of formula (I) according to claim 1, wherein said compound is:

(4aR,8aS)-6-(6-(2-Chloro-4-(trifluoromethoxy)phenoxy)-2-azaspiro[3.3]heptane-2-carbonyl)hexahydro-2H-pyrido[4,3-b][1,4]oxazin-3(4H)-one;

(4aR,8aS)-6-(2-(2-Fluoro-4-(trifluoromethyl)phenoxy)-7-azaspiro[3.5]nonane-7-carbonyl)hexahydro-2H-pyrido[4,3-b][1,4]oxazin-3(4H)-one;

(4aR,8aS)-6-(6-(2-Fluoro-4-(trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(2-Methoxy-5-(trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(2-Fluoro-4-(trifluoromethoxy)phenoxy)-2-azaspiro[3.3]heptane-2-carbonyl)hexahydro-2H-pyrido[4,3-b][1,4]oxazin-3(4H)-one;

(4aR,8aS)-6-(6-(2-Chloro-4-fluorophenoxy)-2-azaspiro[3.3]heptane-2-carbonyl)hexahydro-2H-pyrido[4,3-b][1,4]oxazin-3(4H)-one;

(4aR,8aS)-6-(6-(4-(Trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(4-Chloro-2-(trifluoromethyl)phenoxy)-2-azaspiro[3.3]heptane-2-carbonyl)hexahydro-2H-pyrido[4,3-b][1,4]oxazin-3(4H)-one;

(4aR,8aS)-6-(6-(2,4-Difluorophenoxy)-2-azaspiro[3.3]heptane-2-carbonyl)hexahydro-2H-pyrido[4,3-b][1,4]oxazin-3(4H)-one;

(4aR,8aS)-6-(6-(2-Fluoro-4-(trifluoromethyl)benzyl)-2,6-diazaspiro[3.3]heptane-2-carbonyl)hexahydro-2H-pyrido[4,3-b][1,4]oxazin-3(4H)-one;

(4aR,8aS)-6-(6-((4,5-bis(trifluoromethyl)pyridin-2-yl)oxy)-2-azaspiro[3.3]heptane-2-carbonyl)hexahydro-2H-pyrido[4,3-b][1,4]oxazin-3(4H)-one;

(4aR,8aS)-6-(6-(4-(pentafluoro-16-sulfaneyl)phenyl)-2-azaspiro[3.3]heptane-2-carbonyl)hexahydro-2H-pyrido[4,3-b][1,4]oxazin-3(4H)-one;

(4aR,8aS)-6-(6-(2-fluoro-4-(trifluoromethyl)benzyl)-2-azaspiro[3.3]heptane-2-carbonyl)hexahydro-2H-pyrido[4,3-b][1,4]oxazin-3(4H)-one;

(4aR,8aS)-6-(6-(2,4-difluorobenzyl)-2-azaspiro[3.3]heptane-2-carbonyl)hexahydro-2H-pyrido[4,3-b][1,4]oxazin-3(4H)-one;

(4aR,8aS)-6-(6-(2-methoxy-4-(trifluoromethyl)benzyl)-2-azaspiro[3.3]heptane-2-carbonyl)hexahydro-2H-pyrido[4,3-b][1,4]oxazin-3(4H)-one; or (4aR,8aS)-6-(6-((2-chloro-4-fluorophenoxy)methyl)-2-azaspiro[3.3]heptane-2-carbonyl)hexahydro-2H-pyrido[4,3-b][1,4]oxazin-3(4H)-one, or is a pharmaceutically acceptable salt thereof.

23. A pharmaceutical composition, comprising a compound of formula (I) according to claim 1, or a pharmaceutically acceptable salt thereof, and a therapeutically inert carrier.

24. A pharmaceutical composition, comprising a compound of formula (I) according to claim 21, or a pharmaceutically acceptable salt thereof, and a therapeutically inert carrier.

25. A pharmaceutical composition, comprising a compound of formula (I) according to claim 22, or a pharmaceutically acceptable salt thereof, and a therapeutically inert carrier.

* * * * *